US008153644B2

(12) United States Patent
Bolin et al.

(10) Patent No.: US 8,153,644 B2
(45) Date of Patent: *Apr. 10, 2012

(54) DIACYLGLYCEROL ACYLTRANSFERASE INHIBITORS

(75) Inventors: David Robert Bolin, Montclair, NJ (US); Adrian Wai-Hing Cheung, Glen Rock, NJ (US); Fariborz Firooznia, Florham Park, NJ (US); Matthew Michael Hamilton, Hackettstown, NJ (US); Lee Aopstle McDermott, Parlin, NJ (US); Yimin Qian, Wayne, NJ (US); Jenny Tan, New Providence, NJ (US); Weiya Yun, Warren, NJ (US)

(73) Assignee: Madrigal Pharmaceuticals, Inc., San Francisco, CA (US)

( * ) Notice: Subject to any disclaimer, the term of this patent is extended or adjusted under 35 U.S.C. 154(b) by 127 days.

This patent is subject to a terminal disclaimer.

(21) Appl. No.: 12/113,295

(22) Filed: May 1, 2008

(65) Prior Publication Data
US 2009/0105273 A1   Apr. 23, 2009

Related U.S. Application Data

(60) Provisional application No. 61/037,357, filed on Mar. 18, 2008, provisional application No. 60/931,369, filed on May 22, 2007.

(51) Int. Cl.
*A61K 31/506* (2006.01)
*A61K 31/4525* (2006.01)
*A61K 31/443* (2006.01)
*A61K 31/421* (2006.01)
*C07D 239/34* (2006.01)
*C07D 239/42* (2006.01)
*C07D 211/22* (2006.01)
*C07D 413/14* (2006.01)
*C07D 263/34* (2006.01)

(52) U.S. Cl. ........ 514/272; 514/274; 514/318; 514/343; 514/374; 544/297; 544/316; 546/194; 546/271.4; 548/236

(58) Field of Classification Search .................. None
See application file for complete search history.

(56) References Cited

U.S. PATENT DOCUMENTS

| 3,250,771 | A | 5/1966 | Leonard et al. |
| 3,929,793 | A | 12/1975 | Popelak et al. |
| 4,066,654 | A | 1/1978 | Adelstein et al. |
| 7,015,218 | B1 | 3/2006 | Ushio et al. |
| 7,094,896 | B2 | 8/2006 | Ding et al. |
| 7,148,246 | B2 | 12/2006 | Gretzke et al. |
| 7,160,911 | B2 | 1/2007 | Goerlitzer et al. |
| 7,244,727 | B2 | 7/2007 | Fox et al. |
| 7,317,125 | B2 | 1/2008 | Bolin et al. |
| 7,714,126 | B2 * | 5/2010 | Bolin et al. ............ 544/59 |
| 2004/0019067 | A1 | 1/2004 | Armistead et al. |
| 2007/0123504 | A1* | 5/2007 | Bolin et al. ............ 514/210.02 |
| 2009/0093497 | A1 | 4/2009 | Bolin et al. |
| 2009/0099201 | A1 | 4/2009 | Bolin et al. |
| 2009/0170864 | A1 | 7/2009 | Bolin et al. |
| 2010/0145047 | A1 | 6/2010 | Bolin et al. |
| 2010/0152445 | A1 | 6/2010 | Bolin et al. |

FOREIGN PATENT DOCUMENTS

| AU | 2002333456 A2 | 3/2003 |
| EP | 1 535 915 A | 6/2005 |
| EP | 1535915 A1 | 6/2005 |
| WO | WO-0047558 A1 | 8/2000 |
| WO | WO 03/020269 A1 | 3/2003 |
| WO | WO 2006/134317 A1 | 12/2006 |
| WO | WO 2007/060140 | * 5/2007 |
| WO | WO2007/060140 A | 5/2007 |
| WO | 2008141976 A1 | 11/2008 |
| WO | WO-2010065310 A1 | 6/2010 |
| WO | WO-2010077861 A1 | 7/2010 |

OTHER PUBLICATIONS

The International Search Report and Written Opinion by the International Searching Authority, issued on Jul. 30, 2008, in the PCT application No. PCT/EP2008/055843.
Zhao et al., "Validation of Diacyl Glycerolacyltransferase I as a Novel Target for the Treatment of Obesity and Dyslipidemia Using a Potent and Selective Small Molecule Inhibitor," J. Med. Chem., 2008, 51 (3), pp. 380-383.
The International Search Report and Written Opinion by the International Searching Authority, issued on Mar. 2, 2010, in the PCT application No. PCT/US09/68048. The restriction requirement for U.S. Appl. No. 12/113,275, issued on Mar. 10, 2010.
Birch et al., "Discovery of a potent, selective, and orally efficacious pyrimidinooxazinyl bicyclooctaneacetic acid diacylglycerol acyltransferase-1 inhibitor," J. Med Chem. Mar. 26, 2009;52(6)1558-68.
Mishra et al., "A molecular model for diacylglycerol acyltransferase from *Mortierella ramanniana* var. *angulispora*," Bioinformation. 2009; 3(9): 394-398.
Oh et al., "Diacylglycerol acyltransferase-inhibitory compounds from *Erythrina senegalensis*," Archives of Pharmacal Research, 32(1), pp. 43-47, Jan. 2009.
The International Search Report and Written Opinion by the International Searching Authority, issued on Apr. 2, 2010, in the PCT application No. PCT/US09/64971.
Burger, A., "Isosterism and Bioisosterism in Drug Design," Progress in Drug Research, 1991, pp. 287-328.
Patani, G. and LaVoie, E., "Bioisosterism: A Rational Approach in Drug Design," Chem. Rev. 1996, 96, 3147-3176.

* cited by examiner

*Primary Examiner* — Rebecca Anderson
*Assistant Examiner* — Alicia L Otton
(74) *Attorney, Agent, or Firm* — Mintz Levin Cohn Ferris Glovsky and Popeo, P.C.; Ivor R. Elrifi; Heidi A. Erlacher

(57) ABSTRACT

Provided herein are compounds of the formula (I):

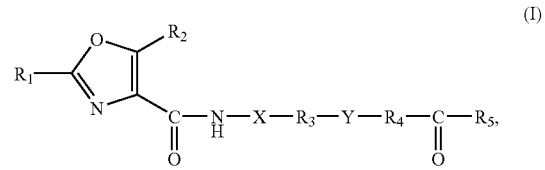

as well as pharmaceutically acceptable salts thereof, wherein the substituents are as those disclosed in the specification. These compounds, and the pharmaceutical compositions containing them, are useful for the treatment of diseases such as, for example, obesity, type II diabetes mellitus and metabolic syndrome.

51 Claims, No Drawings

DIACYLGLYCEROL ACYLTRANSFERASE INHIBITORS

PRIORITY TO RELATED APPLICATION(S)

This application claims the benefit of U.S. Provisional Application No. 61/037,357, filed Mar. 18, 2008, and U.S. Provisional Application No. 60/931,369, filed May 22, 2007 which is hereby incorporated by reference in its entirety.

RELATED APPLICATIONS

This application is related to U.S. Provisional Application Nos. 61/037,341, 61/037,339, and 61/037,348 all of which were filed on Mar. 18, 2008, and U.S. Provisional Application Nos. 60/931,273, 60/931,303 and 60/931,327, all of which were filed on May 22, 2007 all of which are incorporated by reference herein in their entirety.

FIELD OF THE INVENTION

The invention relates to inhibitors of diacylglycerol acyltransferase. The inhibitors are useful for the treatment of diseases such as obesity, type II diabetes mellitus, dyslipidemia and metabolic syndrome.

All documents cited or relied upon below are expressly incorporated herein by reference.

BACKGROUND OF THE INVENTION

Triglycerides or triacylglycerols are the major form of energy storage in eukaryotic organisms. In mammals, these compounds are primarily synthesized in three tissues: the small intestine, liver, and adipocytes. Triglycerides or triacylglycerols support the major functions of dietary fat absorption, packaging of newly synthesized fatty acids and storage in fat tissue (see Subauste and Burant, Current Drug Targets—Immune, Endocrine & Metabolic Disorders (2003) 3, 263-270).

Diacylglycerol O-acyltransferase, also known as diglyceride acyltransferase or DGAT, is a key enzyme in triglyceride synthesis. DGAT catalyzes the final and rate-limiting step in triacylglycerol synthesis from 1,2-diacylglycerol (DAG) and long chain fatty acyl CoA as substrates. Thus, DGAT plays an essential role in the metabolism of cellular diacylglycerol and is critically important for triglyceride production and energy storage homeostasis (see Mayorek et al, European Journal of Biochemistry (1989) 182, 395-400).

DGAT has a specificity for sn-1,2 diacylglycerols and will accept a wide variety of fatty acyl chain lengths (see Farese et al, Current Opinions in Lipidology (2000) 11, 229-234). DGAT activity levels increase in fat cells as they differentiate in vitro and recent evidence suggests that DGAT may be regulated in adipose tissue post-transcriptionally (see Coleman et al, Journal of Molecular Biology (1978) 253, 7256-7261 and Yu et al, Journal of Molecular Biology (2002) 277, 50876-50884). DGAT activity is primarily expressed in the endoplasmic reticulum (see Colman, Methods in Enzymology (1992) 209, 98-104). In hepatocytes, DGAT activity has been shown to be expressed on both the cytosolic and luminal surfaces of the endoplasmic reticular membrane (see Owen et al, Biochemical Journal (1997) 323 (pt 1), 17-21 and Waterman et al, Journal of Lipid Research (2002) 43, 1555-156). In the liver, the regulation of triglyceride synthesis and partitioning, between retention as cytosolic droplets and secretion, is of primary importance in determining the rate of VLDL production (see Shelness and Sellers, Current Opinions in Lipidology (2001) 12, 151-157 and Owen et al, Biochemical Journal (1997) 323 (pt 1), 17-21).

Two forms of DGAT have been cloned and are designated DGAT1 and DGAT2 (see Cases et al, Proceedings of the National Academy of Science, USA (1998) 95, 13018-13023, Lardizabal et al, Journal of Biological Chemistry (2001) 276, 38862-38869 and Cases et al, Journal of Biological Chemistry (2001) 276, 38870-38876). Although both enzymes utilize the same substrates, there is no homology between DGAT1 and DGAT2. Both enzymes are widely expressed however some differences do exist in the relative abundance of expression in various tissues.

The gene encoding mouse DGAT1 has been used to create DGAT knock-out. These mice, although unable to express a functional DGAT enzyme (Dgat−/− mice), are viable and continue to synthesize triglycerides (see Smith et al, Nature Genetics (2000) 25, 87-90). This would suggest that multiple catalytic mechanisms contribute to triglyceride synthesis, such as DGAT2. An alternative pathway has also been shown to form triglycerides from two diacylglycerols by the action of diacylglycerol transacylase (see Lehner and Kuksis, Progress in Lipid Research (1996) 35, 169-210).

Dgat−/− mice are resistant to diet-induced obesity and remain lean. When fed a high fat diet, Dgat−/− mice maintain weights comparable to mice fed a diet with regular fat content. Dgat−/− mice have lower tissue triglyceride levels. The resistance to weight gain seen in the knockout mice, which have a slightly higher food intake, is due to an increased energy expenditure and increased sensitivity to insulin and leptin (see Smith et al, Nature Genetics (2000) 25, 87-90, Chen and Farese, Trends in Cardiovascular Medicine (2000) 10, 188-192, Chen and Farese, Current Opinions in Clinical Nutrition and Metabolic Care (2002) 5, 359-363 and Chen et al, Journal of Clinical Investigation (2002) 109, 1049-1055). Dgat−/− mice have reduced rates of triglyceride absorption, improved triglyceride metabolism, and improved glucose metabolism, with lower glucose and insulin levels following a glucose load, in comparison to wild-type mice (see Buhman et al, Journal of Biological Chemistry (2002) 277, 25474-25479 and Chen and Farese, Trends in Cardiovascular Medicine (2000) 10, 188-192).

Disorders or imbalances in triglyceride metabolism, both absorption as well as de novo synthesis, have been implicated in the pathogenesis of a variety of disease risks These include obesity, insulin resistance syndrome, type II diabetes, dyslipidemia, metabolic syndrome (syndrome X) and coronary heart disease (see Kahn, Nature Genetics (2000) 25, 6-7, Yanovski and Yanovski, New England Journal of Medicine (2002) 346, 591-602, Lewis et al, Endocrine Reviews (2002) 23, 201, Brazil, Nature Reviews Drug Discovery (2002) 1, 408, Malloy and Kane, Advances in Internal Medicine (2001) 47, 111, Subauste and Burant, Current Drug Targets—Immune, Endocrine & Metabolic Disorders (2003) 3, 263-270 and Yu and Ginsberg, Annals of Medicine (2004) 36, 252-261). Compounds that can decrease the synthesis of triglycerides from diacylglycerol by inhibiting or lowering the activity of the DGAT enzyme would be of value as therapeutic agents for the treatment diseases associated with abnormal metabolism of triglycerides.

Known inhibitors of DGAT include: dibenzoxazepinones (see Ramharack, et al, EP1219716 and Burrows et al, 26th National Medicinal Chemistry Symposium (1998) poster C-22), substituted amino-pyrimidino-oxazines (see Fox et al, WO2004047755), chalcones such as xanthohumol (see Tabata et al, Phytochemistry (1997) 46, 683-687 and Casaschi et al, Journal of Nutrition (2004) 134, 1340-1346), substituted benzyl-phosphonates (see Kurogi et al, Journal of Medicinal Chemistry (1996) 39, 1433-1437, Goto, et al, Chemistry and Pharmaceutical Bulletin (1996) 44, 547-551, Ikeda, et al, Thirteenth International Symposium on Atherosclerosis (2003), abstract 2P-0401, and Miyata, et al, JP 2004067635), aryl alkyl acid derivatives (see Smith et al, WO2004100881 and US20040224997), furan and thiophene derivatives (see WO2004022551), pyrrolo[1,2b]pyridazine derivatives (see Fox et al, WO2005103907), and substituted sulfonamides (see Budd Haeberlein and Buckett, WO20050442500).

Also known to be inhibitors of DGAT are: 2-bromo-palmitic acid (see Colman et al, Biochimica et Biophysica Acta (1992) 1125, 203-9), 2-bromo-octanoic acid (see Mayorek and Bar-Tana, Journal of Biological Chemistry (1985) 260, 6528-6532), roselipins (see Noriko et al, (Journal of Antibiotics (1999) 52, 815-826), amidepsin (see Tomoda et al, Journal of Antibiotics (1995) 48, 942-7), isochromophilone, prenylflavonoids (see Chung et al, Planta Medica (2004) 70, 258-260), polyacetylenes (see Lee et al, Planta Medica (2004) 70, 197-200), cochlioquinones (see Lee et al, Journal of Antibiotics (2003) 56, 967-969), tanshinones (see Ko et al, Archives of Pharmaceutical Research (2002) 25, 446-448), gemfibrozil (see Zhu et al, Atherosclerosis (2002) 164, 221-228), and substituted quinolones (see Ko, et al, Planta Medica (2002) 68, 1131-1133). Also known to be modulators of DGAT activity are antisense oligonucleotides (see Monia and Graham, US20040185559).

A need exits in the art, however, for additional DGAT inhibitors that have efficacy for the treatment of metabolic disorders such as, for example, obesity, type II diabetes mellitus and metabolic syndrome. Further, a need exists in the art for DGAT inhibitors having $IC_{50}$ values less than about 1 µM.

SUMMARY OF THE INVENTION

In an embodiment of the present invention, provided is a compound of formula (I):

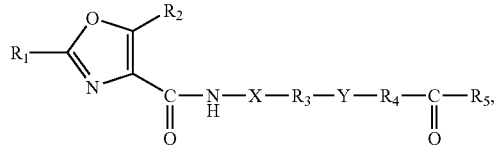

wherein:
$R_1$ is phenyl or 5- or 6-membered heteroaryl, said phenyl and heteroaryl being unsubstituted or substituted with halogen, lower alkyl, alkoxy or O—$CF_3$;
$R_2$ is halogen, lower alkyl, haloloweralkyl or alkoxy;
$R_3$ is nitrogen, oxygen or absent, said nitrogen being unsubstituted or substituted with lower alkyl;
$R_4$ is carbon, nitrogen, oxygen or absent, said carbon or nitrogen being unsubstituted or substituted with lower alkyl, wherein both $R_3$ and $R_4$ are not absent;
$R_5$ is -loweralkyl,
  -alkoxy,
  -hydroxy,
  -amine,
  -lower alkyl amine,
  -haloloweralkyl,
  -lower alkoxy,
  -lower alkenyloxy,
  -cycloloweralkyl, unsubstituted or substituted with one to four substituents from lower alkyl, hydroxy, halogen, —C(O)OH, —C(O)O-lower alkyl or —C(O)O-lower alkyl-phenyl,
  -5- or 6-membered heterocycloalkyl, unsubstituted or substituted, with one to four substituents from lower alkyl, hydroxy, halogen, —$SO_2$-loweralkyl, —C(O)OH, —C(O)O-lower alkyl or —C(O)O-lower alkyl-phenyl,
  -5- or 6-membered aryl, unsubstituted or substituted with one to four substituents from lower alkyl, hydroxy, halogen, —C(O)OH, —C(O)O-lower alkyl or —C(O)O-lower alkyl-phenyl,
  -5- or 6-membered heteroaryl, unsubstituted or substituted with one to four substituents from lower alkyl, hydroxy, halogen, —C(O)OH, C(O)O-lower alkyl or —C(O)O-lower alkyl-phenyl,
  —$(CH_2)_n$C(O)OH,
  —$CH_2$C(lower alkyl)$_2$C(O)OH,
  —$CH_2$(cycloalkyl)C(O)OH,
  -(cycloalkyl)C(O)OH,
  —$CH_2$C($CH_3$)$_3$,
  —$(CH_2)_n$-cycloalkyl,
  -cycloalkenyl,
  -bicycloalkenyl-C(O)OH,
  —$(CH_2)_n$—O-alkyl,
  —O—C(=C)-lower alkyl,
  —O—$(CH_2)_n$-phenyl,
  —$NSO_2$-loweralkyl,
  —$NSO_2$-cycloalkyl,
  —$NSO_2$-aryl,
  —N-lower alkyl,
  —N-cycloalkyl, said cycloalkyl being unsubstituted or substituted with —C(O)OH,
  —N-heterocycloalkyl,
  —N-aryl,
  —N—$(CH_2)_n$-aryl,
  —N-heteroaryl, said heteroaryl being unsubstituted or substituted with alkyl,
  —N—CH(lower alkyl)C(O)OH,
  —N-(cycloalkyl)C(O)OH,
  —N—CH(lower alkyl)C(O)O-lower alkyl,
  -phenyl-C(O)OH,
X is 5- or 6-membered aryl or 5- or 6-membered heteroaryl, said aryl or heteroaryl being unsubstituted or substituted with lower alkyl, halogen or cyano;
Y is phenyl, heteroaryl, cycloloweralkyl, or 5- or 6-membered heterocycloalkyl, —N($CH_2)_n$)N—, said phenyl, cycloloweralkyl or heterocycloalkyl being unsubstituted or substituted with lower alkyl, halogen or cyano; and
n is 1, 2 or 3,
or pharmaceutically acceptable salts thereof, In another embodiment of the present invention, provided is a pharmaceutical composition, comprising a therapeutically effective amount of a compound according to formula I or a pharmaceutically acceptable salt thereof and a pharmaceutically acceptable carrier.

In a further embodiment of the present invention, provided is a method of treating obesity, type II diabetes or metabolic syndrome, comprising the step of administering a therapeutically effective amount of a compound according to formula I to a patient in need thereof.

DETAILED DESCRIPTION OF THE INVENTION

The present invention pertains to DGAT inhibitors In a preferred embodiment, the invention provides compounds of the formula:

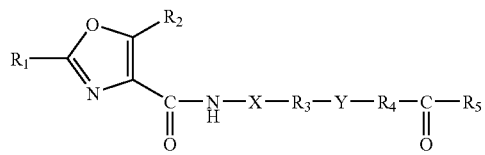

as well as pharmaceutically acceptable salts thereof.

The core structure of formula I above is supported by the examples and associated enabling chemistry which follow. Such exemplification and associated enabling chemistry, however, also support varying substitution patterns for the core structures exemplified and claimed as formula I in each of co-pending applications 60/931,303, 60/931,273 and 60/931,327. It will, therefore, be understood by the skilled chemist that the enabling chemistry presented in exemplification of such other core structures are correspondingly applicable to the core structure of formula I herein.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl" means, for example, a branched or unbranched, cyclic (i.e., "cycloalkyl") or acyclic, saturated or unsaturated (e.g. alkenyl or alkynyl)hydrocarbyl radical which may be substituted or unsubstituted. Where cyclic, the alkyl group is preferably $C_3$ to $C_{12}$, more preferably $C_4$ to $C_{10}$, more preferably $C_4$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

In a preferred embodiment, the "cycloalkyl" moieties can optionally be substituted with one, two, three or four substituents, wherein each substituent is independently, for example, hydroxy, alkyl, alkoxy, halogen or amino, unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a cyclic alkyl ring, wherein one, two or three of the carbon ring atoms is replaced by a heteroatom such as N, O or S. Examples of heterocycloalkyl groups include, but are not limited to, morpholine, thiomorpholine, piperazine, piperidine and the like. The heterocycloalkyl groups may be unsubstituted or substituted.

As used herein, the term "lower alkyl" means, for example, a branched or unbranched, cyclic (e.g., "cycloloweralkyl") or acyclic, saturated or unsaturated hydrocarbyl radical wherein said cyclic lower alkyl group is $C_3$, $C_4$, $C_5$, $C_6$ or $C_7$, and wherein said acyclic lower alkyl group is $C_1$, $C_2$, $C_3$ or $C_4$, and is preferably selected from methyl, ethyl, propyl (n-propyl or isopropyl) or butyl (n-butyl, isobutyl or tertiary-butyl). It will be appreciated therefore that the term "lower alkyl" as used herein includes, for example, lower alkyl (branched or unbranched) and cycloloweralkyl.

As used herein, the term "aryl" means, for example, a substituted or unsubstituted carbocyclic aromatic group. Examples of aryl groups are phenyl, naphthyl and the like.

The term "heteroaryl", alone or in combination with other groups, means a monocyclic or bicyclic radical of 5 to 12 ring atoms having at least one aromatic ring containing one, two, or three ring heteroatoms selected from N, O, and S, the remaining ring atoms being C. One or two ring carbon atoms of the heteroaryl group may be replaced with a carbonyl group. The heteroaryl group described above may be substituted independently with one, two, or three substituents, preferably one or two substituents such as, for example, halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, aminocarbonyl, mono- or di-substituted amino-carbonyl, aminocarbonyl $C_{1-6}$ alkoxy, mono- or di-substituted amino-carbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro, carbamoyl, mono- or di-substituted amino-carbonyl, hydroxy-$C_{1-6}$ alkyl, carboxyl, $C_{1-6}$ alkoxy carbonyl and cyano.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, arloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be, for example, 1 to 3 substitutents present, preferably 1 substituent.

As used herein, the term "alkoxy" means, for example, alkyl-O— and "alkoyl" means, for example, alkyl-CO—. Alkoxy substituent groups or alkoxy-containing substituent groups may be substituted by, for example, one or more alkyl groups.

As used herein, the term "halogen" means a fluorine, chlorine, bromine or iodine radical, preferably a fluorine, chlorine or bromine radical, and more preferably a fluorine or chlorine radical.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

Compounds of the present invention can be prepared beginning with commercially available starting materials and utilizing general synthetic techniques and procedures known to those skilled in the art. Outlined below are reaction schemes suitable for preparing such compounds. Further exemplification is found in the specific examples listed below.

Scheme 1

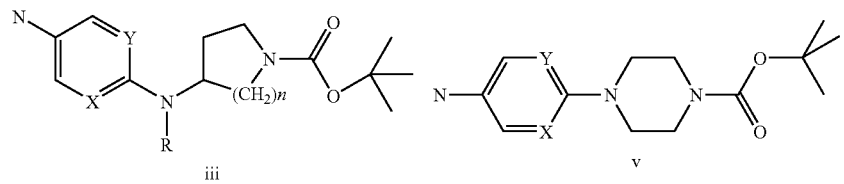

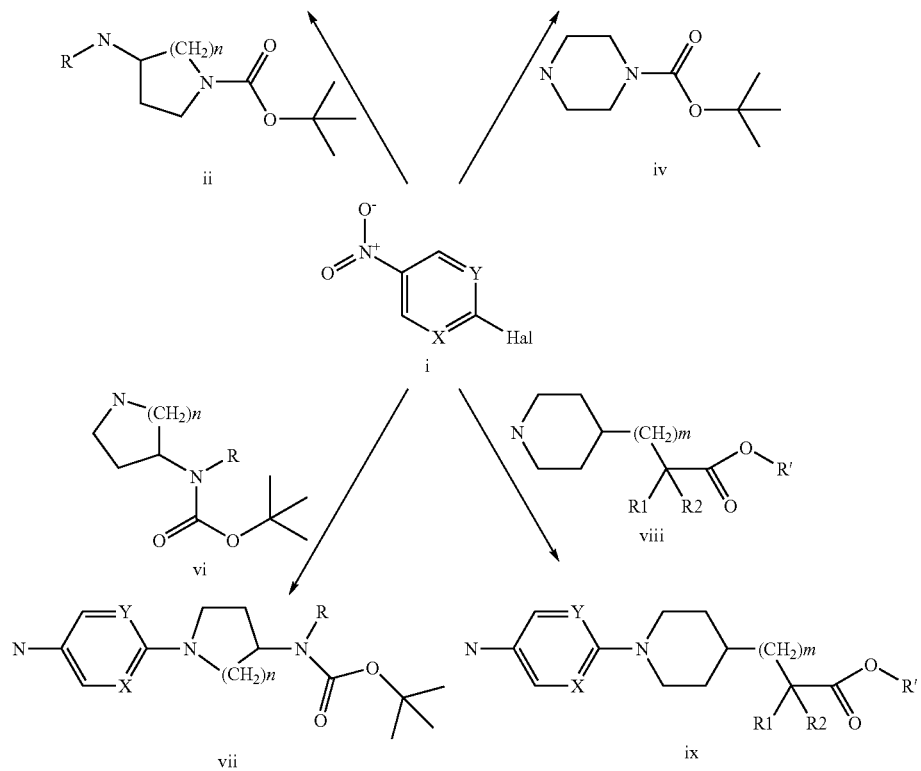

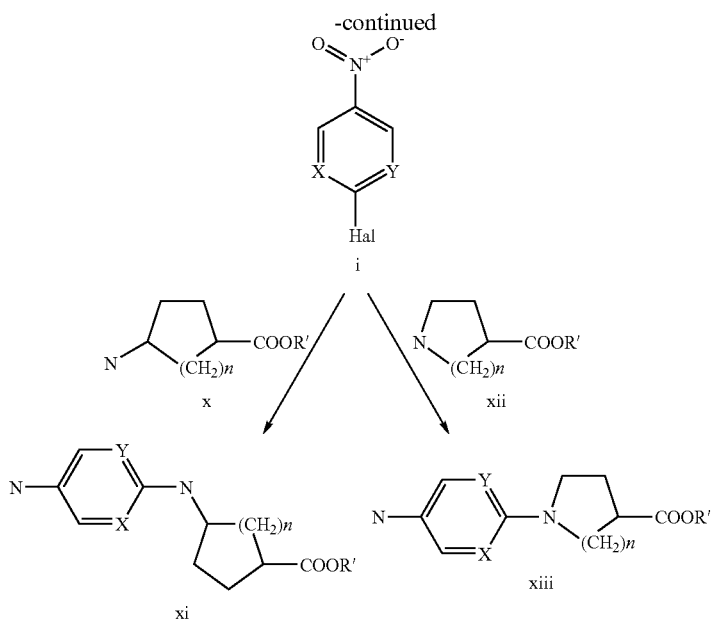

In Scheme 1, compound i (X and Y can be CH or N, Hal can be F, Cl, Br or I) can be treated with various cyclic amines (ii, iv, vi, viii, x, xii) in the presence of base and through nucleophilic aromatic substitution gave the corresponding nitro adduct (iii, v, vii, ix, xi, xiii). The resulting nitro compounds can be reduced to the corresponding amines by catalytic hydrogenation. Each arrow in Scheme 1 represents two individual reactions.

For the formation of compound iii, the cyclic amine can be 3-amino-pyrrolidine-1-carboxylic acid tert-butyl ester (compound ii, n=1) or 4-amino-piperidine-1-carboxylic acid tert-butyl ester (compound ii, n=2) and the exocyclic nitrogen can be alkylated or non-alkylated (compound ii, R=H or lower alkyl group). The configuration of 3-amino-pyrrolidine can be (R) or (S)-stereoisomer.

When the cyclic amine is piperazine-1-carboxylic acid tert-butyl ester (compound iv), substitution and subsequent reduction will generate compound v.

Alternatively, the cyclic amine can be pyrrolidin-3-yl-carbamic acid tert-butyl ester (compound vi, n=1) or piperidin-4-yl-carbamic acid tert-butyl ester (compound vi, n=2) and the carbamate nitrogen can be alkylated or non-alkylated (compound vi, R=H or lower alkyl group). The stereochemistry of pyrrolidin-3-yl-carbamic acid tert-butyl ester can be (R) or (S)-configuration.

Additionally, the cyclic amine can also be a 4-substituted piperidine derivative as in compound viii for the preparation of compound ix (m=0 or 1, R' can be methyl or ethyl).

Applying the same methodology, compounds xi and xiii (n=1 or 2, R' can be methyl or ethyl) can be prepared by reacting compound i with the ester of amino-cycloalkyl-carboxylic acid (compound x) or the ester of pyrrolidine-3-carboxylic acid (compound xii, n=1).

Scheme 2

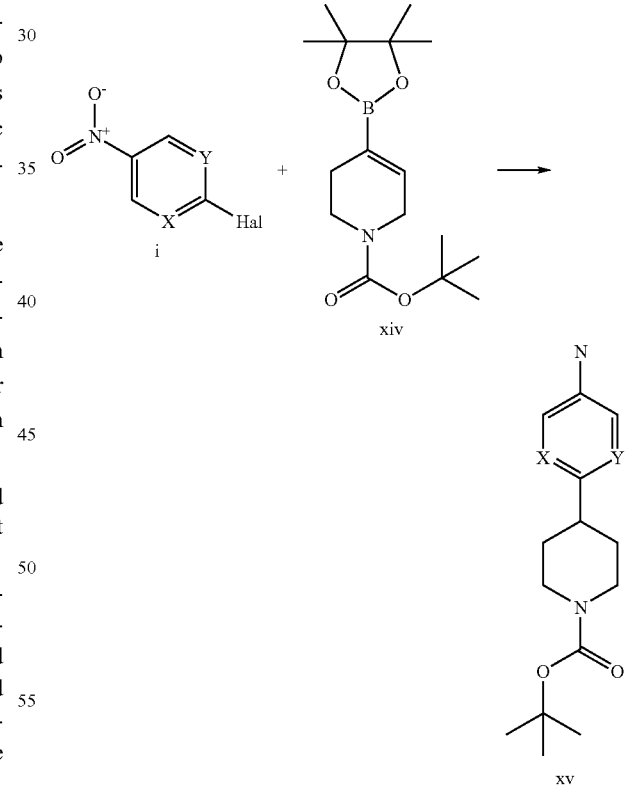

In Scheme 2, the cross-coupling of aryl halide (compound i, Hal can be Cl, Br or I) with a pinacol borate (compound xiv) can be accomplished through a palladium catalyzed reaction according to known procedure (*Tetrahedron Letters*, 2000, 41, 3705). The pinacol borate (compound xiv) can be prepared from 4-trifluoromethylsulfonyloxy-3,6-dihydro-2H-pyridine-1-carboxylic acid tert-butyl ester as described in the literature (*Synthesis,* 1991, 11, 993). The nitro group and the olefin in the coupling product can both be hydrogenated to generate compound xv.

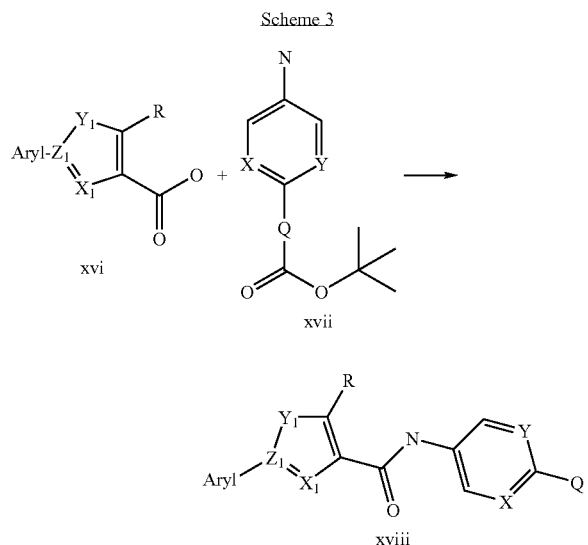

In Scheme 3, amide formation of an aryl-substituted five membered ring heterocyclic carboxylic acid (compound xvi, where $Z_1$ can be carbon or nitrogen, $X_1$ and $Y_1$ can be oxygen, nitrogen, or sulfur, R can be halogen, lower alkyl, fluorine substituted alkyl or alkoxy group) with an aryl amine xvii can be carried out by using general amide coupling methods such as acid chloride, mixed anhydride or coupling reagents. It is understood that a variety of coupling reagents such as EDCl, PyBroP® and many others can be applied.

The chemical structure of compound xvii is meant to encompass those represented by compounds iii, v, vii and xv with the different cyclic amines being represented by spacer Q. The nitrogen that links spacer Q and the tert-butyloxycarbonyl group can be part of the ring (e.g. compound v) or outside of the ring (e.g. compound vii). The tert-butyloxycarbonyl group in the coupling product can be cleaved under acidic condition to generate the corresponding amine xviii.

In addition, heterocyclic carboxylic acid xvi can also be coupled with amine ix, xi and xiii under the same amide formation conditions. The esters of the amide coupling product can further be hydrolyzed to generate the corresponding carboxylic acids.

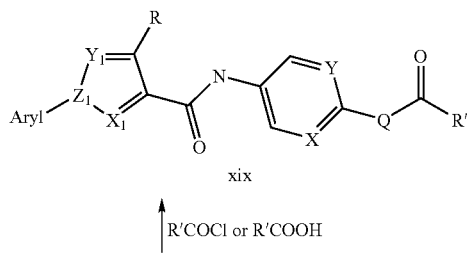

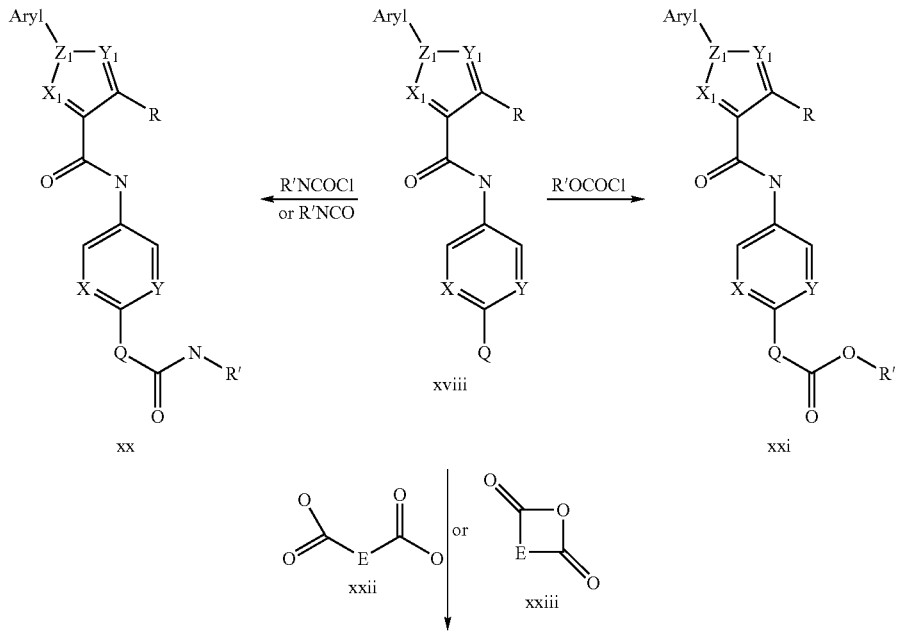

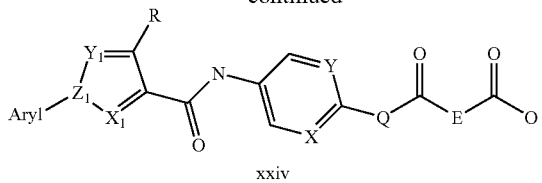

xxiv

The key intermediate xviii in Scheme 3 can be functionalized to form various amides, carbamates and ureas. As shown in Scheme 4, compound xviii can be treated with acyl chloride or carboxylic acid to form amide xix (R' can be cyclic or acyclic alkyl group). For the formation of urea xx, compound xviii can be treated with isocyanate or alkylaminocarbonyl chloride. Finally, the reaction of xviii with alkoxycarbonyl chloride will generate carbamate xxi.

To prepare amides with terminal carboxylic acids, xviii can be treated with anhydride xxiii (E can be cyclic or acyclic alkyl group) to form carboxylic acid xxiv. In case when xxiii is not readily available, the direct coupling of xviii with dicarboxylic acid xxii using coupling reagents can also lead to xxiv.

Alternatively, the dicarboxylic acid in xxii can be transformed to a mono-ester mono-carboxylic acid which can be coupled with xviii, and the cleavage of the resulting ester will generate compound xxiv.

For compound xxii, when spacer E is cyclic, the dicarboxylic acid can be in cis or trans-conformation. For cases where spacer E has stereogenic centers, single enantiomers of compound xxiv can be prepared through chiral separation.

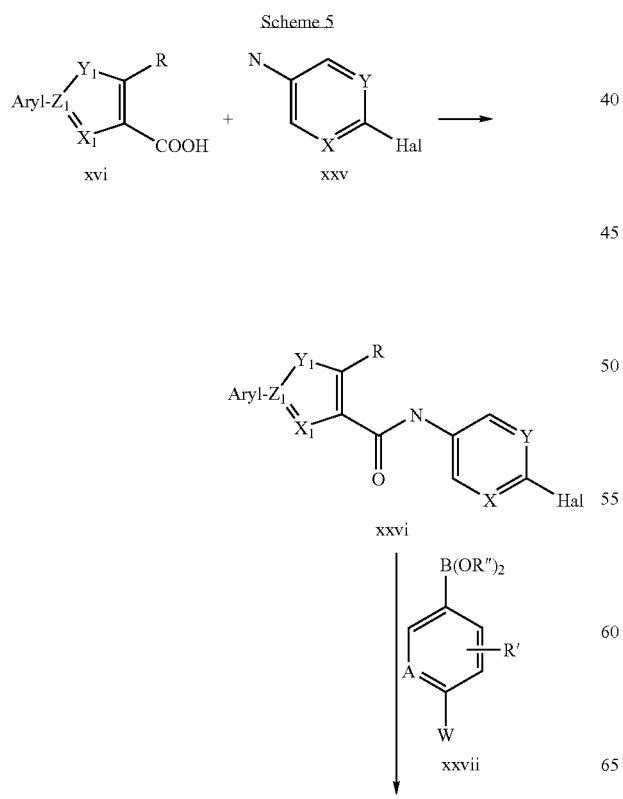

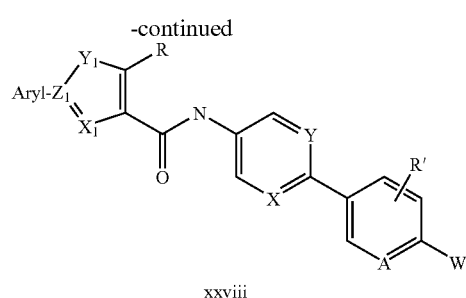

xxviii

Compounds with the structure xxviii, where a biarylamine is linked to a heterocyclic carboxylic acid through an amide linkage, can be prepared by using Suzuki coupling reactions. In Scheme 5, 5-amino-2-halogen substituted aromatic compound xxv (Hal=Cl, Br or I, X and Y can be CH or N) can be coupled with aryl substituted heterocyclic carboxylic acid xvi using general amide coupling conditions as described above to generate compound xxvi. Suzuki coupling of xxvi with aryl boronic acid derivative xxvii (A can be CH or N, R'=H, halogen or simple alkyl, R''=H or alkyl, the boronic acid ester can also be cyclic such as pinocolate, W can be amide, carbamate, urea, ester or carboxylic acid) will generate compound xxviii.

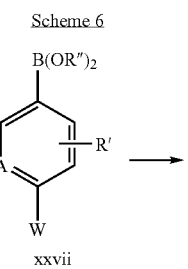

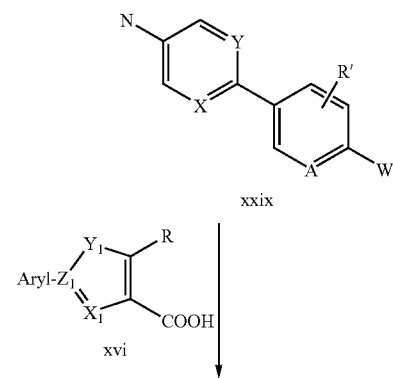

-continued

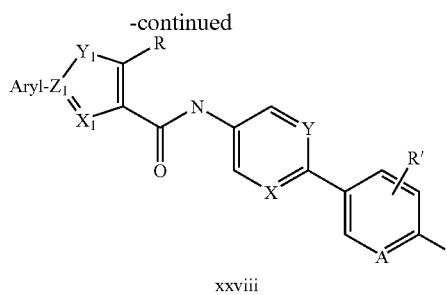

xxviii

An alternative route to prepare compound xxviii is shown in Scheme 6. Compound xxv can be coupled with aryl boronic acid derivative xxvii first to form a biarylamine derivative xxix under Suzuki coupling conditions. The resulting biarylamine can then be reacted with heterocyclic carboxylic acid xvi under amide formation conditions to form compound xxviii.

tion or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules,

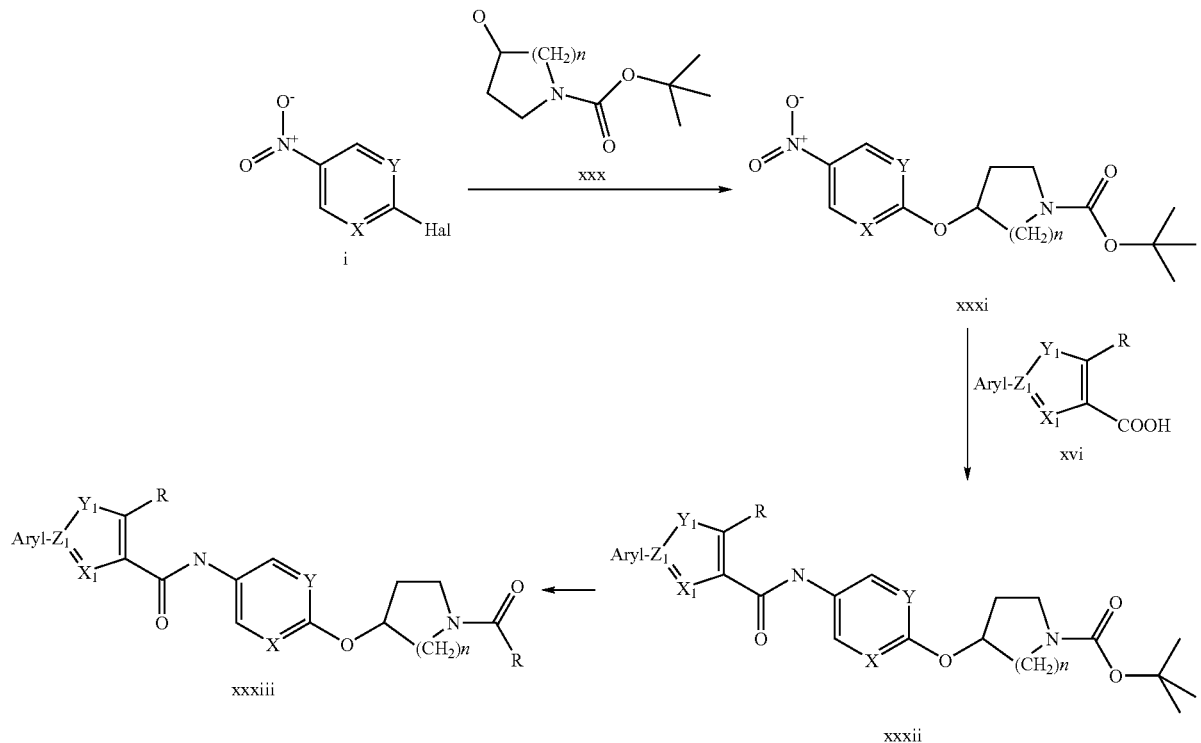

Scheme 7

Shown in Scheme 7 is a general method to prepare claimed compounds with an ether linkage. The hydroxyl substituted heterocycle xxx (n=1 or 2) can be reacted with aryl halide i in the presence of sodium hydride or 4-dimethylaminopyridine to generate an aryl ether xxxi. The nitro group in xxxi can be reduced and the resulting amine can be coupled with heterocyclic carboxylic acid xvi to generate compound xxxii. The tert-butyloxycarbonyl group in xxxii can be cleaved under acidic condition and the resulting amine can be functionalized to generate compound xxxiii, where R represents alkyl, alkoxy, cycloalkyl, and alkyl/cycloalkyl with carboxylic acid.

In the practice of the method of the present invention, an effective amount of any one of the compounds of this invention or a combination of any of the compounds of this invensuppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day The invention will now be further described in the Examples below, which are intended as an illustration only and do not limit the scope of the invention.

EXAMPLES

Part I: Preparation of Preferred Intermediates

Amines

Preparation of (5'-amino-3,4,5,6-tetrahydro-2H-[1,2'] bipyridinyl-4-yl)-acetic acid methyl ester

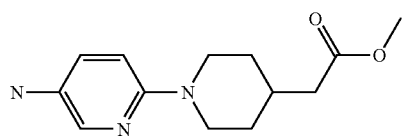

To a mixture of 2-chloro-5-nitropyridine (476 mg, 3.0 mmol) and 4-piperidine acetic acid methyl ester (471 mg, 3.0 mmol) in tetrahydrofuran (10 mL) was added diisopropylethylamine (1.0 mL, 5.74 mmol). The mixture was heated in a microwave at 120° C. for 30 minutes. The mixture was evaporated to dryness and extracted with ethyl acetate and water. The organic layer was dried over sodium sulfate and solvents were evaporated. The residue was purified using flash chromatography (eluting with ethyl acetate and hexanes) to give (5'-nitro-3,4,5,6-tetrahydro-2H-[1,2']bipyridinyl-4-yl)-acetic acid methyl ester as a yellow solid. The NMR spectrum obtained on the sample is compatible with its structure.

To a solution of (5'-nitro-3,4,5,6-tetrahydro-2H-[1,2']bipyridinyl-4-yl)-acetic acid methyl ester (279 mg, 1 mmol) from above in a mixture of tetrahydrofuran (10 mL) and methanol (50 mL) was added 10% palladium on carbon (50 mg). The mixture was hydrogenated at 50 psi for 1 hr. The mixture was filtered and the solvents were evaporated to give (5'-amino-3,4,5,6-tetrahydro-2H-[1,2']bipyridinyl-4-yl)-acetic acid methyl ester that was used in the next step without further purification.

Preparation of 2-(5'-amino-3,4,5,6-tetrahydro-2H-[1, 2']bipyridinyl-4-yl)-2-methyl-propionic acid ethyl ester

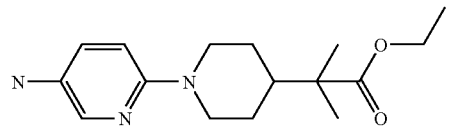

To a solution of diisopropylamine (7.64 mL, 54.5 mmol) in dry tetrahydrofuran (5 mL) at −78° C. was added n-butyl lithium (2.5 M, 20 mL, 50.0 mmol). The mixture was stirred at −65° C. for 30 minutes. Then ethyl isobutyrate (6.09 mL, 45.6 mmol) in tetrahydrofuran (5 mL) was added. The mixture was stirred at −60° C. for 45 minutes. To this solution was added 1-benzylpiperidone (6.15 g, 32.5 mmol) in 5 mL of tetrahydrofuran. The mixture was allowed to warm up to room temperature and stirred overnight. The mixture was quenched with ammonium chloride solution (30 mL) and extracted with ether (100 mL). The organic layer was first washed with brine and then dried over sodium sulfate. Solvents were evaporated and the residue was purified using flash chromatography (eluting with ethyl acetate and hexanes) to give 2-(1-benzyl-4-hydroxy-piperidin-4-yl)-2-methyl-propionic acid ethyl ester (5.87 g) as an oily material. The NMR spectrum obtained on the sample is compatible with its structure. LC-MS calcd for C18H27NO3 (m/e) 305.43, obsd 306.2 (M+H).

2-(1-benzyl-4-hydroxy-piperidin-4-yl)-2-methyl-propionic acid ethyl ester (3.24 g, 10.6 mmol) from above was dissolved in chloroform (13 mL) containing N,N-dimethylformamide (34 µL). To this solution was added thionyl chloride (1.56 mL). The mixture was refluxed overnight. Solvents were evaporated and the residue was extracted with ethyl acetate and sodium hydroxide (1N) solution. The organic layer was washed with brine and dried over sodium sulfate. After evaporation of solvents, the residue was purified using flash chromatography (eluting with ethyl acetate and hexanes) to give 2-(1-benzyl-1,2,3,6-tetrahydro-pyridin-4-yl)-2-methyl-propionic acid ethyl ester (1.17 g) as an oily material. The NMR spectrum obtained on the sample is compatible with its structure. LC-MS calcd for C18H25NO2 (m/e) 287.4, obsd 288.2 (M+H).

2-(1-benzyl-1,2,3,6-tetrahydro-pyridin-4-yl)-2-methyl-propionic acid ethyl ester from above (1.15 g, 4.0 mmol) was dissolved in 50 mL of ethanol and 10% palladium on carbon (600 mg) was added. The mixture was hydrogenated at 50 psi for 20 hrs. The mixture was filtered and solvents were evaporated to give 2-methyl-2-piperidin-4-yl-propionic acid ethyl ester (760 mg) as an oil. The NMR spectrum obtained on the sample is compatible with its structure. LRMS calcd for C11H21NO2 (m/e) 199.29, obsd 200.1 (M+H).

The above 2-methyl-2-piperidin-4-yl-propionic acid ethyl ester (606 mg, 3.82 mmol) was mixed with 2-chloro-5-nitropyridine (760 mg, 3.82 mmol) in 10 mL of tetrahydrofuran. To this solution was added diisopropylethylamine (1.33 mL). The mixture was heated in a microwave at 140° C. for 30 minutes. Solvents were evaporated and the residue was extracted with methylene chloride and water. The organic layer was dried over sodium sulfate, filtered and concentrated. The residue was purified using flash chromatography (eluting with ethyl acetate and hexanes) to give 2-methyl-2-(5'-nitro-3,4,5,6-tetrahydro-2H-[1,2']bipyridinyl-4-yl)-propionic acid ethyl ester as a solid (1.13 g, 92%). The NMR spectrum obtained on the sample is compatible with its structure.

With a method similar to that used for the preparation of (5'-amino-3,4,5,6-tetrahydro-2H-[1,2']bipyridinyl-4-yl)-acetic acid methyl ester above, 2-(5'-amino-3,4,5,6-tetrahydro-2H-[1,2']bipyridinyl-4-yl)-2-methyl-propionic acid ethyl ester was prepared from the hydrogenation of 2-methyl-2-(5'-nitro-3,4,5,6-tetrahydro-2H-[1,2']bipyridinyl-4-yl)-propionic acid ethyl ester. This compound was used in the next step without further purification.

Preparation of 2-(5'-amino-3,4,5,6-tetrahydro-2H-[1, 2']bipyridinyl-4-yl)-2-methyl-propionic acid

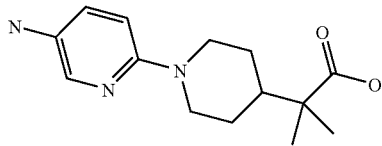

To a solution of 2-methyl-2-(5'-nitro-3,4,5,6-tetrahydro-2H-[1,2']bipyridinyl-4-yl)-propionic acid ethyl ester (321 mg, 1.0 mmol) in tetrahydrofuran (2 mL) and methanol (6 mL) was added sodium hydroxide solution (1N, 2 mL). The mixture was heated in a microwave at 140° C. for 1.5 hr. The mixture was evaporated and the residue was dissolved in hot methanol and water. The clear solution was then acidified with 1N hydrochloric acid (2.5 mL). The resulting pale yellow precipitate was filtered and dried to give 2-methyl-2-(5'-nitro-3,4,5,6-tetrahydro-2H-[1,2']bipyridinyl-4-yl)-propionic acid (210 mg). LC-MS calcd. for C14H19N3O4 (m/e) 293.1, obsd 294.1

With a method similar to that used for the preparation of (5'-amino-3,4,5,6-tetrahydro-2H-[1,2']bipyridinyl-4-yl)-acetic acid methyl ester above, 2-(5'-amino-3,4,5,6-tetrahydro-2H-[1,2']bipyridinyl-4-yl)-2-methyl-propionic acid was prepared from the hydrogenation of 2-methyl-2-(5'-nitro-3,4,5,6-tetrahydro-2H-[1,2']bipyridinyl-4-yl)-propionic acid. This compound was used in the next step without further purification.

Preparation of 3-(5'-amino-3,4,5,6-tetrahydro-2H-[1, 2']bipyridinyl-4-yl)-2,2-dimethyl-propionic acid

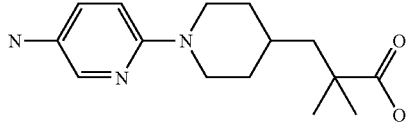

To a solution of 3-(N-Boc-piperidine-4-yl)-propionic acid (4.0 g, 15.6 mmol) in ether (100 mL) was added a solution of diazomethane in ether (0.2 M, 100 ml) in portions until the solution became lightly yellow. The mixture was stirred at room temperature for 1 hr and the solvents were evaporated to give 3-(N-Boc-piperidine-4-yl)-propionic acid methyl ester (4.2 g) as an oil.

3-(N-Boc-piperidine-4-yl)-propionic acid methyl ester (2.0 g, 7.38 mmol) from above was dissolved in tetrahydrofuran (50 mL). The solution was cooled to −78° C. and sodium bis(trimethylsilyl)amide (1.0 M, 9.0 mL) was added. The mixture was stirred at −78° C. for 1 hr and methyl iodide (1.2 mL, 19.5 mmol) was added. The mixture was warmed to room temperature and stirred for 2 hrs. The mixture was extracted with ether and washed with dilute hydrochloric acid. The organic layer was dried, filtered and concentrated. The residue was purified using flash chromatography (eluting with ethyl acetate and hexanes) to give 2-methyl-3-(N-Boc-piperidine-4-yl)-propionic acid methyl ester as an oil (789 mg).

2-methyl-3-(N-Boc-piperidine-4-yl)-propionic acid methyl ester (789 mg, 2.77 mmol) from above was dissolved in dry tetrahydrofuran (2 mL) and cooled to −78° C. To this solution was added lithium diisopropylamide (5.5 mmol, prepared from diisopropylamine and n-butyl lithium). The mixture was stirred at −78° C. for 1 hr and methyl iodide (0.7 mL, 11.24 mmol) was added. The mixture was stirred at −78° C. for 2 hrs until complete consumption of the starting material. The mixture was treated with hydrochloric acid (1N, 10 mL) and extracted with ether. The organic layer was washed with brine and dried over sodium sulfate. After evaporation of the solvents, the residue was purified using flash chromatography (eluting with hexanes and ethyl acetate) to give 2,2-dimethyl-3-(N-Boc-piperidine-4-yl)-propionic acid methyl ester as a colorless oil that slowly turned into a solid (598 mg).

2,2-dimethyl-3-(N-Boc-piperidine-4-yl)-propionic acid methyl ester (598 mg) from above was dissolved in methylene chloride (2 mL) and trifluoroacetic acid (1 mL) was added. The mixture was stirred at room temperature for 1 hr and the solvents were evaporated. The mixture was partitioned between ether and sodium hydroxide solution (1N). The organic layer was washed with brine and dried. Evaporation of solvents gave 2,2-dimethyl-3-(piperidine-4-yl)-propionic acid methyl ester (370 mg) as an oil.

2,2-Dimethyl-3-(piperidine-4-yl)-propionic acid methyl ester (156 mg, 0.78 mmol) from above was mixed with 2-chloro-5-nitropyridine (124 mg, 0.78 mol) in tetrahydrofuran (2 mL) containing triethylamine (0.24 mL). The mixture was heated in a microwave at 140° C. for 30 minutes. The mixture was extracted with ethyl acetate and water. The organic layer was washed with brine and dried. Solvents were evaporated and the residue was triturated with ether to give 2,2-dimethyl-3-(5'-nitro-3,4,5,6-tetrahydro-2H-[1,2']bipyridinyl-4-yl)-propionic acid methyl ester (199 mg) as a crystalline material. The NMR spectrum obtained on the sample is compatible with its structure.

2,2-Dimethyl-3-(5'-nitro-3,4,5,6-tetrahydro-2H-[1,2']bipyridinyl-4-yl)-propionic acid methyl ester (199 mg, 0.62 mmol) from above was dissolved in tetrahydrofuran (2 mL). Then methanol (4 mL) and sodium hydroxide solution (1N, 2 mL) were added. The mixture was stirred and refluxed for 8 hrs. Solvents were evaporated and the residue was dissolved in hot methanol. The solution was cooled to room temperature and hydrochloric acid (1N, 2 mL) was added. The resulting mixture was cooled in an ice bath and the solid was filtered and washed with water. The solid was dried in air to give 2,2-dimethyl-3-(5'-nitro-3,4,5,6-tetrahydro-2H-[1,2']bipyridinyl-4-yl)-propionic acid (181.5 mg). The NMR spectrum obtained on the sample is compatible with its structure. LC-MS calcd for C15H21N3O4 (m/e) 307.34, obsd 308.1 (M+H).

With a method similar to that used for the preparation of (5'-amino-3,4,5,6-tetrahydro-2H-[1,2']bipyridinyl-4-yl)-acetic acid methyl ester above, 3-(5'-amino-3,4,5,6-tetrahydro-2H-[1,2']bipyridinyl-4-yl)-2,2-dimethyl-propionic acid was prepared from the hydrogenation of 2,2-dimethyl-3-(5'-nitro-3,4,5,6-tetrahydro-2H-[1,2']bipyridinyl-4-yl)-propionic acid. This compound was used in the next step without further purification.

Preparation of (S)-3-(5-amino-pyridin-2-ylamino)-pyrrolidine-1-carboxylic acid tert-butyl ester

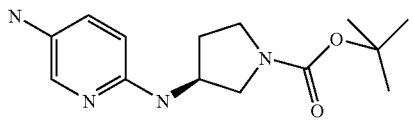

A mixture of 2-chloro-5-nitro-pyridine (3.4 g, 0.021 mol), (S)-(−)-3-amino-pyrrolidine-1-carboxylic acid tert-butyl ester (4 g, 0.021 mol), and potassium carbonate (14.5 g, 0.105 mol) in acetonitrile (50 mL) was heated at reflux for 24 h. The reaction was monitored by LCMS and additional (S)-(−)-3-amino-pyrrolidine-1-carboxylic acid tert-butyl ester was added until the reaction was driven to completion. The reaction mixture was then filtered and concentrated to give (S)-3-(5-nitro-pyridin-2-ylamino)-pyrrolidine-1-carboxylic acid tert-butyl ester (5.1 g, 78.6%) as a yellow solid. LCMS calcd for C14H20N4O4 (m/e) 308, obsd 307.1 (M−H).

A mixture of (S)-3-(5-nitro-pyridin-2-ylamino)-pyrrolidine-1-carboxylic acid tert-butyl ester (500 mg, 1.67 mmol), 10% palladium on carbon (80 mg) in methanol (10 mL) was hydrogenated at 50 psi in a Parr Shaker at room temperature for 2 h. The reaction mixture was then filtered through a plug of celite and the filtration pad was washed with ethyl acetate. The organic layers were collected and concentrated to give (S)-3-(5-amino-pyridin-2-ylamino)-pyrrolidine-1-carboxylic acid tert-butyl ester (490 mg, crude) as a light red solid, which was directly used in the next step without further purification.

Preparation of (R)-3-(5-amino-pyridin-2-ylamino)-pyrrolidine-1-carboxylic acid tert-butyl ester

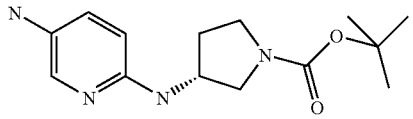

With a method similar to that used for the preparation of (S)-3-(5-nitro-pyridin-2-ylamino)-pyrrolidine-1-carboxylic acid tert-butyl ester above, (R)-3-(5-nitro-pyridin-2-ylamino)-pyrrolidine-1-carboxylic acid tert-butyl ester was prepared from 2-chloro-5-nitro-pyridine and (R)-(−)-3-amino-pyrrolidine-1-carboxylic acid tert-butyl ester. LCMS calcd for C14H20N4O4 (m/e) 308.3, obsd 309 (M+H). This material was a mixture of product and starting material (6:1 ratio) and was used in the next step without further purification.

With a method similar to that used for the preparation of (S)-3-(5-amino-pyridin-2-ylamino)-pyrrolidine-1-carboxylic acid tert-butyl ester above, (R)-3-(5-amino-pyridin-2-ylamino)-pyrrolidine-1-carboxylic acid tert-butyl ester was prepared by the hydrogenation of (R)-3-(5-nitro-pyridin-2-ylamino)-pyrrolidine-1-carboxylic acid tert-butyl ester. This material was used in the next step without further purification.

Preparation of [(S)-1-(5-amino-pyridin-2-yl)-pyrrolidin-3-yl]-carbamic acid tert-butyl ester

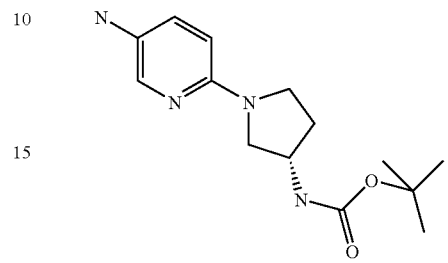

With a method similar to that used for the preparation of (S)-3-(5-nitro-pyridin-2-ylamino)-pyrrolidine-1-carboxylic acid tert-butyl ester above, [(S)-1-(5-nitro-pyridin-2-yl)-pyrrolidin-3-yl]-carbamic acid tert-butyl ester was prepared from 2-chloro-5-nitro-pyridine and (S)-pyrrolidin-3-yl-carbamic acid tert-butyl ester. LCMS calcd for C14H20N4O4 (m/e) 308.34, obsd 309 (M+H).

With a method similar to that used for the preparation of (S)-3-(5-amino-pyridin-2-ylamino)-pyrrolidine-1-carboxylic acid tert-butyl ester above, [(S)-1-(5-amino-pyridin-2-yl)-pyrrolidin-3-yl]-carbamic acid tert-butyl ester was prepared by the hydrogenation of [(S)-1-(5-nitro-pyridin-2-yl)-pyrrolidin-3-yl]-carbamic acid tert-butyl ester. This material was directly used in the next step without further purification.

Preparation of [(R)-1-(5-amino-pyridin-2-yl)-pyrrolidin-3-yl]-carbamic acid tert-butyl ester

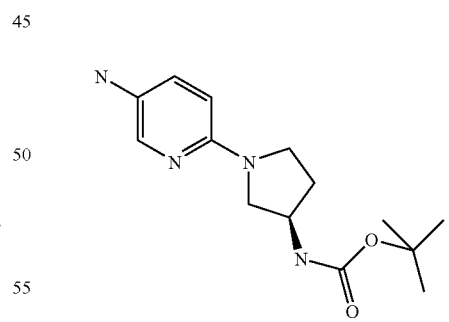

With a method similar to that used for the preparation of (S)-3-(5-nitro-pyridin-2-ylamino)-pyrrolidine-1-carboxylic acid tert-butyl ester above, [(R)-1-(5-nitro-pyridin-2-yl)-pyrrolidin-3-yl]-carbamic acid tert-butyl ester was prepared from 2-chloro-5-nitro-pyridine and (R)-pyrrolidin-3-yl-carbamic acid tert-butyl ester. LCMS calcd for C14H20N4O4 (m/e) 308.34, obsd 309 (M+H). This material was a mixture of product and starting material (10:1 ratio) and was used in the next step without further purification.

With a method similar to that used for the preparation of (S)-3-(5-amino-pyridin-2-ylamino)-pyrrolidine-1-carboxylic acid tert-butyl ester above, [(R)-1-(5-amino-pyridin-2-yl)-pyrrolidin-3-yl]-carbamic acid tert-butyl ester was prepared by the hydrogenation of [(R)-1-(5-nitro-pyridin-2-yl)-pyrrolidin-3-yl]-carbamic acid tert-butyl ester. This material was directly used in the next step without further purification.

Preparation of racemic [1-(5-amino-pyridin-2-yl)-pyrrolidin-3-yl]-methyl-carbamic acid tert-butyl ester

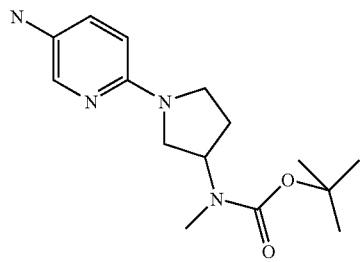

With a method similar to that used for the preparation of (S)-3-(5-nitro-pyridin-2-ylamino)-pyrrolidine-1-carboxylic acid tert-butyl ester above, racemic [1-(5-nitro-pyridin-2-yl)-pyrrolidin-3-yl]-methyl-carbamic acid tert-butyl ester was prepared from 2-chloro-5-nitro-pyridine and racemic 3-(N-tert-butoxycarbonyl-N-methylamino)pyrrolidine. LCMS calcd for C15H22N4O4 (m/e) 322.37, obsd 323.1 (M+H).

With a method similar to that used for the preparation of (S)-3-(5-amino-pyridin-2-ylamino)-pyrrolidine-1-carboxylic acid tert-butyl ester above, racemic [1-(5-amino-pyridin-2-yl)-pyrrolidin-3-yl]-methyl-carbamic acid tert-butyl ester was prepared by the hydrogenation of racemic [1-(5-nitro-pyridin-2-yl)-pyrrolidin-3-yl]-methyl-carbamic acid tert-butyl ester. This material was directly used in the next step without further purification.

Preparation of racemic 1-(5-amino-pyridin-2-yl)-pyrrolidine-3-carboxylic acid methyl ester

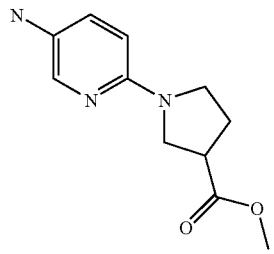

With a method similar to that used for the preparation of (S)-3-(5-nitro-pyridin-2-ylamino)-pyrrolidine-1-carboxylic acid tert-butyl ester above, racemic 1-(5-nitro-pyridin-2-yl)-pyrrolidine-3-carboxylic acid methyl ester was prepared from 2-chloro-5-nitro-pyridine and racemic Pyrrolidine-3-carboxylic acid methyl ester. LCMS calcd for C11H15N3O4 (m/e) 251.3, obsd 252 (M+H).

With a method similar to that used for the preparation of (S)-3-(5-amino-pyridin-2-ylamino)-pyrrolidine-1-carboxylic acid tert-butyl ester above, racemic 1-(5-amino-pyridin-2-yl)-pyrrolidine-3-carboxylic acid methyl ester was prepared by the hydrogenation of racemic 1-(5-nitro-pyridin-2-yl)-pyrrolidine-3-carboxylic acid methyl ester. This material was directly used in the next step without further purification.

Preparation of (1S,3S)-3-(5-amino-pyridin-2-ylamino)-cyclopentanecarboxylic acid methyl ester

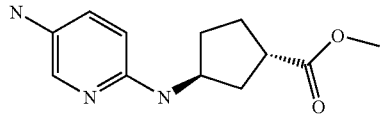

With a method similar to that used for the preparation of (S)-3-(5-nitro-pyridin-2-ylamino)-pyrrolidine-1-carboxylic acid tert-butyl ester above, (1S,3S)-3-(5-nitro-pyridin-2-ylamino)-cyclopentanecarboxylic acid methyl ester was prepared from 2-chloro-5-nitro-pyridine and (1S,3S)-3-amnio-cyclopentanecarboxylic acid methyl ester hydrochloride salt. LCMS calcd for C12H15N3O4 (m/e) 265.3, obsd 266 (M+H). This material was a mixture of product and starting material (76:24 ratio) and was used in the next step without further purification.

With a method similar to that used for the preparation of (S)-3-(5-amino-pyridin-2-ylamino)-pyrrolidine-1-carboxylic acid tert-butyl ester above, (1S,3S)-3-(5-amino-pyridin-2-ylamino)-cyclopentanecarboxylic acid methyl ester was prepared by the hydrogenation of (1S,3S)-3-(5-nitro-pyridin-2-ylamino)-cyclopentanecarboxylic acid methyl ester. This material was directly used in the next step without further purification.

Preparation of (1R,3S)-3-(5-amino-pyridin-2-ylamino)-cyclopentanecarboxylic acid ethyl ester

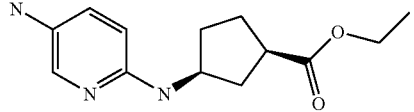

With a method similar to that used for the preparation of (S)-3-(5-nitro-pyridin-2-ylamino)-pyrrolidine-1-carboxylic acid tert-butyl ester above, (1R,3S)-3-(5-nitro-pyridin-2-ylamino)-cyclopentanecarboxylic acid methyl ester was prepared from 2-chloro-5-nitro-pyridine and (1R,3S)-3-amnio-cyclopentanecarboxylic acid methyl ester hydrochloride salt. LCMS calcd for C12H15N3O4 (m/e) 265.3, obsd 266 (M+H).

With a method similar to that used for the preparation of (S)-3-(5-amino-pyridin-2-ylamino)-pyrrolidine-1-carboxylic acid tert-butyl ester above, (1R,3S)-3-(5-amino-pyridin-2-ylamino)-cyclopentanecarboxylic acid methyl ester was prepared by the hydrogenation of (1R,3S)-3-(5-nitro-pyridin- 2-ylamino)-cyclopentanecarboxylic acid methyl ester. This material was directly used in the next step without further purification.

Preparation of 5'-amino-3,4,5,6-tetrahydro-2H-[1,2'] bipyridinyl-4-carboxylic acid ethyl ester

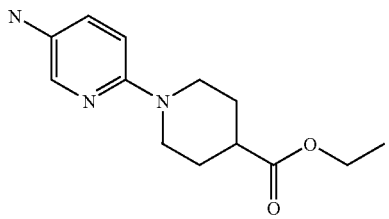

With a method similar to that used for the preparation of (S)-3-(5-nitro-pyridin-2-ylamino)-pyrrolidine-1-carboxylic acid tert-butyl ester above, 5'-nitro-3,4,5,6-tetrahydro-2H-[1,2']bipyridinyl-4-carboxylic acid ethyl ester was prepared from 2-chloro-5-nitro-pyridine and piperidine-4-carboxylic acid ethyl ester. LCMS calcd for C13H17N3O4 (m/e) 279.3, obsd 280 (M+H).

With a method similar to that used for the preparation of (S)-3-(5-amino-pyridin-2-ylamino)-pyrrolidine-1-carboxylic acid tert-butyl ester above, 5'-amino-3,4,5,6-tetrahydro-2H-[1,2']bipyridinyl-4-carboxylic acid ethyl ester was prepared by the hydrogenation of 5'-nitro-3,4,5,6-tetrahydro-2H-[1,2']bipyridinyl-4-carboxylic acid ethyl ester. This material was directly used in the next step without further purification.

Preparation of (S)-3-(5-amino-pyrimidin-2-ylamino)-pyrrolidine-1-carboxylic acid tert-butyl ester

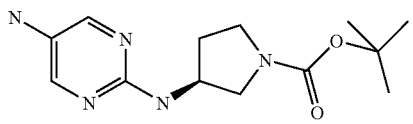

With a method similar to that used for the preparation of (S)-3-(5-nitro-pyridin-2-ylamino)-pyrrolidine-1-carboxylic acid tert-butyl ester above, (S)-3-(5-nitro-pyrimidin-2-ylamino)-pyrrolidine-1-carboxylic acid tert-butyl ester was prepared from 2-chloro-5-nitro-pyrimidine and (S)-3-amino-pyrrolidine-1-carboxylic acid tert-butyl ester. LCMS calcd for C13H19N5O4 (m/e) 309.3, obsd 310 (M+H).

With a method similar to that used for the preparation of (S)-3-(5-amino-pyridin-2-ylamino)-pyrrolidine-1-carboxylic acid tert-butyl ester above, (S)-3-(5-amino-pyrimidin-2-ylamino)-pyrrolidine-1-carboxylic acid tert-butyl ester was prepared by the hydrogenation of (S)-3-(5-nitro-pyrimidin- 2-ylamino)-pyrrolidine-1-carboxylic acid tert-butyl ester. This material was directly used in the next step without further purification.

Preparation of 4-(5-amino-pyridin-2-yl)-piperazine-1-carboxylic acid tert-butyl ester

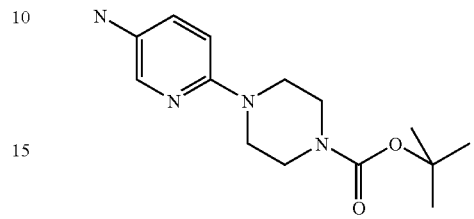

With a method similar to that used for the preparation of (S)-3-(5-nitro-pyridin-2-ylamino)-pyrrolidine-1-carboxylic acid tert-butyl ester above, 4-(5-nitro-pyridin-2-yl)-piperazine-1-carboxylic acid tert-butyl ester was prepared from 2-chloro-5-nitro-pyridine and piperazine-1-carboxylic acid tert-butyl ester. LCMS calcd for C14H20N4O4 (m/e) 308.3, obsd 309 (M+H). This material was a mixture of product and starting material (5:2 ratio) and was used in the next step without further purification.

With a method similar to that used for the preparation of (S)-3-(5-amino-pyridin-2-ylamino)-pyrrolidine-1-carboxylic acid tert-butyl ester above, 4-(5-amino-pyridin-2-yl)-piperazine-1-carboxylic acid tert-butyl ester was prepared by the hydrogenation of 4-(5-nitro-pyridin-2-yl)-piperazine-1-carboxylic acid tert-butyl ester. This material was directly used in the next step without further purification.

Preparation of (S)-3-(4-amino-phenylamino)-pyrrolidine-1-carboxylic acid ethyl ester

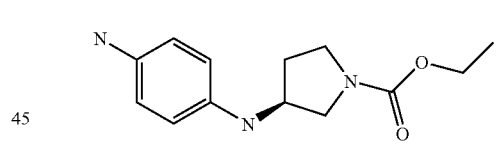

With a method similar to that used for the preparation of (S)-3-(5-nitro-pyridin-2-ylamino)-pyrrolidine-1-carboxylic acid tert-butyl ester above, (S)-3-(4-nitro-phenylamino)-pyrrolidine-1-carboxylic acid tert-butyl ester was prepared from 1-fluoro-4-nitrobenzene and (S)-3-amino-pyrrolidine-1-carboxylic acid tert-butyl ester. LCMS calcd for C15H21N3O4 (m/e) 307.4, obsd 306.2 (M−H).

(S)-3-(4-nitro-phenylamino)-pyrrolidine-1-carboxylic acid tert-butyl ester was deprotected with trifluoroacetic acid according to known procedures. After concentration, the amine trifluoroacetate salt was treated with ethyl chloroformate (1 equiv.) and triethylamine (3 equiv.) in methylene chloride to afford (S)-3-(4-nitro-phenylamino)-pyrrolidine-1-carboxylic acid ethyl ester. LCMS calcd for C13H17N3O4 (m/e) 279.3, obsd 280.1 (M+H).

With a method similar to that used for the preparation of (S)-3-(5-amino-pyridin-2-ylamino)-pyrrolidine-1-carboxylic acid tert-butyl ester above, (S)-3-(4-amino-phenylamino)-pyrrolidine-1-carboxylic acid ethyl ester was prepared by the hydrogenation of (S)-3-(4-nitro-phenylamino)-pyrrolidine- 1-carboxylic acid ethyl ester. This material was directly used in the next step without further purification.

Preparation of [4-(4-amino-phenylamino)-cyclohexyl]-carbamic acid tert-butyl ester

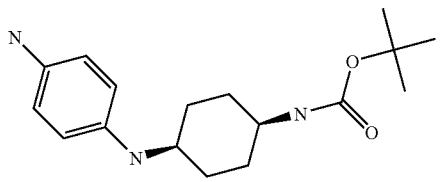

With a method similar to that used for the preparation of (S)-3-(4-amino-phenylamino)-pyrrolidine-1-carboxylic acid ethyl ester, [4-(4-amino-phenylamino)-cyclohexyl]-carbamic acid tert-butyl ester was prepared from (4-amino-cyclohexyl)-carbamic acid tert-butyl ester and 1-fluoro-4-nitrobenzene. LCMS calcd for C17H27N3O2 m/e 305.2, obsd 306 (M+H).

Preparation of (S)-3-[(5-amino-pyridin-2-yl)-methyl-amino]-pyrrolidine-1-carboxylic acid tert-butyl ester

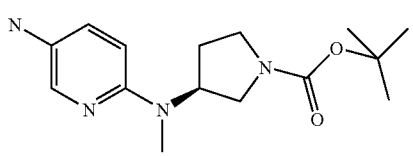

To a solution of (S)-3-(5-nitro-pyridin-2-ylamino)-pyrrolidine-1-carboxylic acid tert-butyl ester described previously (300 mg, 0.97 mmol) in tetrahydrofuran cooled at 0° C. was added sodium hydride (47 mg, 1.95 mmol) gradually. The mixture was stirred at room temperature for 15 min followed by the addition of methyl iodide (166 mg, 1.17 mmol). The reaction mixture was stirred for 2 h and then extracted with ethyl acetate and washed with water. The organic layer was dried over sodium sulfate, filtered and concentrated to give (S)-3-[(5-nitro-pyridin-2-yl)-methyl-amino]-pyrrolidine-1-carboxylic acid tert-butyl ester (295 mg, crude) as a yellow solid, which was directly used in the next step without further purification. LCMS calcd for C15H22N4O4 (m/e) 322, obsd 323 (M+H).

With a method similar to that used for the preparation of (S)-3-(5-amino-pyridin-2-ylamino)-pyrrolidine-1-carboxylic acid tert-butyl ester above, (S)-3-[(5-amino-pyridin-2-yl)-methyl-amino]-pyrrolidine-1-carboxylic acid tert-butyl ester was prepared by the hydrogenation of (S)-3-[(5-nitro-pyridin-2-yl)-methyl-amino]-pyrrolidine-1-carboxylic acid tert-butyl ester. This material was directly used in the next step without further purification.

Preparation of 4-(2-cyano-4-nitro-phenyl)-piperazine-1-carboxylic acid tert-butyl ester

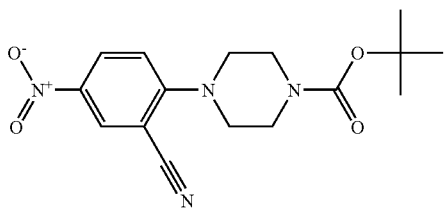

A solution of 2-fluoro-5-nitrobenzonitrile (500 mg, 3.0 mmol) in ethanol (35 mL) was treated with potassium carbonate (420 mg, 3.0 mmol) and piperazine-1-carboxylic acid tert-butyl ester (560 mg, 3.0 mmol). The reaction mixture was stirred at 80° C. for 1 h, then cooled and partitioned between ethyl acetate and water. The organic layer was then collected, dried over sodium sulfate, filtered and evaporated to a yellow residue. Purification using flash chromatography yielded 4-(2-cyano-4-nitro-phenyl)-piperazine-1-carboxylic acid tert-butyl ester (590 mg, 59% yield) as a bright yellow solid. HRMS calcd for C16H20N4O4 (M+Na) 355.1377, obsd 355.1376.

Preparation of 4-(5-amino-pyridin-2-ylamino)-piperidine-1-carboxylic acid tert-butyl ester

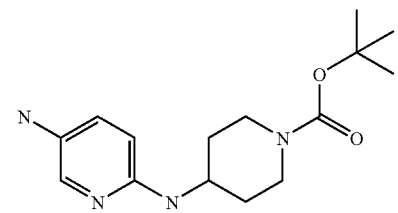

A mixture of 2-bromo-5-nitro-pyridine (5 g, 24.6 mmol), 4-amino-piperidine-1-carboxylic acid tert-butyl ester (5 g, 25 mmol), and triethylamine (5 mL) in N,N-dimethylformamide (30 mL) was stirred at 90° C. for 14 h. The reaction mixture was then partitioned between water and ethyl acetate, and the two layers were separated. The aqueous layer was extracted with ethyl acetate three times. The organic layers were combined, washed with brine, dried over sodium sulfate, filtered, and concentrated. The residue was purified by flash chromatography to give 7.15 g (90%) 4-(5-nitro-pyridin-2-ylamino)-piperidine-1-carboxylic acid tert-butyl ester as a yellow solid. LCMS calcd for C15H22N4O4 (m/e) 322, obsd 323 (M+H).

With a method similar to that used for the preparation of (S)-3-(5-amino-pyridin-2-ylamino)-pyrrolidine-1-carboxylic acid tert-butyl ester above, 4-(5-amino-pyridin-2-ylamino)-piperidine-1-carboxylic acid tert-butyl ester was prepared by the hydrogenation of 4-(5-nitro-pyridin-2-ylamino)-piperidine-1-carboxylic acid tert-butyl ester. This material was directly used in the next step without further purification.

Preparation of (5'-amino-3,4,5,6-tetrahydro-2H-[1,2'] bipyridinyl-4-yl)-methyl-carbamic acid tert-butyl ester

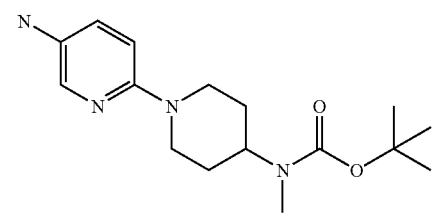

A mixture of 2-bromo-5-nitro-pyridine (4.74 g, 23.3 mmol), methyl-piperidin-4-yl-carbamic acid tert-butyl ester (5 g, 23.3 mmol), and triethylamine (5 mL) in N,N-dimethylformamide (30 mL) was stirred at 90° C. for 14 h. Upon completion of the reaction, the reaction mixture was partitioned between water and ethyl acetate. The aqueous layer was extracted with ethyl acetate twice. The combined organic layers were washed with brine, dried over sodium sulfate, filtered, and concentrated. The residue was recrystallized from methanol and water to give methyl (5'-nitro-3,4,5,6-tetrahydro-2H-[1,2']bipyridinyl-4-yl)-carbamic acid tert-butyl ester (6.7 g, 85.5%) as brown crystals. LCMS calcd for C16H24N4O4 (m/e) 336, obsd 337 (M+H).

A solution of methyl (5'-nitro-3,4,5,6-tetrahydro-2H-[1,2'] bipyridinyl-4-yl)-carbamic acid tert-butyl ester (1.4 g, 4.2 mmol) in ethyl acetate (5 mL) in the presence of 10% palladium on carbon (0.15 g) was shaken under 40 psi of hydrogen at room temperature for 2 h. The reaction mixture was filtered through a plug of celite and the filtration pad was washed with ethyl acetate. The combined washings were concentrated and dried to give 5'-amino-3,4,5,6-tetrahydro-2H-[1,2']bipyridinyl-4-yl)-methyl-carbamic acid tert-butyl ester (1.25 g, 98%) as a brown solid. This material was used in the next step without further purification.

Preparation of (S)-3-(5-nitro-pyridin-2-yloxy)-pyrrolidine-1-carboxylic acid tert-butyl ester

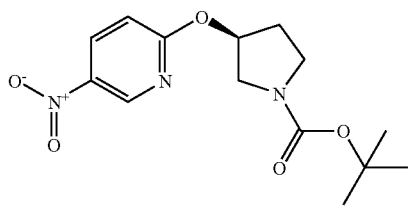

A solution of (S)-3-hydroxy-pyrrolidine-1-carboxylic acid tert-butyl ester (500 mg, 2.67 mmol) in anhydrous tetrahydrofuran (10 mL) was added to sodium hydride (60% in mineral oil, 215 mg, 5.34 mmol) gradually, and the resulting mixture was stirred at room temperature for 1 h. 2-Chloro-5-nitropyridine (425 mg, 2.68 mmol) was added, and the reaction mixture was stirred at room temperature for 3 h, then quenched with water, extracted with ethyl acetate, washed with water, dried over anhydrous sodium sulfate, and concentrated to afford (S)-3-(5-nitro-pyridin-2-yloxy)-pyrrolidine-1-carboxylic acid tert-butyl ester as a brown oil (800 mg, 98% yield). The NMR spectrum obtained on the sample is compatible with its structure.

Preparation of (S)-3-(4-nitro-phenoxy)-pyrrolidine-1-carboxylic acid tert-butyl ester

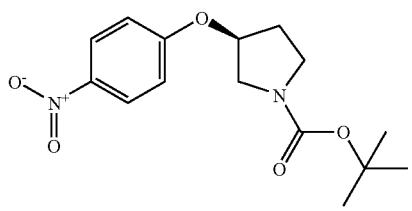

With a method similar to that used for the preparation of (S)-3-(5-nitro-pyridin-2-yloxy)-pyrrolidine-1-carboxylic acid tert-butyl ester, (S)-3-(4-nitro-phenoxy)-pyrrolidine-1-carboxylic acid tert-butyl ester was prepared from (S)-3-hydroxy-pyrrolidine-1-carboxylic acid tert-butyl ester and 1-fluoro-4-nitrobenzene. The NMR spectrum obtained on the sample is compatible with its structure.

Preparation of (S)-3-(5-nitro-pyrimidin-2-yloxy)-pyrrolidine-1-carboxylic acid tert-butyl ester

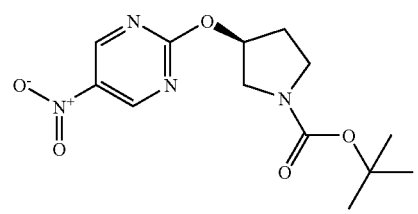

With a method similar to that used for the preparation of (S)-3-(5-nitro-pyridin-2-yloxy)-pyrrolidine-1-carboxylic acid tert-butyl ester, (S)-3-(5-nitro-pyrimidin-2-yloxy)-pyrrolidine-1-carboxylic acid tert-butyl ester was prepared from (S)-3-hydroxy-pyrrolidine-1-carboxylic acid tert-butyl ester and 2-fluoro-5-nitropyrimidine. The NMR spectrum obtained on the sample is compatible with its structure.

Preparation of (2-amino-ethyl)methyl carbamic acid ethyl ester trifluoroacetate salt

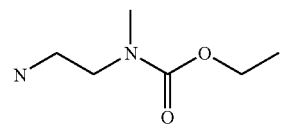

To a solution of N-tert-butoxycarbonyl-2-methylamino-ethylamine hydrochloride salt (1 g, 4.7 mmol) in methylene chloride (30 mL) was added triethylamine (1.63 mL), followed by ethyl chloroformate (450 μL, 4.7 mmol). The reaction mixture was allowed to stir at room temperature overnight. After solvent removal, the residue was extracted with ethyl acetate, dried over anhydrous sodium sulfate and concentrated. The resulting material was treated with trifluoroacetic acid without further purification. The reaction mixture was stirred at room temperature for 1 h and concentrated to yield (2-amino-ethyl)methyl carbamic acid ethyl ester trifluoroacetate salt which was carried on to the next step without further purification.

Preparation of racemic trans-2-(4'-amino-biphenyl-4-carbonyl)-cyclopentanecarboxylic acid

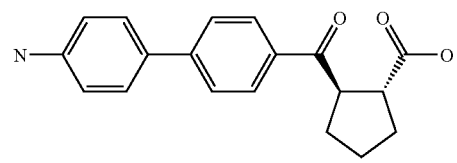

A mixture of 4-aminophenylboronic acid hydrochloride (0.21 g, 1.2 mmol), trans-2-(4-bromo-benzoyl)-cyclopentanecarboxylic acid (0.30 g, 1 mmol), tetrakis(triphenylphosphine) palladium (0) (10 mg), 2 M aqueous sodium carbonate solution (0.5 mL), ethanol (2 mL), and ethylene glycol dimethyl ether (3 mL) was heated under microwave condition to 160° C. for 30 min. The crude reaction mixture was adsorbed onto silica gel and flash chromatography (eluting with ethyl acetate and hexanes) yielded 0.2 g of trans-2-(4'-amino-biphenyl-4-carbonyl)-cyclopentanecarboxylic acid as a brown solid. LCMS calcd for C19H19NO3 (m/e) 309, obsd 310 (M+H).

Preparation of trans-2-(4'-amino-biphenyl-4-carbonyl)-cyclohexanecarboxylic acid

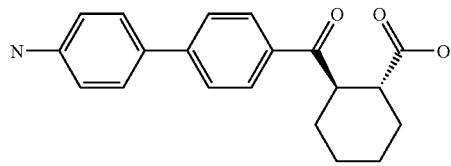

With a method similar to that used for the preparation of trans-2-(4'-amino-biphenyl-4-carbonyl)-cyclopentanecarboxylic acid, trans-2-(4'-amino-biphenyl-4-carbonyl)-cyclohexanecarboxylic acid was prepared from 4-aminophenylboronic acid hydrochloride and trans-2-(4-bromo-benzoyl)-cyclohexanecarboxylic acid. LCMS calcd for C20H21NO3 (m/e) 323, obsd 324 (M+H).

Preparation of 4-(5-amino-pyridin-2-yl)-N-isobutyl-benzamide

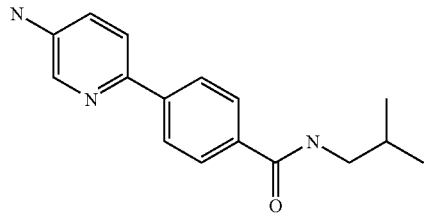

With a method similar to that used for the preparation of trans-2-(4'-amino-biphenyl-4-carbonyl)-cyclopentanecarboxylic acid, 4-(5-amino-pyridin-2-yl)-N-isobutyl-benzamide was prepared from 5-amino-2-bromopyridine and 4-(isobutylaminocarbonyl)benzeneboronic acid. LCMS calcd for C16H19N3O (m/e) 269, obsd 270 (M+H).

Acids

Preparation of rac-trans-cyclopentane-1,2-dicarboxylic acid monoethyl ester

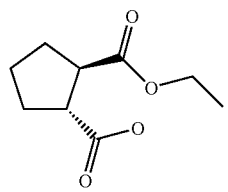

A solution of trans-DL-cyclopentane-1,2-dicarboxylic acid (316 mg, 2 mmol) in 25 mL ethanol was saturated with hydrogen chloride gas by bubbling for 5 minutes. The mixture was heated under reflux overnight, cooled and evaporated under reduced pressure. The residue was dissolved in ethyl acetate, washed with water, dried over magnesium sulfate, filtered and evaporated to dryness under vacuum to give rac-trans-cyclopentane-1,2-dicarboxylic acid diethyl ester (393 mg) that was used in the next step without further purification.

To a solution of rac-trans-cyclopentane-1,2-dicarboxylic acid diethyl ester (393 mg, 1.84 mmol) was added a solution of lithium hydroxide (75.5 mg, 1.8 mmol) in water (7 mL). The reaction mixture was stirred at room temperature for 30 minutes and then heated to 55° C. for 1 hr. The reaction mixture was cooled and evaporated under reduced pressure. The residue was dissolved in 25 mL water and washed with diethyl ether (2×5 mL). The pH of the aqueous layer was adjusted to pH 5 with 1N hydrochloric acid and extracted with methylene chloride (2×5 mL) and ethyl acetate (5 mL). The combined organic layers were dried over magnesium sulfate, filtered and evaporated to dryness under vacuum to give rac-trans-cyclopentane-1,2-dicarboxylic acid monoethyl ester (95 mg) that was used without further purification.

Preparation of 2,2-diethyl-succinic acid 1-methyl ester

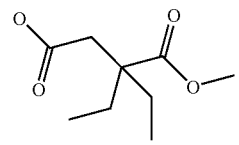

With a method similar to that used for the preparation of rac-trans-cyclopentane-1,2-dicarboxylic acid monoethyl ester, 2,2-diethyl-succinic acid 1-methyl ester was prepared from 2,2-diethyl-succinic acid. This material was used in the next step without further purification.

Preparation of 1-phenyl-3-trifluoromethyl-1H-pyrazole-4-carboxylic acid

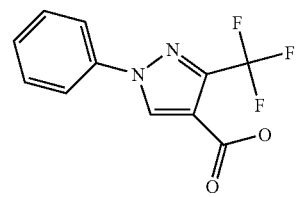

A mixture of 3-trifluoromethyl-1H-pyrazole-4-carboxylic acid ethyl ester (2.5 g, 12.0 mmol), copper (I) iodide (0.69 g, 3.6 mmol) and potassium carbonate (3.49 g, 25.3 mmol) in toluene (12 mL) in a round bottom flask was purged with argon. To the reaction mixture was then added iodobenzene (1.61 mL, 14.4 mmol) and racemic trans-N,N'-dimethyl-cyclohexane-1,2-diamine (1.16 mL, 7.2 mmol). The slurry was heated under Ar in an oil bath at 110° C. for 24 hours. After cooling to room temperature, the reaction mixture was diluted with ethyl acetate and filtered over a bed of celite. The organic washings were combined and concentrated to give a crude which was purified by silica gel chromatography (Isco 120 g column, 0→30% ethyl acetate/hexanes) to give 1-phenyl-3- trifluoromethyl-1H-pyrazole-4-carboxylic acid ethyl ester (2.91 g, 85%) as an off-white solid. The NMR spectrum obtained on the sample is compatible with its structure.

A mixture of 1-phenyl-3-trifluoromethyl-1H-pyrazole-4-carboxylic acid ethyl ester (1.25 g, 4.4 mmol) and 1N aqueous sodium hydroxide solution (17.3 mL) in methanol (20 mL) was stirred at room temperature overnight. The reaction mixture was concentrated and acidified to pH~1 with 1N aqueous hydrochloric acid. The slurry was extracted with methylene chloride and the combined organic layers were washed with saturated sodium chloride and dried over sodium sulfate. Filtration and concentration gave 1-phenyl-3-trifluoromethyl-1H-pyrazole-4-carboxylic acid (1 g, 89% yield) as an off-white solid, which was directly used in the next step without further purification. LCMS calcd for C11H7F3N2O2 (m/e) 256, obsd 255 (M−H).

Preparation of 1-(4-fluoro-phenyl)-3-trifluoromethyl-1H-pyrazole-4-carboxylic acid

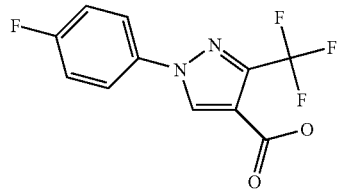

With a method similar to that used for the preparation of 1-phenyl-3-trifluoromethyl-1H-pyrazole-4-carboxylic acid above, 1-(4-fluoro-phenyl)-3-trifluoromethyl-1H-pyrazole-4-carboxylic acid was prepared from 3-trifluoromethyl-1H-pyrazole-4-carboxylic acid ethyl ester and 1-fluoro-4-iodobenzene. LCMS calcd for C11H6F4N2O2 (m/e) 274, obsd 273 (M−H).

Preparation of 1-(2-chloro-phenyl)-3-trifluoromethyl-1H-pyrazole-4-carboxylic acid

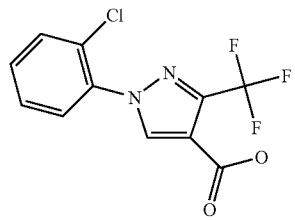

With a method similar to that used for the preparation of 1-phenyl-3-trifluoromethyl-1H-pyrazole-4-carboxylic acid above, 1-(2-chloro-phenyl)-3-trifluoromethyl-1H-pyrazole-4-carboxylic acid was prepared from 3-trifluoromethyl-1H-pyrazole-4-carboxylic acid ethyl ester and 1-chloro-2-iodobenzene. LCMS calcd for C11H6ClF3N2O2 (m/e) 290, obsd 289 (M−H).

Preparation of 1-pyridin-2-yl-3-trifluoromethyl-1H-pyrazole-4-carboxylic acid

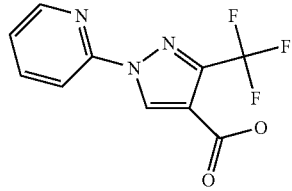

With a method similar to that used for the preparation of 1-phenyl-3-trifluoromethyl-1H-pyrazole-4-carboxylic acid above, 1-pyridin-2-yl-3-trifluoromethyl-1H-pyrazole-4-carboxylic acid was prepared from 3-Trifluoromethyl-1H-pyrazole-4-carboxylic acid ethyl ester and 2-bromopyridine. LCMS calcd for C10H6F3N3O2 (m/e) 257, obsd 258 (M+H).

Preparation of 5-phenyl-2-(2,2,2-trifluoro-ethyl)-2H-pyrazole-3-carboxylic acid

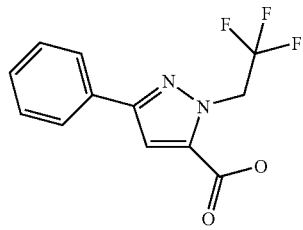

To a mixture of 5-phenyl-2H-pyrazole-3-carboxylic acid ethyl ester (500 mg, 2.31 mmol) in N,N-dimethylformamide (30 mL) at 0° C. was added sodium hydride (60% in mineral oil, 110 mg, 2.75 mmol). The mixture was stirred at 0° C. for 10 minutes and stirred at room temperature for 40 minutes. After the reaction mixture was re-cooled to 0° C., 2,2,2-trifluoro-methanesulfonic acid 2,2,2-trifluoro-ethyl ester (500 mg, 2.39 mmol) was added dropwise. The mixture was warmed up to room temperature and stirred overnight. The reaction was quenched carefully with ice water and neutralized with 1N aqueous hydrochloric acid. The mixture was extracted with methylene chloride and the organic layer was dried over sodium sulfate. Filtration and concentration gave a crude which was purified by silica gel chromatography (Isco 120 g column, 10% ethyl acetate/hexanes) to give 5-phenyl-2-(2,2,2-trifluoro-ethyl)-2H-pyrazole-3-carboxylic acid ethyl ester (360 mg, 52%) as a white solid. The NMR spectrum obtained on the sample is compatible with its structure.

A mixture of 5-phenyl-2-(2,2,2-trifluoro-ethyl)-2H-pyrazole-3-carboxylic acid ethyl ester (360 mg, 1.21 mmol) and 1N aqueous sodium hydroxide solution (3.6 mL, 3.6 mmol) in methanol (10 mL) was stirred at room temperature overnight. The reaction mixture was acidified to pH~2 with 1N aqueous hydrochloric acid and concentrated to give 5-phenyl-2-(2,2, 2-trifluoro-ethyl)-2H-pyrazole-3-carboxylic acid as an off-white solid, which was directly used in the next step without further purification. LCMS calcd for C12H9F3N2O2 (m/e) 270, obsd 271 (M+H).

Preparation of 5-phenyl-2-propyl-2H-pyrazole-3-carboxylic acid

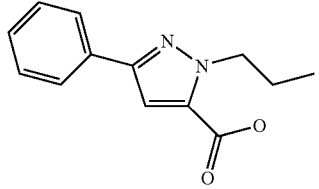

With a method similar to that used for the preparation of 5-phenyl-2-(2,2,2-trifluoro-ethyl)-2H-pyrazole-3-carboxylic acid above, 5-phenyl-2-propyl-2H-pyrazole-3-carboxylic acid was prepared from 5-phenyl-2H-pyrazole-3-carboxylic acid ethyl ester and 1-iodopropane. LCMS calcd for C13H14N2O2 (m/e) 230, obsd 229 (M−H).

Preparation of 2-(2-methoxy-ethyl)-5-phenyl-2H-pyrazole-3-carboxylic acid

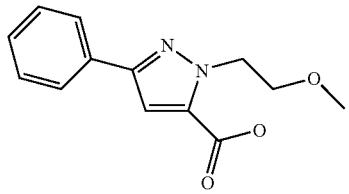

With a method similar to that used for the preparation of 5-phenyl-2-(2,2,2-trifluoro-ethyl)-2H-pyrazole-3-carboxylic acid above, 2-(2-methoxy-ethyl)-5-phenyl-2H-pyrazole-3-carboxylic acid was prepared from 5-phenyl-2H-pyrazole-3-carboxylic acid ethyl ester and 1-iodo-2-methoxy-ethane. LCMS calcd for C13H14N2O3 (m/e) 246, obsd 245 (M−H).

Preparation of 2-propyl-5-thiophen-2-yl-2H-pyrazole-3-carboxylic acid

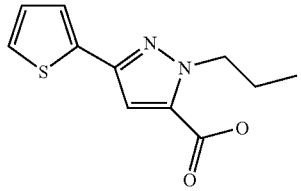

With a method similar to that used for the preparation of 5-phenyl-2-(2,2,2-trifluoro-ethyl)-2H-pyrazole-3-carboxylic acid above, 2-propyl-5-thiophen-2-yl-2H-pyrazole-3-carboxylic acid was prepared from 5-thiophen-2-yl-2H-pyrazole-3-carboxylic acid ethyl ester and 1-iodo-propane. LCMS calcd for C11H12N2O2S (m/e) 236, obsd 235 (M−H).

Advanced Intermediates

Preparation of 2-phenyl-5-trifluoromethyl-oxazole-4-carboxylic acid (6-piperazin-1-yl-pyridin-3-yl)-amide; hydrochloride

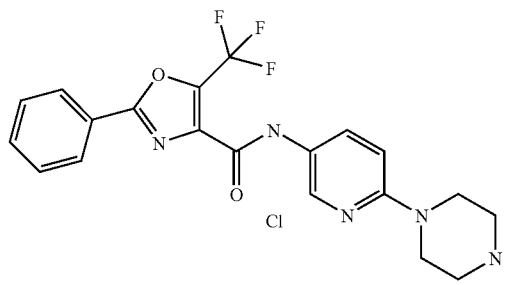

4-(5-Amino-pyridin-2-yl)-piperazine-1-carboxylic acid tert-butyl ester described above was mixed with 2-phenyl-5-trifluoromethyloxazole-4-carboxylic acid (771 mg, 3.0 mmol) and bromotrispyrrolidinophosphonium hexafluorophosphate (1.40 g, 3.0 mmol) in N,N-dimethylformamide (20 mL) and methylene chloride (5 mL) containing triethylamine (0.85 mL). The mixture was stirred at room temperature overnight and the solvents were evaporated. The residue was partitioned between ethyl acetate and water. The organic layer was dried over sodium sulfate and solvent was evaporated. The residue was triturated with ethyl acetate and the solid was filtered to give 4-{5-[(2-phenyl-5-trifluoromethyl-oxazole-4-carbonyl)-amino]-pyridin-2-yl}-piperazine-1-carboxylic acid tert-butyl ester (1.09 g). LC-MS calcd for C25H26F3N5O4 (m/e) 517.5, obsd 518.1 (M+H). The NMR spectrum obtained on the sample is compatible with its structure.

4-{5-[(2-phenyl-5-trifluoromethyl-oxazole-4-carbonyl)-amino]-pyridin-2-yl}-piperazine-1-carboxylic acid tert-butyl ester (300 mg, 0.58 mmol) from above was suspended in methylene chloride (5 mL) and methanol (5 mL). To this mixture was added hydrogen chloride in ether (4N, 3 mL). The mixture was stirred at room temperature overnight. The solvents were evaporated and the residue was dried in vacuum. The resulting solid was triturated with dry ether and then filtered to give a hydrochloride salt of 2-phenyl-5-trifluoromethyl-oxazole-4-carboxylic acid (6-piperazin-1-yl-pyridin-3-yl)-amide (274 mg). LC-MS calcd C20H18F3N5O2 (m/e) 417.39, obsd 418.0 (M+H). The NMR spectrum obtained on the sample is compatible with its structure.

Preparation of 2-phenyl-5-trifluoromethyl-oxazole-4-carboxylic acid (2-piperazin-1-yl-pyrimidin-5-yl)-amide; hydrochloride

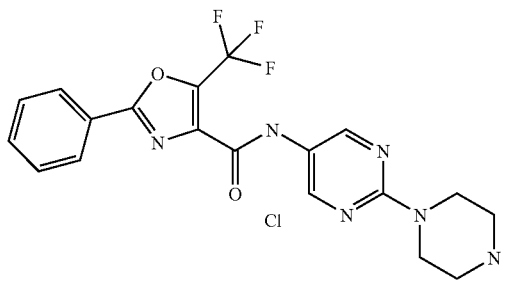

To a solution of 4-(5-nitro-pyrimidin-2-yl)-piperazine-1-carboxylic acid tert-butyl ester (927 mg, 3 mmol, prepared from 2-chloro-5-nitropyrimidine and N-Boc-piperazine) in tetrahydrofuran (20 mL) and methanol (30 mL) was added 10% palladium on carbon (240 mg) and the mixture was hydrogenated at 50 psi for 1 hr. The mixture was filtered and the solvents were evaporated. The residue was dried in vacuum to give 4-(5-amino-pyrimidin-2-yl)-piperazine-1-carboxylic acid tert-butyl ester.

To a suspension of 2-phenyl-5-trifluoromethyloxazole-4-carboxylic acid (771 mg, 3 mmol) in methylene chloride (10 mL) was added oxalyl chloride (2M, 3 mL, 6.0 mmol) and one drop of N,N-dimethylformamide. The mixture was stirred at room temperature for 1 hr and the solvents were evaporated. The residue was treated with benzene (5 mL) and the solvents were again evaporated. The oily residue was dried in vacuum and then dissolved in methylene chloride (10 mL). The solution was cooled in an ice bath. To this solution was added a methylene chloride solution of 4-(5-amino-pyrimidin-2-yl)-piperazine-1-carboxylic acid tert-butyl ester (3 mmol) and pyridine (0.73 mL). The mixture was stirred at 0° C. for 10 minutes and room temperature for 2 hrs. After concentration, the residue was partitioned between methylene chloride and water. The organic layer was washed with aqueous citric acid solution and dried over sodium sulfate. The solvents were evaporated and the residue was dried in vacuum. The resulting material was triturated with ethyl acetate and the precipitate was filtered to give 4-{5-[(2-phenyl-5-trifluoromethyl-oxazole-4-carbonyl)-amino]-pyrimidin-2-yl}-piperazine-1-carboxylic acid tert-butyl ester (1.38 g). LC-MS calcd for C24H25F3N6O4 (m/e) 518.5, obsd 519.1 (M+H). The NMR spectrum obtained on the sample is compatible with its structure.

With a method similar to that used for the preparation of 2-phenyl-5-trifluoromethyl-oxazole-4-carboxylic acid (6-piperazin-1-yl-pyridin-3-yl)-amide above, hydrochloride salt of 2-phenyl-5-trifluoromethyl-oxazole-4-carboxylic acid (2-piperazin-1-yl-pyrimidin-5-yl)-amide was prepared from 4-{5-[(2-phenyl-5-trifluoromethyl-oxazole-4-carbonyl)-amino]-pyrimidin-2-yl}-piperazine-1-carboxylic acid tert-butyl ester. LC-MS calcd for the free base C19H17F3N6O2 (m/e) 418.39, obsd 419.0 (M+H). The NMR spectrum obtained on the sample is compatible with its structure.

Preparation of 2-phenyl-5-trifluoromethyl-oxazole-4-carboxylic acid (4-piperidin-4-yl-phenyl)-amide

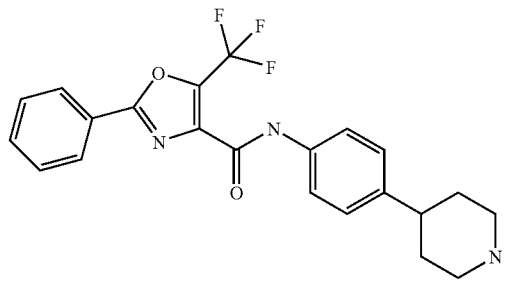

With a method similar to that used for the preparation of 4-{5-[(2-phenyl-5-trifluoromethyl-oxazole-4-carbonyl)-amino]-pyrimidin-2-yl}-piperazine-1-carboxylic acid tert-butyl ester above, 4-{4-[(2-phenyl-5-trifluoromethyl-oxazole-4-carbonyl)-amino]-phenyl}-piperidine-1-carboxylic acid tert-butyl ester was prepared from 2-phenyl-5-trifluoromethyloxazole-4-carboxylic acid and 4-(4-aminophenyl)-piperidine-1-carboxylic acid tert-butyl ester. The NMR spectrum obtained on the sample is compatible with its structure.

4-{4-[(2-Phenyl-5-trifluoromethyl-oxazole-4-carbonyl)-amino]-phenyl}-piperidine-1-carboxylic acid tert-butyl ester (245 mg, 0.475 mmol) from above was dissolved in methylene chloride (2 mL) and trifluoroacetic acid (1 mL). The mixture was stirred at room temperature and the solvents were evaporated. The residue was partitioned between methylene chloride and dilute sodium hydroxide solution. The organic layer was washed with brine and dried over sodium sulfate. Evaporation of solvents gave 2-phenyl-5-trifluoromethyl-oxazole-4-carboxylic acid (4-piperidin-4-yl-phenyl)-amide (183 mg) as a white solid. LC-MS calcd for C22H20F3N3O2 (m/e) 415.41, obsd 416.0. The NMR spectrum obtained on the sample is compatible with its structure.

Preparation of 2-phenyl-5-trifluoromethyl-oxazole-4-carboxylic acid (1',2',3',4',5',6'-hexahydro-[2,4']bipyridinyl-5-yl)-amide

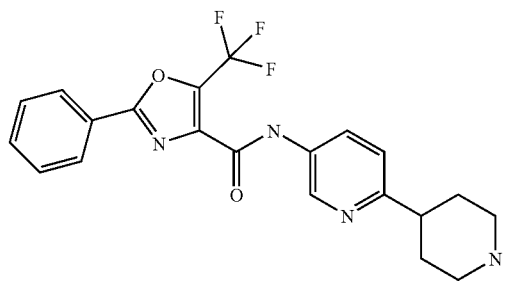

4-Trifluoromethanesulfonyloxy-3,6-dihydro-2H-pyridine-1-carboxylic acid tert-butyl ester (prepared according to known procedures *Synthesis*, 1991, 11, 993) was reacted with bis(pinacolato)diboron to generate N-tert-butoxycarbonyl-1,2,3,6-tetrahydropyridine-4-boronic acid pinacol ester according to literature procedures (*Tetrahedron Letters*, 2000, 41, 3705).

To a mixture of 2-bromo-5-nitropyridine (0.5 g, 2.46 mmol) and N-tert-butoxycarbonyl-1,2,3,6-tetrahydropyridine-4-boronic acid pinacol ester (0.913 g, 2.95 mmol) in toluene (4 mL) and ethanol (1.0 mL) was added potassium carbonate solution (2M, 2 mL) and $PdCl_2dppf$ (180 mg, 0.246 mmol). The mixture was degassed with argon and heated to 100° C. in a microwave for 40 minutes with stirring. The solvents were evaporated and the residue was extracted with ethyl acetate. After evaporation of the solvents, the residue was purified using flash chromatography (eluting with ethyl acetate and hexanes) to give 5-nitro-3',6'-dihydro-2'H-[2,4']bipyridinyl-1'-carboxylic acid tert-butyl ester as a solid (400 mg). The NMR spectrum obtained on the sample is compatible with its structure.

5-nitro-3',6'-dihydro-2'H-[2,4']bipyridinyl-1'-carboxylic acid tert-butyl ester (400 mg) from above was dissolved in methanol (50 mL) and tetrahydrofuran (10 mL). To this mixture was added 10% palladium on carbon (100 mg). The mixture was hydrogenated at 50 psi for 2 hrs. The mixture was filtered and the solvents were evaporated to give 5-amino-3',4',5',6'-tetrahydro-2'H-[2,4']bipyridinyl-1'-carboxylic acid tert-butyl ester as a white solid (363 mg). The NMR spectrum obtained on the sample is compatible with its structure.

With a method similar to that used for the preparation of 4-{5-[(2-phenyl-5-trifluoromethyl-oxazole-4-carbonyl)-amino]-pyrimidin-2-yl}-piperazine-1-carboxylic acid tert-butyl ester above, 5-[(2-phenyl-5-trifluoromethyl-oxazole-4-carbonyl)-amino]-3',4',5',6'-tetrahydro-2'H-[2,4']bipyridinyl-1'-carboxylic acid tert-butyl ester was prepared from 2-phenyl-5-trifluoromethyloxazole-4-carboxylic acid and 5-amino-3',4',5',6'-tetrahydro-2'H-[2,4']bipyridinyl-1'-carboxylic acid tert-butyl ester. The NMR spectrum obtained on the sample is compatible with its structure.

5-[(2-phenyl-5-trifluoromethyl-oxazole-4-carbonyl)-amino]-3',4',5',6'-tetrahydro-2'H-[2,4']bipyridinyl-1'-carboxylic acid tert-butyl ester (535 mg) from above was dissolved in a mixture of methylene chloride (35 mL) and trifluoroacetic acid (9 mL). The mixture was stirred at room temperature for 2 hrs. The solvents were evaporated and the residues were partitioned between methylene chloride and dilute sodium hydroxide solution. The organic layer was washed with brine and dried over sodium sulfate. Evaporation of solvents gave 2-phenyl-5-trifluoromethyl-oxazole-4-carboxylic acid (1',2',3',4',5',6'-hexahydro-[2,4']bipyridinyl-5-yl)-amide (360 mg) as a solid. LC-MS calcd for $C_{21}H_{19}F_3N_4O_2$ (m/e) 416.1, obsd 417.1 (M+H). The NMR spectrum obtained on the sample is compatible with its structure.

Preparation of 2-phenyl-5-trifluoromethyl-oxazole-4-carboxylic acid (4-piperazin-1-yl-phenyl)-amide

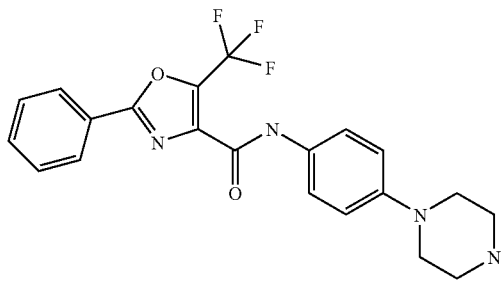

A solution of di-tert-butyldicarbonate (5.79 g, 26.5 mmol) in 20 mL dioxane was added dropwise to a solution of 1-(4-nitro-phenyl)-piperazine (5 g, 24.1 mmol) in 150 mL dioxane and stirred at room temperature for 1 hr. The reaction mixture was diluted with 250 mL ethyl acetate, washed with water, dried over sodium sulfate and filtered. The organic filtrate was evaporated under reduced pressure to yield 7.9 g of 4-(4-nitro-phenyl)-piperazine-1-carboxylic acid tert-butyl ester that was used in the next step without further purification.

A mixture of 4-(4-nitro-phenyl)-piperazine-1-carboxylic acid tert-butyl ester (3 g, 9.76 mmol) and 10% palladium on carbon (300 mg) in 50 mL ethanol and 20 mL ethyl acetate was hydrogenated at room temperature under a 50 psi hydrogen atmosphere for 2 hrs. The reaction mixture was filtered through a plug of Celite and evaporated under reduced pressure to give 4-(4-amino-phenyl)-piperazine-1-carboxylic acid tert-butyl ester that was used in the in the next step without further purification.

2-Phenyl-5-trifluoromethyl-oxazole-4-carboxylic acid (2.5 g, 9.76 mmol), 4-(4-amino-phenyl)-piperazine-1-carboxylic acid tert-butyl ester (2.65 g, 10.34 mmol), and triethylamine (4.1 mL, 29.3 mmol) were dissolved in 50 mL of 1-methyl-2-pyrrolidinone. To this solution was added (benzotriazol-1-yloxy)tris(dimethylamino)phosphonium hexafluorophosphate (BOP, 4.51 g, 10.34 mmol) in one portion. The mixture was stirred at room temperature overnight and then diluted with 250 mL of ethyl acetate. The organic layer was washed with saturated sodium bicarbonate (2×50 mL), dried over magnesium sulfate, filtered and evaporated to dryness under vacuum. The residue was purified by chromatography over a silica gel plug (eluting with ethyl acetate/methylene chloride) to yield 4-{4-[(2-phenyl-5-trifluoromethyl-oxazole-4-carbonyl)-amino]-phenyl}-piperazine-1-carboxylic acid tert-butyl ester as an amorphous solid. ES-MS calcd for $C_{26}H_{27}F_3N_4O_4$ (m/e) 516.52, obsd 517 (M+H).

With a method similar to that used for the preparation of 2-phenyl-5-trifluoromethyl-oxazole-4-carboxylic acid (1',2',3',4',5',6'-hexahydro-[2,4']bipyridinyl-5-yl)-amide above, 2-phenyl-5-trifluoromethyl-oxazole-4-carboxylic acid (4-piperazin-1-yl-phenyl)-amide was prepared from 4-{4-[(2-phenyl-5-trifluoromethyl-oxazole-4-carbonyl)-amino]-phenyl}-piperazine-1-carboxylic acid tert-butyl ester. LC-MS calcd. for $C_{21}H_{19}F_3N_4O_2$ (m/e) 416.1, obsd 417.1 (M+H). The NMR spectrum obtained on the sample is compatible with its structure.

Preparation of 2-phenyl-5-trifluoromethyl-oxazole-4-carboxylic acid (3-cyano-4-piperazin-1-yl-phenyl)-amide

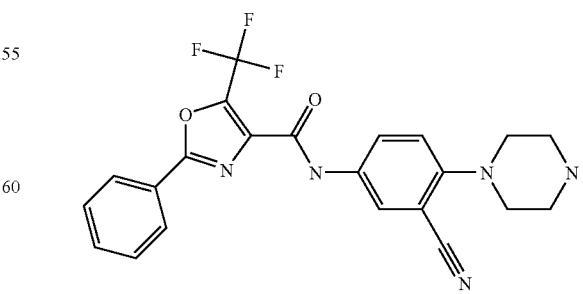

4-(2-Cyano-4-nitro-phenyl)-piperazine-1-carboxylic acid tert-butyl ester (587 mg, 1.77 mmol) was dissolved in methanol (50 mL) and to this solution was added ammonium chloride (945 mg, 17.66 mmol) and zinc (1155 mg, 17.66 mmol). The mixture was magnetically stirred for 3 hr and the mixture was filtered through a pad of celite. The solids were rinsed with methanol and the combined filtrate was concentrated to a yellow solid. This crude intermediate was dissolved in ethyl acetate (400 mL) and the resulting solution was washed with water (400 mL) and brine (200 mL). The organic layer was collected, dried over sodium sulfate, and concentrated to give 4-(4-amino-2-cyano-phenyl)-piperazine-1-carboxylic acid tert-butyl ester that was used in the next step without further purification.

Crude 4-(4-amino-2-cyano-phenyl)-piperazine-1-carboxylic acid tert-butyl ester from above was dissolved in methylene chloride (10 mL) and to the resulting solution was added 2-phenyl-5-trifluoromethyl-oxazole-4-carboxylic acid (454 mg), triethylamine (247 μL) and 1-[3-(dimethylamino)propyl]-3-ethylcarbodiimide hydrochloride (EDCl, 337 mg). The reaction mixture was stirred at room temperature for 3 hr. Another portion of 1-[3-(dimethylamino)propyl]-3-ethylcarbodiimide hydrochloride (0.5 eq) was added. The reaction mixture was stirred at 50° C. for 3 hr and at room temperature for 3.5 days. The reaction mixture was partitioned between ethyl acetate and water. The organic layer was dried over sodium sulfate, filtered and evaporated. Purification by flash chromatography afforded 4-{2-cyano-4-[(2-phenyl-5-trifluoromethyl-oxazole-4-carbonyl)-amino]-phenyl}-piperazine-1-carboxylic acid tert-butyl ester (240 mg, 25% yield) as a yellow solid. LCMS calcd for C27H26F3N5O4 (m/e) 541, obsd 542 (M+H).

With a method similar to that used for the preparation of 2-phenyl-5-trifluoromethyl-oxazole-4-carboxylic acid (1',2',3',4',5',6'-hexahydro-[2,4']bipyridinyl-5-yl)-amide above, 2-phenyl-5-trifluoromethyl-oxazole-4-carboxylic acid (3-cyano-4-piperazin-1-yl-phenyl)-amide was prepared from 4-{2-cyano-4-[(2-phenyl-5-trifluoromethyl-oxazole-4-carbonyl)-amino]-phenyl}-piperazine-1-carboxylic acid tert-butyl ester. LCMS calcd for C22H18F3N5O2 (m/e) 441, obsd 442 (M+H).

Preparation of 2-phenyl-5-trifluoromethyl-oxazole-4-carboxylic acid [6-(piperidin-4-ylamino)-pyridin-3-yl]-amide trifluoroacetate salt

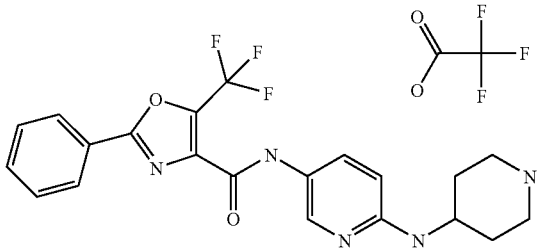

A mixture of 2-phenyl-5-trifluoromethyl-oxazole-4-carboxylic acid (0.67 g, 2.6 mmol), 4-(5-amino-pyridin-2-ylamino)-piperidine-1-carboxylic acid tert-butyl ester (0.76 g, 2.6 mmol), bromo-tris-pyrrolidino-phosphonium hexafluorophosphate (PyBrop, 1.45 g, 3.1 mmol), and diisopropylethylamine (0.9 mL, 5.2 mmol) in anhydrous dichloromethane (15 mL) was stirred at room temperature overnight. The reaction mixture was then concentrated and purified by flash chromatography (Merck silica gel 60, 230-400 mesh, eluted with ethyl acetate and hexane) to give 4-{5-[(2-phenyl-5-trifluoromethyl-oxazole-4-carbonyl)-amino]-pyridin-2-ylamino}-piperidine-1-carboxylic acid tert-butyl ester (0.78 g, 56%) as a white solid. LCMS calcd for C26H28F3N5O4 (m/e) 531, obsd 532 (M+H).

With a method similar to that used for the preparation of 2-phenyl-5-trifluoromethyl-oxazole-4-carboxylic acid (1',2',3',4',5',6'-hexahydro-[2,4']bipyridinyl-5-yl)-amide above, 2-phenyl-5-trifluoromethyl-oxazole-4-carboxylic acid [6-(piperidin-4-ylamino)-pyridin-3-yl]-amide trifluoroacetate salt was prepared from 4-{5-[(2-phenyl-5-trifluoromethyl-oxazole-4-carbonyl)-amino]-pyridin-2-ylamino}-piperidine-1-carboxylic acid tert-butyl ester. LCMS calcd for C21H20F3N5O2 (m/e) 431, obsd 432 (M+H).

Preparation of 2-phenyl-5-trifluoromethyl-oxazole-4-carboxylic acid (4-methylamino-3,4,5,6-tetrahydro-2H-[1,2']bipyridinyl-5'-yl)-amide trifluoroacetate salt

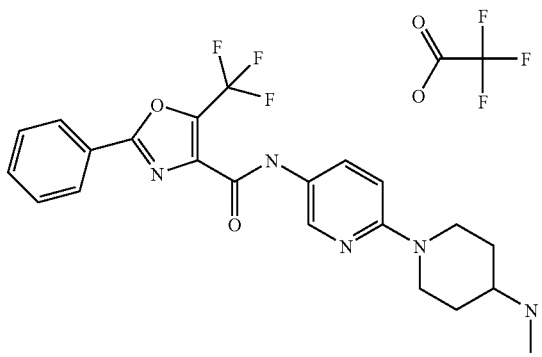

A mixture of 2-phenyl-5-trifluoromethyl-oxazole-4-carboxylic acid (0.91 g, 3.54 mmol), 5'-amino-3,4,5,6-tetrahydro-2H-[1,2']bipyridinyl-4-yl)-methyl-carbamic acid tert-butyl ester (1.25 g, 4 mmol), bromo-tris-pyrrolidino-phosphonium hexafluorophosphate (PyBrop, 1.86 g, 4 mmol), and diisopropylethylamine (0.8 mL, 4.6 mmol) in anhydrous dichloromethane (15 mL) was stirred at room temperature overnight. After concentration, the crude was partitioned between water and ethyl acetate. The organic layer was washed with brine, dried over sodium sulfate, and concentrated to give a solid. The crude product was purified by flash chromatography (Merck silica gel 60, 230-400 mesh, 0%-100% ethyl acetate in hexane) to give methyl-{5'-[(2-phenyl-trifluoromethyl-oxazole-4-carbonyl)-amino]-3,4,5,6-tetrahydro-2H-[1,2']bipyridinyl-4-yl}-carbamic acid tert-butyl ester in quantitative yield (1.9 g) as an off-white solid. LCMS calcd for C27H30F3N5O4 (m/e) 545, obsd 546 (M+H).

With a method similar to that used for the preparation of 2-phenyl-5-trifluoromethyl-oxazole-4-carboxylic acid (1',2',3',4',5',6'-hexahydro-[2,4']bipyridinyl-5-yl)-amide above, 2-phenyl-5-trifluoromethyl-oxazole-4-carboxylic acid (4-methylamino-3,4,5,6-tetrahydro-2H-[1,2']bipyridinyl-5'-yl)-amide trifluoroacetate salt was prepared from methyl-{5'-

[(2-phenyl-trifluoromethyl-oxazole-4-carbonyl)-amino]-3,4,5,6-tetrahydro-2H-[1,2']bipyridinyl-4-yl}-carbamic acid tert-butyl ester.

Preparation of 2-phenyl-5-trifluoromethyl-oxazole-4-carboxylic acid (6-bromo-pyridin-3-yl)-amide

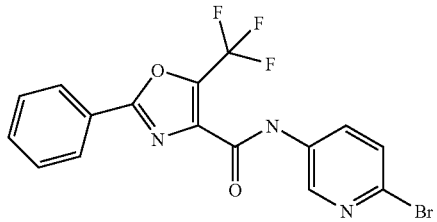

A mixture of 2-phenyl-5-trifluoromethyl-oxazole-4-carboxylic acid (3.0 g, 11.7 mmol), 6-bromo-pyridin-3-ylamine (2.0 g, 11.7 mmol), 1-hydroxy-7-azabenzotriazole (HOAT) (2.4 g, 17.5 mmol), and 1-ethyl-3-(3-dimethylaminopropyl) carbodiimide hydrochloride (3.4 g, 17.5 mmol) in anhydrous dichloromethane (100 mL) was stirred at room temperature overnight. The reaction mixture was concentrated and partitioned between water and ethyl acetate. The organic layer was washed with brine, dried and concentrated to give a solid. Recrystallization of the crude solid from ethyl acetate/hexane/methanol gave 4.04 g of 2-phenyl-5-trifluoromethyl-oxazole-4-carboxylic acid (6-bromo-pyridin-3-yl)-amide. The mother liquor was purified by flash chromatography (Merck silica gel 60, 230-400 mesh, 0%-100% ethyl acetate in hexane) to give an additional 200 mg of 2-phenyl-5-trifluoromethyl-oxazole-4-carboxylic acid (6-bromo-pyridin-3-yl)-amide (4.24 g in total, 88%) as a light brown solid. LCMS calcd for C16H9BrF3N3O2 (m/e) 412, obsd 413 (M+H).

Preparation of 2-phenyl-5-trifluoromethyl-oxazole-4-carboxylic acid (4-iodo-phenyl)-amide

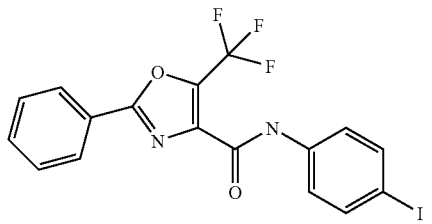

With a method similar to that used for the preparation of 2-phenyl-5-trifluoromethyl-oxazole-4-carboxylic acid (6-bromo-pyridin-3-yl)-amide above, 2-phenyl-5-trifluoromethyl-oxazole-4-carboxylic acid (4-iodo-phenyl)-amide was prepared from 2-phenyl-5-trifluoromethyl-oxazole-4-carboxylic acid and 4-iodo-phenylamine. LCMS calcd for C17H10F3IN2O2 (m/e) 458, obsd 459 (M+H).

Preparation of 2-phenyl-5-trifluoromethyl-oxazole-4-carboxylic acid (4-bromo-3-fluoro-phenyl)-amide

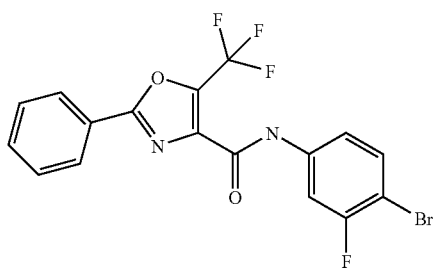

With a method similar to that used for the preparation of 2-phenyl-5-trifluoromethyl-oxazole-4-carboxylic acid (6-bromo-pyridin-3-yl)-amide above, 2-phenyl-5-trifluoromethyl-oxazole-4-carboxylic acid (4-bromo-3-fluoro-phenyl)-amide was prepared from 2-phenyl-5-trifluoromethyl-oxazole-4-carboxylic acid and 4-bromo-3-fluoro-phenylamine. LCMS calcd for C17H9BrF4N2O2 (m/e) 429, obsd 430 (M+H).

Preparation of 2,2-dimethyl-4-oxo-4-{4'-[(2-phenyl-5-trifluoromethyl-oxazole-4-carbonyl)-amino]-biphenyl-4-yl}-butyric acid methyl ester

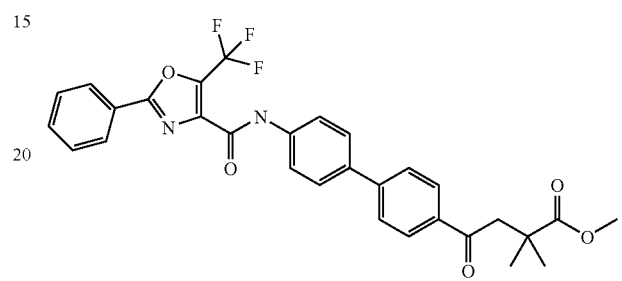

With a method similar to that used for the preparation of 2-phenyl-5-trifluoromethyl-oxazole-4-carboxylic acid (6-bromo-pyridin-3-yl)-amide, 2,2-dimethyl-4-oxo-4-{4'-[(2-phenyl-5-trifluoromethyl-oxazole-4-carbonyl)-amino]-biphenyl-4-yl}-butyric acid methyl ester was prepared from 2-phenyl-5-trifluoromethyl-oxazole-4-carboxylic acid and 4-(4'-amino-biphenyl-4-yl)-2,2-dimethyl-4-oxo-butyric acid methyl ester (prepared according to the procedure described in US 20040224997). LCMS calcd for C30H25F3N2O5 (m/e) 550, obsd 551 (M+H).

Preparation of 1-(2-chloro-phenyl)-3-trifluoromethyl-1H-pyrazole-4-carboxylic acid (4-piperidin-4-yl-phenyl)-amide; hydrochloride

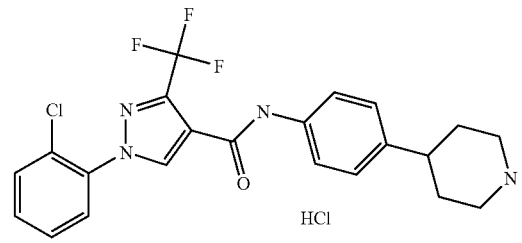

To 1-(2-chloro-phenyl)-3-trifluoromethyl-1H-pyrazole-4-carboxylic acid described above (320 mg, 1.10 mmol) in methylene chloride (10 mL) was added bromotrispyrrolidinophosphonium hexafluorophosphate (770 mg, 1.65 mmol). The reaction was stirred for 10 minutes and then 4-(4-aminophenyl)-piperidine-1-carboxylic acid tert-butyl ester (320 mg, 1.10 mmol) followed by diisopropylethylamine (0.60 mL, 3.30 mmol) were added. The reaction was stirred at room temperature overnight. The crude mixture was diluted in methanol (100 mL), loaded onto silica gel and purified using Isco chromatography (eluting with ethyl acetate and hexanes) to give 4-(4-{[1-(2-chloro-phenyl)-3-trifluoromethyl-1H-pyrazole-carbonyl]-amino}-phenyl)-piperidine-1-carboxylic acid tert-butyl ester. The NMR spectrum obtained on the sample is compatible with its structure.

4-(4-{[1-(2-chloro-phenyl)-3-trifluoromethyl-1H-pyrazole-carbonyl]-amino}-phenyl)-piperidine-1-carboxylic acid tert-butyl ester (400 mg, 0.73 mmol) from above was dissolved in dioxane (10 mL). To this reaction mixture was bubbled in HCl gas for 1 minute. Reaction was stirred at room temperature for 2 hours. The solvents were evaporated to give 400 mg of 1-(2-chloro-phenyl)-3-trifluoromethyl-1H-pyrazole-4-carboxylic acid (4-piperidin-4-yl-phenyl)-amide hydrochloride salt. The NMR spectrum obtained on this sample is compatible with its structure.

Preparation of 4-{4-[(1-pyridin-2-yl-3-trifluoromethyl-1H-pyrazole-4-carbonyl)-amino]-phenyl}-piperidine-1-carboxylic acid tert-butyl ester

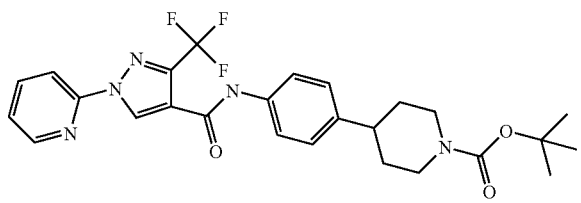

With a method similar to that used for the preparation of 4-{4-[(1-(2-chloro-phenyl-3-trifluoromethyl-1H-pyrazole-4-carbonyl]-amino}-phenyl)-piperidine-1-carboxylic acid tert butyl ester, 4-{4-[(1-pyridin-2-yl-3-trifluoromethyl-1H-pyrazole-4-carbonyl]-amino}-phenyl)-piperidine-1-carboxylic acid tert butyl ester was prepared from 1-pyridin-2-yl-3-trifluoromethyl-1H-pyrazole-carboxylic acid and 4-(4-amino-phenyl)-piperidine-1-carboxylic acid tert butyl ester. The NMR spectrum obtained on the sample is compatible with its structure.

Preparation of 1-pyridin-2-yl-3-trifluoromethyl-1H-pyrazole-4-carboxylic acid (4-piperidin-4-yl-phenyl)-amide; hydrochloride

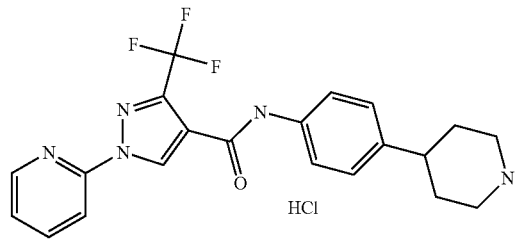

With a similar method to that used for the preparation of 1-(2-chloro-phenyl)-3-trifluoro-methyl-1H-pyrazole-4-carboxylic acid (4-piperidine-4-yl-phenyl)-amide hydrochloride, 1-pyridin-2-yl-3-trifluoromethyl-1H-pyrazole-4-carboxylic acid (4-piperidine-4-yl-phenyl)-amide hydrochloride was prepared from 4-{4-[(1-pyridin-2-yl-3-trifluoromethyl-1H-pyrazole-4-carbonyl)-amino]-phenyl)-piperidine-1-carboxylic acid tert-butyl ester.

Preparation of 4-{4-[(5-phenyl-2-trifluoromethyl-furan-3-carbonyl)-amino]-phenyl}-piperazine-1-carboxylic acid tert-butyl ester

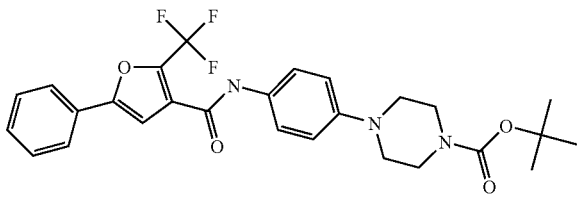

With a method similar to that used for the preparation of 4-(4-{[1-(2-chloro-phenyl)-3-trifluoromethyl-1H-pyrazole-carbonyl]-amino}-phenyl)-piperidine-1-carboxylic acid tert-butyl ester, 4-{4-[(5-phenyl-2-trifluoromethyl-furan-3-carbonyl)-amino]-phenyl}-piperazine-1-carboxylic acid tert-butyl ester was prepared from 5-phenyl-2-trifluoromethyl-furan-3-carboxylic acid and 4-[4-amino-phenyl]-piperazine-1-carboxylic acid tert-butyl ester. HRMS m/z calcd. for C27H29F3N3O4 [M+H]+: 516.2105; found 516.2105.

Preparation of (1R,2R)-2-(4-{4-[(5-phenyl-2-trifluoromethyl-furan-3-carbonyl)-amino]-phenyl}-piperazine-1-carbonyl)-cyclopentanecarboxylic acid benzyl ester

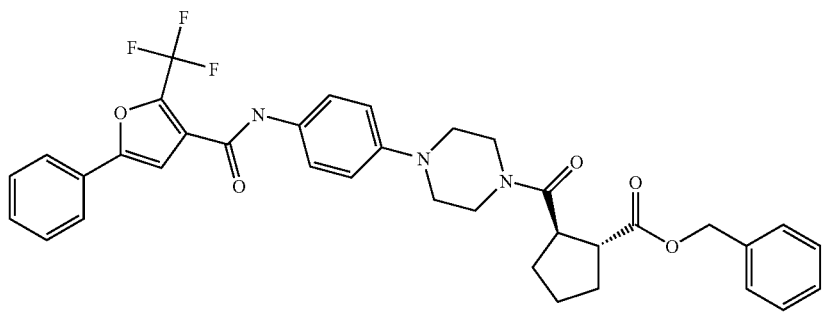

With a method similar to that used for the preparation of 4-(4-{[1-(2-chloro-phenyl)-3-trifluoromethyl-1H-pyrazole-carbonyl]-amino}-phenyl)-piperidine-1-carboxylic acid tert-butyl ester, (1R,2R)-2-(4-{4-[(5-phenyl-2-trifluoromethyl-furan-3-carbonyl)-amino]-phenyl}-piperazine-1-carbonyl)-cyclopentanecarboxylic acid benzyl ester was prepared from 5-phenyl-2-trifluoromethyl-furan-3-carboxylic acid (4-piperazin-1-yl-phenyl)-amide and (1R,2R)-cyclopentane-1,2-dicarboxylic acid monobenzyl ester. The product was isolated as a white solid (225 mg, 61% yield). HRMS m/z calcd. for C36H35F3N3O5 [M+H]+: 646.2524; found: 646.2524.

Preparation of (4-{4-[(2-phenyl-5-trifluoromethyl-oxazole-4-carbonyl)-amino]-phenylamino}-cyclohexyl)-carbamic acid tert-butyl ester

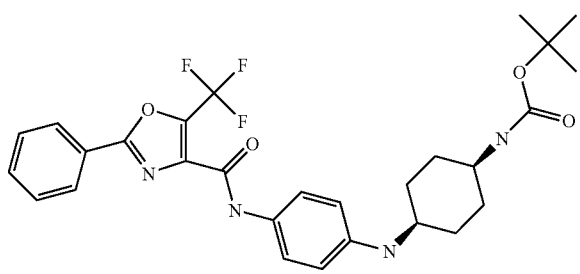

With a method similar to that used for the preparation of 4-(4-{[1-(2-chloro-phenyl)-3-trifluoromethyl-1H-pyrazole-carbonyl]-amino}-phenyl)-piperidine-1-carboxylic acid tert-butyl ester, (4-{4-[(2-phenyl-5-trifluoromethyl-oxazole-4-carbonyl)-amino]-phenylamino}-cyclohexyl)-carbamic acid tert-butyl ester was prepared from [4-(4-amino-phenylamino)-cyclohexyl]-carbamic acid tert-butyl ester and 2-phenyl-5-trifluoromethyl-oxazole-4-carboxylic acid. HRMS m/z calcd. for C28H32F3N4O4 [M+H]+: 545.2370; found: 545.2370.

Preparation of rac-trans-2-(4'-nitro-biphenyl-4-ylcarbamoyl)-cyclopentanecarboxylic acid

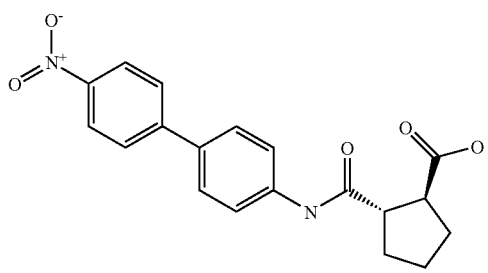

With a method similar to that used for the preparation of 4-(4-{[1-(2-chloro-phenyl)-3-trifluoromethyl-1H-pyrazole-carbonyl]-amino}-phenyl)-piperidine-1-carboxylic acid tert-butyl ester, rac-trans-2-(4'-nitro-biphenyl-4-ylcarbamoyl)-cyclopentanecarboxylic acid was prepared from 4'-nitro-biphenyl-4-ylamine and rac-trans-cyclopentane-1,2-dicarboxylic acid. LCMS calcd for C19H18N2O5 (m/e) 354, obsd 355 (M+H).

Preparation of rac-trans-2-[(4'-amino-biphenyl-4-yl)-methyl-carbamoyl]-cyclopentanecarboxylic acid

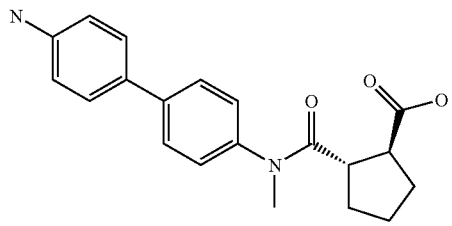

To a solution of rac-trans-2-(4'-nitro-biphenyl-4-ylcarbamoyl)-cyclopentanecarboxylic acid (3.54 g, 10 mmol) in DMF cooled at 0° C. was added sodium hydride (0.48 g, 12 mmol) gradually. The mixture was stirred at room temperature for 15 min followed by the addition of methyl iodide (0.7 mL). The reaction mixture was stirred for 2 h. The reaction was then mixed with water and extracted with ethyl acetate. The organic layer was washed with water and brine. The organic layer dried over sodium sulfate, filtered and concentrated to give rac-trans-2-[methyl-(4'-nitro-biphenyl-4-yl)-carbamoyl]-cyclopentanecarboxylic acid as a yellow solid. With a method similar to that used above, trans-2-[(4'-amino-biphenyl-4-yl)-methyl-carbamoyl]-cyclopentanecarboxylic acid was prepared by the hydrogenation of trans-2-[methyl-(4'-nitro-biphenyl-4-yl)-carbamoyl]-cyclopentanecarboxylic acid. This material was directly used in the next step without further purification. LCMS calcd for C20H22N2O3 (m/e) 338, obsd 339 (M+H).

Preparation of 2-phenyl-5-trifluoromethyl-oxazole-4-carboxylic acid (2-piperazin-1-yl-pyrimidin-5-yl)-amide hydrochloride salt

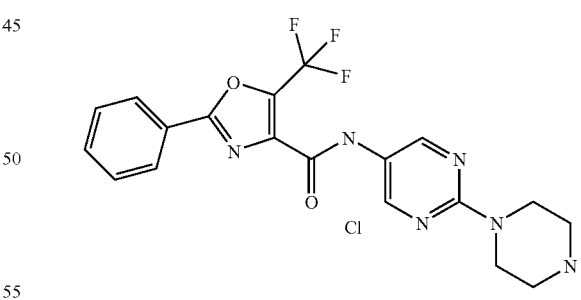

To a solution of 4-(5-nitro-pyrimidin-2-yl)-piperazine-1-carboxylic acid tert-butyl ester (927 mg, 3 mmol, prepared from 2-chloro-5-nitropyrimidine and N-Boc-piperazine) in tetrahydrofuran (20 mL) and methanol (30 mL) was added 10% palladium on carbon (240 mg) and the mixture was hydrogenated at 50 psi for 1 hr. The mixture was filtered and the solvents were evaporated. The residue was dried in vacuum to give 4-(5-amino-pyrimidin-2-yl)-piperazine-1-carboxylic acid tert-butyl ester.

To a suspension of 2-phenyl-5-trifluoromethyloxazole-4-carboxylic acid (771 mg, 3 mmol) in methylene chloride (10 mL) was added oxalyl chloride (2M, 3 mL, 6.0 mmol) and one drop of N,N-dimethylformamide. The mixture was stirred at room temperature for 1 hr and the solvents were evaporated. The residue was treated with benzene (5 mL) and the solvents were again evaporated. The oily residue was dried in vacuum and then dissolved in methylene chloride (10 mL). The solution was cooled in an ice bath. To this solution was added a methylene chloride solution of 4-(5-amino-pyrimidin-2-yl)-piperazine-1-carboxylic acid tert-butyl ester (3 mmol) and pyridine (0.73 mL). The mixture was stirred at 0° C. for 10 minutes and room temperature for 2 hrs. After concentration, the residue was partitioned between methylene chloride and water. The organic layer was washed with aqueous citric acid solution and dried over sodium sulfate. The solvents were evaporated and the residue was dried in vacuum. The resulting material was triturated with ethyl acetate and the precipitate was filtered to give 4-{5-[(2-phenyl-5-trifluoromethyl-oxazole-4-carbonyl)-amino]-pyrimidin-2-yl}-piperazine-1-carboxylic acid tert-butyl ester (1.38 g). LC-MS calcd for C24H25F3N6O4 (m/e) 518.5, obsd 519.1 (M+H). The NMR spectrum obtained on the sample is compatible with its structure.

4-{5-[(2-phenyl-5-trifluoromethyl-oxazole-4-carbonyl)-amino]-pyrimidin-2-yl}-piperazine-1-carboxylic acid tert-butyl ester from above was suspended in methylene chloride and methanol. To this mixture was added hydrogen chloride in ether (4N, 3 mL). The mixture was stirred at room temperature overnight. The solvents were evaporated and the residue was dried in vacuum. The resulting solid was triturated with dry ether and then filtered to give 2-phenyl-5-trifluoromethyl-oxazole-4-carboxylic acid (2-piperazin-1-yl-pyrimidin-5-yl)-amide hydrochloride salt. LC-MS calcd for C19H17F3N6O2 (m/e) 418.39, obsd 419.0 (M+H). The NMR spectrum obtained on the sample is compatible with its structure.

Preparation of 2-phenyl-5-trifluoromethyl-oxazole-4-carboxylic acid [2-(4-methylamino-piperidin-1-yl)-pyrimidin-5-yl]-amide hydrochloride salt

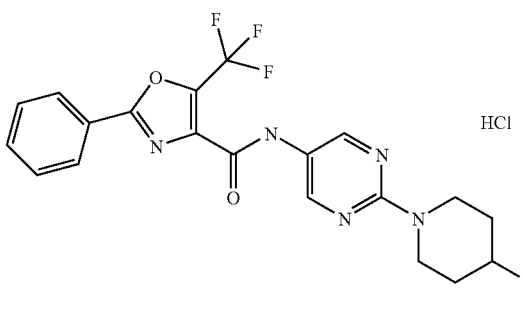

With a method similar to that used for the preparation of 2-phenyl-5-trifluoromethyl-oxazole-4-carboxylic acid (2-piperazin-1-yl-pyrimidin-5-yl)-amide above, 2-phenyl-5-trifluoromethyl-oxazole-4-carboxylic acid [2-(4-methylamino-piperidin-1-yl)-pyrimidin-5-yl]-amide hydrochloride salt was prepared from 2-phenyl-5-trifluoromethyloxazole-4-carboxylic acid, 2-chloro-5-nitropyrimidine and methyl-piperidin-4-yl-carbamic acid tert-butyl ester. LCMS calcd for C21H21F3N6O2 (m/e) 446, obsd 447 (M+H).

Preparation of 2-phenyl-5-trifluoromethyl-oxazole-4-carboxylic acid [2-(4-amino-piperidin-1-yl)-pyrimidin-5-yl]-amide hydrochloride salt

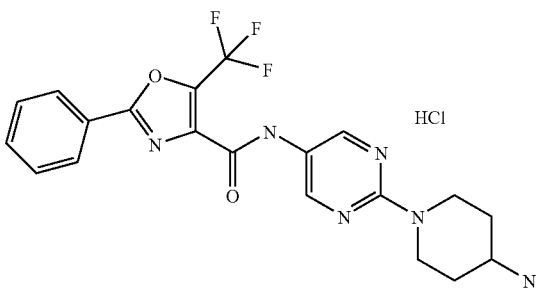

With a method similar to that used for the preparation of hydrochloride salt of 2-phenyl-5-trifluoromethyl-oxazole-4-carboxylic acid (2-piperazin-1-yl-pyrimidin-5-yl)-amide above, 2-phenyl-5-trifluoromethyl-oxazole-4-carboxylic acid [2-(4-amino-piperidin-1-yl)-pyrimidin-5-yl]-amide hydrochloride salt was prepared from 2-phenyl-5-trifluoromethyloxazole-4-carboxylic acid, 2-chloro-5-nitropyrimidine and piperidin-4-yl-carbamic acid tert-butyl ester. LCMS calcd for C20H19F3N6O2 (m/e) 432, obsd 433 (M+H).

Preparation of 5'-nitro-3,4,5,6-tetrahydro-2H-[1,2']bipyridinyl-4-carboxylic acid amide

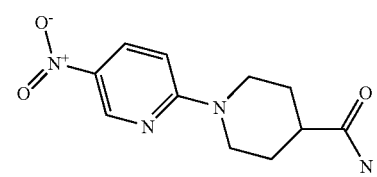

A mixture of 5-nitro-2-chloro-pyridine (2 g, 12.6 mmol), piperidine-4-carboxylic acid amide (1.78 g, 13.9 mmol), and potassium carbonate (3.48 g, 25.2 mmol) in anhydrous 1,4 dioxane (65 mL) was heated in an oil bath at 100° C. for 5 hr. The reaction was diluted with water (500 mL) and extracted with ethyl acetate (500 mL). The resulting yellow precipitate that form in both layers was filtered off and washed with minimal ethyl acetate, dichloromethane, and hexanes, and dried. The aqueous layer was extracted with dichloromethane (three times with 200 mL each). This dichloromethane layer was washed with brine, combined with the original ethyl acetate extract dried over sodium sulfate, and concentrated to a yellow solid. The yellow solid and the original yellow filtered precipitate were combined to give 5'-nitro-3,4,5,6-tetrahydro-2H-[1,2']bipyridinyl-4-carboxylic acid amide (2.93 g, 112%) as a yellow solid. LCMS calcd for C11H14N4O3 (m/e) 250, obsd 251 (M+H).

Preparation of 4-(1H-tetrazol-5-yl)-cyclohexanecarboxylic acid

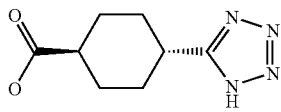

A mixture of 4-(1H-tetrazol-5-yl)-cyclohexanecarboxylic acid methyl ester (304 mg, 2.74 mmol), lithium hydroxide (121 mg 2.89), THF and water were stirred at RT overnight. The reaction was concentrated and diluted with water acidified with concentrated HCl to pH 1 and extracted with ethyl acetate to give 4-(1H-tetrazol-5-yl)-cyclohexanecarboxylic acid (173 mg, 61%) as an off white solid. LCMS calcd C8H12N4O2 (m/e) 196, obsd 197 (M+H).

Preparation of 4-(1H-tetrazol-5-yl)-cyclohexanecarboxylic acid methyl ester

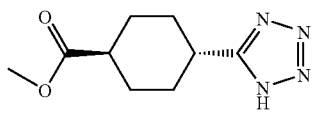

A mixture of azidotributyltin (1.51 mL, 5.48 mmol), and 4-cyano-cyclohexanecarboxylic acid methyl ester (458 mg, 2.74 mmol) in 1,4 dioxane were sealed in a vial and heated in an oil bath at 145° C. for 4 days. The reaction was concentrated, diluted with aqueous sodium bicarbonate (saturated, 200 mL), washed with ethyl acetate (200 mL), acidified to pH 1 with concentrated HCl, and extracted with ethyl acetate (2×200 mL). The organic layer was washed with brine (200 mL), dried over sodium sulfate, concentrated, and tritrated with mixtures of hexanes and ethyl acetate to give 4-(1H-tetrazol-5-yl)-cyclohexanecarboxylic acid methyl ester (304 mg, 52%) as an off white solid. LCMS calcd for C9H14N4O2 (m/e) 210, obsd 211 (M+H).

Preparation of 4-(5-oxo-4,5-dihydro-[1,2,4]oxadiazol-3-yl)-cyclohexanecarboxylic acid

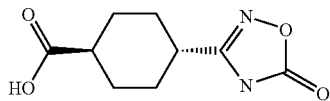

A mixture of aqueous lithium hydroxide (215 mg, 5.13 mmol, 10 mL H2O), 4-(5-oxo-4,5-dihydro-[1,2,4]oxadiazol-3-yl)-cyclohexanecarboxylic acid methyl ester (580 mg, 2.56 mmol) and THF (40 mL) were stirred at room temperature for 5 hr. The reaction was then concentrated, diluted with aqueous sodium hydroxide (0.1 M, 100 mL) washed with ethyl acetate (100 mL). The basic solution was acidified with concentrated HCl and extracted with ethyl acetate (125 mL). The organic layer was washed with brine (100 mL), dried over sodium sulfate, concentrated, and dried from dichloromethane to give 4-(5-oxo-4,5-dihydro-[1,2,4]oxadiazol-3-yl)-cyclohexanecarboxylic acid (104 mg, 20%) as a white solid. LCMS calcd for C9H12N2O4 (m/e) 212, obsd 213 (M+H) and 211 (M−H).

Preparation of 4-(5-oxo-4,5-dihydro-[1,2,4]oxadiazol-3-yl)-cyclohexanecarboxylic acid methyl ester

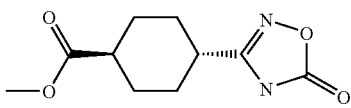

A mixture of carbodiimidazole (624 mg, 3.85 mmol) and 4-(N-hydroxycarbamimidoyl)-cyclohexanecarboxylic acid methyl ester (770 mg, 3.85 mmol) in anhydrous 1,4 dioxane (15 mL) was heated in a sealed vial in an oil bath at 100° C. for 30 min. The reaction was concentrated, diluted with ethyl acetate (200 mL) washed with aqueous ammonium chloride (sat'd, 200 mL) and brine (200 mL), dried over sodium sulfate, and concentrated to give 4-(5-oxo-4,5-dihydro-[1,2,4]oxadiazol-3-yl)-cyclohexanecarboxylic acid methyl ester (580 mg 67%) as a clear light yellow oil. LCMS calcd for C10H14N2O4 (m/e) 226, obsd 225 (M−H).

Preparation of 4-(N-hydroxycarbamimidoyl)-cyclohexanecarboxylic acid methyl ester

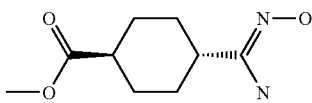

A mixture of 4-cyano-cyclohexanecarboxylic acid methyl ester (1070 mg, 6.40 mmol), N-hydroxyamine as a free base solution was prepared by the addition of triethylamine (9.8 mL, 64 mmol) to a solution of N-hydroxyamine HCl salt (4.4 g, 64 mmol) in DMSO (40 mL), stirred at room temperature for 5 min, filtered, and rinsed with THF. The reaction was heated in a sealed vial in an oil bath at 80° C. overnight. The reaction was diluted with ethyl acetate (200 mL) washed with aqueous saturated ammonium chloride (200 mL) and brine (200 mL). The water layer was extracted with ethyl acetate (200 mL) and the resulting second organic layer was washed with brine (200 mL). The organic layers were combined, dried over sodium sulfate, and concentrated to give 4-(N-hydroxycarbamimidoyl)-cyclohexanecarboxylic acid methyl ester (770 mg, 60%) as a white solid. LCMS calcd for C9H16N2O3 (m/e) 200, obsd 201 (M+H).

Preparation of 4-cyano-cyclohexanecarboxylic acid methyl ester

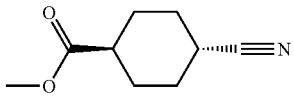

To a mixture of 4-carbamoyl-cyclohexanecarboxylic acid methyl ester (2.14 g, 11.6 mmol) in trimethyl phosphate (14 mL) cooled in an ice bath was dripped in diphosgene (2.24 g 11.6 mmol) and the reaction was allowed to warm to room temperature over 2 hr. The material was diluted with ethyl acetate (200 mL) and washed with an aqueous sodium bicarbonate (saturated, 200 mL) and brine (200 mL), dried over sodium sulfate, and concentrated as a clear oil. The oil was triturated with hexanes to give 4-cyano-cyclohexanecarboxylic acid methyl ester (687 mg 36%) as a clear oil. LCMS calcd for C9H13NO2 (m/e) 167, obsd 168 (M+H).

Preparation of Carbamoyl-Cyclohexanecarboxylic Acid Methyl Ester

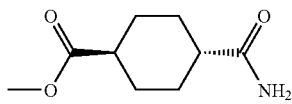

To a mixture cyclohexane-1,4-dicarboxylic acid monomethyl ester (3 g, 16.1 mmol) and triethylamine (2.24 mL, 16.1 mmol) in chloroform cooled in an icebath was dripped in of ethyl chloroformate (1.54 g, 16.1 mmol) followed by bubbling of ammonia gas for 15 min. The reaction was stirred for 1 hr, filtered, the precipitate washed with chloroform, the filtrate diluted with dichloromethane (500 mL) and washed with aqueous sodium bicarbonate (saturated, 500 mL) and brine (250 mL), dried over sodium sulfate, and concentrated to give carbamoyl-cyclohexanecarboxylic acid methyl ester (2.1 g, 72%) as a white solid. LCMS calcd for C9H15NO3 (m/e) 185, obsd 186 (M+H).

Preparation of 4-{4-[(2-phenyl-5-trifluoromethyl-oxazole-4-carbonyl)-amino]-phenyl}-piperidine-1-carboxylic acid 4-nitro-phenyl ester

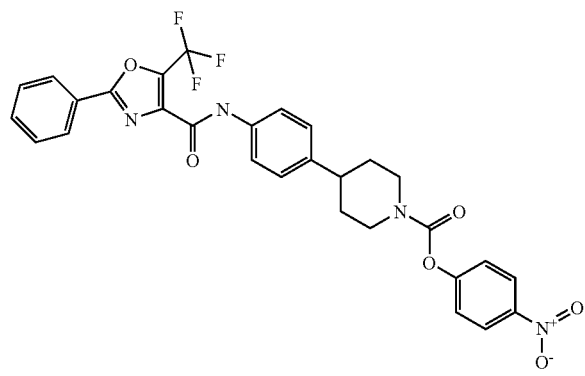

To a mixture of 2-phenyl-5-trifluoromethyl-oxazole-4-carboxylic acid (4-piperidin-4-yl-phenyl)-amide hydrochloride salt (2.0 g, 4.43 mmol) in methylene chloride (20 mL) at room temperature was added p-nitrophenyl chloroformate (1.11 g, 5.52 mmol) followed by pyridine (1.1 mL, 13.6 mmol). The mixture was stirred at room temperature overnight. The slurry was filtered and the filtrate was evaporated to give a crude material (2.4 g). The crude was triturated with methanol and filtration gave 4-{4-[(2-phenyl-5-trifluoromethyl-oxazole-4-carbonyl)-amino]-phenyl}-piperidine-1-carboxylic acid 4-nitro-phenyl ester (850 mg, crude) as a white solid, which was directly used in the next step without further purification. LCMS calcd for C29H23F3N4O6 (m/e) 580, obsd 581 (M+H). The NMR spectrum obtained on the sample is compatible with its structure.

Preparation of 4-(4-amino-3-fluoro-phenyl)-piperazine-1-carboxylic acid tert-butyl ester

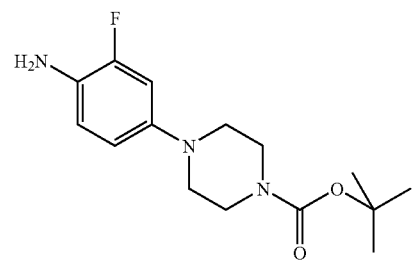

A mixture of 2,4-difluoro-nitro-benzene (2.2 mL, 20 mmol), piperazine-1-carboxylic acid tert-butyl ester (3.7 g, 20 mmol), and triethylamine (10 mL) in anhydrous DMF (20 mL) was stirred at 90° C. for 16 hr. After the reaction, the reaction mixture was mixed with water and ethyl acetate, and two layers were separated. The aqueous layer was extracted with ethyl acetate twice. Organic layers were collected, combined, washed with brine, dried over sodium sulfate, filtered, and concentrated. The residue was applied on a silica gel flash column with ethyl acetate and hexanes as eluenting solvents to give 4-(3-fluoro-4-nitro-phenyl)-piperazine-1-carboxylic acid tert-butyl ester (2.1 gm, 32%) as a brown solid. LCMS calcd for C15H20FN3O4 (m/e) 325, obsd 326 (M+H).

The solution of 4-(3-fluoro-4-nitro-phenyl)-piperazine-1-carboxylic acid tert-butyl ester (2.1 g, 6.4 mmol) in ethyl acetate (20 mL) in the presence of 10% palladium on carbon was shaken under the hydrogen with a pressure of 50 psi at room temperature for 2 hr. The reaction mixture was filtered through a plug of celite and the filtration pad was washed with ethyl acetate. The organic layer was collected, concentrated, and dried to give 4-(4-amino-3-fluoro-phenyl)-piperazine-1-carboxylic acid tert-butyl ester (1.90 g, crude) as a light red solid, which was directly used in the next step reaction without further purification.

Preparation of methyl-[1-(4-nitro-phenyl)-piperidin-4-yl]-carbamic acid tert-butyl ester

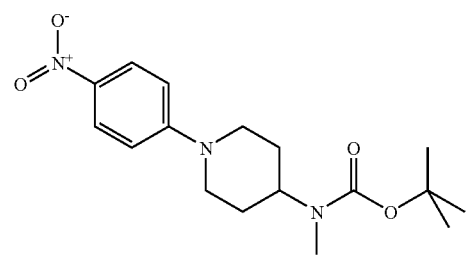

With a method similar to that used for the preparation of 3-hydroxy-3-[1-(4-nitro-phenyl)-piperidin-4-yl]-propionic acid ethyl ester above, methyl-[1-(4-nitro-phenyl)-piperidin-4-yl]-carbamic acid tert-butyl ester was prepared from 4-fluoro-1-nitro-benzene and methyl-piperidin-4-yl-carbamic acid tert-butyl ester. LCMS calcd for C17H25N3O4 (m/e) 335, obsd 336 (M+H).

Preparation of [1-(4-amino-phenyl)-piperidin-4-yl]-methyl-carbamic acid tert-butyl ester

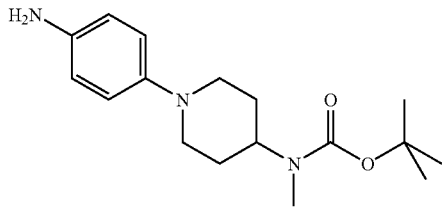

With a method similar to that used for the preparation of 3-[1-(4-amino-phenyl)-piperidin-4-yl]-3-hydroxy-propionic acid ethyl ester above, [1-(4-amino-phenyl)-piperidin-4-yl]-methyl-carbamic acid tert-butyl ester was prepared from methyl-[1-(4-nitro-phenyl)-piperidin-4-yl]-carbamic acid tert-butyl ester. LCMS calcd for C17H27N3O2 (m/e) 305, obsd 306 (M+H).

Preparation of methyl-(5'-nitro-3,4,5,6-tetrahydro-2H-[1,2']bipyridinyl-4-yl)-carbamic acid tert-butyl ester

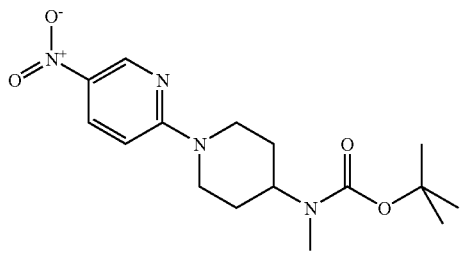

With a method similar to that used for the preparation of methyl-[1-(4-nitro-phenyl)-piperidin-4-yl]-carbamic acid tert-butyl ester, methyl-(5'-nitro-3,4,5,6-tetrahydro-2H-[1,2']bipyridinyl-4-yl)-carbamic acid tert-butyl ester was prepared from 2-chloro-5-nitro-pyridine and methyl-piperidin-4-yl-carbamic acid tert-butyl ester. LCMS calcd for C16H24N4O4 (m/e) 336 obsd 337 (M+H).

Preparation of (5'-amino-3,4,5,6-tetrahydro-2H-[1,2'] bipyridinyl-4-yl)-methyl-carbamic acid tert-butyl ester

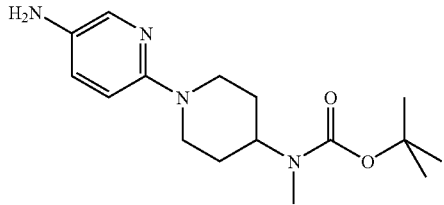

With a method similar to that used for the preparation of [1-(4-amino-phenyl)-piperidin-4-yl]-methyl-carbamic acid tert-butyl ester above, (5'-amino-3,4,5,6-tetrahydro-2H-[1,2'] bipyridinyl-4-yl)-methyl-carbamic acid tert-butyl ester was prepared from methyl-(5'-nitro-3,4,5,6-tetrahydro-2H-[1,2'] bipyridinyl-4-yl)-carbamic acid tert-butyl ester. LCMS calcd for C16H26N4O2 (m/e) 306, obsd 307 (M+H).

Preparation of 2-phenyl-5-trifluoromethyl-oxazole-4-carboxylic acid [4-(piperidin-3-yloxy)-phenyl]-amide

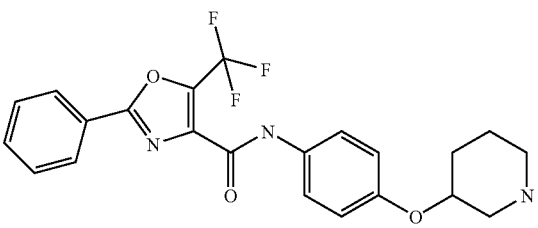

A solution of 3-(4-nitro-phenoxy)-piperidine-1-carboxylic acid tert-butyl ester (352 mg, 1.09 mmol) in 20 mL ethanol was hydrogenated at 40 psi for 1 hr with 50 mg 10% Pd/C. The reaction was filtered and evaporated to dryness. The intermediate amine was dissolved in 3 mL DMF and treated with 2-phenyl-5-trifluoromethyl-oxazole-4-carboxylic acid (280 mg, 1.09 mmol), triethylamine (457 uL, 3.27 mmol) and BOP (461 mg, 1.09 mmol) for 1 hr and diluted with 40 mL ethyl acetate. The organic phase was washed with saturated sodium bicarbonate (10 mL), 2.5% KHSO4 (2×10 mL) and saturated sodium chloride (10 mL). The organic layer was dried over MgSO4, filtered and evaporated to dryness under vacuum. The residue was purified by flash chromatography to yield 3-{4-[(2-phenyl-5-trifluoromethyl-oxazole-4-carbonyl)-amino]-phenoxy}-piperidine-1-carboxylic acid tert-butyl (354 mg, 61%). ES-MS calcd for C27H28F3N3O5 (m/e) 531.54, obsd 532 (M+H).

A solution of 3-{4-[(2-phenyl-5-trifluoromethyl-oxazole-4-carbonyl)-amino]-phenoxy}-piperidine-1-carboxylic acid tert-butyl (0.350 mg, 0.659 mmol) in 4 mL 25% TFA/CH2Cl2 was stirred at room temperature for 30 minutes. The reaction mixture was concentrated under vacuum, taken up in ethyl acetate (25 mL) and washed with 0.05N NaOH (2×5 mL) and saturated sodium chloride (5 mL). MgSO4, filtered and evaporated to dryness under vacuum to yield 2-phenyl-5-trifluoromethyl-oxazole-4-carboxylic acid [4-(piperidin-3- yloxy)-phenyl]-amide as a tan solid (301 mg). ES-MS calcd for C22H20F3N3O3 (m/e) 431.42, obsd 432 (M+H).

Part II: Preparation of Preferred Compounds

Example 1

Preparation of 4-oxo-4-(4-{4-[(2-phenyl-5-trifluoromethyl-oxazole-4-carbonyl)-amino]-phenyl}-piperazin-1-yl)-butyric acid

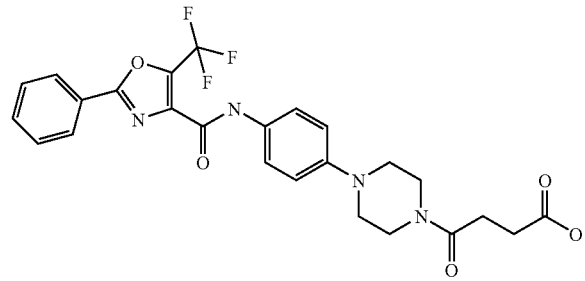

A solution of dioxane (10 mL) that was saturated with hydrogen chloride gas was added to 4-{4-[(2-Phenyl-5-trifluoromethyl-oxazole-4-carbonyl)-amino]-phenyl}-piperazine-1-carboxylic acid tert-butyl ester (300 mg, 0.581 mmol). The reaction mixture was stirred for 30 minutes at room temperature and then the volatiles were evaporated under reduced pressure. The residue was triturated with diethyl ether to yield 2-phenyl-5-trifluoromethyl-oxazole-4-carboxylic acid (4-piperazin-1-yl-phenyl)-amide hydrochloride as a white powder (226 mg).

2-Phenyl-5-trifluoromethyl-oxazole-4-carboxylic acid (4-piperazin-1-yl-phenyl)-amide hydrochloride (100 mg, 0.204 mmol), triethylamine (57.5 µL, 0.408 mmol) and succinic anhydride (22.4 mg, 0.224 mmol) in 5 mL toluene and 3 mL dimethylsulfoxide were stirred at room temperature. After 3 hrs, an additional 5.5 mg of succinic anhydride was added and stirred for an additional 1 hr. The reaction mixture was diluted with 50 mL ethyl acetate, washed with 500 mL water, dried over magnesium sulfate, filtered and evaporated to dryness under vacuum. The residue was dissolved in acetonitrile and water and lyophilized to yield 4-oxo-4-(4-{4-[(2-phenyl-5-trifluoromethyl-oxazole-4-carbonyl)-amino]-phenyl}-piperazin-1-yl)-butyric acid as an amorphous, light yellow solid (83 mg, 78%). ES-MS calcd for C25H23F3N4O5 (m/e) 516.48, obsd 517 (M+H).

Example 2

Preparation of 2,2-dimethyl-4-oxo-4-(4-{4-[(2-phenyl-5-trifluoromethyl-oxazole-4-carbonyl)-amino]-phenyl}-piperazin-1-yl)-butyric acid

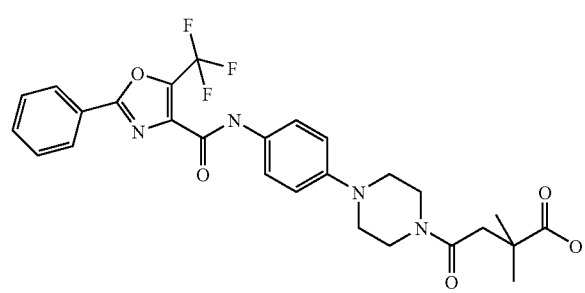

With a method similar to that used for the preparation of 4-oxo-4-(4-{4-[(2-phenyl-5-trifluoromethyl-oxazole-4-carbonyl)-amino]-phenyl}-piperazin-1-yl)-butyric acid above, 2,2-dimethyl-4-oxo-4-(4-{4-[(2-phenyl-5-trifluoromethyl-oxazole-4-carbonyl)-amino]-phenyl}-piperazin-1-yl)-butyric acid was prepared from 2-phenyl-5-trifluoromethyl-oxazole-4-carboxylic acid (4-piperazin-1-yl-phenyl)-amide hydrochloride and dimethylsuccinic anhydride. ES-MS calcd for C27H27F3N4O5 (m/e) 544.53, obsd 545.1 (M+H).

Example 3

Preparation of 1-[2-oxo-2-(4-{4-[(2-phenyl-5-trifluoromethyl-oxazole-4-carbonyl)-amino]-phenyl}-piperazin-1-yl)-ethyl]-cyclopentanecarboxylic acid

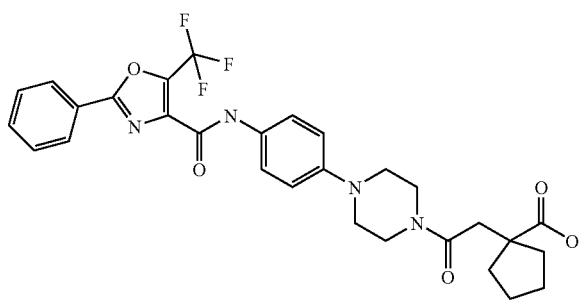

With a method similar to that used for the preparation of 4-oxo-4-(4-{4-[(2-phenyl-5-trifluoromethyl-oxazole-4-carbonyl)-amino]-phenyl}-piperazin-1-yl)-butyric acid above, 1-[2-oxo-2-(4-{4-[(2-phenyl-5-trifluoromethyl-oxazole-4-carbonyl)-amino]-phenyl}-piperazin-1-yl)-ethyl]-cyclopentanecarboxylic acid was prepared from 2-Phenyl-5-trifluoromethyl-oxazole-4-carboxylic acid (4-piperazin-1-yl-phenyl)-amide hydrochloride and 2-oxa-spiro[4.4]nonane-1,3-dione. ES-MS calcd for C29H29F3N4O5 (m/e) 570.57, obsd 571 (M+H).

Example 4

Preparation of 1-[2-oxo-2-(4-{4-[(2-phenyl-5-trifluoromethyl-oxazole-4-carbonyl)-amino]-phenyl}-piperazin-1-yl)-ethyl]-cyclohexanecarboxylic acid

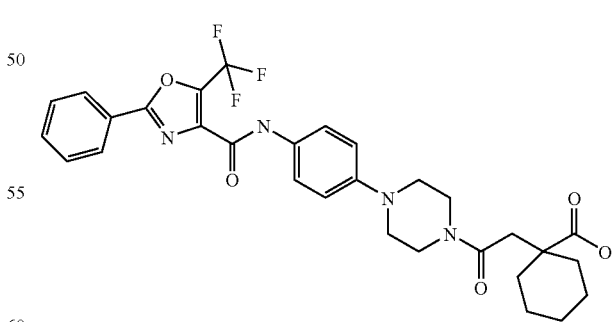

With a method similar to that used for the preparation of 4-oxo-4-(4-{4-[(2-phenyl-5-trifluoromethyl-oxazole-4-carbonyl)-amino]-phenyl}-piperazin-1-yl)-butyric acid above, 1-[2-oxo-2-(4-{4-[(2-phenyl-5-trifluoromethyl-oxazole-4-carbonyl)-amino]-phenyl}-piperazin-1-yl)-ethyl]-cyclohexanecarboxylic acid was prepared from 2-phenyl-5-trifluororomethyl-oxazole-4-carboxylic acid (4-piperazin-1-yl-phenyl)-amide hydrochloride and 2-oxa-spiro[4.5]decane-1,3-dione. ES-MS calcd for C30H31F3N4O5 (m/e) 584.60, obsd 585.1 (M+H).

Example 5

Preparation of 2,2-dimethyl-4-oxo-4-(4-{5-[(2-phenyl-5-trifluoromethyl-oxazole-4-carbonyl)-amino]-pyridin-2-yl}-piperazin-1-yl)-butyric acid

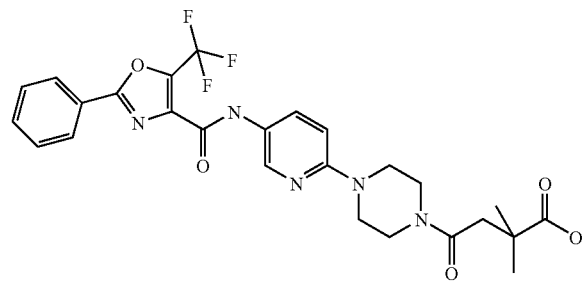

With a method similar to that used for the preparation of 4-oxo-4-(4-{4-[(2-phenyl-5-trifluoromethyl-oxazole-4-carbonyl)-amino]-phenyl}-piperazin-1-yl)-butyric acid above, 2,2-dimethyl-4-oxo-4-(4-{5-[(2-phenyl-5-trifluoromethyl-oxazole-4-carbonyl)-amino]-pyridin-2-yl}-piperazin-1-yl)-butyric acid was prepared from 2-Phenyl-5-trifluoromethyl-oxazole-4-carboxylic acid (6-piperazin-1-yl-pyridin-3-yl)-amide hydrochloride and dimethylsuccinic anhydride. ES-MS calcd for C26H26F3N5O5 (m/e) 545.2, obsd 546.1 (M+H). The NMR spectrum obtained on the sample is compatible with its structure.

Example 6

Preparation of 4-oxo-4-(4-{5-[(2-phenyl-5-trifluoromethyl-oxazole-4-carbonyl)-amino]-pyridin-2-yl}-piperazin-1-yl)-butyric acid

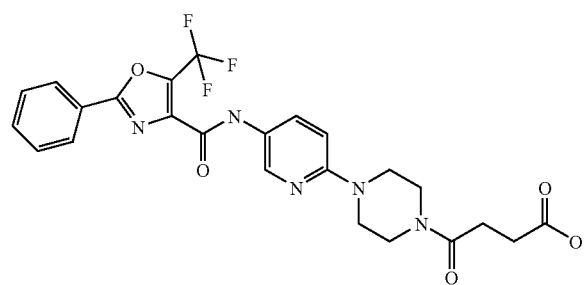

With a method similar to that used for the preparation of 4-oxo-4-(4-{4-[(2-phenyl-5-trifluoromethyl-oxazole-4-carbonyl)-amino]-phenyl}-piperazin-1-yl)-butyric acid above, 4-oxo-4-(4-{5-[(2-phenyl-5-trifluoromethyl-oxazole-4-carbonyl)-amino]-pyridin-2-yl}-piperazin-1-yl)-butyric acid was prepared from 2-phenyl-5-trifluoromethyl-oxazole-4-carboxylic acid (6-piperazin-1-yl-pyridin-3-yl)-amide hydrochloride and succinic anhydride. ES-MS calcd for C24H22F3N5O5 (m/e) 517.2, obsd 518.1 (M+H). The NMR spectrum obtained on the sample is compatible with its structure.

Example 7

Preparation of 2,2-dimethyl-4-oxo-4-(4-{5-[(2-phenyl-5-trifluoromethyl-oxazole-4-carbonyl)-amino]-pyrimidin-2-yl}-piperazin-1-yl)-butyric acid

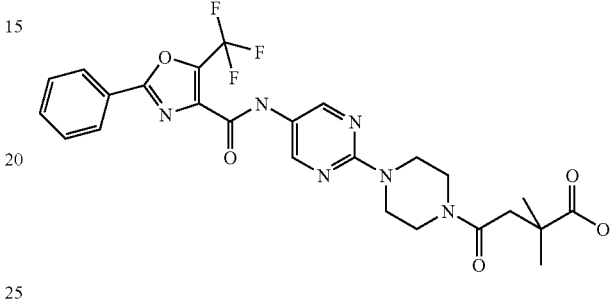

With a method similar to that used for the preparation of 4-oxo-4-(4-{4-[(2-phenyl-5-trifluoromethyl-oxazole-4-carbonyl)-amino]-phenyl}-piperazin-1-yl)-butyric acid above, 2,2-dimethyl-4-oxo-4-(4-{5-[(2-phenyl-5-trifluoromethyl-oxazole-4-carbonyl)-amino]-pyrimidin-2-yl}-piperazin-1-yl)-butyric acid was prepared from 2-phenyl-5-trifluoromethyl-oxazole-4-carboxylic acid (2-piperazin-1-yl-pyrimidin-5-yl)-amide and 2,2-dimethylsuccinic anhydride. ES-MS calcd for C25H25F3N6O5 (m/e) 546.2, obsd 547.0 (M+H). The NMR spectrum obtained on the sample is compatible with its structure.

Example 8

Preparation of 4-oxo-4-(4-{5-[(2-phenyl-5-trifluoromethyl-oxazole-4-carbonyl)-amino]-pyrimidin-2-yl}-piperazin-1-yl)-butyric acid

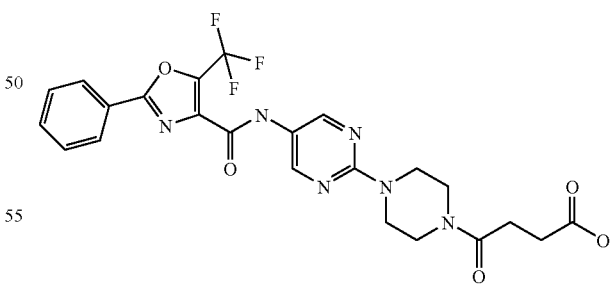

With a method similar to that used for the preparation of 4-oxo-4-(4-{4-[(2-phenyl-5-trifluoromethyl-oxazole-4-carbonyl)-amino]-phenyl}-piperazin-1-yl)-butyric acid above, 4-oxo-4-(4-{5-[(2-phenyl-5-trifluoromethyl-oxazole-4-carbonyl)-amino]-pyrimidin-2-yl}-piperazin-1-yl)-butyric acid was prepared from 2-phenyl-5-trifluoromethyl-oxazole-4-carboxylic acid (2-piperazin-1-yl-pyrimidin-5-yl)-amide and succinic anhydride. ES-MS calcd for C23H21F3N6O5 (m/e)

518.2, obsd 519.0 (M+H). The NMR spectrum obtained on the sample is compatible with its structure.

Example 9

Preparation of 2,2-dimethyl-4-oxo-4-(4-{4-[(2-phenyl-5-trifluoromethyl-oxazole-4-carbonyl)-amino]-phenyl}-piperidin-1-yl)-butyric acid

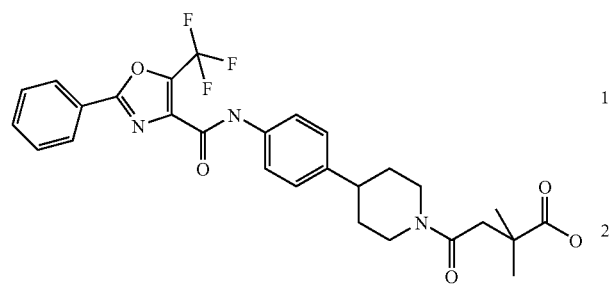

With a method similar to that used for the preparation of 4-oxo-4-(4-{4-[(2-phenyl-5-trifluoromethyl-oxazole-4-carbonyl)-amino]-phenyl}-piperazin-1-yl)-butyric acid above, 2,2-Dimethyl-4-oxo-4-(4-{4-[(2-phenyl-5-trifluoromethyl-oxazole-4-carbonyl)-amino]-phenyl}-piperidin-1-yl)-butyric acid was prepared from 2-phenyl-5-trifluoromethyl-oxazole-4-carboxylic acid (4-piperidin-4-yl-phenyl)-amide and 2,2-dimethylsuccinic anhydride. ES-MS calcd for C28H28F3N3O5 (m/e) 543.2, obsd 544.0 (M+H). The NMR spectrum obtained on the sample is compatible with its structure.

Example 10

Preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester

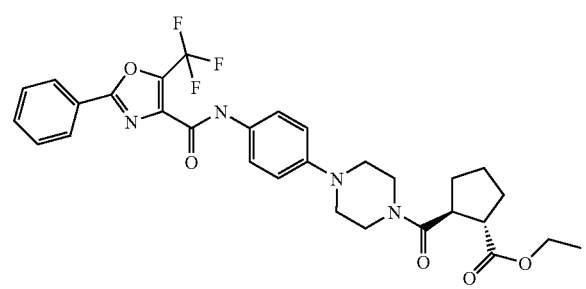

To a solution of 2-phenyl-5-trifluoromethyl-oxazole-4-carboxylic acid (4-piperazin-1-yl-phenyl)-amide hydrochloride (212 mg, 0.435 mmol), racemic trans-cyclopentane-1,2-dicarboxylic acid monoethyl ester (81 mg, 0.435 mmol) and triethylamine (305 µL, 2.17 mmol) in 5 mL 1-methyl-2-pyrrolidinone was added (benzotriazol-1-yloxy)tris(dimethylamino) phosphonium hexafluorophosphate (BOP, 202 mg, 0.456 mmol) in one portion and the mixture was stirred at room temperature overnight. The reaction mixture was diluted with ethyl acetate, washed with water, saturated aqueous sodium bicarbonate, dried over magnesium sulfate, filtered, and evaporated under reduced pressure. The residue was purified by flash chromatography (eluted with ethyl acetate/hexane) to yield rac-2-(4-{4-[(2-phenyl-5-trifluoromethyl-oxazole-4-carbonyl)-amino]-phenyl}-piperazine-1-carbonyl)-cyclopentanecarboxylic acid ethyl ester as an amorphous solid (236 mg, 93%). ES-MS calcd for C30H31F3N4O5 (m/e) 584.60, obsd 585 (M+H).

Example 11

Preparation of 2,2-diethyl-4-oxo-4-(4-{4-[(2-phenyl-5-trifluoromethyl-oxazole-4-carbonyl)-amino]-phenyl}-piperazin-1-yl)-butyric acid methyl ester

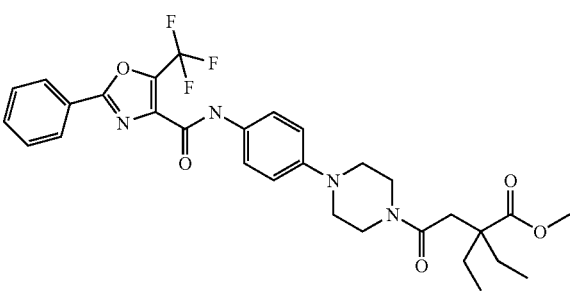

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 2,2-diethyl-4-oxo-4-(4-{4-[(2-phenyl-5-trifluoromethyl-oxazole-4-carbonyl)-amino]-phenyl}-piperazin-1-yl)-butyric acid methyl ester was prepared from 2-Phenyl-5-trifluoromethyl-oxazole-4-carboxylic acid (4-piperazin-1-yl-phenyl)-amide hydrochloride and 2,2-diethyl-succinic acid 1-methyl ester. ES-MS calcd for C30H33F3N4O5 (m/e) 586.61, obsd 587 (M+H).

Example 12

Preparation of 4-(4-{4-[(2-phenyl-5-trifluoromethyl-oxazole-4-carbonyl)-amino]-phenyl}-piperazine-1-carbonyl)-cyclohexanecarboxylic acid methyl ester

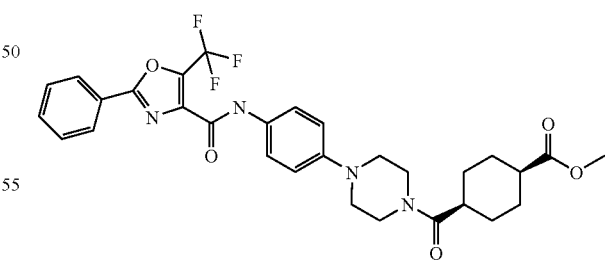

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 4-(4-{4-[(2-phenyl-5-trifluoromethyl-oxazole-4-carbonyl)-amino]-phenyl}-piperazine-1-carbonyl)-cyclohexanecarboxylic acid methyl ester was prepared from 2-Phenyl-5-trifluoromethyl-oxazole-4-carboxylic acid (4-piperazin-1-yl-phenyl)-amide hydrochloride and cis-cyclohexane-1,4-dicarboxylic acid monomethyl ester. ES-MS calcd for C30H31F3N4O5 (m/e) 584.60, obsd 585.1 (M+H).

and trans-1,4-cyclohexanedicarboxylic acid. ES-MS calcd for C29H29F3N4O5 (m/e) 570.57, obsd 571 (M+H).

Example 13

Preparation of 2,2-diethyl-4-oxo-4-(4-{4-[(2-phenyl-5-trifluoromethyl-oxazole-4-carbonyl)-amino]-phenyl}-piperazin-1-yl)-butyric acid

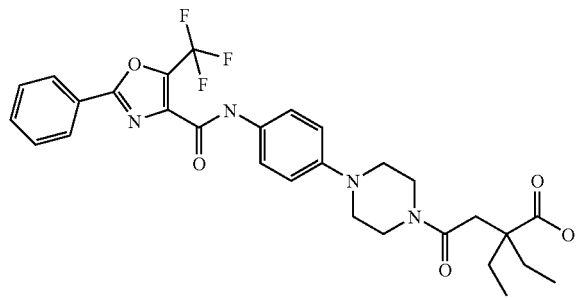

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 2,2-diethyl-4-oxo-4-(4-{4-[(2-phenyl-5-trifluoromethyl-oxazole-4-carbonyl)-amino]-phenyl}-piperazin-1-yl)-butyric acid was prepared from 2-phenyl-5-trifluoromethyl-oxazole-4-carboxylic acid (4-piperazin-1-yl-phenyl)-amide hydrochloride and 2,2-diethylsuccinic acid. ES-MS calcd for C29H31F3N4O5 (m/e) 572.58, obsd 573 (M+H).

Example 14

Preparation of 4-(4-{4-[(2-phenyl-5-trifluoromethyl-oxazole-4-carbonyl)-amino]-phenyl}-piperazine-1-carbonyl)-cyclohexanecarboxylic acid

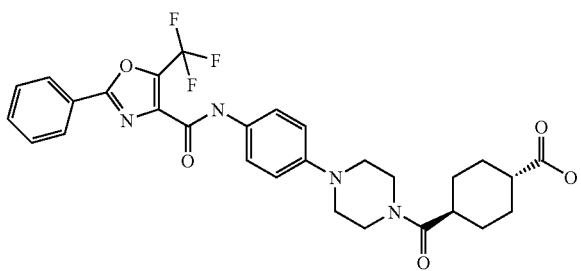

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 4-(4-{4-[(2-phenyl-5-trifluoromethyl-oxazole-4-carbonyl)-amino]-phenyl}-piperazine-1-carbonyl)-cyclohexanecarboxylic acid was prepared from 2-Phenyl-5-trifluoromethyl-oxazole-4-carboxylic acid (4-piperazin-1-yl-phenyl)-amide hydrochloride Example 15

Preparation of rac-3-(4-{4-[(2-phenyl-5-trifluoromethyl-oxazole-4-carbonyl)-amino]-phenyl}-piperazine-1-carbonyl)-cyclohexanecarboxylic acid methyl ester

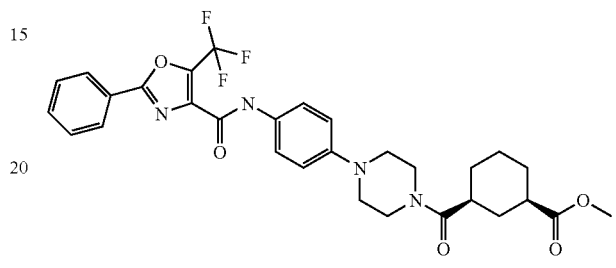

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, rac-3-(4-{4-[(2-phenyl-5-trifluoromethyl-oxazole-4-carbonyl)-amino]-phenyl}-piperazine-1-carbonyl)-cyclohexanecarboxylic acid methyl ester was prepared from 2-phenyl-5-trifluoromethyl-oxazole-4-carboxylic acid (4-piperazin-1-yl-phenyl)-amide hydrochloride and racemic cis-cyclohexane-1,3-dicarboxylic acid monomethyl ester. ES-MS calcd for C30H31F3N4O5 (m/e) 584.57, obsd 585.1 (M+H).

Example 16

Preparation of (1R,3S)-1,2,2-trimethyl-3-(4-{4-[(2-phenyl-5-trifluoromethyl-oxazole-4-carbonyl)-amino]-phenyl}-piperazine-1-carbonyl)-cyclopentanecarboxylic acid

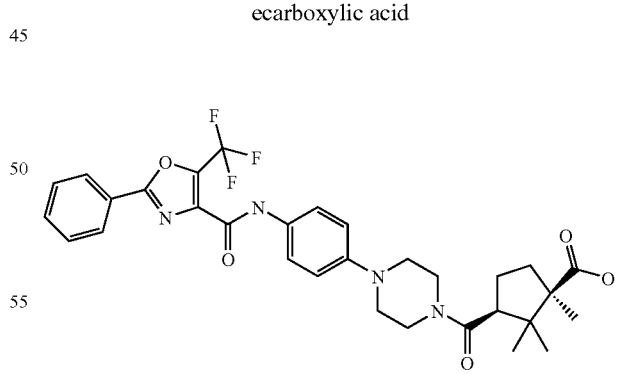

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, (1R,3S)-1,2,2-trimethyl-3-(4-{4-[(2-phenyl-5-trifluoromethyl-oxazole-4-carbonyl)-amino]-phenyl}-piperazine-1-carbonyl)-cyclopentanecarboxylic acid was prepared from 2-Phenyl-5-trifluoromethyl-oxazole-4-carboxylic acid (4-piperazin-1- yl-phenyl)-amide hydrochloride and d-camphoric acid. ES-MS calcd for C31H33F3N4O5 (m/e) 598.62, obsd 599.2 (M+H).

Example 17

Preparation of rac-2-(4-{4-[(2-phenyl-5-trifluoromethyl-oxazole-4-carbonyl)-amino]-phenyl}-piperidine-1-carbonyl)-cyclopentanecarboxylic acid

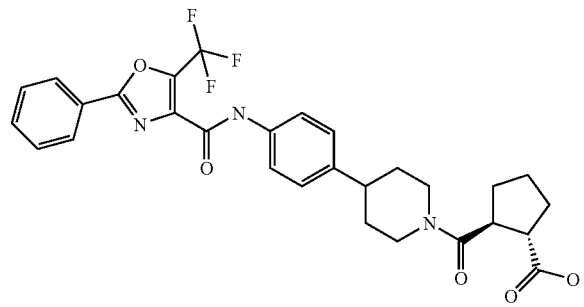

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-(4-{4-[(2-phenyl-5-trifluoromethyl-oxazole-4-carbonyl)-amino]-phenyl}-piperidine-1-carbonyl)-cyclopentanecarboxylic acid was prepared from 2-phenyl-5-trifluoromethyl-oxazole-4-carboxylic acid (4-piperidin-4-yl-phenyl)-amide and racemic 1,2-trans-cyclopetane dicarboxylic acid. ES-MS calcd for C29H28F3N3O5 (m/e) 555.2, obsd 556.1 (M+H). The NMR spectrum obtained on the sample is compatible with its structure.

Example 18

Preparation of (1R,2R)-2-(4-{4-[(2-Phenyl-5-trifluoromethyl-oxazole-4-carbonyl)-amino]-phenyl}-piperidine-1-carbonyl)-cyclopentanecarboxylic acid

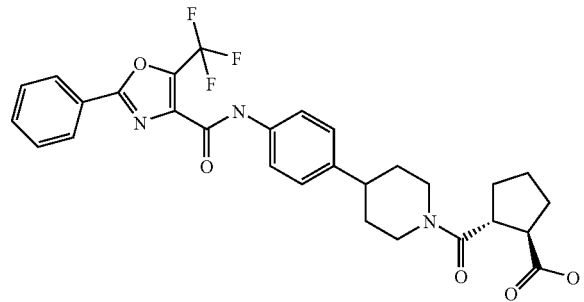

The racemic mixture of 2-(4-{4-[(2-phenyl-5-trifluoromethyl-oxazole-4-carbonyl)-amino]-phenyl}-piperidine-1-carbonyl)-cyclopentanecarboxylic acid from above was separated under supercritical fluid chromatography (SFC) conditions (chiral OJ column, 25% methanol in liquid carbon dioxide, flow rate 70 mL/min, pressure 100 bar at 30° C.). The earlier eluting fraction provided (1R,2R)-2-(4-{4-[(2-phenyl-5-trifluoromethyl-oxazole-4-carbonyl)-amino]-phenyl}-piperidine-1-carbonyl)-cyclopentanecarboxylic acid $[\alpha]_D=-$24.2 (4.5 mg/mL in ethyl acetate). HRMS calcd for C29H28F3N3O5 (M+H)$^+$ 556.2054, obsd 556.2052. The NMR spectrum obtained on the sample is compatible with its structure.

Example 19

Preparation of (1S,2S)-2-(4-{4-[(2-Phenyl-5-trifluoromethyl-oxazole-4-carbonyl)-amino]-phenyl}-piperidine-1-carbonyl)-cyclopentanecarboxylic acid

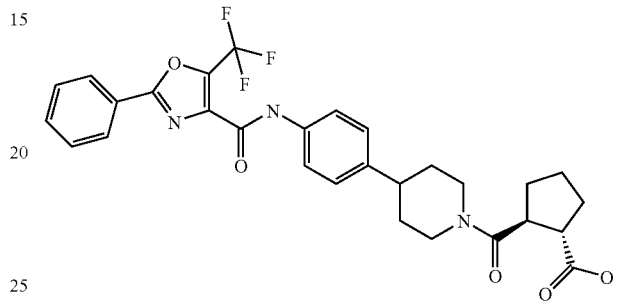

The racemic mixture of 2-(4-{4-[(2-phenyl-5-trifluoromethyl-oxazole-4-carbonyl)-amino]-phenyl}-piperidine-1-carbonyl)-cyclopentanecarboxylic acid from above was separated under supercritical fluid chromatography (SFC) conditions (chiral OJ column, 25% methanol in liquid carbon dioxide, flow rate 70 mL/min, pressure 100 bar at 30° C.). The later eluting fraction provided (1S,2S)-2-(4-{4-[(2-phenyl-5-trifluoromethyl-oxazole-4-carbonyl)-amino]-phenyl}-piperidine-1-carbonyl)-cyclopentanecarboxylic acid. $[\alpha]_D=+$25.3 (3.2 mg/mL in ethyl acetate). LC-MS calcd for C29H28F3N3O5 (m/e) 555.2, obsd 556.1 (M+H). The NMR spectrum obtained on the sample is compatible with its structure.

Example 20

Preparation of 4-(4-{4-[(2-phenyl-5-trifluoromethyl-oxazole-4-carbonyl)-amino]-phenyl}-piperidine-1-carbonyl)-cyclohexanecarboxylic acid

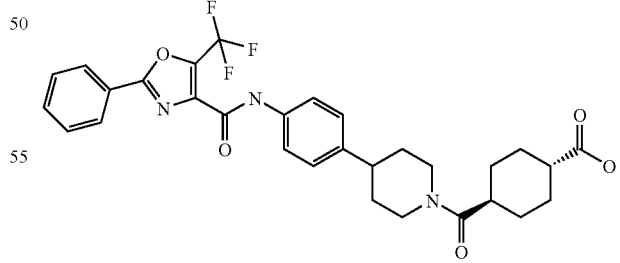

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 4-(4-{4-[(2-phenyl-5-trifluoromethyl-oxazole-4-carbonyl)-amino]-phenyl}-piperidine-1-carbonyl)-cyclohexanecarboxylic acid was prepared from 2-phenyl-5-trifluoromethyl-oxazole-4-carboxylic acid (4-piperidin-4-yl-phenyl)-amide and 1,4-trans-cyclohexane dicarboxylic acid. HRMS calcd for C30H30F3N3O5 (M+H)+ 570.2211 obsd 570.2210

Example 21

Preparation of rac-2-(4-{4-[(2-phenyl-5-trifluoromethyl-oxazole-4-carbonyl)-amino]-phenyl}-piperidine-1-carbonyl)-cyclobutanecarboxylic acid

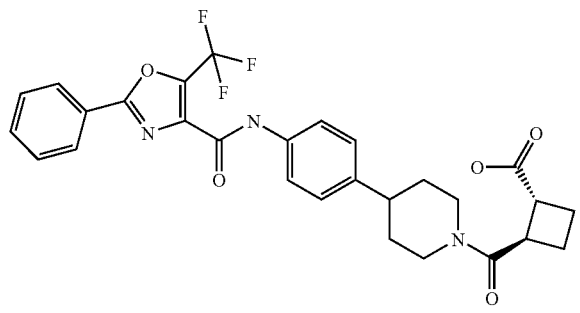

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-(4-{4-[(2-phenyl-5-trifluoromethyl-oxazole-4-carbonyl)-amino]-phenyl}-piperidine-1-carbonyl)-cyclobutanecarboxylic acid was prepared from 2-phenyl-5-trifluoromethyl-oxazole-4-carboxylic acid (4-piperidin-4-yl-phenyl)-amide and racemic 1,2-trans-cyclobutane dicarboxylic acid. LC-MS calcd for C28H26F3N3O5 (m/e) 541.2, obsd 542.3 (M+H).

Example 22

Preparation of rac-2-(4-{5-[(2-phenyl-5-trifluoromethyl-oxazole-4-carbonyl)-amino]-pyridin-2-yl}-piperazine-1-carbonyl)-cyclopentanecarboxylic acid

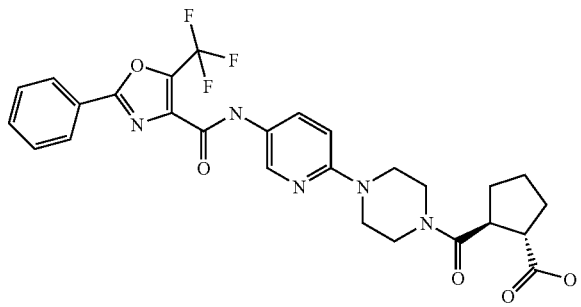

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-(4-{5-[(2-phenyl-5-trifluoromethyl-oxazole-4-carbonyl)-amino]-pyridin-2-yl}-piperazine-1-carbonyl)-cyclopentanecarboxylic acid was prepared from 2-phenyl-5-trifluoromethyl-oxazole-4-carboxylic acid (6-piperazin-1-yl-pyridin-3-yl)-amide and racemic 1,2-trans-cyclopentane dicarboxylic acid. LC-MS calcd for C27H26F3N5O5 (m/e) 557.2, obsd 558.1 (M+H).

Example 23

Preparation of (1S,2S)-2-(4-{[5-[(2-phenyl-5-trifluoromethyl-oxazole-4-carbonyl)-amino]-pyridin-2-yl}-piperazine-1-carbonyl)-cyclopentanecarboxylic acid]

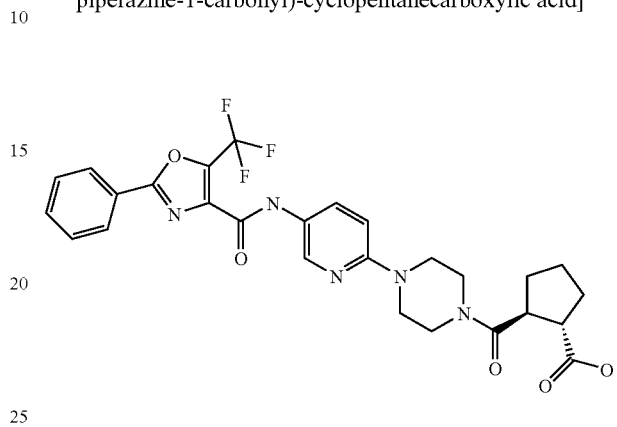

The racemic mixture of 2-(4-{5-[(2-phenyl-5-trifluoromethyl-oxazole-4-carbonyl)-amino]-pyridin-2-yl}-piperazine-1-carbonyl)-cyclopentanecarboxylic acid from above was separated under supercritical fluid chromatography (SFC) conditions as described earlier. The earlier eluting fraction provided (1S,2S)-2-(4-{5-[(2-phenyl-5-trifluoromethyl-oxazole-4-carbonyl)-amino]-pyridin-2-yl}-piperazine-1-carbonyl)-cyclopentanecarboxylic acid. $[\alpha]_D$=+21.8 (4.3 mg/mL in ethyl acetate). LC-MS calcd for C27H26F3N5O5 (m/e) 557.2, obsd 558.1 (M+H).

Example 24

Preparation of (1R,2R)-2-(4-{5-[(2-phenyl-5-trifluoromethyl-oxazole-4-carbonyl)-amino]-pyridin-2-yl}-piperazine-1-carbonyl)-cyclopentanecarboxylic acid

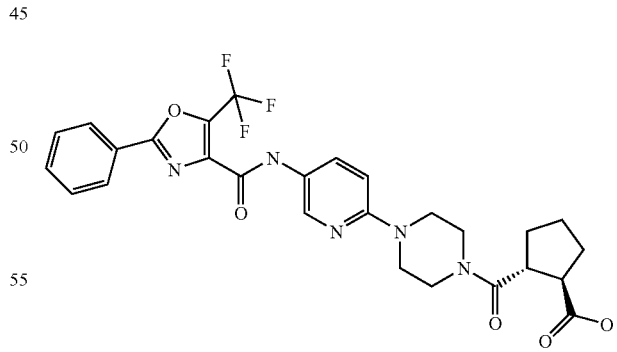

The racemic mixture of 2-(4-{5-[(2-Phenyl-5-trifluoromethyl-oxazole-4-carbonyl)-amino]-pyridin-2-yl}-piperazine-1-carbonyl)-cyclopentanecarboxylic acid from above was separated under supercritical fluid chromatography (SFC) conditions as described earlier. The later eluting fraction provided (1R,2R)-2-(4-{5-[(2-phenyl-5-trifluoromethyl-oxazole-4-carbonyl)-amino]-pyridin-2-yl}-piperazine-1-carbonyl)-cyclopentanecarboxylic acid. $[\alpha]_D$=−21.6

(4.2 mg/mL in ethyl acetate). LC-MS calcd for C27H26F3N5O5 (m/e) 557.2, obsd 558.1 (M+H).

Example 25

Preparation of rac-2-(4-{5-[(2-phenyl-5-trifluoromethyl-oxazole-4-carbonyl)-amino]-pyrimidin-2-yl}-piperazine-1-carbonyl)-cyclopentanecarboxylic acid

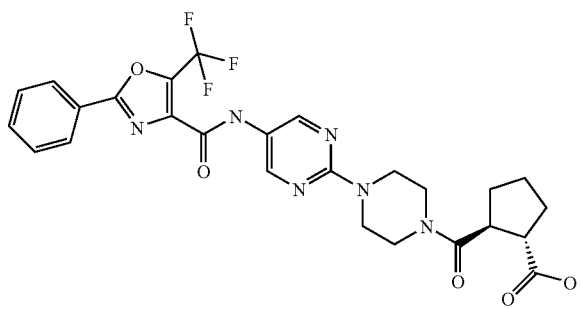

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-(4-{5-[(2-phenyl-5-trifluoromethyl-oxazole-4-carbonyl)-amino]-pyrimidin-2-yl}-piperazine-1-carbonyl)-cyclopentanecarboxylic acid was prepared from 2-phenyl-5-trifluoromethyl-oxazole-4-carboxylic acid (2-piperazin-1-yl-pyrimidin-5-yl)-amide and racemic 1,2-trans-cyclopentane dicarboxylic acid. LC-MS calcd for C26H25F3N6O5 (m/e) 558.2, obsd 559.1 (M+H).

Example 26

Preparation of (1R,2R)-2-(4-{5-[(2-phenyl-5-trifluoromethyl-oxazole-4-carbonyl)-amino]-pyrimidin-2-yl}-piperazine-1-carbonyl)-cyclopentanecarboxylic acid

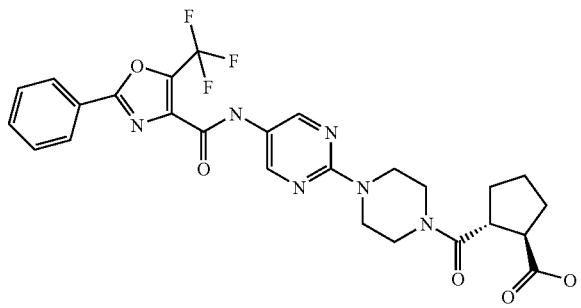

The racemic mixture of 2-(4-{5-[(2-Phenyl-5-trifluoromethyl-oxazole-4-carbonyl)-amino]-pyrimidin-2-yl}-piperazine-1-carbonyl)-cyclopentanecarboxylic acid from above was separated under supercritical fluid chromatography (SFC) conditions as described earlier. The earlier eluting fraction provided (1R,2R)-2-(4-{5-[(2-phenyl-5-trifluoromethyl-oxazole-4-carbonyl)-amino]-pyrimidin-2-yl}-piperazine-1-carbonyl)-cyclopentanecarboxylic acid. $[\alpha]_D=-19.3$ (4.2 mg/mL in ethyl acetate). LC-MS calcd for C26H25F3N6O5 (m/e) 558.2, obsd 559.1 (M+H).

Example 27

Preparation of (1S,2S)-2-(4-{5-[(2-phenyl-5-trifluoromethyl-oxazole-4-carbonyl)-amino]-pyrimidin-2-yl}-piperazine-1-carbonyl)-cyclopentanecarboxylic acid

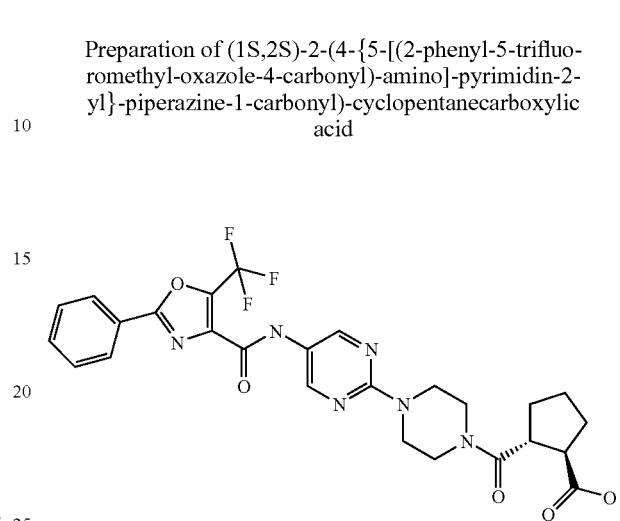

The racemic mixture of 2-(4-{5-[(2-phenyl-5-trifluoromethyl-oxazole-4-carbonyl)-amino]-pyrimidin-2-yl}-piperazine-1-carbonyl)-cyclopentanecarboxylic acid from above was separated under supercritical fluid chromatography (SFC) conditions as described earlier. The later eluting fraction provided (1S,2S)-2-(4-{5-[(2-phenyl-5-trifluoromethyl-oxazole-4-carbonyl)-amino]-pyrimidin-2-yl}-piperazine-1-carbonyl)-cyclopentane carboxylic acid. $[\alpha]_D=+20.6$ (4.4 mg/mL in ethyl acetate). LC-MS calcd for C26H25F3N6O5 (m/e) 558.2, obsd 559.1 (M+H).

Example 28

Preparation of 4-{5-[(2-phenyl-5-trifluoromethyl-oxazole-4-carbonyl)-amino]-3',4',5',6'-tetrahydro-2'H-[2,4']bipyridinyl-1'-carbonyl}-cyclohexanecarboxylic acid

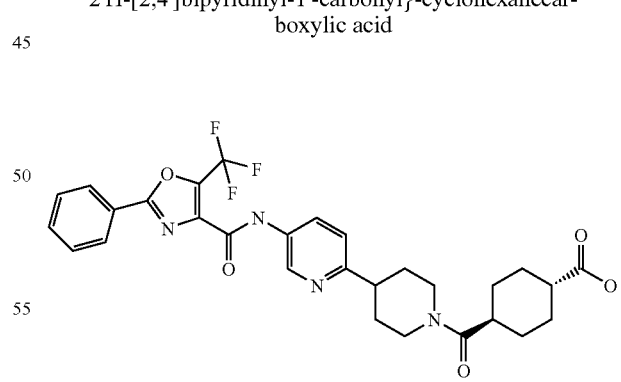

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 4-{5-[(2-phenyl-5-trifluoromethyl-oxazole-4-carbonyl)-amino]-3',4',5',6'-tetrahydro-2'H-[2,4']bipyridinyl-1'-carbonyl}-cyclohexanecarboxylic acid was prepared from 2-phenyl-5-trifluoromethyl-oxazole-4-carboxylic acid (1',2',3',4',5',6'-hexahydro-[2,4']bipyridinyl-5-yl)-amide and 1,4-trans-cyclohexane dicarboxylic acid. LC-MS calcd for C29H29F3N4O5 (m/e) 570.2, obsd 571.4 (M+H).

Example 29

Preparation of 4-(4-{5-[(2-phenyl-5-trifluoromethyl-oxazole-4-carbonyl)-amino]-pyridin-2-yl}-piperazine-1-carbonyl)-cyclohexanecarboxylic acid

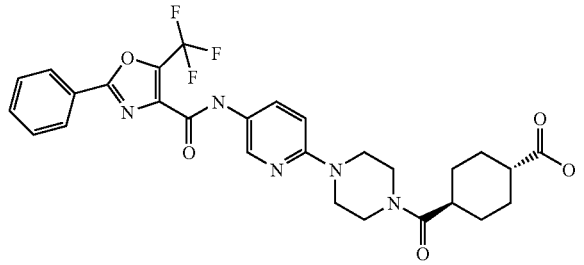

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 4-(4-{5-[(2-phenyl-5-trifluoromethyl-oxazole-4-carbonyl)-amino]-pyridin-2-yl}-piperazine-1-carbonyl)-cyclohexanecarboxylic acid was prepared from 2-phenyl-5-trifluoromethyl-oxazole-4-carboxylic acid (6-piperazin-1-yl-pyridin-3-yl)-amide and 1,4-trans-cyclohexane dicarboxylic acid. LC-MS calcd for C28H28F3N5O5 (m/e) 571.2, obsd 572.2 (M+H).

Example 30

Preparation of rac-2-{5-[(2-Phenyl-5-trifluoromethyl-oxazole-4-carbonyl)-amino]-3',4',5',6'-tetrahydro-2'H-[2,4']bipyridinyl-1'-carbonyl}-cyclopentanecarboxylic acid

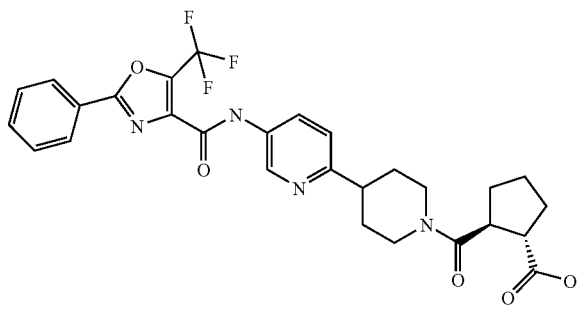

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-{5-[(2-phenyl-5-trifluoromethyl-oxazole-4-carbonyl)-amino]-3',4',5',6'-tetrahydro-2'H-[2,4']bipyridinyl-1'-carbonyl}-cyclopentanecarboxylic acid was prepared from 2-phenyl-5-trifluoromethyl-oxazole-4-carboxylic acid (1',2',3',4',5',6'-hexahydro-[2,4']bipyridinyl-5-yl)-amide and 1,2-trans-cyclopentane dicarboxylic acid. LC-MS calcd for C28H27F3N4O5 (m/e) 556.2, obsd 557.3 (M+H).

Example 31

Preparation of racemic 2-(4-{5-[(5-phenyl-2-propyl-2H-pyrazole-3-carbonyl)-amino]-pyridin-2-yl}-piperazine-1-carbonyl)-cyclopentanecarboxylic acid

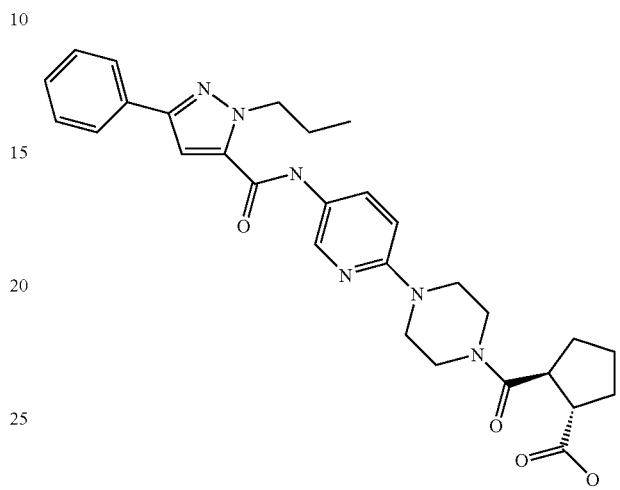

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-(4-{5-[(5-phenyl-2-propyl-2H-pyrazole-3-carbonyl)-amino]-pyridin-2-yl}-piperazine-1-carbonyl)cyclopentanecarboxylic acid was prepared from 5-phenyl-2-propyl-2H-pyrazole-3-carboxylic acid (6-piperazin-1-yl-pyridin-3-yl)-amide and racemic trans-cyclopentane-1,2-dicarboxylic acid. LCMS calcd for C29H34N6O4 (m/e) 530, obsd 531 (M+H).

Example 32

Preparation of racemic 2-(4-{5-[(1-phenyl-3-trifluoromethyl-1H-pyrazole-4-carbonyl)-amino]-pyridin-2-yl}-piperazine-1-carbonyl)-cyclopentanecarboxylic acid

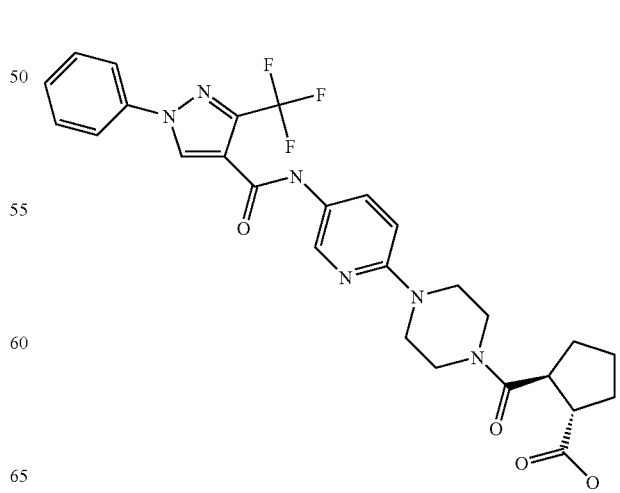

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 2-(4-{5-[(1-phenyl-3-trifluoromethyl-1H-pyrazole-4-carbonyl)-amino]-pyridin-2-yl}-piperazine-1-carbonyl)-cyclopentanecarboxylic acid was prepared from 1-phenyl-3-trifluoromethyl-1H-pyrazole-4-carboxylic acid (6-piperazin-1-yl-pyridin-3-yl)-amide and racemic trans-Cyclopentane-1,2-dicarboxylic acid. LCMS calcd for C27H27F3N6O4 (m/e) 556, obsd 557 (M+H).

clopentane-1,2-dicarboxylic acid. LCMS calcd for C30H35N5O4 (m/e) 529, obsd 530 (M+H).

Example 34

Preparation of racemic 2-(4-{4-[(1-phenyl-3-trifluoromethyl-1H-pyrazole-4-carbonyl)-amino]-phenyl}-piperazine-1-carbonyl)-cyclopentanecarboxylic acid

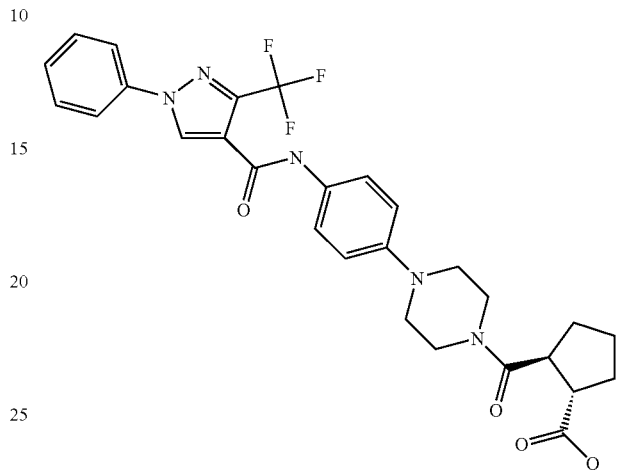

Example 33

Preparation of racemic 2-(4-{4-[(5-phenyl-2-propyl-2H-pyrazole-3-carbonyl)-amino]-phenyl}-piperazine-1-carbonyl)-cyclopentanecarboxylic acid

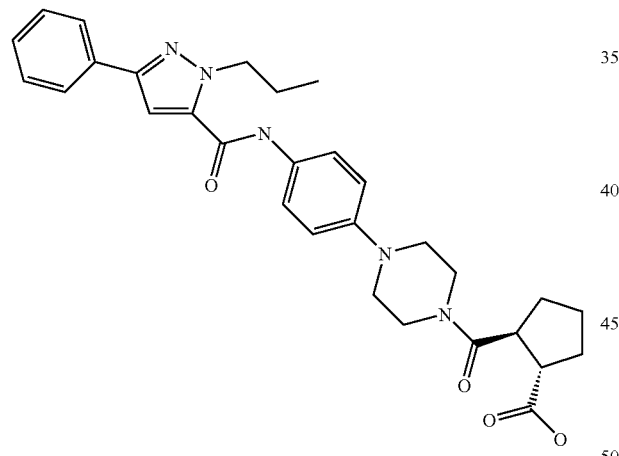

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-(4-{4-[(1-phenyl-3-trifluoromethyl-1H-pyrazole-4-carbonyl)-amino]-phenyl}-piperazine-1-carbonyl)-cyclopentanecarboxylic acid was prepared from 1-phenyl-3-trifluoromethyl-1H-pyrazole-4-carboxylic acid (4-piperazin-1-yl-phenyl)-amide and racemic trans-cyclopentane-1,2-dicarboxylic acid. LCMS calcd for C28H28F3N5O4 (m/e) 555, obsd 556 (M+H). The NMR spectrum obtained on the sample is compatible with its structure.

Example 35

Preparation of racemic 2-(4-{5-[(5-Methyl-2-phenyl-2H-[1,2,3]triazole-4-carbonyl)-amino]-pyridin-2-yl}-piperazine-1-carbonyl)-cyclopentanecarboxylic acid

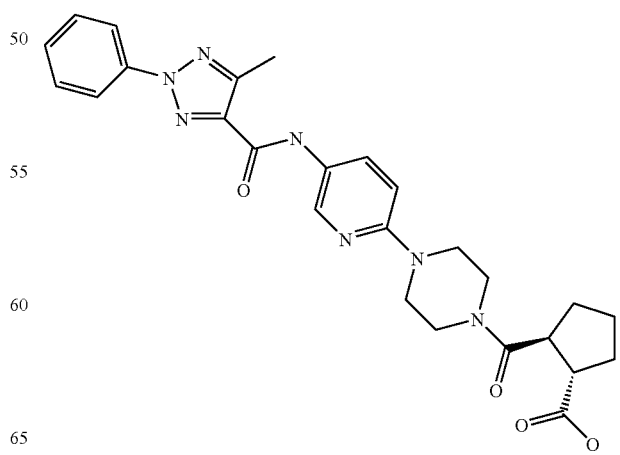

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-(4-{4-[(5-phenyl-2-propyl-2H-pyrazole-3-carbonyl)-amino]-phenyl}-piperazine-1-carbonyl)-cyclopentanecarboxylic acid was prepared from 5-phenyl-2-propyl-2H-pyrazole-3-carboxylic acid (4-piperazin-1-yl-phenyl)-amide and racemic trans-cy- With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-(4-{5-[(5-Methyl-2-phenyl-2H-[1,2,3]triazole-4-carbonyl)-amino]-pyridin-2-yl}-piperazine-1-carbonyl)cyclopentane carboxylic acid was prepared from 5-Methyl-2-phenyl-2H-[1,2,3]triazole-4-carboxylic acid (6-piperazin-1-yl-pyridin-3-yl)-amide and racemic trans-cyclopentane-1,2-dicarboxylic acid. LCMS calcd for C26H29N7O4 (m/e) 503, obsd 504 (M+H).

Example 36

Preparation of racemic 2-[4-(5-{[1-(4-fluoro-phenyl)-3-trifluoromethyl-1H-pyrazole-4-carbonyl]-amino}-pyridin-2-yl)-piperazine-1-carbonyl]-cyclopentanecarboxylic acid

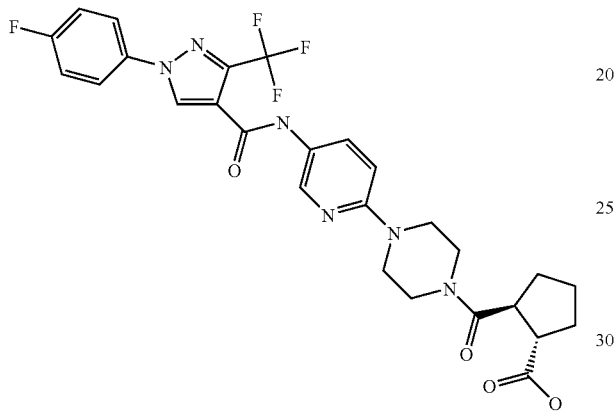

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 2-[4-(5-{[1-(4-fluoro-phenyl)-3-trifluoromethyl-1H-pyrazole-4-carbonyl]-amino}-pyridin-2-yl)-piperazine-1-carbonyl]-cyclopentanecarboxylic acid was prepared from 1-(4-fluoro-phenyl)-3-trifluoromethyl-1H-pyrazole-4-carboxylic acid (6-piperazin-1-yl-pyridin-3-yl)-amide and racemic trans-cyclopentane-1,2-dicarboxylic acid. LCMS calcd for C27H26F4N6O4 (m/e) 574, obsd 575 (M+H).

Example 37

Preparation of racemic 2-[4-(5-{[2-(2-methoxy-ethyl)-5-phenyl-2H-pyrazole-3-carbonyl]-amino}-pyridin-2-yl)-piperazine-1-carbonyl]-cyclopentanecarboxylic acid

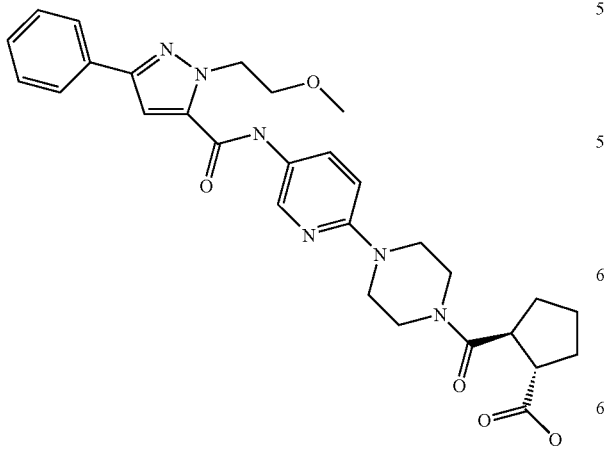

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-[4-(5-{[2-(2-methoxy-ethyl)-5-phenyl-2H-pyrazole-3-carbonyl]-amino}-pyridin-2-yl)-piperazine-1-carbonyl]-cyclopentanecarboxylic acid was prepared from 2-(2-methoxy-ethyl)-5-phenyl-2H-pyrazole-3-carboxylic acid (6-piperazin-1-yl-pyridin-3-yl)-amide and racemic trans-cyclopentane-1,2-dicarboxylic acid. LCMS calcd for C29H34N6O5 (m/e) 546, obsd 547 (M+H).

Example 38

Preparation of racemic 2-(4-{5-[(2-propyl-5-thiophen-2-yl-2H-pyrazole-3-carbonyl)-amino]-pyridin-2-yl}-piperazine-1-carbonyl)-cyclopentanecarboxylic acid

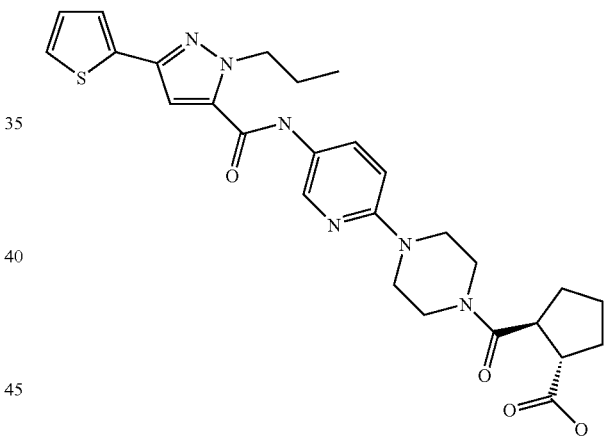

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-(4-{5-[(2-propyl-5-thiophen-2-yl-2H-pyrazole-3-carbonyl)-amino]-pyridin-2-yl}-piperazine-1-carbonyl)-cyclopentanecarboxylic acid was prepared from 2-propyl-5-thiophen-2-yl-2H-pyrazole-3-carboxylic acid (6-piperazin-1-yl-pyridin-3-yl)-amide and racemic trans-cyclopentane-1,2-dicarboxylic acid. LCMS calcd for C27H32N6O4S (m/e) 536, obsd 537 (M+H).

Example 39

Preparation of racemic 2-(4-{4-[(2-phenyl-5-trifluoromethyl-oxazole-4-carbonyl)-amino]-phenyl}-piperazine-1-carbonyl)-cyclopentanecarboxylic acid methyl ester

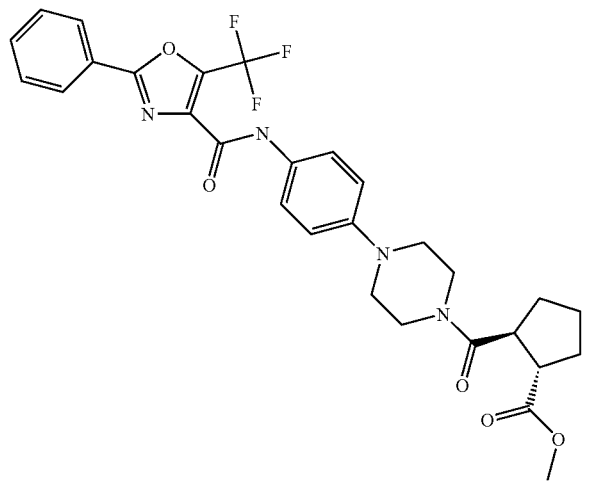

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-(4-{4-[(2-phenyl-5-trifluoromethyl-oxazole-4-carbonyl)-amino]-phenyl}-piperazine-1-carbonyl)-cyclopentanecarboxylic acid methyl ester was prepared from 2-phenyl-5-trifluoromethyl-oxazole-4-carboxylic acid (4-piperazin-1-yl-phenyl)-amide and racemic trans-cyclopentane-1,2-dicarboxylic acid methyl ester. LCMS calcd for C29H29F3N4O5 (m/e) 570, obsd 571 (M+H). The NMR spectrum obtained on the sample is compatible with its structure.

Example 40

Preparation of rac-2-(4-{4-[(1-phenyl-3-trifluoromethyl-1H-pyrazole-4-carbonyl)-amino]-phenyl}-piperidine-1-carbonyl)-cyclopentanecarboxylic acid

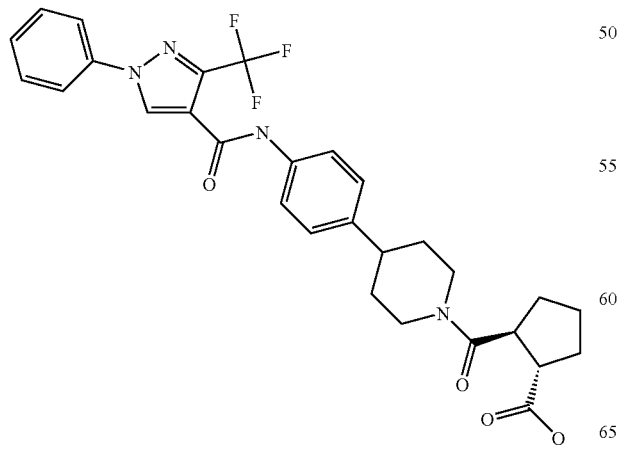

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-(4-{4-[(1-phenyl-3-trifluoromethyl-1H-pyrazole-4-carbonyl)-amino]-phenyl}-piperidine-1-carbonyl)-cyclopentanecarboxylic acid was prepared from 1-phenyl-3-trifluoromethyl-1H-pyrazole-4-carboxylic acid (4-piperidin-4-yl-phenyl)-amide and racemic trans-cyclopentane-1,2-dicarboxylic acid. LCMS calcd for C29H29F3N4O4 (m/e) 554, obsd 555 (M+H).

Example 41

Preparation of 4-(4-{4-[(1-phenyl-3-trifluoromethyl-1H-pyrazole-4-carbonyl)-amino]-phenyl}-piperidine-1-carbonyl)-cyclohexanecarboxylic acid

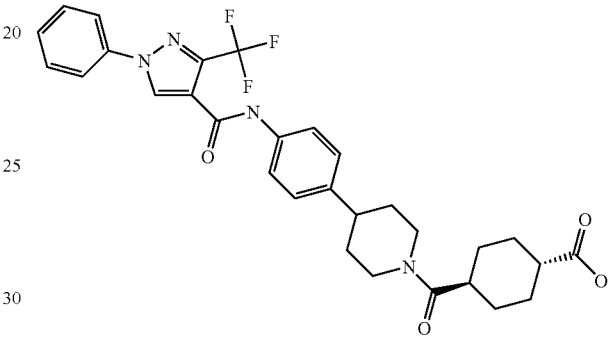

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 4-(4-{4-[(1-phenyl-3-trifluoromethyl-1H-pyrazole-4-carbonyl)-amino]-phenyl}-piperidine-1-carbonyl)-cyclohexanecarboxylic acid was prepared from 1-phenyl-3-trifluoromethyl-1H-pyrazole-4-carboxylic acid (4-piperidin-4-yl-phenyl)-amide and trans-1,4-cyclohexanedicarboxylic acid. LCMS calcd for C30H31F3N4O4 (m/e) 568, obsd 569 (M+H).

Example 42

Preparation of racemic 2-[4-(4-{[1-(4-fluoro-phenyl)-3-trifluoromethyl-1H-pyrazole-4-carbonyl]-amino}-phenyl)-piperidine-1-carbonyl]-cyclopentanecarboxylic acid

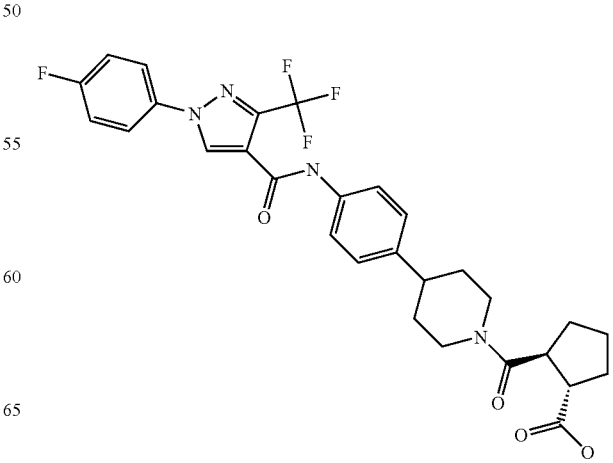

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-[4-(4-{[1-(4-fluoro-phenyl)-3-trifluoromethyl-1H-pyrazole-4-carbonyl]-amino}-phenyl)-piperidine-1-carbonyl]-cyclopentanecarboxylic acid was prepared from 1-(4-fluoro-phenyl)-3-trifluoromethyl-1H-pyrazole-4-carboxylic acid (4-piperidin-4-yl-phenyl)-amide and racemic trans-cyclopentane-1,2-dicarboxylic acid. LCMS calcd for C29H28F4N4O4 (m/e) 572, obsd 573 (M+H).

Example 43

Preparation of 4-[4-(4-{[1-(4-fluoro-phenyl)-3-trifluoromethyl-1H-pyrazole-4-carbonyl]-amino}-phenyl)-piperidine-1-carbonyl]-cyclohexanecarboxylic acid

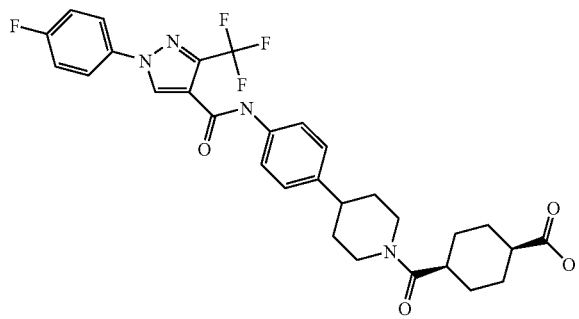

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 4-[4-(4-{[1-(4-fluoro-phenyl)-3-trifluoromethyl-1H-pyrazole-4-carbonyl]-amino}-phenyl)-piperidine-1-carbonyl]-cyclohexanecarboxylic acid was prepared from 1-(4-fluoro-phenyl)-3-trifluoromethyl-1H-pyrazole-4-carboxylic acid (4-piperidin-4-yl-phenyl)-amide and cis-cyclohexane-1,4-dicarboxylic acid. LCMS calcd for C30H30F4N4O4 (m/e) 586, obsd 585 (M−H).

Example 44

Preparation of 4-[4-(4-{[1-(2-chloro-phenyl)-3-trifluoromethyl-1H-pyrazole-4-carbonyl]-amino}-phenyl)-piperidine-1-carbonyl]-cyclohexanecarboxylic acid

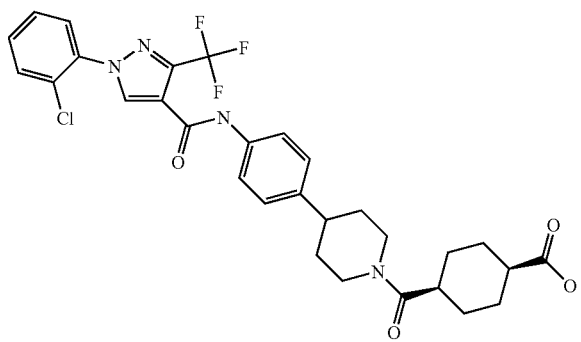

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 4-[4-(4-{[1-(2-chloro-phenyl)-3-trifluoromethyl-1H-pyrazole-4-carbonyl]-amino}-phenyl)-piperidine-1-carbonyl]-cyclohexanecarboxylic acid was prepared from 1-(2-chloro-phenyl)-3-trifluoromethyl-1H-pyrazole-4-carboxylic acid (4-piperidin-4-yl-phenyl)-amide and cis-cyclohexane-1,4-dicarboxylic acid. LCMS calcd for C30H30ClF3N4O4 (m/e) 603, obsd 602 (M−H). The NMR spectrum obtained on the sample is compatible with its structure.

Example 45

Preparation of 4-[4-(4-{[1-(2-chloro-phenyl)-3-trifluoromethyl-1H-pyrazole-4-carbonyl]-amino}-phenyl)-piperidine-1-carbonyl]-cyclohexanecarboxylic acid

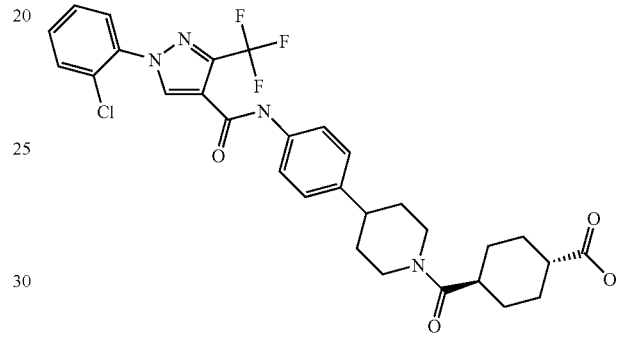

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 4-[4-(4-{[1-(2-chloro-phenyl)-3-trifluoromethyl-1H-pyrazole-4-carbonyl]-amino}-phenyl)-piperidine-1-carbonyl]-cyclohexanecarboxylic acid was prepared from 1-(2-chloro-phenyl)-3-trifluoromethyl-1H-pyrazole-4-carboxylic acid (4-piperidin-4-yl-phenyl)-amide and trans-cyclohexane-1,4-dicarboxylic acid. LCMS calcd for C30H30ClF3N4O4 (m/e) 603, obsd 602 (M−H). The NMR spectrum obtained on the sample is compatible with its structure.

Example 46

Preparation of racemic 2-[4-(4-{[1-(2-chloro-phenyl)-3-trifluoromethyl-1H-pyrazole-4-carbonyl]-amino}-phenyl)-piperidine-1-carbonyl]-cyclopentanecarboxylic acid

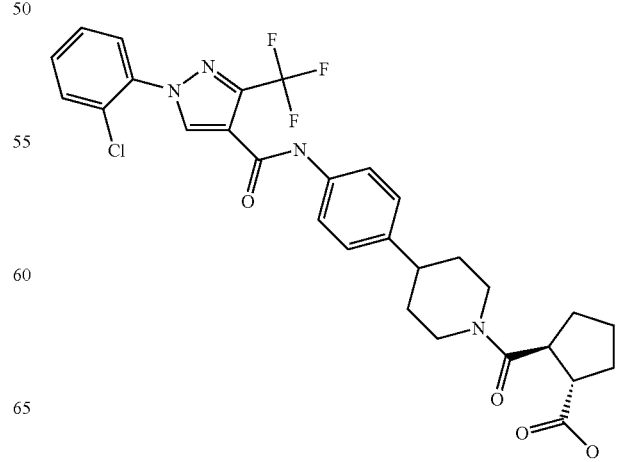

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-[4-(4-{[1-(2-chloro-phenyl)-3-trifluoromethyl-1H-pyrazole-4-carbonyl]-amino}-phenyl)-piperidine-1-carbonyl]-cyclopentanecarboxylic acid was prepared from 1-(2-chloro-phenyl)-3-trifluoromethyl-1H-pyrazole-4-carboxylic acid (4-piperidin-4-yl-phenyl)-amide and racemic trans-cyclopentane-1,2-dicarboxylic acid. LCMS calcd for C29H28ClF3N4O4 (m/e) 589, obsd 588 (M−H). The NMR spectrum obtained on the sample is compatible with its structure.

Example 47

Preparation of 4-[4-(4-{[1-(4-fluoro-phenyl)-3-trifluoromethyl-1H-pyrazole-4-carbonyl]-amino}-phenyl)-piperidine-1-carbonyl]-cyclohexanecarboxylic acid

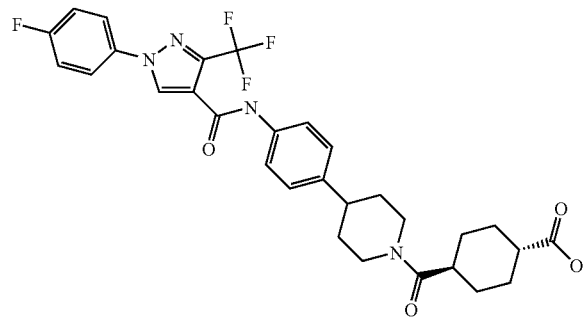

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 4-[4-(4-{[1-(4-fluoro-phenyl)-3-trifluoromethyl-1H-pyrazole-4-carbonyl]-amino}-phenyl)-piperidine-1-carbonyl]-cyclohexanecarboxylic acid was prepared from 1-(4-fluoro-phenyl)-3-trifluoromethyl-1H-pyrazole-4-carboxylic acid (4-piperidin-4-yl-phenyl)-amide and trans-cyclohexane-1,4-dicarboxylic acid. LCMS calcd for C30H30F4N4O4 (m/e) 586, obsd 585 (M−H).

Example 48

Preparation of (1R,2R)-2-((S)-3-{5-[(2-phenyl-5-trifluoromethyl-oxazole-4-carbonyl)-amino]-pyridin-2-ylamino}-pyrrolidine-1-carbonyl)-cyclopentanecarboxylic acid

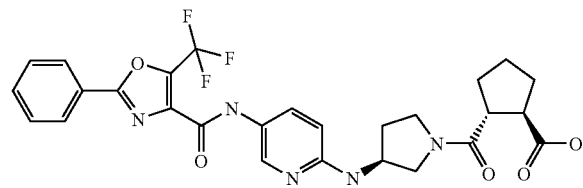

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, (1R,2R)-2-((S)-3-{5-[(2-phenyl-5-trifluoromethyl-oxazole-4-carbonyl)-amino]-pyridin-2-ylamino}-pyrrolidine-1-carbonyl)-cyclopentanecarboxylic acid was prepared from (S)-2-phenyl-5-trifluoromethyl-oxazole-4-carboxylic acid [6-(pyrrolidin-3-ylamino)-pyridin-3-yl]-amide and racemic trans-cyclopentane-1,2-dicarboxylic acid. The mixture of diasteriomers were then separated by chiral SFC to give (1R, 2R)-2-((S)-3-{5-[(2-phenyl-5-trifluoromethyl-oxazole-4-carbonyl)-amino]-pyridin-2-ylamino}-pyrrolidine-1-carbonyl)-cyclopentanecarboxylic acid. LCMS calcd for C27H26F3N5O5 (m/e) 557.53, obsd 558.53 (M+H). The NMR spectrum obtained on the sample is compatible with its structure.

Example 49

Preparation of (1S,2S)-2-((S)-3-{5-[(2-phenyl-5-trifluoromethyl-oxazole-4-carbonyl)-amino]-pyridin-2-ylamino}-pyrrolidine-1-carbonyl)-cyclopentanecarboxylic acid

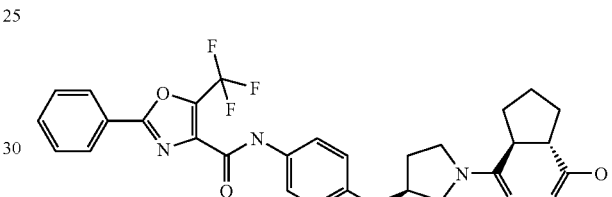

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, (1S,2S)-2-((S)-3-{5-[(2-phenyl-5-trifluoromethyl-oxazole-4-carbonyl)-amino]-pyridin-2-ylamino}-pyrrolidine-1-carbonyl)-cyclopentanecarboxylic acid was prepared from (S)-2-phenyl-5-trifluoromethyl-oxazole-4-carboxylic acid [6-(pyrrolidin-3-ylamino)-pyridin-3-yl]-amide and racemic trans-cyclopentane-1,2-dicarboxylic acid. The mixture of diasteriomers were then separated by chiral SFC to give (1S, 2S)-2-((S)-3-{5-[(2-phenyl-5-trifluoromethyl-oxazole-4-carbonyl)-amino]-pyridin-2-ylamino}-pyrrolidine-1-carbonyl)-cyclopentanecarboxylic acid. LCMS calcd for C27H26F3N5O5 (m/e) 557.53, obsd 558.53 (M+H). The NMR spectrum obtained on the sample is compatible with its structure.

Example 50

Preparation of 4-((S)-3-{5-[(2-phenyl-5-trifluoromethyl-oxazole-4-carbonyl)-amino]-pyridin-2-ylamino}-pyrrolidine-1-carbonyl)-cyclohexanecarboxylic acid

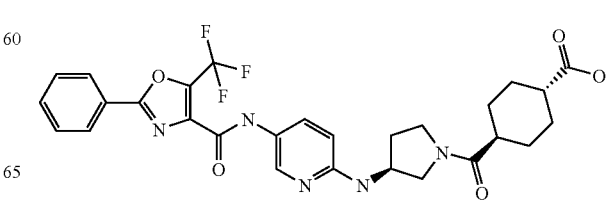

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 4-((S)-3-{5-[(2-phenyl-5-trifluoromethyl-oxazole-4-carbonyl)-amino]-pyridin-2-ylamino}-pyrrolidine-1-carbonyl)-cyclohexanecarboxylic acid was prepared from 2-phenyl-5-trifluoromethyl-oxazole-4-carboxylic acid [6-((S)-pyrrolidin-3-ylamino)-pyridin-3-yl]-amide and trans-cyclohexane-1,4-dicarboxylic acid. LCMS calcd for C28H28F3N5O5 (m/e) 571.55, obsd 572.21 (M+H).

Example 51

Preparation of 4-(4-{4-[(2-phenyl-5-trifluoromethyl-oxazole-4-carbonyl)-amino]-phenyl}-piperidine-1-carbonyl)-cyclohexanecarboxylic acid

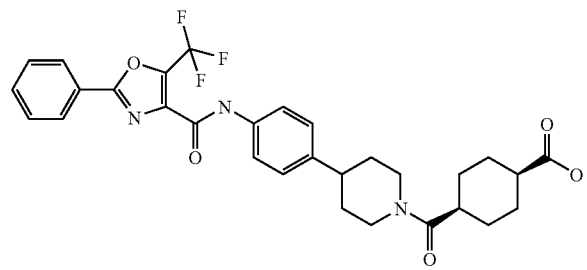

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 4-(4-{4-[(2-phenyl-5-trifluoromethyl-oxazole-4-carbonyl)-amino]-phenyl}-piperidine-1-carbonyl)-cyclohexanecarboxylic acid was prepared from 2-phenyl-5-trifluoromethyl-oxazole-4-carboxylic acid (4-piperidin-4-yl-phenyl)-amide and cis-cyclohexane-1,4-dicarboxylic acid. LCMS calcd for C30H30F3N3O5 (m/e) 569.58, obsd 570.22 (M+H).

Example 52

Preparation of rac-2-(4-{2-cyano-4-[(2-phenyl-5-trifluoromethyl-oxazole-4-carbonyl)-amino]-phenyl}-piperazine-1-carbonyl)-cyclopentanecarboxylic acid

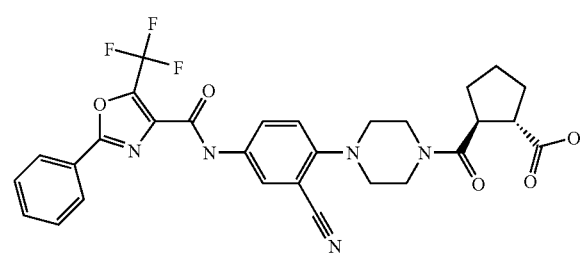

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-(4-{2-cyano-4-[(2-phenyl-5-trifluoromethyl-oxazole-4-carbonyl)-amino]-phenyl}-piperazine-1-carbonyl)-cyclopentanecarboxylic acid was prepared from 2-phenyl-5-trifluoromethyl-oxazole-4-carboxylic acid (3-cyano-4-piperazin-1-yl-phenyl)-amide and racemic trans-cyclopentane-1,2-dicarboxylic acid. LCMS calcd for C29H26F3N5O5 (m/e) 581, obsd. 582 (M+H).

Example 53

Preparation of rac-2-phenyl-5-trifluoromethyl-oxazole-4-carboxylic acid {4-[1-(tetrahydro-furan-2-carbonyl)-piperidin-4-yl]-phenyl}-amide

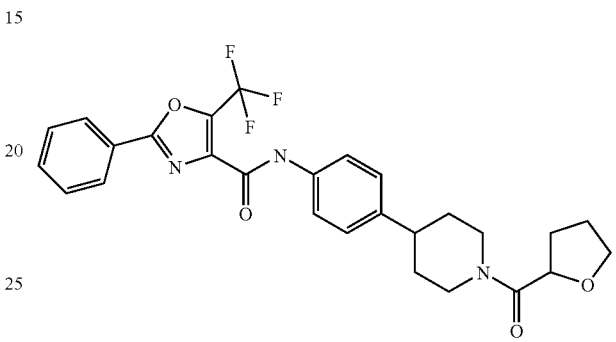

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-phenyl-5-trifluoromethyl-oxazole-4-carboxylic acid {4-[1-(tetrahydro-furan-2-carbonyl)-piperidin-4-yl]-phenyl}-amide was prepared from 2-phenyl-5-trifluoromethyl-oxazole-4-carboxylic acid (4-piperidin-4-yl-phenyl)-amide and racemic tetrahydrofuran-2-carboxylic acid. LC-MS calcd for C27H26F3N3O4 (m/e) 513.2, obsd 514.4 (M+H). The NMR spectrum obtained on the sample is compatible with its structure.

Example 54

Preparation of rac-2-phenyl-5-trifluoromethyl-oxazole-4-carboxylic acid {4-[1-(tetrahydro-furan-3-carbonyl)-piperidin-4-yl]-phenyl}-amide

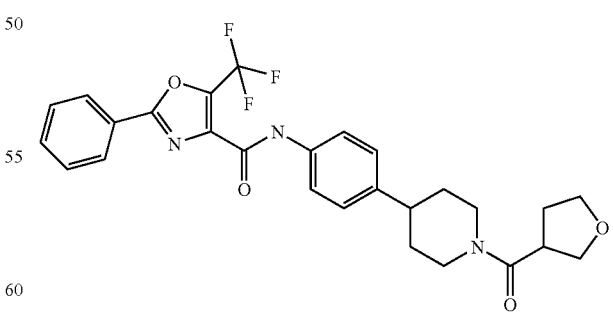

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, racemic 2-phenyl-5-trifluoromethyl-oxazole-4-carboxylic acid {4-[1-(tetrahydrofuran-3-carbonyl)-piperidin-4-yl]-phenyl}-amide was prepared from 2-phenyl-5-trifluoromethyl-oxazole-4-carboxylic acid (4-piperidin-4-yl-phenyl)-amide and racemic tetrahydrofuran-3-carboxylic acid. LC-MS calcd for C27H26F3N3O4 (m/e) 513.2, obsd 514.4 (M+H). The NMR spectrum obtained on the sample is compatible with its structure.

Example 55

Preparation of 2-phenyl-5-trifluoromethyl-oxazole-4-carboxylic acid {6-[4-(cyclopent-3-enecarbonyl)-piperazin-1-yl]-pyridin-3-yl}-amide

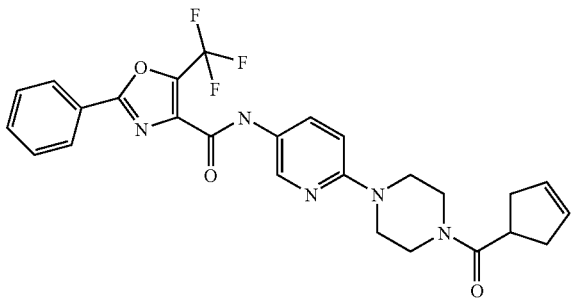

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 2-phenyl-5-trifluoromethyl-oxazole-4-carboxylic acid {6-[4-(cyclopent-3-enecarbonyl)-piperazin-1-yl]-pyridin-3-yl}-amide was prepared from 2-phenyl-5-trifluoromethyl-oxazole-4-carboxylic acid (6-piperazin-1-yl-pyridin-3-yl)-amide and 3-cyclopentene carboxylic acid. LC-MS calcd for C26H24F3N5O3 (m/e) 511.2, obsd 512.1 (M+H). The NMR spectrum obtained on the sample is compatible with its structure.

Example 56

Preparation of 2-phenyl-5-trifluoromethyl-oxazole-4-carboxylic acid {4-[1-(cyclopent-3-enecarbonyl)-piperidin-4-yl]-phenyl}-amide

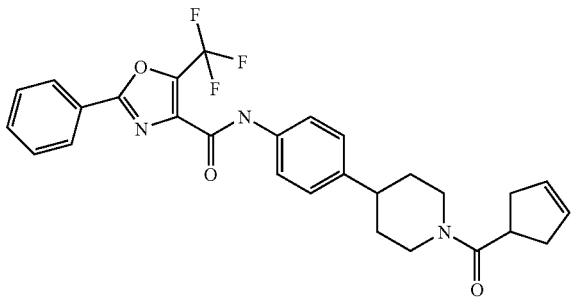

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 2-phenyl-5-trifluoromethyl-oxazole-4-carboxylic acid {4-[1-(cyclopent-3- enecarbonyl)-piperidin-4-yl]-phenyl}-amide was prepared from 2-phenyl-5-trifluoromethyl-oxazole-4-carboxylic acid (4-piperidin-4-yl-phenyl)-amide and 3-cyclopentene carboxylic acid. LC-MS calcd for C28H26F3N3O3 (m/e) 509.2, obsd 510.2 (M+H). The NMR spectrum obtained on the sample is compatible with its structure.

Example 57

Preparation of 2-phenyl-5-trifluoromethyl-oxazole-4-carboxylic acid (1'-cyclopropanecarbonyl-1',2',3',4',5',6'-hexahydro-[2,4']bipyridinyl-5-yl)-amide

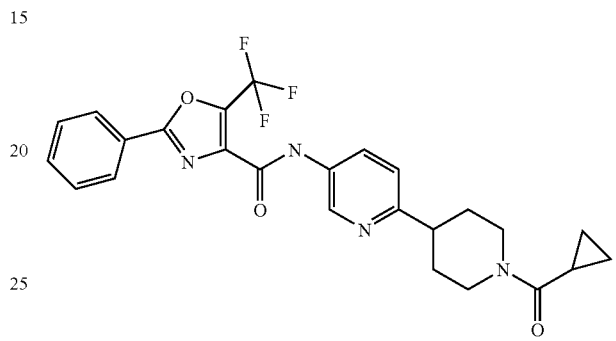

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 2-phenyl-5-trifluoromethyl-oxazole-4-carboxylic acid (1'-cyclopropanecarbonyl-1',2',3',4',5',6'-hexahydro-[2,4']bipyridinyl-5-yl)-amide was prepared from 2-phenyl-5-trifluoromethyl-oxazole-4-carboxylic acid (1',2',3',4',5',6'-hexahydro-[2,4']bipyridinyl-5-yl)-amide and cyclopropane carboxylic acid. LC-MS calcd for C25H23F3N4O3 (m/e) 484.2, obsd 485.1 (M+H). The NMR spectrum obtained on the sample is compatible with its structure.

Example 58

Preparation of 2-phenyl-5-trifluoromethyl-oxazole-4-carboxylic acid [4-(4-cyclopropanecarbonyl-piperazin-1-yl)-phenyl]-amide

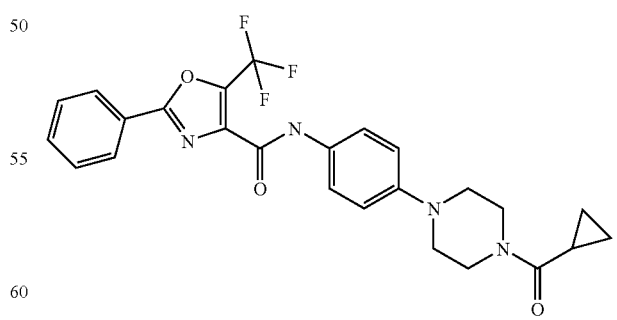

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid ethyl ester above, 2-phenyl-5-trifluoromethyl-oxazole-4-carboxylic acid [4-(4- cyclopropanecarbonyl-piperazin-1-yl)-phenyl]-amide was prepared from 2-phenyl-5-trifluoromethyl-oxazole-4-carboxylic acid (4-piperazin-1-yl-phenyl)-amide and cyclopropane carboxylic acid. LC-MS calcd for C25H23F3N4O3 (m/e) 484.2, obsd 485.1 (M+H). The NMR spectrum obtained on the sample is compatible with its structure.

Example 59

Preparation of 4-{5-[(2-phenyl-5-trifluoromethyl-oxazole-4-carbonyl)-amino]-pyridin-2-yl}-piperazine-1-carboxylic acid tert-butyl ester

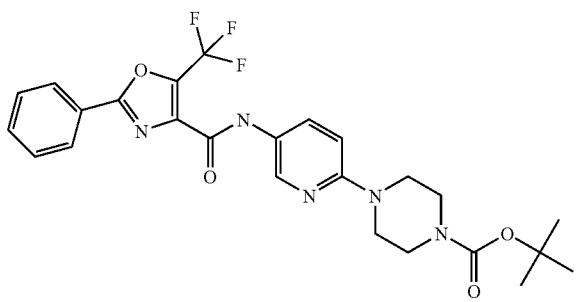

4-(5-Amino-pyridin-2-yl)-piperazine-1-carboxylic acid tert-butyl ester was mixed with 2-phenyl-5-trifluoromethyloxazole-4-carboxylic acid (771 mg, 3.0 mmol) and bromotrispyrrolidinophosphonium hexafluorophosphate (1.40 g, 3.0 mmol) in N,N-dimethylformamide (20 mL) and methylene chloride (5 mL) containing triethylamine (0.85 mL). The mixture was stirred at room temperature overnight and the solvents were evaporated. The residue was extracted with ethyl acetate and water. The organic layer was dried over sodium sulfate, filtered and concentrated. The residue was triturated with ethyl acetate and the solid was filtered to give 4-{5-[(2-phenyl-5-trifluoromethyl-oxazole-4-carbonyl)-amino]-pyridin-2-yl}-piperazine-1-carboxylic acid tert-butyl ester (1.09 g). LC-MS calcd for C25H26F3N5O4 (m/e) 517.5, obsd 518.1 (M+H). The NMR spectrum obtained on the sample is compatible with its structure.

Example 60

Preparation of (1-{4-[(2-phenyl-5-trifluoromethyl-oxazole-4-carbonyl)-amino]-phenyl}-piperidin-4-yl)-acetic acid ethyl ester

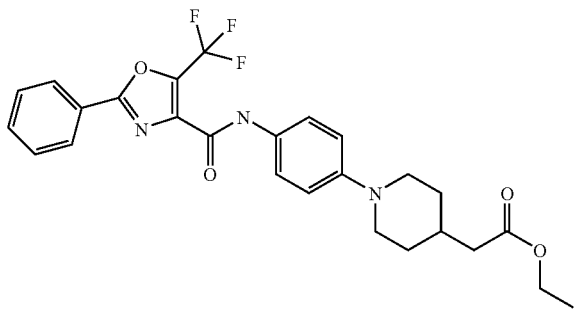

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (1-{4-[(2-phenyl-5-trifluoromethyl-oxazole-4-carbonyl)-amino]-phenyl}-piperidin-4-yl)-acetic acid ethyl ester was prepared from 2-phenyl-5-trifluoromethyl-oxazole-4-carboxylic acid and [1-(4-aminophenyl)-piperidine-4-yl]-acetic acid ethyl ester. LC-MS calcd for C26H26F3N3O4 (m/e) 501.2, obsd 502.1 (M+H). The NMR spectrum obtained on the sample is compatible with its structure.

Example 61

Preparation of {5'-[(2-phenyl-5-trifluoromethyl-oxazole-4-carbonyl)-amino]-3,4,5,6-tetrahydro-2H-[1,2']bipyridinyl-4-yl}-acetic acid methyl ester

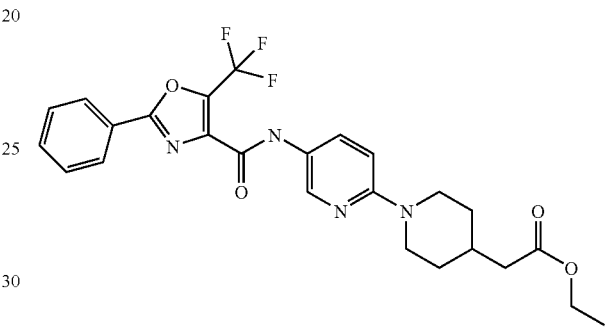

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, {5'-[(2-phenyl-5-trifluoromethyl-oxazole-4-carbonyl)-amino]-3,4,5,6-tetrahydro-2H-[1,2']bipyridinyl-4-yl}-acetic acid methyl ester was prepared from 2-phenyl-5-trifluoromethyl-oxazole-4-carboxylic acid and (5'-amino-3,4,5,6-tetrahydro-2H-[1,2']bipyridinyl-4-yl)-acetic acid methyl ester. LC-MS calcd for C24H23F3N4O4 (m/e) 488.2, obsd 489.1 (M+H). The NMR spectrum obtained on the sample is compatible with its structure.

Example 62

Preparation of 2-Methyl-2-{5'-[(2-phenyl-5-trifluoromethyl-oxazole-4-carbonyl)-amino]-3,4,5,6-tetrahydro-2H-[1,2']bipyridinyl-4-yl}-propionic acid ethyl ester

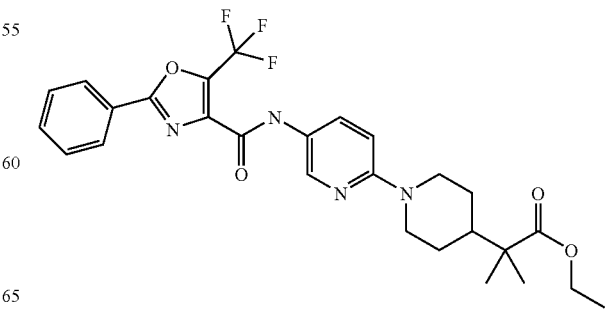

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 2-methyl-2-{5'-[(2-phenyl-5-trifluoromethyl-oxazole-4-carbonyl)-amino]-3,4,5,6-tetrahydro-2H-[1,2']bipyridinyl-4-yl}-propionic acid ethyl ester was prepared from 2-phenyl-5-trifluoromethyl-oxazole-4-carboxylic acid and 2-(5'-amino-3,4,5,6-tetrahydro-2H-[1,2']bipyridinyl-4-yl)-2-methyl-propionic acid ethyl ester. LC-MS calcd for C27H29F3N4O4 (m/e) 530.2, obsd 531.1 (M+H). The NMR spectrum obtained on the sample is compatible with its structure.

Example 63

Preparation of 4-{5-[(1-phenyl-3-trifluoromethyl-1H-pyrazole-4-carbonyl)-amino]-pyridin-2-yl}-piperazine-1-carboxylic acid tert-butyl ester

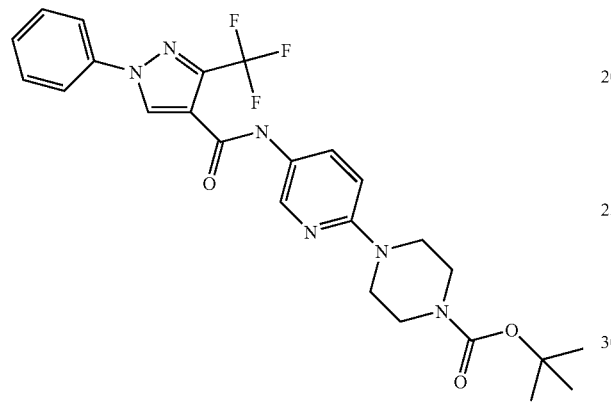

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-{5-[(1-phenyl-3-trifluoromethyl-1H-pyrazole-4-carbonyl)-amino]-pyridin-2-yl}-piperazine-1-carboxylic acid tert-butyl ester was prepared from 1-phenyl-3-trifluoromethyl-1H-pyrazole-4-carboxylic acid and 4-(5-amino-pyridin-2-yl)-piperazine-1-carboxylic acid tert-butyl ester. LCMS calcd for C25H27F3N6O3 (m/e) 516, obsd 517 (M+H).

Example 64

Preparation of 4-(5-{[5-phenyl-2-(2,2,2-trifluoro-ethyl)-2H-pyrazole-3-carbonyl]-amino}-pyridin-2-yl)-piperazine-1-carboxylic acid tert-butyl ester

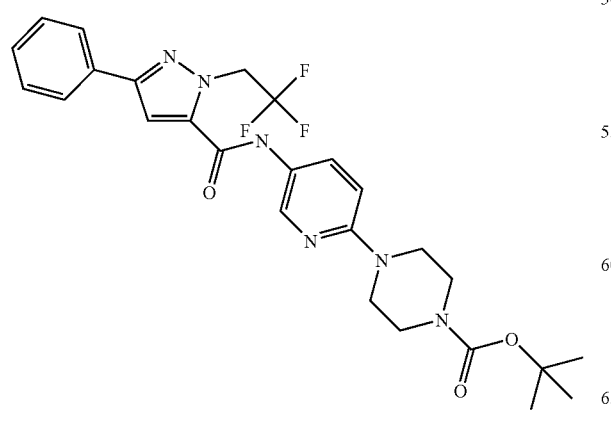

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-(5-{[5-phenyl-2-(2,2,2-trifluoro-ethyl)-2H-pyrazole-3-carbonyl]-amino}-pyridin-2-yl)-piperazine-1-carboxylic acid tert-butyl ester was prepared from 5-phenyl-2-(2,2,2-trifluoro-ethyl)-2H-pyrazole-3-carboxylic acid and 4-(5-amino-pyridin-2-yl)-piperazine-1-carboxylic acid tert-butyl ester. LCMS calcd for C26H29F3N6O3 (m/e) 530, obsd 531 (M+H). The NMR spectrum obtained on the sample is compatible with its structure.

Example 65

Preparation of 4-{5-[(5-phenyl-2-propyl-2H-pyrazole-3-carbonyl)-amino]-pyridin-2-yl}-piperazine-1-carboxylic acid tert-butyl ester

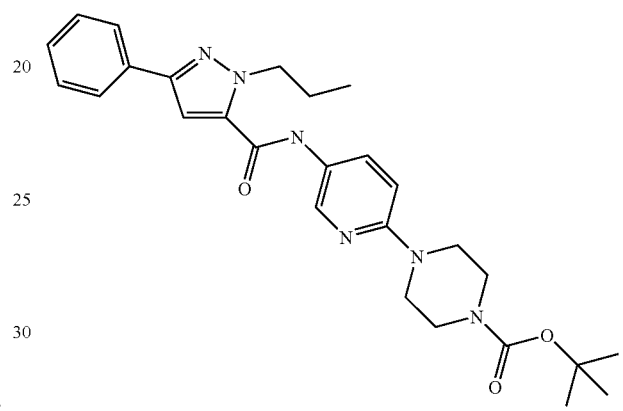

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-{5-[(5-phenyl-2-propyl-2H-pyrazole-3-carbonyl)-amino]-pyridin-2-yl}-piperazine-1-carboxylic acid tert-butyl ester was prepared from 5-phenyl-2-propyl-2H-pyrazole-3-carboxylic acid and 4-(5-amino-pyridin-2-yl)-piperazine-1-carboxylic acid tert-butyl ester. LCMS calcd for C27H34N6O3 (m/e) 490, obsd 491 (M+H). The NMR spectrum obtained on the sample is compatible with its structure.

Example 66

Preparation of 4-{5-[(5-methoxymethyl-2-phenyl-2H-[1,2,3]triazole-4-carbonyl)-amino]-pyridin-2-yl}-piperazine-1-carboxylic acid tert-butyl ester

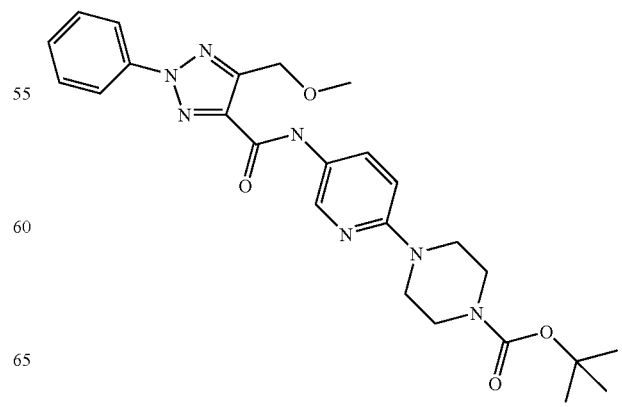

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-{5-[(5-methoxymethyl-2-phenyl-2H-[1,2,3]triazole-4-carbonyl)-amino]-pyridin-2-yl}-piperazine-1-carboxylic acid tert-butyl ester was prepared from 5-methoxymethyl-2-phenyl-2H-[1,2,3]triazole-4-carboxylic acid and 4-(5-amino-pyridin-2-yl)-piperazine-1-carboxylic acid tert-butyl ester. LCMS calcd for C25H31N7O4 (m/e) 493, obsd 494 (M+H). The NMR spectrum obtained on the sample is compatible with its structure.

Example 67

Preparation of 4-(5-{[2-(2-methoxy-ethyl)-5-phenyl-2H-pyrazole-3-carbonyl]-amino}-pyridin-2-yl)-piperazine-1-carboxylic acid tert-butyl ester

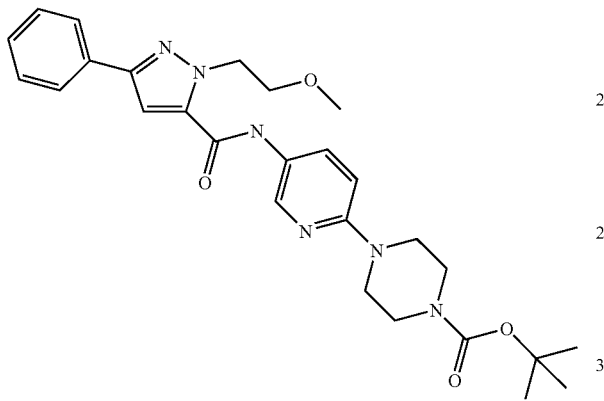

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-(5-{[2-(2-methoxy-ethyl)-5-phenyl-2H-pyrazole-3-carbonyl]-amino}-pyridin-2-yl)-piperazine-1-carboxylic acid tert-butyl ester was prepared from 2-(2-methoxy-ethyl)-5-phenyl-2H-pyrazole-3-carboxylic acid and 4-(5-amino-pyridin-2-yl)-piperazine-1-carboxylic acid tert-butyl ester. LCMS calcd for C27H34N6O4 (m/e) 506, obsd 507 (M+H). The NMR spectrum obtained on the sample is compatible with its structure.

Example 68

Preparation of 4-(5-{[1-(4-fluoro-phenyl)-3-trifluoromethyl-1H-pyrazole-4-carbonyl]-amino}-pyridin-2-yl)-piperazine-1-carboxylic acid tert-butyl ester

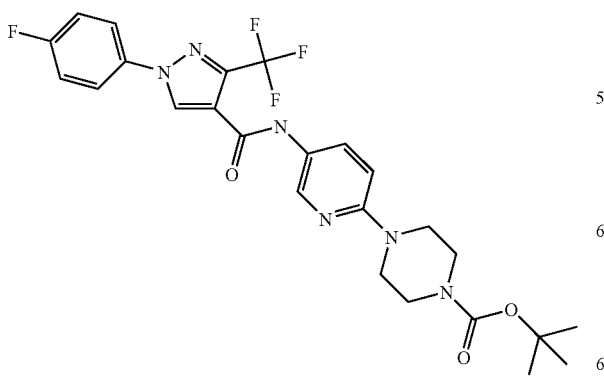

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-(5-{[1-(4-fluoro-phenyl)-3-trifluoromethyl-1H-pyrazole-4-carbonyl]-amino}-pyridin-2-yl)-piperazine-1-carboxylic acid tert-butyl ester was prepared from 1-(4-fluoro-phenyl)-3-trifluoromethyl-1H-pyrazole-4-carboxylic acid and 4-(5-amino-pyridin-2-yl)-piperazine-1-carboxylic acid tert-butyl ester. LCMS calcd for C25H26F4N6O3 (m/e) 534, obsd 535 (M+H).

Example 69

Preparation of 4-{5-[(2-propyl-5-thiophen-2-yl-2H-pyrazole-3-carbonyl)-amino]-pyridin-2-yl}-piperazine-1-carboxylic acid tert-butyl ester

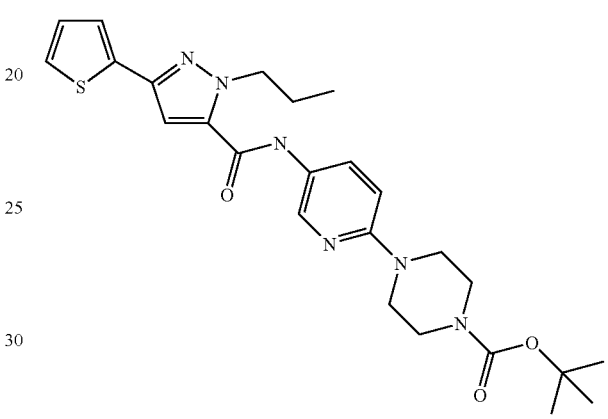

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-{5-[(2-propyl-5-thiophen-2-yl-2H-pyrazole-3-carbonyl)-amino]-pyridin-2-yl}-piperazine-1-carboxylic acid tert-butyl ester was prepared from 2-propyl-5-thiophen-2-yl-2H-pyrazole-3-carboxylic acid and 4-(5-amino-pyridin-2-yl)-piperazine-1-carboxylic acid tert-butyl ester. LCMS calcd for C25H32N6O3S (m/e) 496, obsd 497 (M+H). The NMR spectrum obtained on the sample is compatible with its structure.

Example 70

Preparation of 4-{5-[(1-phenyl-3-trifluoromethyl-1H-pyrazole-4-carbonyl)-amino]-pyridin-2-yl}-benzoic acid

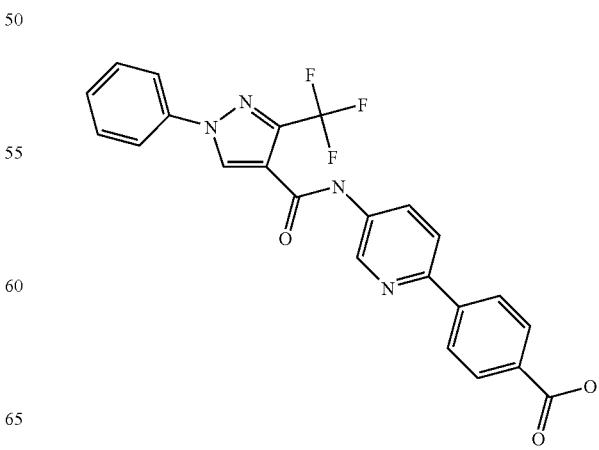

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-{5-[(1-phenyl-3-trifluoromethyl-1H-pyrazole-4-carbonyl)-amino]-pyridin-2-yl}-benzoic acid was prepared from 1-phenyl-3-trifluoromethyl-1H-pyrazole-4-carboxylic acid and 4-(5-amino-pyridin-2-yl)-benzoic acid methyl ester followed by basic hydrolysis of the methyl ester. LCMS calcd for C23H15F3N4O3 (m/e) 452, obsd 453 (M+H). The NMR spectrum obtained on the sample is compatible with its structure.

Example 71

Preparation of 4'-{[1-(4-fluoro-phenyl)-3-trifluoromethyl-1H-pyrazole-4-carbonyl]-amino}-biphenyl-4-carboxylic acid

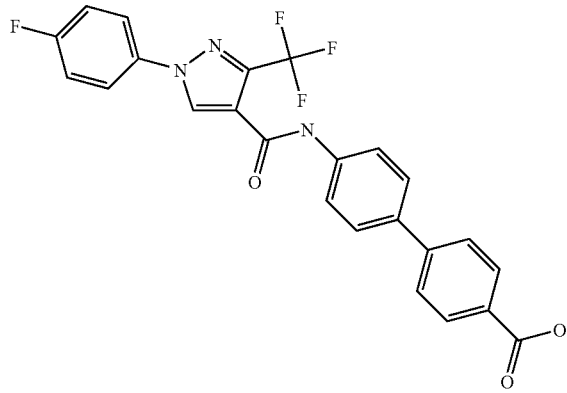

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4'-{[1-(4-fluoro-phenyl)-3-trifluoromethyl-1H-pyrazole-4-carbonyl]-amino}-biphenyl-4-carboxylic acid was prepared from 1-(4-fluoro-phenyl)-3-trifluoromethyl-1H-pyrazole-4-carboxylic acid and 4'-amino-biphenyl-4-carboxylic acid methyl ester followed by basic hydrolysis of the methyl ester. LCMS calcd for C24H15F4N3O3 (m/e) 469, obsd 470 (M+H).

Example 72

Preparation of 4-{5-[(4-methyl-2-pyridin-2-yl-thiazole-5-carbonyl)-amino]-pyridin-2-yl}-benzoic acid

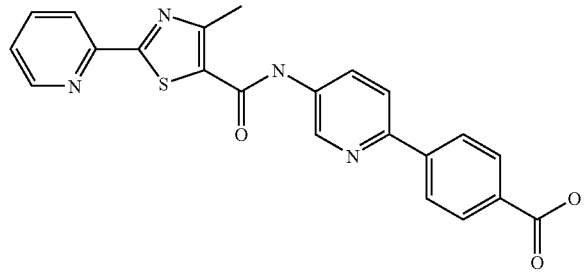

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-{5-[(4-methyl-2-pyridin-2-yl-thiazole-5-carbonyl)-amino]-pyridin-2-yl}-benzoic acid was prepared from 4-methyl-2-pyridin-2-yl-thiazole-5-carboxylic acid and 4-(5-amino-pyridin-2-yl)-benzoic acid methyl ester followed by basic hydrolysis of the methyl ester. LCMS calcd for C22H16N4O3S (m/e) 416, obsd 417 (M+H).

Example 73

Preparation of 4-(5-{[1-(4-fluoro-phenyl)-3-trifluoromethyl-1H-pyrazole-4-carbonyl]-amino}-pyridin-2-yl)-benzoic acid

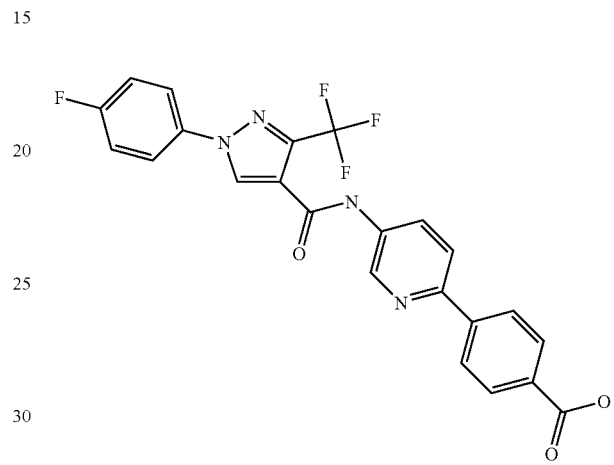

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-(5-{[1-(4-fluoro-phenyl)-3-trifluoromethyl-1H-pyrazole-4-carbonyl]-amino}-pyridin-2-yl)-benzoic acid was prepared from 1-(4-fluoro-phenyl)-3-trifluoromethyl-1H-pyrazole-4-carboxylic acid and 4-(5-amino-pyridin-2-yl)-benzoic acid methyl ester followed by basic hydrolysis of the methyl ester. LCMS calcd for C23H14F4N4O3 (m/e) 470, obsd 471 (M+H). The NMR spectrum obtained on the sample is compatible with its structure.

Example 74

Preparation of 4-{5-[(1-phenyl-5-trifluoromethyl-1H-pyrazole-4-carbonyl)-amino]-pyridin-2-yl}-piperazine-1-carboxylic acid tert-butyl ester

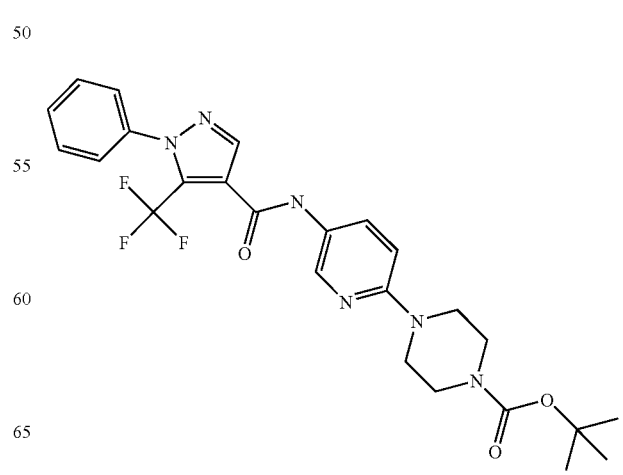

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-{5-[(1-phenyl-5-trifluoromethyl-1H-pyrazole-4-carbonyl)-amino]-pyridin-2-yl}-piperazine-1-carboxylic acid tert-butyl ester was prepared from 1-phenyl-5-trifluoromethyl-1H-pyrazole-4-carboxylic acid and 4-(5-amino-pyridin-2-yl)-piperazine-1-carboxylic acid tert-butyl ester. LCMS calcd for C25H27F3N6O3 (m/e) 516, obsd 517 (M+H). The NMR spectrum obtained on the sample is compatible with its structure.

Example 75

Preparation of 4-{4-[(1-pyridin-2-yl-3-trifluoromethyl-1H-pyrazole-4-carbonyl)-amino]-phenyl}-piperidine-1-carboxylic acid tert-butyl ester

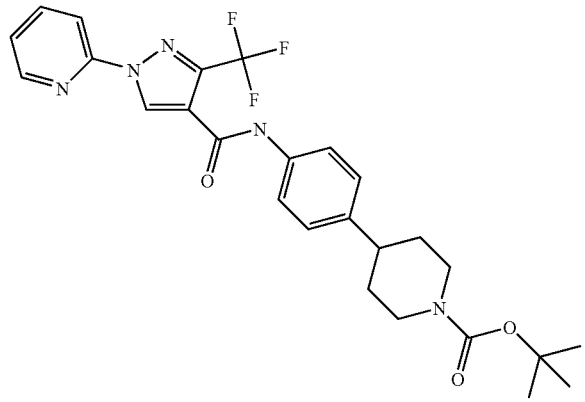

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-{4-[(1-pyridin-2-yl-3-trifluoromethyl-1H-pyrazole-4-carbonyl)-amino]-phenyl}-piperidine-1-carboxylic acid tert-butyl ester was prepared from 1-pyridin-2-yl-3-trifluoromethyl-1H-pyrazole-4-carboxylic acid and 4-(4-amino-phenyl)-piperidine-1-carboxylic acid tert-butyl ester. LCMS calcd for C26H28F3N5O3 (m/e) 515, obsd 516 (M+H). The NMR spectrum obtained on the sample is compatible with its structure.

Example 76

Preparation of 2-methyl-2-{5'-[(2-phenyl-5-trifluoromethyl-oxazole-4-carbonyl)-amino]-3,4,5,6-tetrahydro-2H-[1,2']bipyridinyl-4-yl}-propionic acid

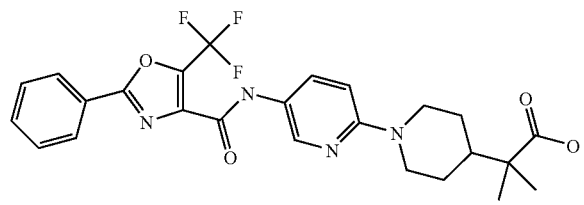

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 2-methyl-2-{5'-[(2-phenyl-5-trifluoromethyl-oxazole-4-carbonyl)-amino]-3,4,5,6-tetrahydro-2H-[1,2']bipyridinyl-4-yl}-propionic acid was prepared from 2-phenyl-5-trifluoromethyl-oxazole-4-carboxylic acid and 2-(5'-amino-3,4,5,6-tetrahydro-2H-[1,2']bipyridinyl-4-yl)-2-methyl-propionic acid. LC-MS calcd for C25H25F3N4O4 (m/e) calcd 502.2, obsd 503.1 (M+H). The NMR spectrum obtained on the sample is compatible with its structure.

Example 77

Preparation of (S)-3-{5-[(2-phenyl-5-trifluoromethyl-oxazole-4-carbonyl)-amino]-pyridin-2-ylamino}-pyrrolidine-1-carboxylic acid tert-butyl ester

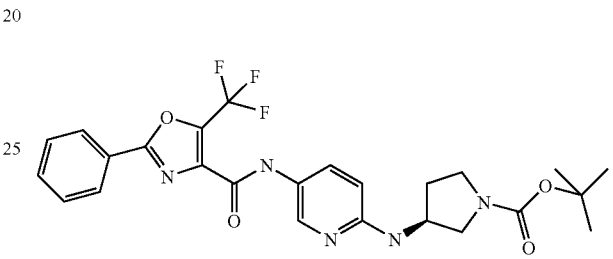

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-{5-[(2-phenyl-5-trifluoromethyl-oxazole-4-carbonyl)-amino]-pyridin-2-ylamino}-pyrrolidine-1-carboxylic acid tert-butyl ester was prepared from 2-phenyl-5-trifluoromethyl-oxazole-4-carboxylic acid and (S)-3-(5-amino-pyridin-2-ylamino)-pyrrolidine-1-carboxylic acid tert-butyl ester. LCMS calcd for C25H26F3N5O4 (m/e) 517.6, obsd 518.2 (M+H).

Example 78

Preparation of (S)-3-(5-{[2-(2-trifluoromethoxy-phenyl)-5-trifluoromethyl-oxazole-4-carbonyl]-amino}-pyrimidin-2-ylamino)-pyrrolidine-1-carboxylic acid ethyl ester

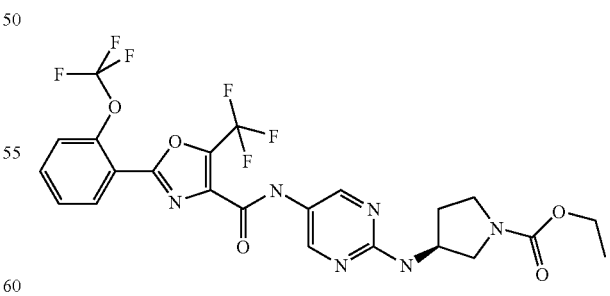

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-(5-{[2-(2-trifluoromethoxy-phenyl)-5-trifluoromethyl-oxazole-4-carbonyl]-amino}-pyrimidin-2-ylamino)-pyrrolidine-1-carboxylic acid tert-butyl ester was prepared from 2-(2-trifluoromethoxy-phenyl)-5-trifluoromethyl-oxazole-4-carboxylic acid and (S)-3-(5-amino-pyrimidin-2-ylamino)-pyrrolidine-1-carboxylic acid ethyl ester. LCMS calcd for C23H20F6N6O5 (m/e) 574.4, obsd 575.2 (M+H).

Example 79

Preparation of (S)-3-{5-[(4-methyl-2-pyridin-2-yl-thiazole-5-carbonyl)-amino]-pyridin-2-ylamino}-pyrrolidine-1-carboxylic acid tert-butyl ester

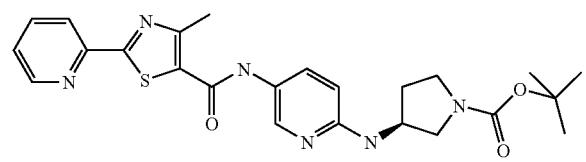

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-{5-[(4-methyl-2-pyridin-2-yl-thiazole-5-carbonyl)-amino]-pyridin-2-ylamino}-pyrrolidine-1-carboxylic acid tert-butyl ester was prepared from 4-methyl-2-pyridin-2-yl-thiazole-5-carboxylic acid and (S)-3-(5-amino-pyridin-2-ylamino)-pyrrolidine-1-carboxylic acid tert-butyl ester. LCMS calcd for C24H28N6O3S (m/e) 480.6, obsd 481.2 (M+H).

Example 80

Preparation of 4-{5-[(4-methyl-2-pyridin-2-yl-thiazole-5-carbonyl)-amino]-pyridin-2-yl}-piperazine-1-carboxylic acid tert-butyl ester

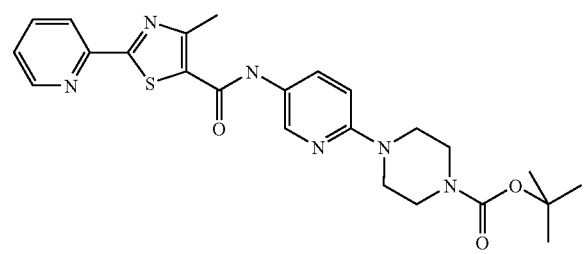

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-{5-[(4-methyl-2-pyridin-2-yl-thiazole-5-carbonyl)-amino]-pyridin-2-yl}-piperazine-1-carboxylic acid tert-butyl ester was prepared from 4-methyl-2-pyridin-2-yl-thiazole-5-carboxylic acid and 4-(5-amino-pyridin-2-yl)-piperazine-1-carboxylic acid tert-butyl ester. LCMS calcd for C24H28N6O3S (m/e) 480.6, obsd 481.2 (M+H).

Example 81

Preparation of 4-{5-[(2-pyridin-3-yl-thiazole-4-carbonyl)-amino]-pyridin-2-yl}-piperazine-1-carboxylic acid tert-butyl ester

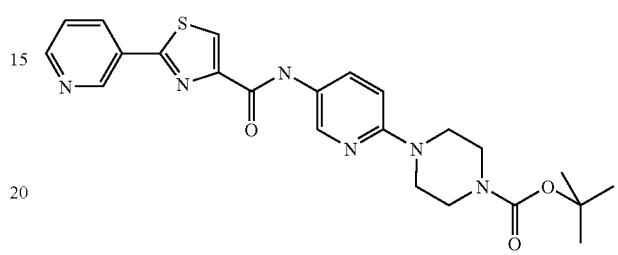

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-{5-[(2-pyridin-3-yl-thiazole-4-carbonyl)-amino]-pyridin-2-yl}-piperazine-1-carboxylic acid tert-butyl ester was prepared from 2-pyridin-3-yl-thiazole-4-carboxylic acid and 4-(5-amino-pyridin-2-yl)-piperazine-1-carboxylic acid tert-butyl ester. LCMS calcd for C23H26N6O3S (m/e) 466.6, obsd 467.2 (M+H).

Example 82

Preparation of 4-{5-[(4-methyl-2-pyridin-3-yl-thiazole-5-carbonyl)-amino]-pyridin-2-yl}-piperazine-1-carboxylic acid tert-butyl ester

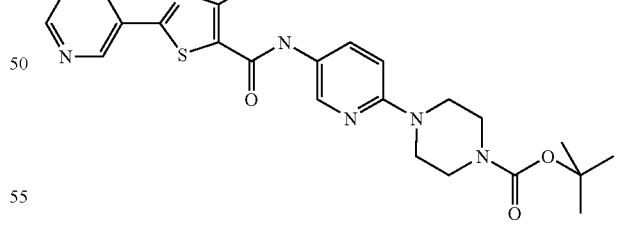

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-{5-[(4-methyl-2-pyridin-3-yl-thiazole-5-carbonyl)-amino]-pyridin-2-yl}-piperazine-1-carboxylic acid tert-butyl ester was prepared from 4-methyl-2-pyridin-3-yl-thiazole-5-carboxylic acid and 4-(5-amino-pyridin-2- yl)-piperazine-1-carboxylic acid tert-butyl ester. LCMS calcd for C24H28N6O3S (m/e) 480.6, obsd 481.2 (M+H).

Example 83

Preparation of (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid ethyl ester

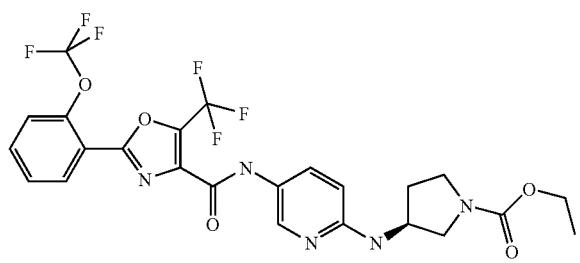

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid tert-butyl ester was prepared from 2-(2-trifluoromethoxy-phenyl)-5-trifluoromethyl-oxazole-4-carboxylic acid and (S)-3-(5-amino-pyridin-2-ylamino)-pyrrolidine-1-carboxylic acid tert-butyl ester. LCMS calcd for C26H25F6N5O5 (m/e) 601.5, obsd 601.9 (M+H).

To a flask containing (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid tert-butyl ester (150 mg, 0.249 mmol) was added trifluoroacetic acid (5 mL). When all the starting material was consumed, as indicated by TLC, the reaction mixture was concentrated to dryness. The residue was dissolved in dichloromethane (10 mL) and then cooled to 0° C. Ethyl chloroformate (24 μL, 0.249 mmol) and triethylamine (75.5 mg, 0.747 mmol) were added dropwise, and the reaction mixture was stirred for 2 h at room temperature and then concentrated. The crude product was purified by flash chromatography (Merck silica gel 60, 230-400 mesh, gradient elution with 0%-100% ethyl acetate in hexane) to give (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid ethyl ester (61 mg, 42.7% yield) as a light yellow solid. LCMS for C24H21F6N5O5 calculated (m/e) 573.46, found 574.15 (M+H).

Example 84

Preparation of (S)-3-{4-[(2-phenyl-5-trifluoromethyl-oxazole-4-carbonyl)-amino]-phenylamino}-pyrrolidine-1-carboxylic acid ethyl ester

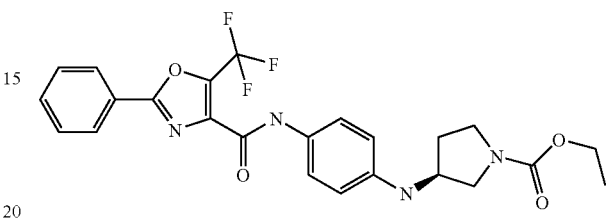

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-{4-[(2-phenyl-5-trifluoromethyl-oxazole-4-carbonyl)-amino]-phenylamino}-pyrrolidine-1-carboxylic acid tert-butyl ester was prepared from 2-phenyl-5-trifluoromethyl-oxazole-4-carboxylic acid and (S)-3-(4-amino-phenylamino)-pyrrolidine-1-carboxylic acid tert-butyl ester. The NMR spectrum obtained on the sample is compatible with its structure.

With a method similar to that used for the preparation of (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid ethyl ester above, (S)-3-{4-[(2-Phenyl-5-trifluoromethyl-oxazole-4-carbonyl)-amino]-phenylamino}-pyrrolidine-1-carboxylic acid ethyl ester was from (S)-3-{4-[(2-phenyl-5-trifluoromethyl-oxazole-4-carbonyl)-amino]-phenylamino}-pyrrolidine-1-carboxylic acid tert-butyl ester and ethyl chloroformate. LCMS calcd for C24H23F3N4O4 (m/e) 488.47, obsd 489.17 (M+H).

Example 85

Preparation of (R)-3-{5-[(2-phenyl-5-trifluoromethyl-oxazole-4-carbonyl)-amino]-pyridin-2-ylamino}-pyrrolidine-1-carboxylic acid tert-butyl ester

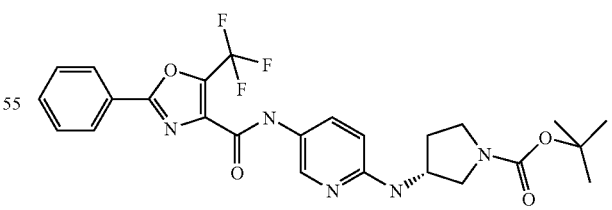

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (R)-3-{5-[(2-phenyl-5-trifluoromethyl-oxazole-4-carbonyl)-amino]-pyridin-2-ylamino}-pyrrolidine-1-carboxylic acid tert-butyl ester was prepared from 2-phenyl-5-trifluoromethyl-oxazole-4-carboxylic acid and (R)-3-(5-amino-pyridin-2-ylamino)-pyrrolidine-1-carboxylic acid tert-butyl ester. LCMS calcd for C25H26F3N5O4 (m/e) 517.6, obsd 518.2 (M+H).

Example 86

Preparation of (R)-(1-{5-[(2-phenyl-5-trifluoromethyl-oxazole-4-carbonyl)-amino]-pyrimidin-2-yl}-pyrrolidin-3-yl)-carbamic acid tert-butyl ester

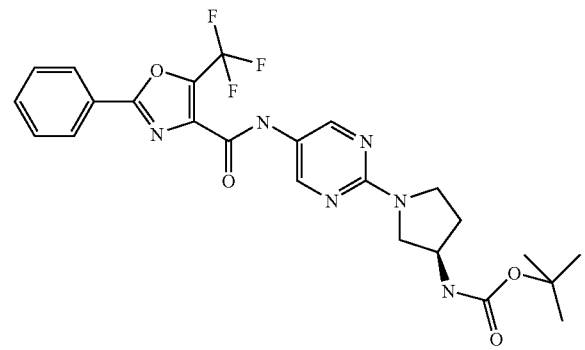

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (R)-(1-{5-[(2-phenyl-5-trifluoromethyl-oxazole-4-carbonyl)-amino]-pyrimidin-2-yl}-pyrrolidin-3-yl)-carbamic acid tert-butyl ester was prepared from 2-phenyl-5-trifluoromethyl-oxazole-4-carboxylic acid and (R)-1-(5-amino-pyrimidin-2-ylamino)-pyrrolidin-3-yl-carbamic acid tert-butyl ester. LCMS calcd for C24H25F3N6O4 (m/e) 518.5, obsd 519.2 (M+H).

Example 87

Preparation of (S)-3-(methyl-{5-[(2-phenyl-5-trifluoromethyl-oxazole-4-carbonyl)-amino]-pyridin-2-yl}-amino)-pyrrolidine-1-carboxylic acid tert-butyl ester

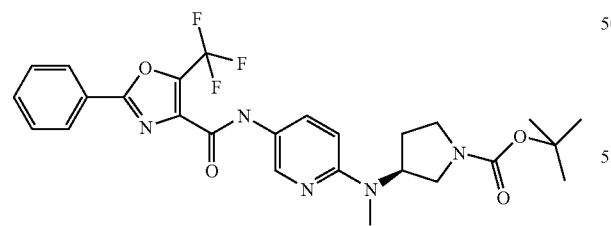

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-(methyl-{5-[(2-phenyl-5-trifluoromethyl-oxazole-4-carbonyl)-amino]-pyridin-2-yl}-amino)-pyrrolidine-1-carboxylic acid tert-butyl ester was prepared from 2-phenyl-5-trifluoromethyl-oxazole-4-carboxylic acid and (S)-3-[(5-amino-pyridin-2-yl)-methyl-amino]-pyrrolidine-1-carboxylic acid tert-butyl ester. LCMS calcd for C26H28F3N5O4 (m/e) 531.5, obsd 532.2 (M+H).

Example 88

Preparation of (S)-(1-{5-[(2-phenyl-5-trifluoromethyl-oxazole-4-carbonyl)-amino]-pyridin-2-yl}-pyrrolidin-3-yl)-carbamic acid tert-butyl ester

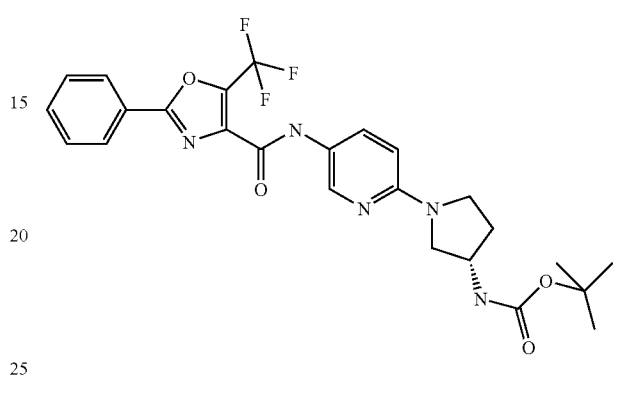

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-(1-{5-[(2-phenyl-5-trifluoromethyl-oxazole-4-carbonyl)-amino]-pyridin-2-yl}-pyrrolidin-3-yl)-carbamic acid tert-butyl ester was prepared from 2-phenyl-5-trifluoromethyl-oxazole-4-carboxylic acid and (S)-[1-(5-amino-pyridin-2-yl)-pyrrolidin-3-yl]-carbamic acid tert-butyl ester. LCMS calcd for C25H26F3N5O4 (m/e) 517.6, obsd 518.2 (M+H).

Example 89

Preparation of (R)-(1-{5-[(2-phenyl-5-trifluoromethyl-oxazole-4-carbonyl)-amino]-pyridin-2-yl}-pyrrolidin-3-yl)-carbamic acid tert-butyl ester

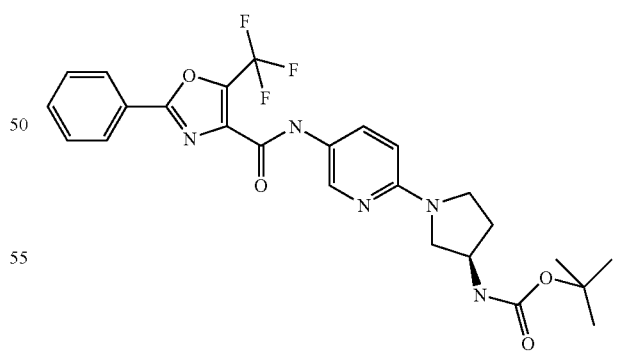

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (R)-(1-{5-[(2-phenyl-5-trifluoromethyl-oxazole-4-carbonyl)-amino]-pyridin-2-yl}-pyrrolidin-3-yl)-carbamic acid tert-butyl ester was prepared from 2-phenyl-5-trifluoromethyl-oxazole-4-carboxylic acid and (R)-[1-(5- amino-pyridin-2-yl)-pyrrolidin-3-yl]-carbamic acid tert-butyl ester. LCMS calcd for C25H26F3N5O4 (m/e) 517.6, obsd 518.2 (M+H).

Example 90

Preparation of rac-methyl-(1-{5-[(2-phenyl-5-trifluoromethyl-oxazole-4-carbonyl)-amino]-pyridin-2-yl}-pyrrolidin-3-yl)-carbamic acid tert-butyl ester

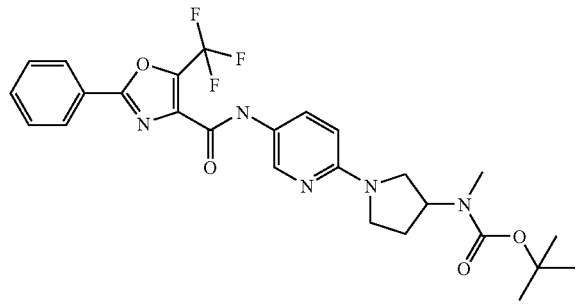

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, racemic methyl-(1-{5-[(2-phenyl-5-trifluoromethyl-oxazole-4-carbonyl)-amino]-pyridin-2-yl}-pyrrolidin-3-yl)-carbamic acid tert-butyl ester was prepared from 2-phenyl-5-trifluoromethyl-oxazole-4-carboxylic acid and racemic [1-(5-amino-pyridin-2-yl)-pyrrolidin-3-yl]-methyl-carbamic acid tert-butyl ester. LCMS calcd for C26H28F3N5O4 (m/e) 531.5, obsd 532.2 (M+H).

Example 91

Preparation of 2-phenyl-5-trifluoromethyl-oxazole-4-carboxylic acid {6-[(R)-3-(acetyl-methyl-amino)-pyrrolidin-1-yl]-pyridin-3-yl}-amide

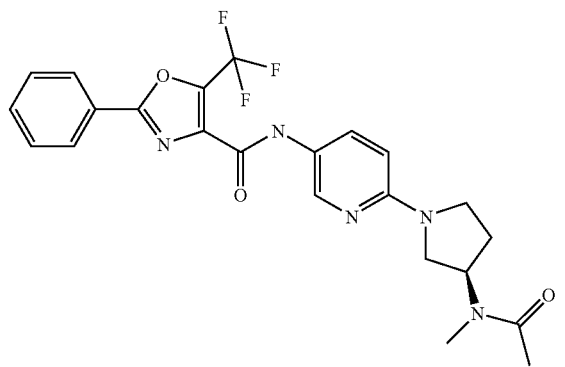

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 2-phenyl-5-trifluoromethyl-oxazole-4-carboxylic acid {6-[(R)-3-(acetyl-methyl-amino)-pyrrolidin-1-yl]-pyridin-3-yl}-amide was prepared from 2-phenyl-5-trifluoromethyl-oxazole-4-carboxylic acid and racemic N-[1-(5-amino-pyridin-2-yl)-pyrrolidin-3-yl]-N-methyl-acetamide followed by chiral SFC. LCMS calcd for C23H22F3N5O3 (m/e) 473.45, obsd 474.17 (M+H). [α]$_D$=−15.2

Example 92

Preparation of rac-1-{5-[(2-phenyl-5-trifluoromethyl-oxazole-4-carbonyl)-amino]-pyridin-2-yl}-pyrrolidine-3-carboxylic acid methyl ester

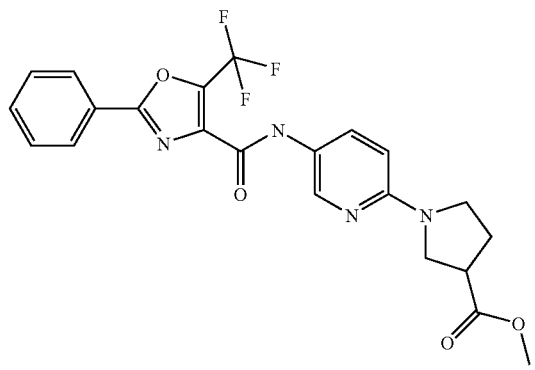

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, racemic 1-{5-[(2-phenyl-5-trifluoromethyl-oxazole-4-carbonyl)-amino]-pyridin-2-yl}-pyrrolidine-3-carboxylic acid methyl ester was prepared from 2-phenyl-5-trifluoromethyl-oxazole-4-carboxylic acid and racemic 1-(5-amino-pyridin-2-yl)-pyrrolidine-3-carboxylic acid methyl ester. LCMS calcd for C22H19F3N4O4 (m/e) 460.4, obsd 461.1 (M+H).

Example 93

Preparation of 5'-[(2-phenyl-5-trifluoromethyl-oxazole-4-carbonyl)-amino]-3,4,5,6-tetrahydro-2H-[1,2']bipyridinyl-4-carboxylic acid ethyl ester

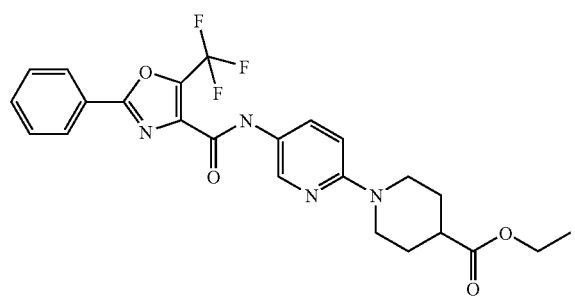

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 5'-[(2-phenyl-5-trifluoromethyl-oxazole-4-carbonyl)-amino]-3,4,5,6-tetrahydro-2H-[1,2']bipyridinyl-4-carboxylic acid ethyl ester was prepared from 2-phenyl-5-trifluoromethyl-oxazole-4-carboxylic acid and 5'-amino-3,4, 5,6-tetrahydro-2H-[1,2']bipyridinyl-4-carboxylic acid ethyl ester. LCMS calcd for C24H23F3N4O4 (m/e) 488.46, obsd 489.17 (M+H).

Example 94

Preparation of (1S,3S)-3-{5-[(2-phenyl-5-trifluoromethyl-oxazole-4-carbonyl)-amino]-pyridin-2-ylamino}-cyclopentanecarboxylic acid methyl ester

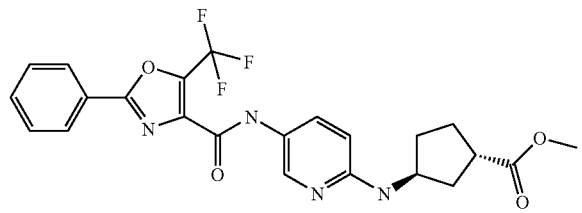

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (1S,3S)-3-{5-[(2-phenyl-5-trifluoromethyl-oxazole-4-carbonyl)-amino]-pyridin-2-ylamino}-cyclopentanecarboxylic acid methyl ester was prepared from 2-phenyl-5-trifluoromethyl-oxazole-4-carboxylic acid and (1S,3S)-3-(5-amino-pyridin-2-ylamino)-cyclopentanecarboxylic acid methyl ester. LCMS calcd for C23H21F3N4O4 (m/e) 474.44, obsd 475.16 (M+H).

Example 95

Preparation of (1R,3S)-3-{5-[(2-phenyl-5-trifluoromethyl-oxazole-4-carbonyl)-amino]-pyridin-2-ylamino}-cyclopentanecarboxylic acid ethyl ester

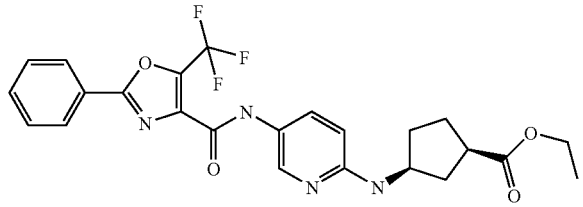

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (1R,3S)-3-{5-[(2-phenyl-5-trifluoromethyl-oxazole-4-carbonyl)-amino]-pyridin-2-ylamino}-cyclopentanecarboxylic acid ethyl ester was prepared from 2-phenyl-5-trifluoromethyl-oxazole-4-carboxylic acid and (1R,3S)-3-(5-amino-pyridin-2-ylamino)-cyclopentanecarboxylic acid ethyl ester. LCMS calcd for C24H23F3N4O4 (m/e) 488.46, obsd 489.17 (M+H).

Example 96

Preparation of (S)-3-{5-[(2-phenyl-5-trifluoromethyl-oxazole-4-carbonyl)-amino]-pyrimidin-2-ylamino}-pyrrolidine-1-carboxylic acid tert-butyl ester

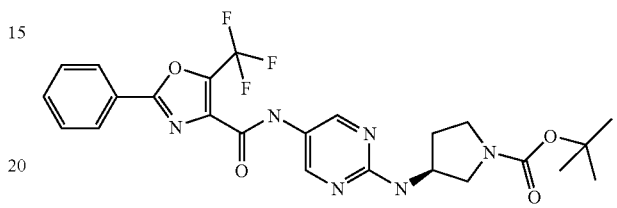

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-{5-[(2-phenyl-5-trifluoromethyl-oxazole-4-carbonyl)-amino]-pyrimidin-2-ylamino}-pyrrolidine-1-carboxylic acid tert-butyl ester was prepared from 2-phenyl-5-trifluoromethyl-oxazole-4-carboxylic acid and (S)-3-(5-amino-pyrimidin-2-ylamino)-pyrrolidine-1-carboxylic acid tert-butyl ester. LCMS calcd for C24H25F3N6O4 (m/e) 518.49, obsd 519.2 (M+H).

Example 97

Preparation of 2-phenyl-5-trifluoromethyl-oxazole-4-carboxylic acid [6-((1S,3R)-3-dimethylcarbamoyl-cyclopentylamino)-pyridin-3-yl]-amide

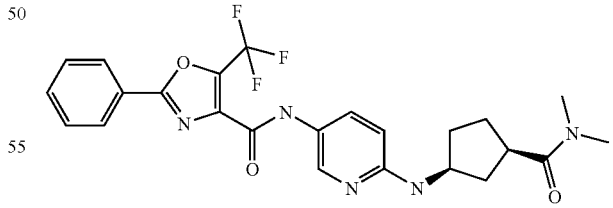

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 2-phenyl-5-trifluoromethyl-oxazole-4-carboxylic acid [6-((1S,3R)-3-dimethylcarbamoyl-cyclopentylamino)-pyridin-3-yl]-amide was prepared from (1R,3S)-3-{5-[(2-phenyl-5-trifluoromethyl-oxazole-4-carbonyl)-amino]-pyridin-2-ylamino}-cyclopentanecarboxylic acid and dimethylamine hydrochloride. LCMS calcd for C24H24F3N5O3 (m/e) 487.48, obsd 488.19 (M+H).

Example 98

Preparation of 2-phenyl-5-trifluoromethyl-oxazole-4-carboxylic acid [6-((1S,3S)-3-dimethylcarbamoyl-cyclopentylamino)-pyridin-3-yl]-amide

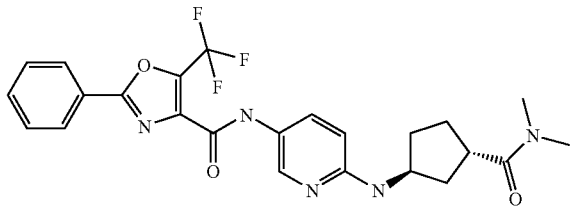

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 2-phenyl-5-trifluoromethyl-oxazole-4-carboxylic acid [6-((1S,3S)-3-dimethylcarbamoyl-cyclopentylamino)-pyridin-3-yl]-amide was prepared from (1S,3S)-3-{5-[(2-phenyl-5-trifluoromethyl-oxazole-4-carbonyl)-amino]-pyridin-2-ylamino}-cyclopentanecarboxylic acid and dimethylamine hydrochloride. LCMS calcd for C24H24F3N5O3 (m/e) 487.48, obsd 488.19 (M+H).

Example 99

Preparation of 5'-[(2-phenyl-5-trifluoromethyl-oxazole-4-carbonyl)-amino]-3,4,5,6-tetrahydro-2H-[1,2']bipyridinyl-4-carboxylic acid dimethylamide

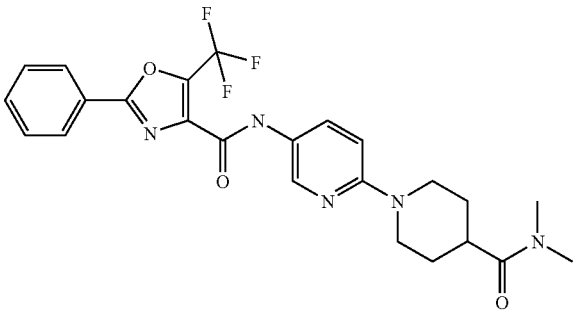

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 5'-[(2-phenyl-5-trifluoromethyl-oxazole-4-carbonyl)-amino]-3,4,5,6-tetrahydro-2H-[1,2']bipyridinyl-4-carboxylic acid dimethylamide was prepared from 5'-[(2-phenyl-5-trifluoromethyl-oxazole-4-carbonyl)-amino]-3,4,5,6-tetrahydro-2H-[1,2']bipyridinyl-4-carboxylic acid and dimethylamine hydrochloride. LCMS calcd for C24H24F3N5O3 (m/e) 487.48, obsd 488.19 (M+H).

Example 100

Preparation of racemic trans-2-{4'-[(2-phenyl-5-trifluoromethyl-oxazole-4-carbonyl)-amino]-biphenyl-4-carbonyl}-cyclopentanecarboxylic acid

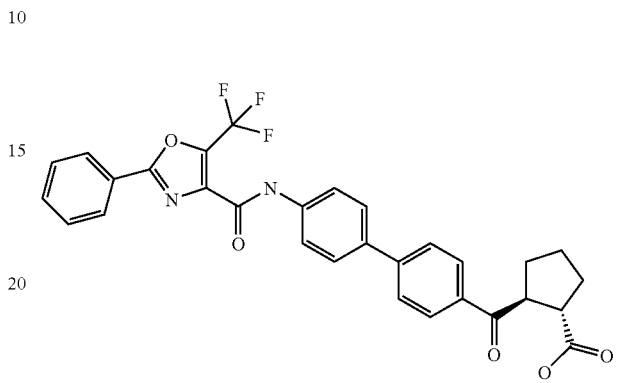

To a solution of 2-phenyl-5-trifluoromethyl-oxazole-4-carboxylic acid (0.25 g, 1 mmol) and bromo-tris-pyrrolidino-phosphonium hexafluorophosphate (0.47 g, 1 mmol) in methylene chloride was added racemic trans-2-(4'-amino-biphenyl-4-carbonyl)-cyclopentanecarboxylic acid (0.20 g, 0.78 mmol) and diisopropylethylamine (0.35 mL, 2 mmol). The mixture was stirred at ambient temperature for 3 h. The reaction mixture was concentrated and the residue was re-dissolved in DMSO and acetonitrile. HPLC reverse phase purification with acetonitrile and water afforded 44 mg of racemic trans-2-{4'-[(2-phenyl-5-trifluoromethyl-oxazole-4-carbonyl)-amino]-biphenyl-4-carbonyl}-cyclopentanecarboxylic acid as a white solid. LCMS calcd for C30H23F3N2O5 (m/e) 548, obsd 549 (M+H).

Example 101

Preparation of (1R,2R)-2-{4'-[(2-phenyl-5-trifluoromethyl-oxazole-4-carbonyl)-amino]-biphenyl-4-carbonyl}-cyclopentanecarboxylic acid (or enantiomer)

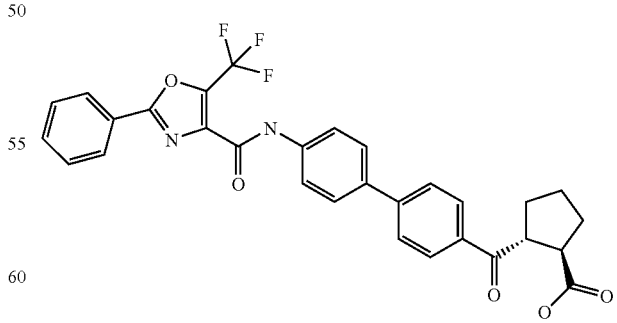

Racemic trans-2-{4'-[(2-phenyl-5-trifluoromethyl-oxazole-4-carbonyl)-amino]-biphenyl-4-carbonyl}-cyclopentanecarboxylic acid from above was separated by chiral SFC to afford (1R,2R)-2-{4'-[(2-phenyl-5-trifluoromethyl-oxazole-4-carbonyl)-amino]-biphenyl-4-carbonyl}-cyclopentanecarboxylic acid (or enantiomer). [α]_D: −36.7° in CHCl_3.

Example 102

Preparation of (1S,2S)-2-{4'-[(2-phenyl-5-trifluoromethyl-oxazole-4-carbonyl)-amino]-biphenyl-4-carbonyl}-cyclopentanecarboxylic acid (or enantiomer)

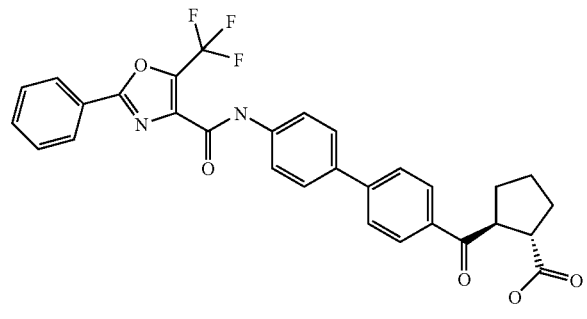

Racemic trans-2-{4'-[(2-phenyl-5-trifluoromethyl-oxazole-4-carbonyl)-amino]-biphenyl-4-carbonyl}-cyclopentanecarboxylic acid from above was separated by chiral SFC to afford (1S,2S)-2-{4'-[(2-phenyl-5-trifluoromethyl-oxazole-4-carbonyl)-amino]-biphenyl-4-carbonyl}-cyclopentanecarboxylic acid (or enantiomer). [α]_D: +37.6° in CHCl_3.

Example 103

Preparation of (1R,2R)-2-{4'-[(2-phenyl-5-trifluoromethyl-oxazole-4-carbonyl)-amino]-biphenyl-4-carbonyl}-cyclohexanecarboxylic acid (or enantiomer)

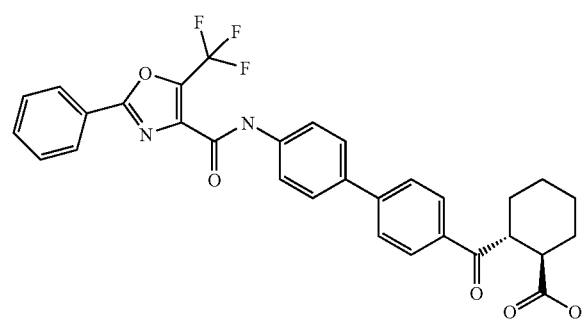

With a method similar to that used for the preparation of racemic trans-2-{4'-[(2-phenyl-5-trifluoromethyl-oxazole-4-carbonyl)-amino]-biphenyl-4-carbonyl}-cyclopentanecarboxylic acid above, racemic 2-{4'-[(2-phenyl-5-trifluoromethyl-oxazole-4-carbonyl)-amino]-biphenyl-4-carbonyl}-cyclohexanecarboxylic acid was prepared from 2-phenyl-5-trifluoromethyl-oxazole-4-carboxylic acid and racemic trans-2-(4'-amino-biphenyl-4-carbonyl)-cyclohexanecarboxylic acid. The racemic product obtained was separated by chiral SFC to afford (1R,2R)-2-{4'-[(2-phenyl-5-trifluoromethyl-oxazole-4-carbonyl)-amino]-biphenyl-4-carbonyl}- cyclohexanecarboxylic acid (or enantiomer). [α]_D: +25.4° in DMSO. LCMS calcd for C31H25F3N2O5 (m/e) 562, obsd 563 (M+H).

Example 104

Preparation of (1S,2S)-2-{4'-[(2-phenyl-5-trifluoromethyl-oxazole-4-carbonyl)-amino]-biphenyl-4-carbonyl}-cyclohexanecarboxylic acid (or enantiomer)

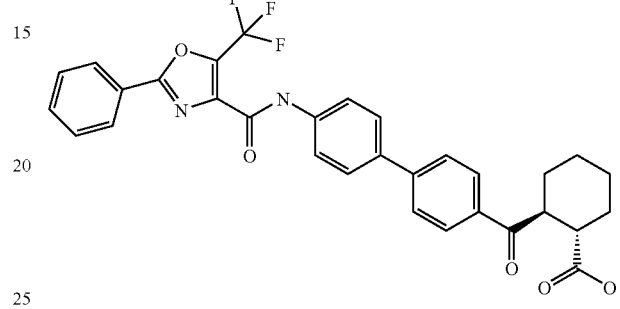

With a method similar to that used for the preparation of racemic trans-2-{4'-[(2-phenyl-5-trifluoromethyl-oxazole-4-carbonyl)-amino]-biphenyl-4-carbonyl}-cyclopentanecarboxylic acid above, racemic 2-{4'-[(2-phenyl-5-trifluoromethyl-oxazole-4-carbonyl)-amino]-biphenyl-4-carbonyl}-cyclohexanecarboxylic acid was prepared from 2-phenyl-5-trifluoromethyl-oxazole-4-carboxylic acid and racemic trans-2-(4'-amino-biphenyl-4-carbonyl)-cyclohexanecarboxylic acid. The racemic product obtained was separated by chiral SFC to afford (1S,2S)-2-{4'-[(2-phenyl-5-trifluoromethyl-oxazole-4-carbonyl)-amino]-biphenyl-4-carbonyl}-cyclohexanecarboxylic acid (or enantiomer). [α]_D: −23° in DMSO. LCMS calcd for C31H25F3N2O5 (m/e) 562, obsd 563 (M+H).

Example 105

Preparation of (1R,2S)-2-{4'-[(2-phenyl-5-trifluoromethyl-oxazole-4-carbonyl)-amino]-biphenyl-4-carbonyl}-cyclohexanecarboxylic acid (or enantiomer)

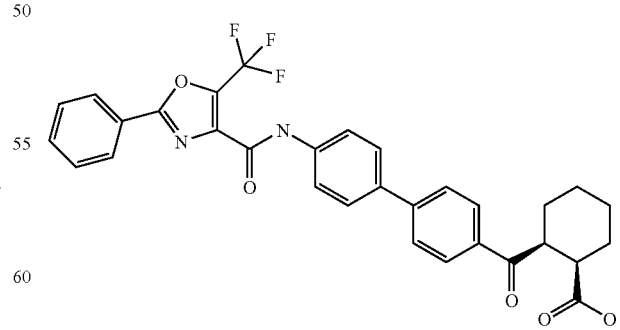

With a method similar to that used for the preparation of racemic trans-2-{4'-[(2-phenyl-5-trifluoromethyl-oxazole-4-carbonyl)-amino]-biphenyl-4-carbonyl}-cyclopentanecarboxylic acid above, racemic 2-{4'-[(2-phenyl-5-trifluoromethyl-oxazole-4-carbonyl)-amino]-biphenyl-4-carbonyl}-cyclohexanecarboxylic acid was prepared from 2-phenyl-5-trifluoromethyl-oxazole-4-carboxylic acid and racemic cis-2-(4'-amino-biphenyl-4-carbonyl)-cyclohexanecarboxylic acid. The racemic product was separated by chiral SFC to afford (1R,2S)-2-{4'-[(2-phenyl-5-trifluoromethyl-oxazole-4-carbonyl)-amino]-biphenyl-4-carbonyl}-cyclohexanecarboxylic acid (or enantiomer). [α]$_D$: +11.7° in DMSO. LCMS calcd for C31H25F3N2O5 (m/e) 562, obsd 563 (M+H).

Example 106

Preparation of (1S,2R)-2-{4'-[(2-phenyl-5-trifluoromethyl-oxazole-4-carbonyl)-amino]-biphenyl-4-carbonyl}-cyclohexanecarboxylic acid (or enantiomer)

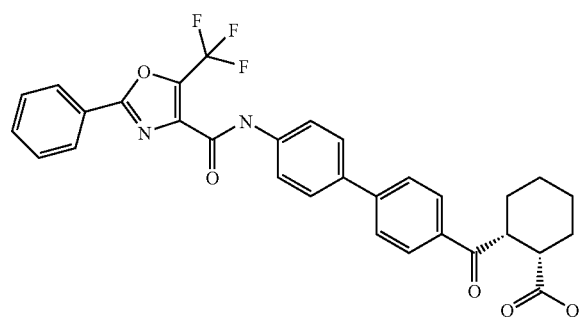

With a method similar to that used for the preparation of racemic trans-2-{4'-[(2-phenyl-5-trifluoromethyl-oxazole-4-carbonyl)-amino]-biphenyl-4-carbonyl}-cyclopentanecarboxylic acid above, racemic 2-{4'-[(2-phenyl-5-trifluoromethyl-oxazole-4-carbonyl)-amino]-biphenyl-4-carbonyl}-cyclohexanecarboxylic acid was prepared from 2-phenyl-5-trifluoromethyl-oxazole-4-carboxylic acid and cis-2-(4'-amino-biphenyl-4-carbonyl)-cyclohexanecarboxylic acid. The racemic product was separated by chiral SFC to afford (1S,2R)-2-{4'-[(2-phenyl-5-trifluoromethyl-oxazole-4-carbonyl)-amino]-biphenyl-4-carbonyl}-cyclohexanecarboxylic acid (or enantiomer). [α]$_D$: −23.8° in DMSO. LCMS calcd for C31H25F3N2O5 (m/e) 562, obsd 563 (M+H).

Example 107

Preparation of 2,2-dimethyl-3-{5'-[(2-phenyl-5-trifluoromethyl-oxazole-4-carbonyl)-amino]-3,4,5,6-tetrahydro-2H-[1,2']bipyridinyl-4-yl}-propionic acid

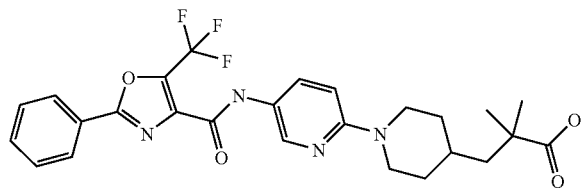

To a suspension of 2,2-dimethyl-3-(5'-nitro-3,4,5,6-tetrahydro-2H-[1,2']bipyridinyl-4-yl)-propionic acid (153.5 mg, 0.5 mmol) in methanol (30 mL) and tetrahydrofuran (5 mL) was added 0% of palladium on carbon (30 mg). The mixture was hydrogenated at 50 psi for 2 hrs. The mixture was filtered and the solvents were evaporated. The resulting aminopyridine derivative was reacted with 2-phenyl-5-trifluoromethyl-oxazole-4-carbonyl chloride (prepared from the corresponding carboxylic acid (128.5 mg, 0.5 mmol), oxalyl chloride and catalytic amount of N,N-dimethylformamide) at room temperature. After concentration, the residue was partitioned between methylene chloride and water. The organic layer was washed with aqueous citric acid solution and dried over sodium sulfate. The solvents were evaporated and the residue was dried in vacuum. The crude product was triturated with methanol (4 mL) and the solid was filtered to give 2,2-dimethyl-3-{5'-[(2-phenyl-5-trifluoromethyl-oxazole-4-carbonyl)-amino]-3,4,5,6-tetrahydro-2H-[1,2']bipyridinyl-4-yl}-propionic acid (87 mg). LC-MS calcd. For C26H27F3N4O4 (m/e) 516.1984, obsd 517.1 (M+H). The NMR spectrum obtained on the sample is compatible with its structure.

Example 108

Preparation of rac-2-(4-{4-[(2-phenyl-5-trifluoromethyl-oxazole-4-carbonyl)-amino]-phenyl}-piperazine-1-carbonyl)-cyclopentanecarboxylic acid

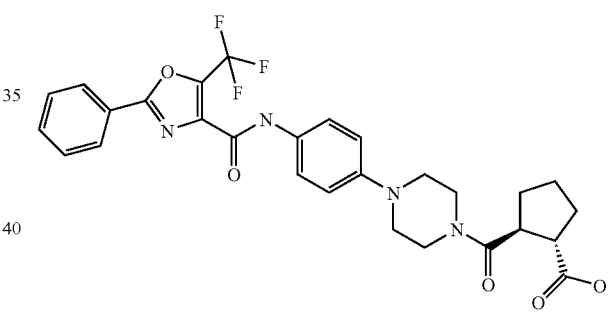

To a solution of racemic 2-(4-{4-[(2-phenyl-5-trifluoromethyl-oxazole-4-carbonyl)-amino]-phenyl}-piperazine-1-carbonyl)-cyclopentanecarboxylic acid ethyl ester (100 mg, 0.171 mmol) in 10 mL ethanol was added a solution of lithium hydroxide (14 mg, 0.342 mmol) in 5 mL water. The reaction mixture was stirred at room temperature for 4 hrs and then heated to 50° C. for 1 hr. The reaction mixture was cooled, diluted with water, and washed with diethyl ether. The pH of the aqueous layer was adjusted to pH 5 with 1N hydrochloric acid and extracted with ethyl acetate. The ethyl acetate layers were dried over magnesium sulfate, filtered and evaporated to dryness. The residue was purified by flash chromatography (eluted with ethyl acetate/methylene chloride) to yield rac-2-(4-{4-[(2-phenyl-5-trifluoromethyl-oxazole-4-carbonyl)-amino]-phenyl}-piperazine-1-carbonyl)-cyclopentanecarboxylic acid (27 mg, 28%). ES-MS calcd for C28H27F3N4O5 (m/e) 556.54, obsd 557.1 (M+H).

Example 109

Preparation of (1R,2R)-2-(4-{4-[(2-phenyl-5-trifluoromethyl-oxazole-4-carbonyl)-amino]-phenyl}-piperazine-1-carbonyl)-cyclopentanecarboxylic acid

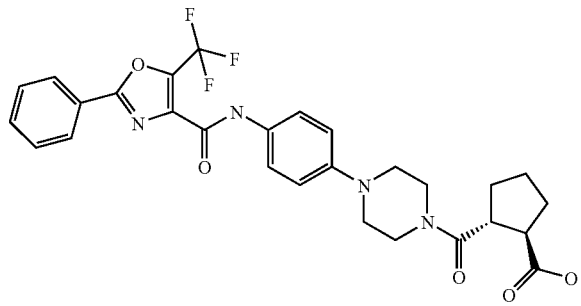

The racemic mixture of 2-(4-{4-[(2-phenyl-5-trifluoromethyl-oxazole-4-carbonyl)-amino]-phenyl}-piperazine-1-carbonyl)-cyclopentanecarboxylic acid described above was purified by chiral supercritical fluid chromatography (first eluting peak) to yield (1R,2R)-2-(4-{4-[(2-phenyl-5-trifluoromethyl-oxazole-4-carbonyl)-amino]-phenyl}-piperazine-1-carbonyl)-cyclopentanecarboxylic acid as an off-white solid. ES-MS calcd for C28H27F3N4O5 (m/e) 556.54, obsd 557 (M+H); $[\alpha]_D$ −16.7°.

Example 110

Preparation of (1S,2S)-2-(4-{4-[(2-phenyl-5-trifluoromethyl-oxazole-4-carbonyl)-amino]-phenyl}-piperazine-1-carbonyl)-cyclopentanecarboxylic acid

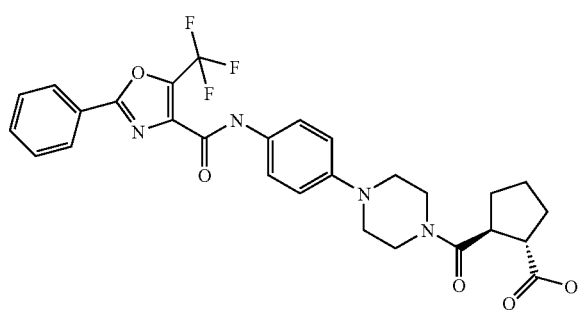

The racemic mixture of 2-(4-{4-[(2-phenyl-5-trifluoromethyl-oxazole-4-carbonyl)-amino]-phenyl}-piperazine-1-carbonyl)-cyclopentanecarboxylic acid described above was purified by chiral supercritical fluid chromatography (second eluting peak) to yield (S,S)-2-(4-{4-[(2-phenyl-5-trifluoromethyl-oxazole-4-carbonyl)-amino]-phenyl}-piperazine-1-carbonyl)-cyclopentanecarboxylic acid as an off-white solid. ES-MS calcd for C28H27F3N4O5 (m/e) 556.54, obsd 557 (M+H); $[\alpha]_D$ +16.7°.

Example 111

Preparation of 4-(4-{4-[(2-phenyl-5-trifluoromethyl-oxazole-4-carbonyl)-amino]-phenyl}-piperazine-1-carbonyl)-cyclohexanecarboxylic acid

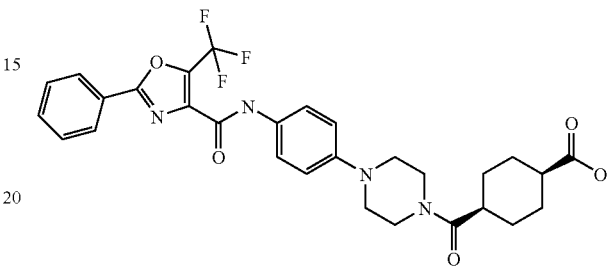

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid above, 4-(4-{4-[(2-phenyl-5-trifluoromethyl-oxazole-4-carbonyl)-amino]-phenyl}-piperazine-1-carbonyl)-cyclohexanecarboxylic acid was prepared from 4-(4-{4-[(2-phenyl-5-trifluoromethyl-oxazole-4-carbonyl)-amino]-phenyl}-piperazine-1-carbonyl)-cyclohexanecarboxylic acid methyl ester and lithium hydroxide. ES-MS calcd for C29H29F3N4O5 (m/e) 570.57, obsd 571.2 (M+H).

Example 112

Preparation of (1R,3S)-3-(4-{4-[(2-phenyl-5-trifluoromethyl-oxazole-4-carbonyl)-amino]-phenyl}-piperazine-1-carbonyl)-cyclohexanecarboxylic acid

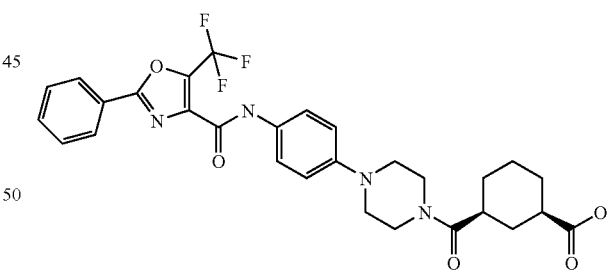

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid above, racemic 3-(4-{4-[(2-phenyl-5-trifluoromethyl-oxazole-4-carbonyl)-amino]-phenyl}-piperazine-1-carbonyl)-cyclohexanecarboxylic acid was prepared from 3-(4-{4-[(2-phenyl-5-trifluoromethyl-oxazole-4-carbonyl)-amino]-phenyl}-piperazine-1-carbonyl)-cyclohexanecarboxylic acid methyl ester and lithium hydroxide. The crude racemate was purified by chiral supercritical fluid chromatography to yield (1R,3S)-3-(4-{4-[(2-phenyl-5-trifluoromethyl-oxazole-4-carbonyl)-amino]-phenyl}-piperazine-1-carbonyl)-cyclohexanecarboxylic acid as an off-white solid (first eluting peak). ES-MS calcd for C29H29F3N4O5 (m/e) 570.57, obsd 571.1 (M+H).

Example 113

Preparation of (1S,3R)-3-(4-{4-[(2-phenyl-5-trifluoromethyl-oxazole-4-carbonyl)-amino]-phenyl}-piperazine-1-carbonyl)-cyclohexanecarboxylic acid

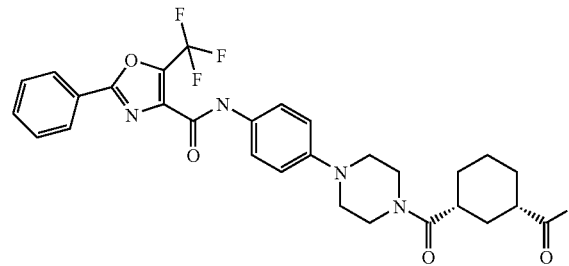

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid above, racemic 3-(4-{4-[(2-phenyl-5-trifluoromethyl-oxazole-4-carbonyl)-amino]-phenyl}-piperazine-1-carbonyl)-cyclohexanecarboxylic acid was prepared from 3-(4-{4-[(2-phenyl-5-trifluoromethyl-oxazole-4-carbonyl)-amino]-phenyl}-piperazine-1-carbonyl)-cyclohexanecarboxylic acid methyl ester and lithium hydroxide. The crude racemate was purified by chiral supercritical fluid chromatography (second eluting peak) to yield (1S,3R)-3-(4-{4-[(2-phenyl-5-trifluoromethyl-oxazole-4-carbonyl)-amino]-phenyl}-piperazine-1-carbonyl)-cyclohexanecarboxylic acid as an off-white solid. ES-MS calcd for C29H29F3N4O5 (m/e) 570.57, obsd 571.1 (M+H).

Example 114

Preparation of (1-{4-[(2-phenyl-5-trifluoromethyl-oxazole-4-carbonyl)-amino]-phenyl}-piperidin-4-yl)-acetic acid

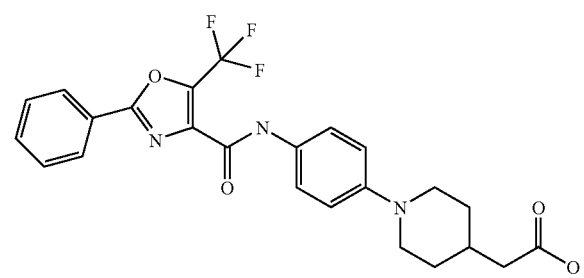

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid above, (1-{4-[(2-phenyl-5-trifluoromethyl-oxazole-4-carbonyl)-amino]-phenyl}-piperidin-4-yl)-acetic acid was prepared from (1-{4-[(2-phenyl-5-trifluoromethyl-oxazole-4-carbonyl)-amino]-phenyl}-piperidin-4-yl)-acetic acid ethyl ester and lithium hydroxide. LC-MS calcd for C24H22F3N3O4 (m/e) 473.2, obsd 474.0 (M+H). The NMR spectrum obtained on the sample is compatible with its structure.

Example 115

Preparation of {5'-[(2-phenyl-5-trifluoromethyl-oxazole-4-carbonyl)-amino]-3,4,5,6-tetrahydro-2H-[1,2']bipyridinyl-4-yl}-acetic acid

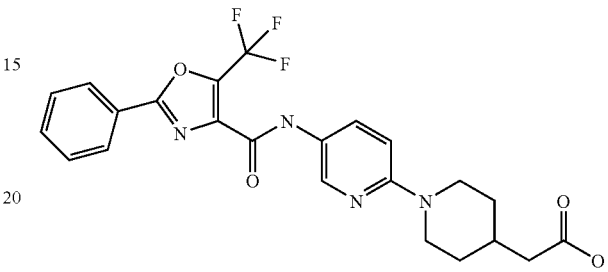

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid above, {5'-[(2-phenyl-5-trifluoromethyl-oxazole-4-carbonyl)-amino]-3,4,5,6-tetrahydro-2H-[1,2']bipyridinyl-4-yl}-acetic acid was prepared from {5'-[(2-phenyl-5-trifluoromethyl-oxazole-4-carbonyl)-amino]-3,4,5,6-tetrahydro-2H-[1,2']bipyridinyl-4-yl}-acetic acid ethyl ester and lithium hydroxide. LC-MS calcd for C23H21F3N4O4 (m/e) 474.2, obsd 475.1 (M+H). The NMR spectrum obtained on the sample is compatible with its structure.

Example 116

Preparation of rac-2-[(4-{4-[(2-phenyl-5-trifluoromethyl-oxazole-4-carbonyl)-amino]-phenyl}-piperazine-1-carbonyl)-amino]-cyclopentanecarboxylic acid

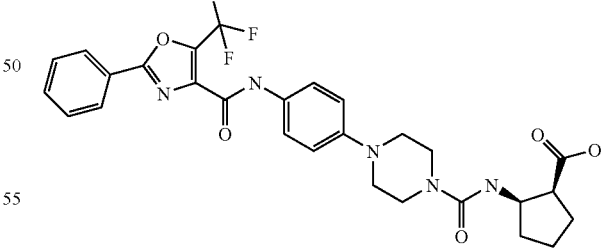

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid above, racemic 2-[(4-{4-[(2-phenyl-5-trifluoromethyl-oxazole-4-carbonyl)-amino]-phenyl}-piperazine-1-carbonyl)-amino]-cyclopentanecarboxylic acid was prepared from racemic 2-[(4-{4-[(2-phenyl-5-trifluoromethyl-oxazole-4-carbonyl)-amino]-phenyl}-piperazine-1-carbonyl)-amino]-cyclopentanecarboxylic acid methyl ester and lithium hydroxide. LC-MS calcd for C28H28F3N5O5 (m/e) 571.6, obsd 572 (M+H).

Example 117

Preparation of rac-1-(4-{4-[(2-phenyl-5-trifluoromethyl-oxazole-4-carbonyl)-amino]-phenyl}-piperazine-1-carbonyl)-pyrrolidine-3-carboxylic acid

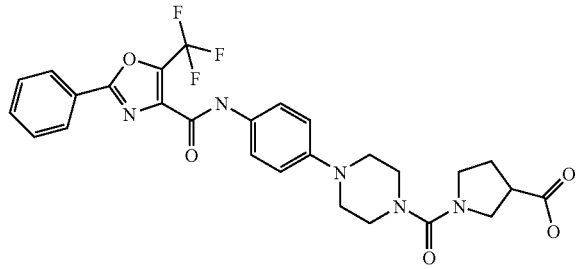

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid above, racemic 1-(4-{4-[(2-phenyl-5-trifluoromethyl-oxazole-4-carbonyl)-amino]-phenyl}-piperazine-1-carbonyl)-pyrrolidine-3-carboxylic acid was prepared from racemic 1-(4-{4-[(2-phenyl-5-trifluoromethyl-oxazole-4-carbonyl)-amino]-phenyl}-piperazine-1-carbonyl)-pyrrolidine-3-carboxylic acid methyl ester and lithium hydroxide. LC-MS calcd for C27H26F3N5O5 (m/e) 557.5, obsd 558.1 (M+H).

Example 118

Preparation of (1S,3S)-3-{5-[(2-phenyl-5-trifluoromethyl-oxazole-4-carbonyl)-amino]-pyridin-2-ylamino}-cyclopentanecarboxylic acid

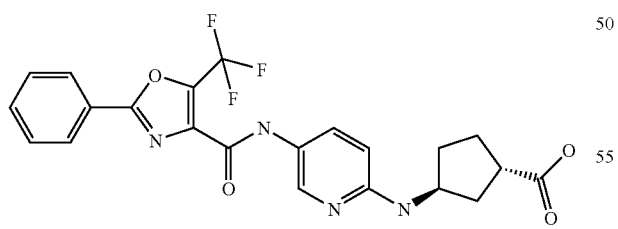

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid above, (1S,3S)-3-{5-[(2-phenyl-5-trifluoromethyl-oxazole-4-carbonyl)-amino]-pyridin-2-ylamino}-cyclopentanecarboxylic acid was prepared from (1S,3S)-3-{5-[(2-phenyl-5-trifluoromethyl-oxazole-4-carbonyl)-amino]-pyridin-2-ylamino}-cyclopentanecarboxylic acid methyl ester and lithium hydroxide. LCMS calcd for C22H19F3N4O4 (m/e) 460.41, obsd 461.14 (M+H).

Example 119

Preparation of (1R,3S)-3-{5-[(2-Phenyl-5-trifluoromethyl-oxazole-4-carbonyl)-amino]-pyridin-2-ylamino}-cyclopentanecarboxylic acid

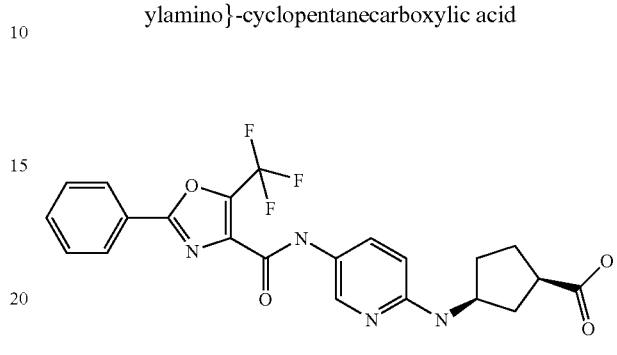

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid above, (1R,3S)-3-{5-[(2-phenyl-5-trifluoromethyl-oxazole-4-carbonyl)-amino]-pyridin-2-ylamino}-cyclopentanecarboxylic acid was prepared from (1R,3S)-3-{5-[(2-phenyl-5-trifluoromethyl-oxazole-4-carbonyl)-amino]-pyridin-2-ylamino}-cyclopentanecarboxylic acid methyl ester and lithium hydroxide. LCMS calcd for C22H19F3N4O4 (m/e) 460.41, obsd 461.14 (M+H).

Example 120

Preparation of 5'-[(2-phenyl-5-trifluoromethyl-oxazole-4-carbonyl)-amino]-3,4,5,6-tetrahydro-2H-[1,2']bipyridinyl-4-carboxylic acid

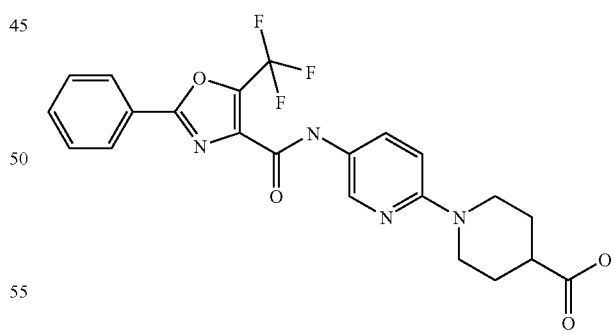

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid above, 5'-[(2-phenyl-5-trifluoromethyl-oxazole-4-carbonyl)-amino]-3,4,5,6-tetrahydro-2H-[1,2']bipyridinyl-4-carboxylic acid was prepared from 5'-[(2-phenyl-5-trifluoromethyl-oxazole-4-carbonyl)-amino]-3,4,5,6-tetrahydro-2H-[1,2']bipyridinyl-4-carboxylic acid methyl ester and lithium hydroxide. LCMS calcd for C22H19F3N4O4 (m/e) 460.41, obsd 461.14 (M+H).

Example 121

Preparation of 2,2-dimethyl-4-oxo-4-{4'-[(2-phenyl-5-trifluoromethyl-oxazole-4-carbonyl)-amino]-biphenyl-4-yl}-butyric acid

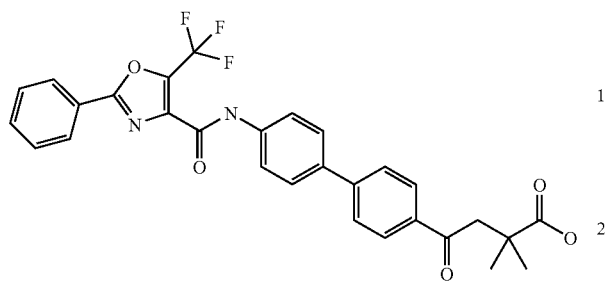

With a method similar to that used for the preparation of rac-2-(4-{4-[(2-phenyl-5-trifluoromethyl-oxazole-4-carbonyl)-amino]-phenyl}-piperazine-1-carbonyl)-cyclopentanecarboxylic acid above, 2,2-dimethyl-4-oxo-4-{4'-[(2-phenyl-5-trifluoromethyl-oxazole-4-carbonyl)-amino]-biphenyl-4-yl}-butyric acid was prepared from 2,2-dimethyl-4-oxo-4-{4'-[(2-phenyl-5-trifluoromethyl-oxazole-4-carbonyl)-amino]-biphenyl-4-yl}-butyric acid methyl ester and lithium hydroxide. LCMS calcd for C29H23F3N2O5 (m/e) 536, obsd 537 (M+H).

Example 122

Preparation of 2-phenyl-5-trifluoromethyl-oxazole-4-carboxylic acid [6-(4-acetyl-piperazin-1-yl)-pyridin-3-yl]-amide

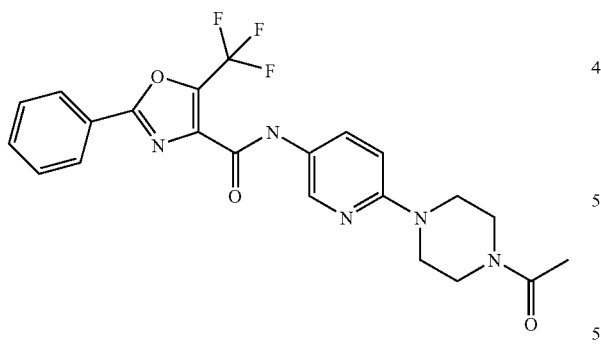

To a suspension of 2-phenyl-5-trifluoromethyl-oxazole-4-carboxylic acid (6-piperazin-1-yl-pyridin-3-yl)-amide hydrochloride salt (65 mg, 0.13 mmol) in methylene chloride (5 mL) was added triethylamine (0.15 mL). The mixture was cooled in an ice bath and acetyl chloride (12 μL) was added. The mixture was stirred at room temperature for 30 minutes and partitioned between methylene chloride and brine. The organic layer was dried over sodium sulfate and the solvents were evaporated. The residue was first dried in vacuum and then triturated with methanol (3 mL) to give 2-phenyl-5-trifluoromethyl-oxazole-4-carboxylic acid [6-(4-acetyl-piperazin-1-yl)-pyridin-3-yl]-amide (21 mg) as a solid. LC-MS calcd for C22H20F3N5O3 (m/e) 459.2, obsd 460.0 (M+H). The NMR spectrum obtained on the sample is compatible with its structure.

Example 123

Preparation of 2-phenyl-5-trifluoromethyl-oxazole-4-carboxylic acid [6-(4-isobutyryl-piperazin-1-yl)-pyridin-3-yl]-amide

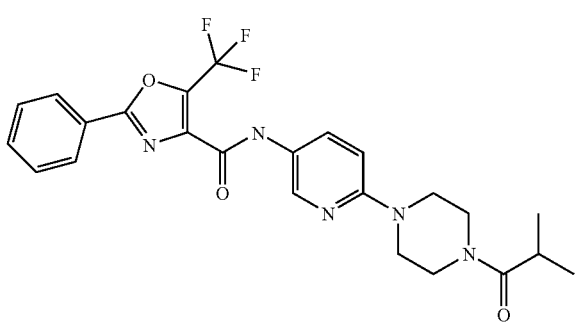

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [6-(4-isobutyryl-piperazin-1-yl)-pyridin-3-yl]-amide was prepared from 2-phenyl-5-trifluoromethyl-oxazole-4-carboxylic acid (6-piperazin-1-yl-pyridin-3-yl)-amide hydrochloride salt and isobutyryl chloride. LC-MS calcd for C24H24F3N5O3 (m/e) 487.2, obsd. 488.1 (M+H). The NMR spectrum obtained on the sample is compatible with its structure.

Example 124

Preparation of 2-phenyl-5-trifluoromethyl-oxazole-4-carboxylic acid [6-(4-cyclopropanecarbonyl-piperazin-1-yl)-pyridin-3-yl]-amide

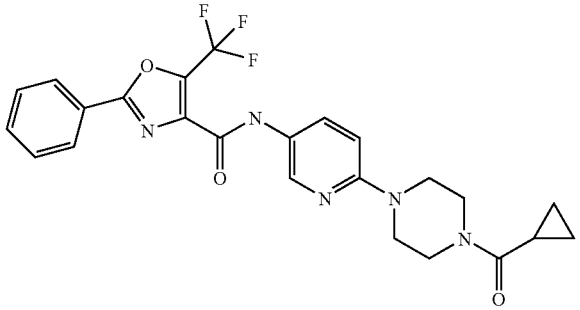

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [6-(4-cyclopropanecarbonyl-piperazin-1-yl)-pyridin-3-yl]-amide was prepared from 2-phenyl-5-trifluoromethyl-oxazole-4-carboxylic acid (6-piperazin-1-yl-pyridin-3-yl)-amide hydrochloride salt and cyclopropanecarbonyl chloride. LC-MS calcd for C24H22F3N5O3 (m/e) 485.2, obsd 486.1 (M+H). The NMR spectrum obtained on the sample is compatible with its structure.

Example 125

Preparation of 2-phenyl-5-trifluoromethyl-oxazole-4-carboxylic acid [6-(4-propionyl-piperazin-1-yl)-pyridin-3-yl]-amide

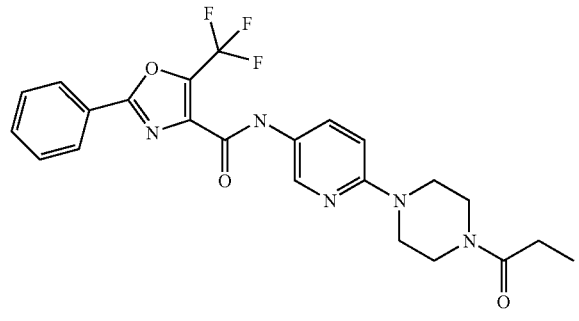

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [6-(4-propionyl-piperazin-1-yl)-pyridin-3-yl]-amide was prepared from 2-phenyl-5-trifluoromethyl-oxazole-4-carboxylic acid (6-piperazin-1-yl-pyridin-3-yl)-amide hydrochloride salt and propionyl chloride. LC-MS calcd for C23H22F3N5O3 (m/e) 473.2, obsd 474.1 (M+H). The NMR spectrum obtained on the sample is compatible with its structure.

Example 126

Preparation of 2-phenyl-5-trifluoromethyl-oxazole-4-carboxylic acid {6-[4-(2,2-dimethyl-propionyl)-piperazin-1-yl]-pyridin-3-yl}-amide

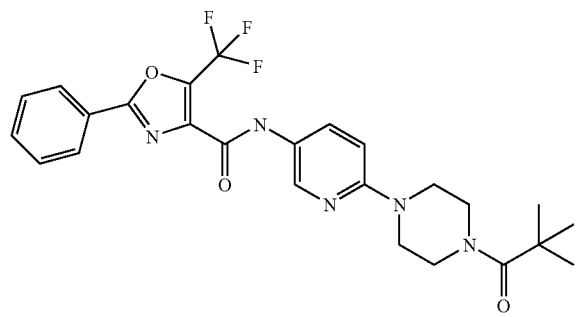

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid {6-[4-(2,2-dimethyl-propionyl)-piperazin-1-yl]-pyridin-3-yl}-amide was prepared from 2-phenyl-5-trifluoromethyl-oxazole-4-carboxylic acid (6-piperazin-1-yl-pyridin-3-yl)-amide hydrochloride salt and pivaloyl chloride. LC-MS calcd for C25H26F3N5O3 (m/e) 501.2, obsd 502.1 (M+H). The NMR spectrum obtained on the sample is compatible with its structure.

Example 127

Preparation of 2-phenyl-5-trifluoromethyl-oxazole-4-carboxylic acid [4-(1-cyclopropanecarbonyl-piperidin-4-yl)-phenyl]-amide

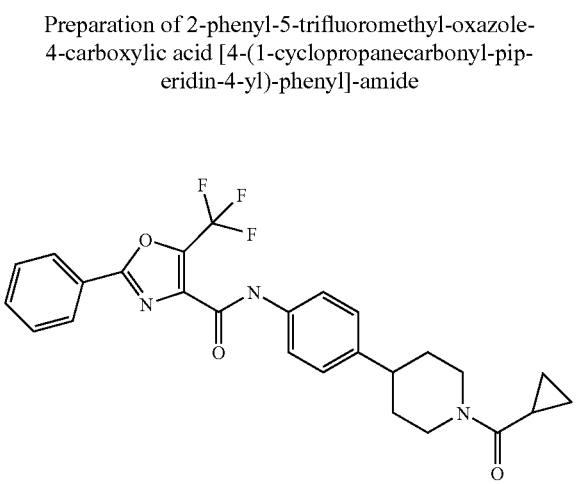

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [4-(1-cyclopropanecarbonyl-piperidin-4-yl)-phenyl]-amide was prepared from 2-phenyl-5-trifluoromethyl-oxazole-4-carboxylic acid (4-piperidin-4-yl-phenyl)-amide and cyclopropanecarbonyl chloride. LC-MS calcd for C26H24F3N3O3 (m/e) 483.2, obsd 484.3 (M+H). The NMR spectrum obtained on the sample is compatible with its structure.

Example 128

Preparation of 2-phenyl-5-trifluoromethyl-oxazole-4-carboxylic acid [6-((S)-1-isobutyryl-pyrrolidin-3-ylamino)-pyridin-3-yl]-amide

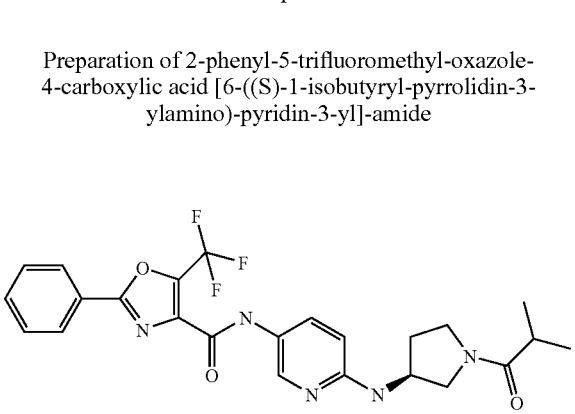

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [6-((S)-1-isobutyryl-pyrrolidin-3-ylamino)-pyridin-3-yl]-amide was prepared from 2-phenyl-5-trifluoromethyl-oxazole-4-carboxylic acid [6-((S)-pyrrolidin-3-ylamino)-pyridin-3-yl]-

Example 129

Preparation of 2-phenyl-5-trifluoromethyl-oxazole-4-carboxylic acid [6-((S)-1-methanesulfonyl-pyrrolidin-3-ylamino)-pyridin-3-yl]-amide

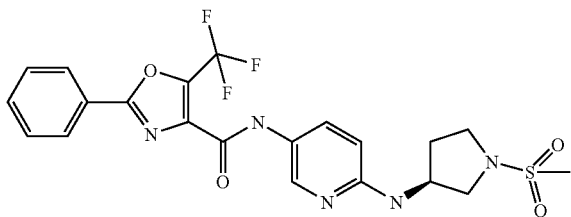

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [6-((S)-1-methanesulfonyl-pyrrolidin-3-ylamino)-pyridin-3-yl]-amide was prepared from 2-phenyl-5-trifluoromethyl-oxazole-4-carboxylic acid [6-((S)-pyrrolidin-3-ylamino)-pyridin-3-yl]-amide and methane sulfonyl chloride. LCMS calcd for C21H20F3N5O4S (m/e) 495.5, obsd 496.1 (M+H).

Example 130

Preparation of rac-2-phenyl-5-trifluoromethyl-oxazole-4-carboxylic acid {6-[3-(isobutyryl-methyl-amino)-pyrrolidin-1-yl]-pyridin-3-yl}-amide

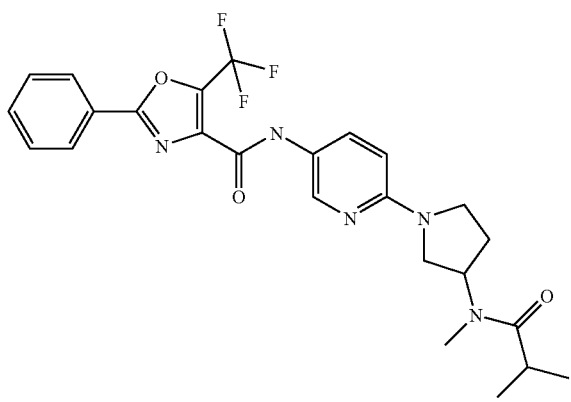

With a method similar to that used for the preparation of 2-phenyl-5-trifluoromethyl-oxazole-4-carboxylic acid [6-(4-acetyl-piperazin-1-yl)-pyridin-3-yl]-amide above, racemic 2-phenyl-5-trifluoromethyl-oxazole-4-carboxylic acid {6-[3-(isobutyryl-methyl-amino)-pyrrolidin-1-yl]-pyridin-3-yl}-amide was prepared from 2-phenyl-5-trifluoromethyl-oxazole-4-carboxylic acid [6-(3-methylamino-pyrrolidin-1-yl)-pyridin-3-yl]-amide and isobutyryl chloride. LCMS calcd for C25H26F3N5O3 (m/e) 501.51, obsd 502.21 (M+H).

Example 131

Preparation of 2-phenyl-5-trifluoromethyl-oxazole-4-carboxylic acid [6-(1-cyclopropanecarbonyl-piperidin-4-ylamino)-pyridin-3-yl]-amide

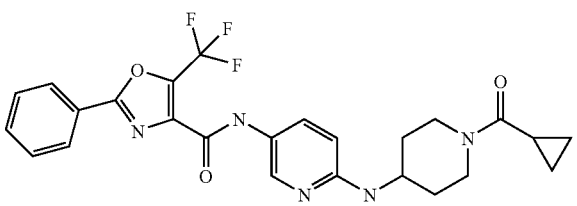

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [6-(1-cyclopropanecarbonyl-piperidin-4-ylamino)-pyridin-3-yl]-amide was prepared from 2-phenyl-5-trifluoromethyl-oxazole-4-carboxylic acid [6-(piperidin-4-ylamino)-pyridin-3-yl]-amide trifluoroacetate and cyclopropanecarbonyl chloride. LCMS calcd for C25H24F3N5O3 (m/e) 499, obsd 500 (M+H).

Example 132

Preparation of 2-phenyl-5-trifluoromethyl-oxazole-4-carboxylic acid [6-(1-phenylacetyl-piperidin-4-ylamino)-pyridin-3-yl]-amide

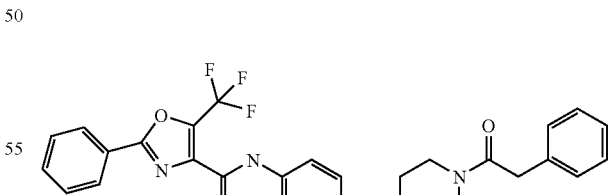

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [6-(1-cyclopropanecarbonyl-piperidin-4-ylamino)-pyridin-3-yl]-amide was prepared from 2-phenyl-5-trifluoromethyl-oxazole-4-carboxylic acid [6-(piperidin-4-ylamino)-pyridin-3-yl]- amide trifluoroacetate and phenyl-acetyl chloride. LCMS calcd for C29H26F3N5O3 (m/e) 549, obsd 550 (M+H).

Example 133

Preparation of 2-phenyl-5-trifluoromethyl-oxazole-4-carboxylic acid {6-[1-(2,2,2-trifluoro-acetyl)-piperidin-4-ylamino]-pyridin-3-yl}-amide

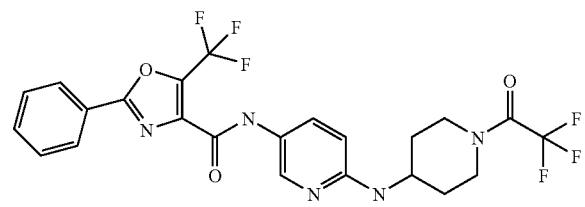

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid {6-[1-(2,2,2-trifluoro-acetyl)-piperidin-4-ylamino]-pyridin-3-yl}-amide was prepared from 2-phenyl-5-trifluoromethyl-oxazole-4-carboxylic acid [6-(piperidin-4-ylamino)-pyridin-3-yl]-amide trifluoroacetate and trifluoroacetic anhydride. LCMS calcd for C23H19F6N5O3 (m/e) 527, obsd 528 (M+H).

Example 134

Preparation of 2-phenyl-5-trifluoromethyl-oxazole-4-carboxylic acid {6-[1-(3,3-dimethyl-butyryl)-piperidin-4-ylamino]-pyridin-3-yl}-amide

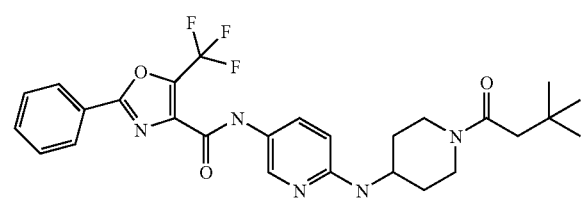

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid {6-[1-(3,3-dimethyl-butyryl)-piperidin-4-ylamino]-pyridin-3-yl}-amide was prepared from 2-phenyl-5-trifluoromethyl-oxazole-4-carboxylic acid [6-(piperidin-4-ylamino)-pyridin-3-yl]-amide trifluoroacetate and 3,3-dimethyl-butyryl chloride. LCMS calcd for C27H30F3N5O3 (m/e) 529, obsd 530 (M+H).

Example 135

Preparation of 2-phenyl-5-trifluoromethyl-oxazole-4-carboxylic acid [6-(1-butyryl-piperidin-4-ylamino)-pyridin-3-yl]-amide

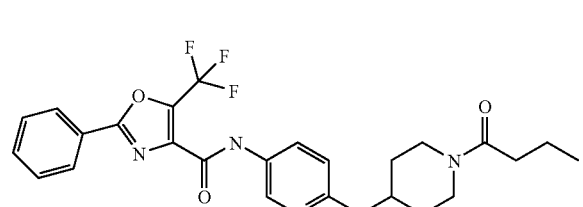

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [6-(1-butyryl-piperidin-4-ylamino)-pyridin-3-yl]-amide was prepared from 2-phenyl-5-trifluoromethyl-oxazole-4-carboxylic acid [6-(piperidin-4-ylamino)-pyridin-3-yl]-amide trifluoroacetate and butyryl chloride. LCMS calcd for C25H26F3N5O3 (m/e) 501, obsd 502 (M+H).

Example 136

Preparation of 2-phenyl-5-trifluoromethyl-oxazole-4-carboxylic acid [6-(1-isobutyryl-piperidin-4-ylamino)-pyridin-3-yl]-amide

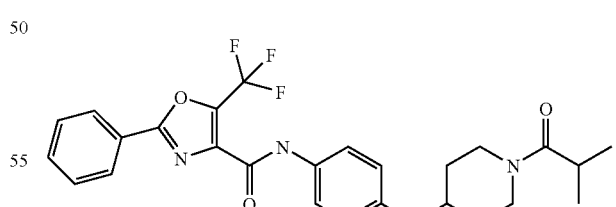

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [6-(1-isobutyryl-piperidin-4-ylamino)-pyridin-3-yl]-amide was prepared from 2-phenyl-5-trifluoromethyl-oxazole-4-carboxylic acid [6-(piperidin-4-ylamino)-pyridin-3-yl]-amide trifluoroacetate and isobutyryl chloride. LCMS calcd for C25H26F3N5O3 (m/e) 501, obsd 502 (M+H).

Example 137

Preparation of 2-phenyl-5-trifluoromethyl-oxazole-4-carboxylic acid [6-(1-propionyl-piperidin-4-ylamino)-pyridin-3-yl]-amide

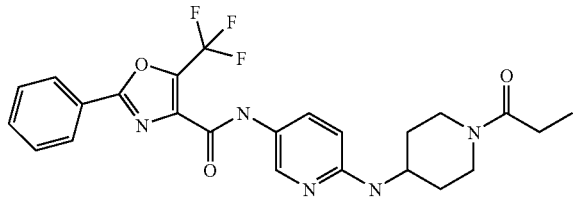

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [6-(1-propionyl-piperidin-4-ylamino)-pyridin-3-yl]-amide was prepared from 2-phenyl-5-trifluoromethyl-oxazole-4-carboxylic acid [6-(piperidin-4-ylamino)-pyridin-3-yl]-amide trifluoroacetate and propionyl chloride. LCMS calcd for C24H24F3N5O3 (m/e) 487, obsd 488 (M+H).

Example 138

Preparation of 2-phenyl-5-trifluoromethyl-oxazole-4-carboxylic acid [6-(1-pentanoyl-piperidin-4-ylamino)-pyridin-3-yl]-amide

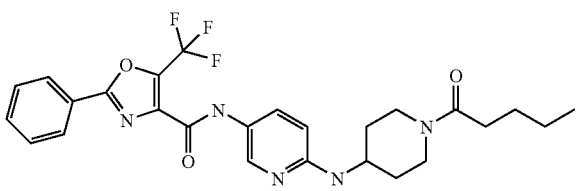

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [6-(1-pentanoyl-piperidin-4-ylamino)-pyridin-3-yl]-amide was prepared from 2-phenyl-5-trifluoromethyl-oxazole-4-carboxylic acid [6-(piperidin-4-ylamino)-pyridin-3-yl]-amide trifluoroacetate and pentanoyl chloride. LCMS calcd for C26H28F3N5O3 (m/e) 515, obsd 516 (M+H).

Example 139

Preparation of 2-phenyl-5-trifluoromethyl-oxazole-4-carboxylic acid {6-[1-(2-cyclopentyl-acetyl)-piperidin-4-ylamino]-pyridin-3-yl}-amide

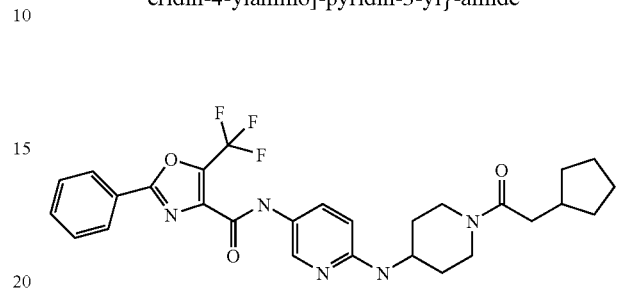

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid {6-[1-(2-cyclopentyl-acetyl)-piperidin-4-ylamino]-pyridin-3-yl}-amide was prepared from 2-phenyl-5-trifluoromethyl-oxazole-4-carboxylic acid [6-(piperidin-4-ylamino)-pyridin-3-yl]-amide trifluoroacetate and cyclopentyl-acetyl chloride. LCMS calcd for C28H30F3N5O3 (m/e) 541, obsd 542 (M+H).

Example 140

Preparation of 2-phenyl-5-trifluoromethyl-oxazole-4-carboxylic acid {6-[1-(3-methyl-butyryl)-piperidin-4-ylamino]-pyridin-3-yl}-amide

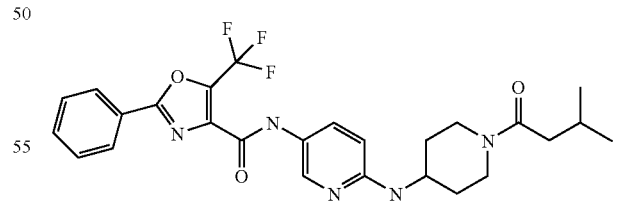

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid {6-[1-(3-methyl-butyryl)-piperidin-4-ylamino]-pyridin-3-yl}-amide was prepared from 2-phenyl-5-trifluoromethyl-oxazole-4-carboxylic acid [6-(piperidin-4-ylamino)-pyridin-3-yl]-amide trifluoroacetate and 3-methyl-butyryl chloride. LCMS calcd for C26H28F3N5O3 (m/e) 515, obsd 516 (M+H).

Example 141

Preparation of 2-phenyl-5-trifluoromethyl-oxazole-4-carboxylic acid {6-[1-(4-methyl-pentanoyl)-piperidin-4-ylamino]-pyridin-3-yl}-amide

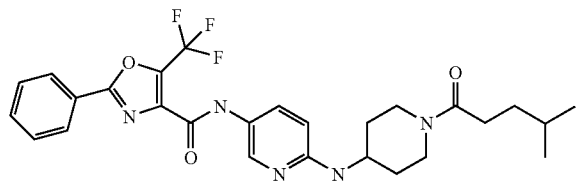

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid {6-[1-(4-methyl-pentanoyl)-piperidin-4-ylamino]-pyridin-3-yl}-amide was prepared from 2-phenyl-5-trifluoromethyl-oxazole-4-carboxylic acid [6-(piperidin-4-ylamino)-pyridin-3-yl]-amide trifluoroacetate and 4-methyl-pentanoyl chloride. LCMS calcd for C27H30F3N5O3 (m/e) 529, obsd 530 (M+H).

Example 142

Preparation of 2-phenyl-5-trifluoromethyl-oxazole-4-carboxylic acid [4-(methyl-pentanoyl-amino)-3,4,5,6-tetrahydro-2H-[1,2']bipyridinyl-5'-yl]-amide

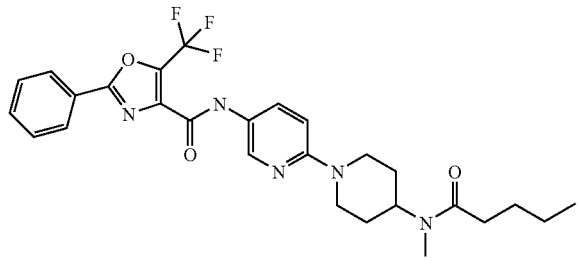

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [4-(methyl-pentanoyl-amino)-3,4,5,6-tetrahydro-2H-[1,2']bipyridinyl-5'-yl]-amide was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and pentanoyl chloride. LCMS calcd for C27H30F3N5O3 (m/e) 529, obsd 530 (M+H).

Example 143

Preparation of 2-phenyl-5-trifluoromethyl-oxazole-4-carboxylic acid {4-[(2-cyclopentyl-acetyl)-methyl-amino]-3,4,5,6-tetrahydro-2H-[1,2']bipyridinyl-5'-yl}-amide

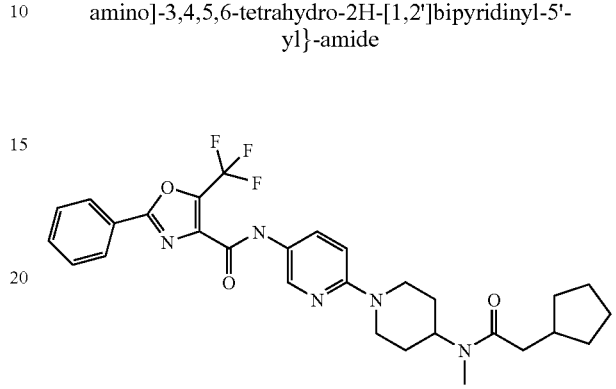

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid {4-[(2-cyclopentyl-acetyl)-methyl-amino]-3,4,5,6-tetrahydro-2H-[1,2'] bipyridinyl-5'-yl}-amide was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and cyclopentylacetyl chloride. LCMS calcd for C29H32F3N5O3 (m/e) 555, obsd 556 (M+H).

Example 144

Preparation of 2-phenyl-5-trifluoromethyl-oxazole-4-carboxylic acid [4-(cyclopropanecarbonyl-methyl-amino)-3,4,5,6-tetrahydro-2H-[1,2']bipyridinyl-5'-yl]-amide

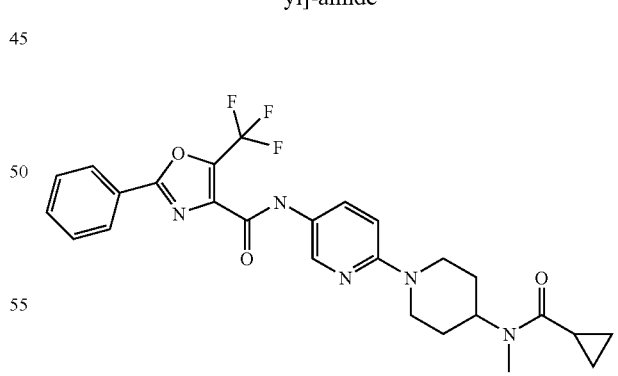

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [4-(cyclopropanecarbonyl-methyl-amino)-3,4,5,6-tetrahydro-2H-[1,2'] bipyridinyl-5'-yl]-amide was prepared from 2-phenyl-5-trifluoromethyl-oxazole-4-carboxylic acid (4-methylamino-3,4,5,6-tetrahydro-2H-[1,2']bipyridinyl-5'-yl)-amide

Example 145

Preparation of 2-phenyl-5-trifluoromethyl-oxazole-4-carboxylic acid [4-(methyl-propionyl-amino)-3,4,5,6-tetrahydro-2H-[1,2']bipyridinyl-5'-yl]-amide

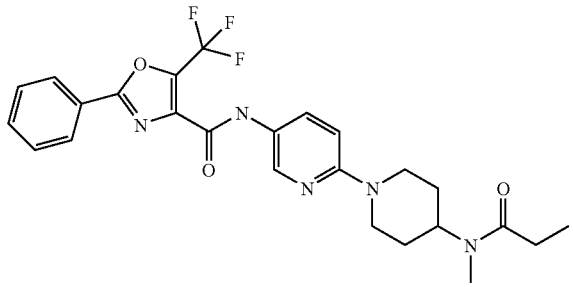

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [4-(methyl-propionyl-amino)-3,4,5,6-tetrahydro-2H-[1,2']bipyridinyl-5'-yl]-amide was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and propionyl chloride. LCMS calcd for C25H26F3N5O3 (m/e) 501, obsd 502 (M+H).

Example 146

Preparation of 2-phenyl-5-trifluoromethyl-oxazole-4-carboxylic acid {4-[(3,3-dimethyl-butyryl)-methyl-amino]-3,4,5,6-tetrahydro-2H-[1,2']bipyridinyl-5'-yl}-amide

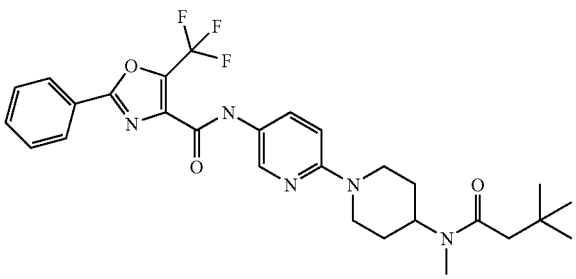

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid {4-[(3,3-dimethyl-butyryl)-methyl-amino]-3,4,5,6-tetrahydro-2H-[1,2']bipyridinyl-5'-yl}-amide was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and tert-butylacetyl chloride. LCMS calcd for C28H32F3N5O3 (m/e) 543, obsd 544 (M+H).

Example 147

Preparation of 2-phenyl-5-trifluoromethyl-oxazole-4-carboxylic acid [4-(isobutyryl-methyl-amino)-3,4,5,6-tetrahydro-2H-[1,2']bipyridinyl-5'-yl]-amide

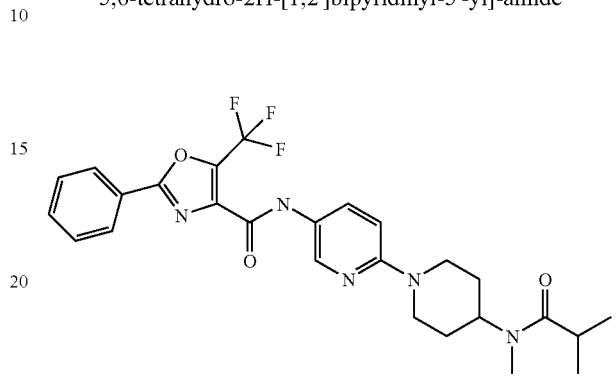

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [4-(isobutyryl-methyl-amino)-3,4,5,6-tetrahydro-2H-[1,2']bipyridinyl-5'-yl]-amide was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and isobutyryl chloride. LCMS calcd for C26H28F3N5O3 (m/e) 515, obsd 516 (M+H).

Example 148

Preparation of 2-phenyl-5-trifluoromethyl-oxazole-4-carboxylic acid {4-[methyl-(3-methyl-butyryl)-amino]-3,4,5,6-tetrahydro-2H-[1,2']bipyridinyl-5'-yl}-amide

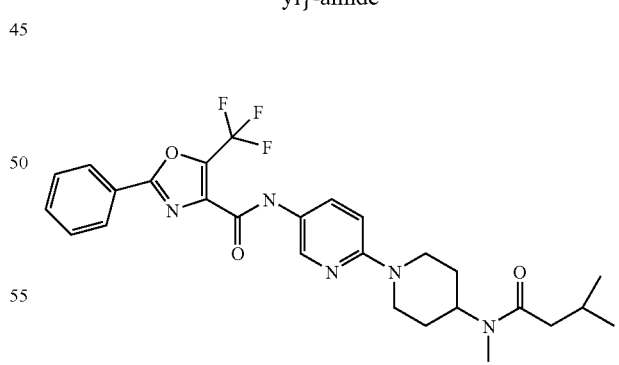

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid {4-[methyl-(3-methyl-butyryl)-amino]-3,4,5,6-tetrahydro-2H-[1,2']bipyridinyl-5'-yl}-amide was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and isovaleryl chloride. LCMS calcd for C27H30F3N5O3 (m/e) 529, obsd 530 (M+H).

Example 149

Preparation of 2-phenyl-5-trifluoromethyl-oxazole-4-carboxylic acid [4-(butyryl-methyl-amino)-3,4,5,6-tetrahydro-2H-[1,2']bipyridinyl-5'-yl]-amide

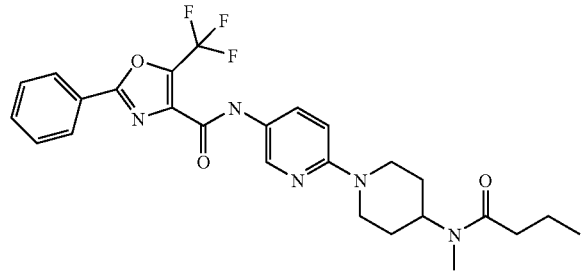

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid [4-(butyryl-methyl-amino)-3,4,5,6-tetrahydro-2H-[1,2']bipyridinyl-5'-yl]-amide was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and butyryl chloride. LCMS calcd for C26H28F3N5O3 (m/e) 515, obsd 516 (M+H).

Example 150

Preparation of 2-phenyl-5-trifluoromethyl-oxazole-4-carboxylic acid {4-[methyl-(3,3,3-trifluoro-propionyl)-amino]-3,4,5,6-tetrahydro-2H-[1,2']bipyridinyl-5'-yl}-amide

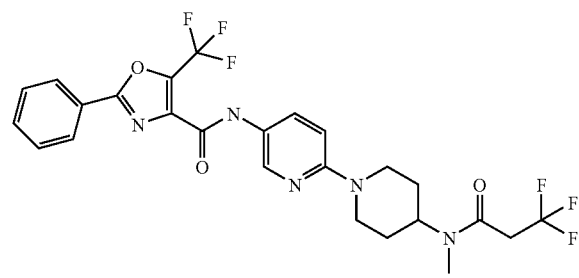

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid {4-[methyl-(3,3,3-trifluoro-propionyl)-amino]-3,4,5,6-tetrahydro-2H-[1,2']bipyridinyl-5'-yl}-amide was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and 3,3,3-trifluoropropionyl chloride. LCMS calcd for C25H23F6N5O3 (m/e) 555, obsd 556 (M+H).

Example 151

Preparation of 2-phenyl-5-trifluoromethyl-oxazole-4-carboxylic acid {4-[methyl-(4-methyl-pentanoyl)-amino]-3,4,5,6-tetrahydro-2H-[1,2']bipyridinyl-5'-yl}-amide

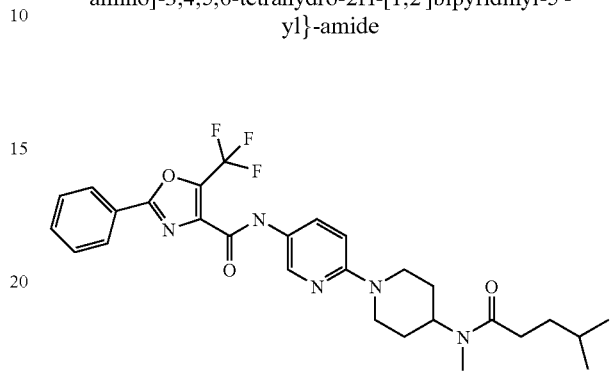

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid {4-[methyl-(4-methyl-pentanoyl)-amino]-3,4,5,6-tetrahydro-2H-[1,2'] bipyridinyl-5'-yl}-amide was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and 4-methyl-pentanoyl chloride. LCMS calcd for C28H32F3N5O3 (m/e) 543, obsd 544 (M+H).

Example 152

Preparation of 2-phenyl-5-trifluoromethyl-oxazole-4-carboxylic acid {4-[(2-methoxy-acetyl)-methyl-amino]-3,4,5,6-tetrahydro-2H-[1,2']bipyridinyl-5'-yl}-amide

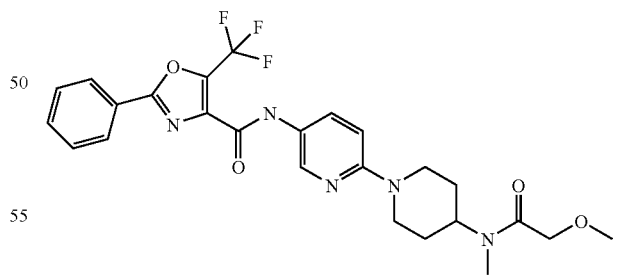

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid {4-[(2-methoxy-acetyl)-methyl-amino]-3,4,5,6-tetrahydro-2H-[1,2'] bipyridinyl-5'-yl}-amide was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and methoxyacetyl chloride. LCMS calcd for C25H26F3N5O4 (m/e) 517, obsd 518 (M+H).

Example 153

Preparation of 2-phenyl-5-trifluoromethyl-oxazole-4-carboxylic acid {4-[methyl-(2,2,2-trifluoro-acetyl)-amino]-3,4,5,6-tetrahydro-2H-[1,2']bipyridinyl-5'-yl}-amide

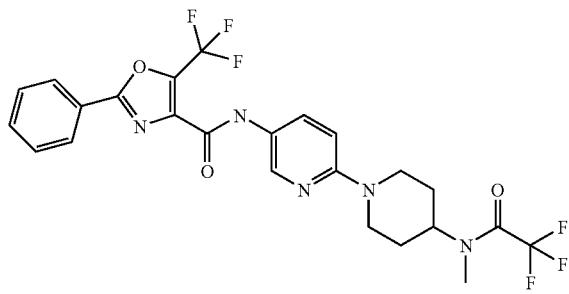

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid {4-[methyl-(2,2,2-trifluoro-acetyl)-amino]-3,4,5,6-tetrahydro-2H-[1,2']bipyridinyl-5'-yl}-amide was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and trifluoroacetic anhydride. LCMS calcd for C24H21F6N5O3 (m/e) 541, obsd 542 (M+H).

Example 154

Preparation of 4-{5-[(2-phenyl-5-trifluoromethyl-oxazole-4-carbonyl)-amino]-pyridin-2-yl}-piperazine-1-carboxylic acid isopropyl ester

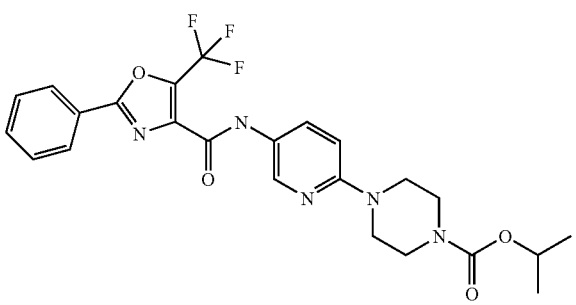

To a suspension of 2-phenyl-5-trifluoromethyl-oxazole-4-carboxylic acid (6-piperazin-1-yl-pyridin-3-yl)-amide hydrochloride salt (50 mg, 0.102 mmol) in methylene chloride (6 mL) was added triethylamine (0.1 mL). The clear solution was cooled in an ice bath and isopropylchloroformate (1M in toluene, 0.2 mL) was added. The mixture was stirred at 0° C. for 30 minutes and at room temperature for 1 hr. The solvents were evaporated and the residue was triturated with methanol. The precipitate was filtered and dried to give 4-{5-[(2-phenyl-5-trifluoromethyl-oxazole-4-carbonyl)-amino]-pyridin-2-yl}-piperazine-1-carboxylic acid isopropyl ester (32.4 mg). LC-MS calcd for C24H24F3N5O4 (m/e) 503.2, obsd 503.8 (M+H). The NMR spectrum obtained on the sample is compatible with its structure.

Example 155

Preparation of 4-{5-[(2-phenyl-5-trifluoromethyl-oxazole-4-carbonyl)-amino]-pyridin-2-yl}-piperazine-1-carboxylic acid ethyl ester

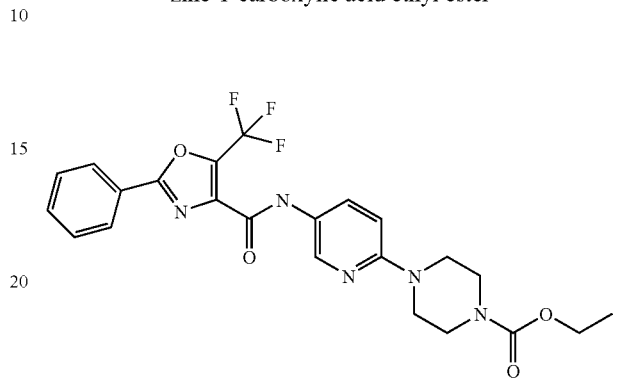

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{5-[(2-phenyl-5-trifluoromethyl-oxazole-4-carbonyl)-amino]-pyridin-2-yl}-piperazine-1-carboxylic acid ethyl ester was prepared from 2-phenyl-5-trifluoromethyl-oxazole-4-carboxylic acid (6-piperazin-1-yl-pyridin-3-yl)-amide hydrochloride salt and ethyl chloroformate. LC-MS calcd for C23H22F3N5O4 (m/e) 489.2, obsd 490.0 (M+H). The NMR spectrum obtained on the sample is compatible with its structure.

Example 156

Preparation of 4-{5-[(2-phenyl-5-trifluoromethyl-oxazole-4-carbonyl)-amino]-pyridin-2-yl}-piperazine-1-carboxylic acid methyl ester

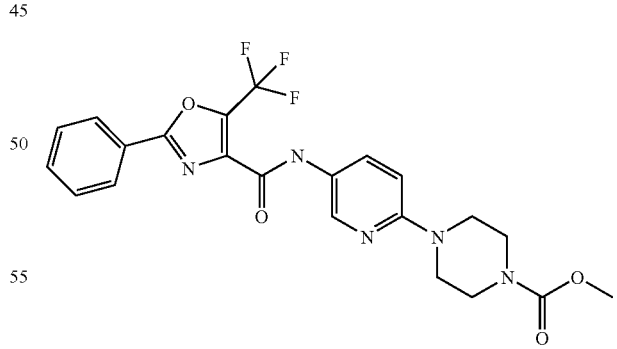

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{5-[(2-phenyl-5-trifluoromethyl-oxazole-4-carbonyl)-amino]-pyridin-2-yl}-piperazine-1-carboxylic acid methyl ester was prepared from 2-phenyl-5-trifluoromethyl-oxazole-4-carboxylic acid (6-piperazin-1-yl-pyridin-3-yl)-amide hydrochloride salt and methyl chloroformate. LC- MS calcd for C22H20F3N5O4 (m/e) 475.1, obsd 476.1 (M+H). The NMR spectrum obtained on the sample is compatible with its structure.

Example 157

Preparation of 4-{5-[(2-phenyl-5-trifluoromethyl-oxazole-4-carbonyl)-amino]-pyridin-2-yl}-piperazine-1-carboxylic acid propyl ester

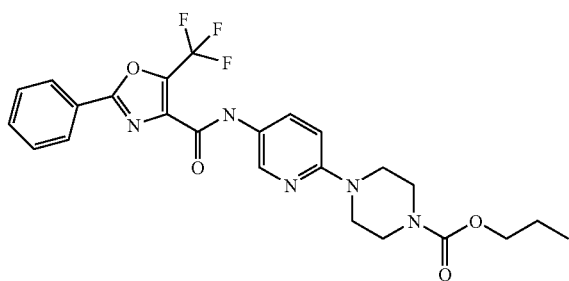

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{5-[(2-phenyl-5-trifluoromethyl-oxazole-4-carbonyl)-amino]-pyridin-2-yl}-piperazine-1-carboxylic acid propyl ester was prepared from 2-phenyl-5-trifluoromethyl-oxazole-4-carboxylic acid (6-piperazin-1-yl-pyridin-3-yl)-amide hydrochloride salt and propyl chloroformate. LC-MS calcd for C24H24F3N5O4 (m/e) 503.2, obsd 504.0 (M+H). The NMR spectrum obtained on the sample is compatible with its structure.

Example 158

Preparation of 4-{5-[(2-phenyl-5-trifluoromethyl-oxazole-4-carbonyl)-amino]-pyridin-2-yl}-piperazine-1-carboxylic acid isobutyl ester

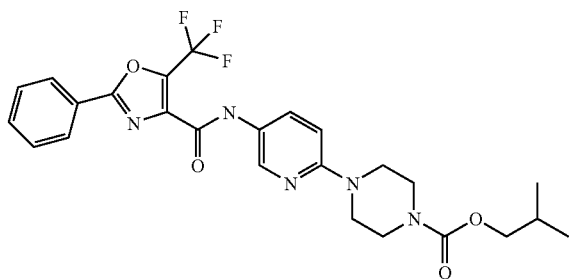

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{5-[(2-phenyl-5-trifluoromethyl-oxazole-4-carbonyl)-amino]-pyridin-2-yl}-piperazine-1-carboxylic acid isobutyl ester was prepared from 2-phenyl-5-trifluoromethyl-oxazole-4-carboxylic acid (6-piperazin-1-yl-pyridin-3-yl)-amide hydrochloride salt and isobutyl chloroformate. LC- MS calcd for C25H26F3N5O4 (m/e) 517.2, obsd 518.1 (M+H). The NMR spectrum obtained on the sample is compatible with its structure.

Example 159

Preparation of 4-{5-[(2-phenyl-5-trifluoromethyl-oxazole-4-carbonyl)-amino]-pyrimidin-2-yl}-piperazine-1-carboxylic acid methyl ester

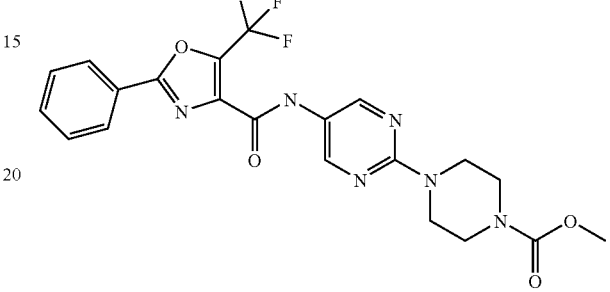

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{5-[(2-phenyl-5-trifluoromethyl-oxazole-4-carbonyl)-amino]-pyrimidin-2-yl}-piperazine-1-carboxylic acid methyl ester was prepared from 2-phenyl-5-trifluoromethyl-oxazole-4-carboxylic acid (2-piperazin-1-yl-pyrimidin-5-yl)-amide and methyl chloroformate. LC-MS calcd for C21H19F3N6O4 (m/e) 476.1, obsd 477.0 (M+H). The NMR spectrum obtained on the sample is compatible with its structure.

Example 160

Preparation of 4-{4-[(2-phenyl-5-trifluoromethyl-oxazole-4-carbonyl)-amino]-phenyl}-piperidine-1-carboxylic acid methyl ester

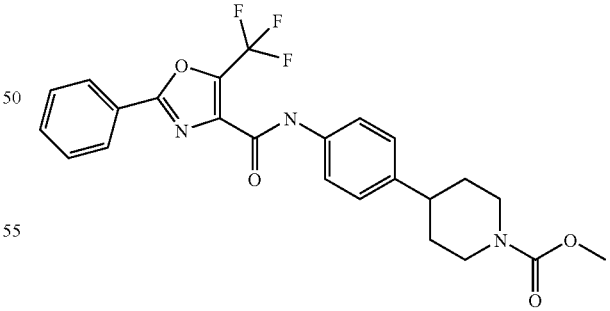

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{4-[(2-phenyl-5-trifluoromethyl-oxazole-4-carbonyl)-amino]-phenyl}-piperidine-1-carboxylic acid methyl ester was prepared from 2-phenyl-5-trifluoromethyl-oxazole-4-carboxylic acid (4-piperidin-4-yl-phenyl)-amide and methyl chloroformate. LC-MS calcd for C24H22F3N3O4 (m/e) 473.2, obsd 474.1 (M+H). The NMR spectrum obtained on the sample is compatible with its structure.

Example 161

Preparation of 5-[(2-phenyl-5-trifluoromethyl-oxazole-4-carbonyl)-amino]-3',4',5',6'-tetrahydro-2'H-[2,4']bipyridinyl-1'-carboxylic acid methyl ester

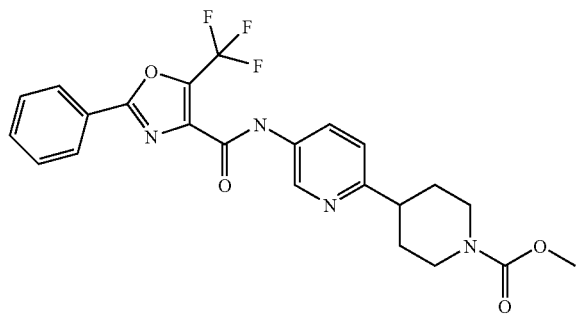

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 5-[(2-phenyl-5-trifluoromethyl-oxazole-4-carbonyl)-amino]-3',4',5',6'-tetrahydro-2'H-[2,4']bipyridinyl-1'-carboxylic acid methyl ester was prepared from 2-phenyl-5-trifluoromethyl-oxazole-4-carboxylic acid (1',2',3',4',5',6'-hexahydro-[2,4']bipyridinyl-5-yl)-amide and methyl chloroformate. LC-MS calcd for C23H21F3N4O4 (m/e) 474.2, obsd 475.1 (M+H). The NMR spectrum obtained on the sample is compatible with its structure.

Example 162

Preparation of 4-{4-[(2-phenyl-5-trifluoromethyl-oxazole-4-carbonyl)-amino]-phenyl}-piperazine-1-carboxylic acid methyl ester

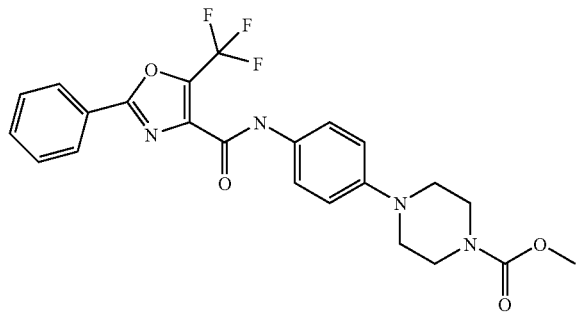

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{4-[(2-phenyl-5-trifluoromethyl-oxazole-4-carbonyl)-amino]-phenyl}-piperazine-1-carboxylic acid methyl ester was prepared from 2-phenyl-5-trifluoromethyl-oxazole-4-carboxylic acid (4-piperazin-1-yl-phenyl)-amide and methyl chloroformate. LC-MS calcd for C23H21F3N4O4 (m/e) 474.2, obsd 475.1 (M+H). The NMR spectrum obtained on the sample is compatible with its structure.

Example 163

Preparation of 4-(5-{[1-(4-fluoro-phenyl)-3-trifluoromethyl-1H-pyrazole-4-carbonyl]-amino}-pyridin-2-yl)-piperazine-1-carboxylic acid ethyl ester

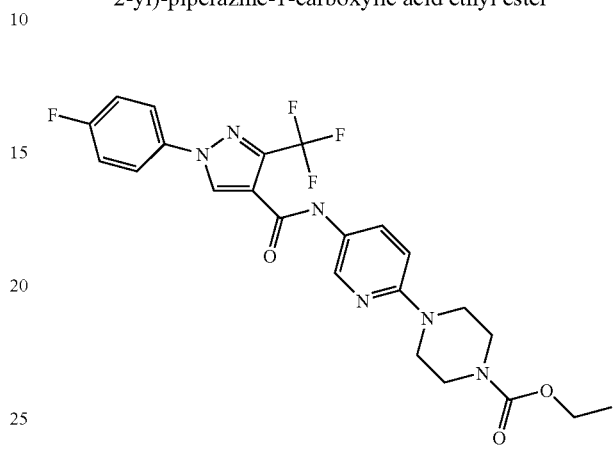

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-(5-{[1-(4-fluoro-phenyl)-3-trifluoromethyl-1H-pyrazole-4-carbonyl]-amino}-pyridin-2-yl)-piperazine-1-carboxylic acid ethyl ester was prepared from 1-(4-fluoro-phenyl)-3-trifluoromethyl-1H-pyrazole-4-carboxylic acid (6-piperazin-1-yl-pyridin-3-yl)-amide and ethyl chloroformate. LCMS calcd for C23H22F4N6O3 (m/e) 506, obsd 507 (M+H). The NMR spectrum obtained on the sample is compatible with its structure.

Example 164

Preparation of 4-{5-[(5-methyl-2-phenyl-2H-[1,2,3]triazole-4-carbonyl)-amino]-pyridin-2-yl}-piperazine-1-carboxylic acid ethyl ester

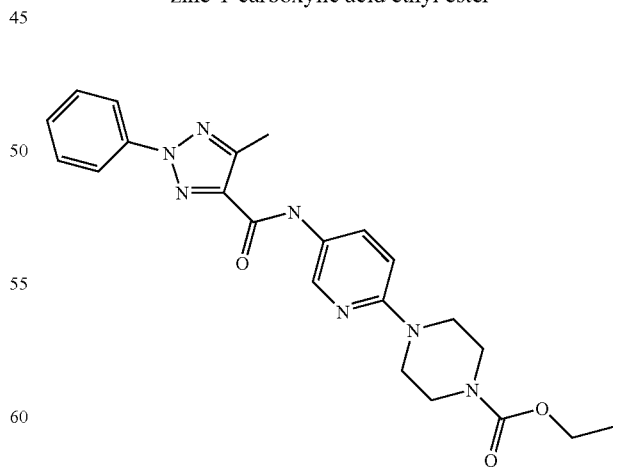

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{5-[(5-methyl-2-phenyl-2H-[1,2,3]triazole-4-carbonyl)-amino]-pyridin-2-yl}-piperazine-1-carboxylic acid ethyl ester was prepared from 5-methyl-2-phenyl-2H-[1,2,3]triazole-4-carboxylic acid (6-piperazin-1-yl-pyridin-3-yl)-amide and ethyl chloroformate. LCMS calcd for C22H25N7O3 (m/e) 435, obsd 436 (M+H). The NMR spectrum obtained on the sample is compatible with its structure.

Example 165

Preparation of 4-{4-[(1-phenyl-3-trifluoromethyl-1H-pyrazole-4-carbonyl)-amino]-phenyl}-piperidine-1-carboxylic acid methyl ester

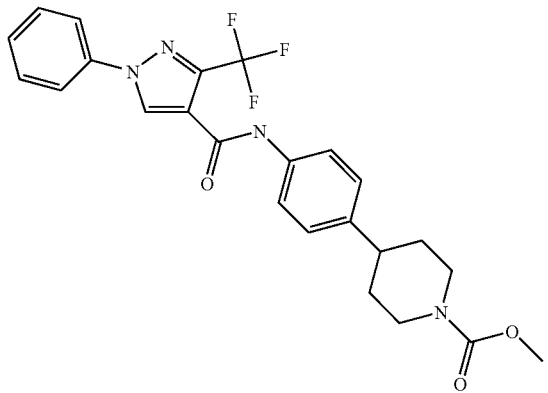

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{4-[(1-phenyl-3-trifluoromethyl-1H-pyrazole-4-carbonyl)-amino]-phenyl}-piperidine-1-carboxylic acid methyl ester was prepared from 1-phenyl-3-trifluoromethyl-1H-pyrazole-4-carboxylic acid (4-piperidin-4-yl-phenyl)-amide and methyl chloroformate. LCMS calcd for C24H23F3N4O3 (m/e) 472, obsd 473 (M+H). The NMR spectrum obtained on the sample is compatible with its structure.

Example 166

Preparation of 4-{4-[(1-phenyl-3-trifluoromethyl-1H-pyrazole-4-carbonyl)-amino]-phenyl}-piperidine-1-carboxylic acid ethyl ester

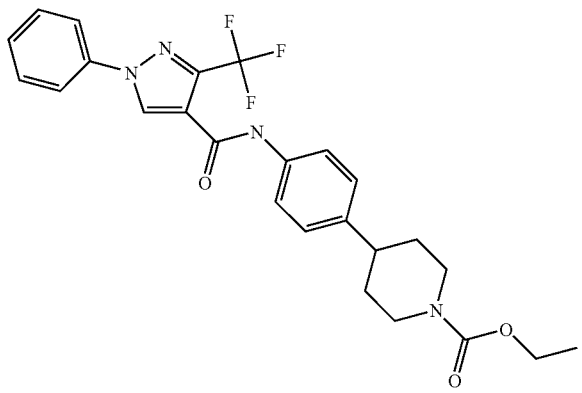

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{4-[(1-phenyl-3-trifluoromethyl-1H-pyrazole-4-carbonyl)-amino]-phenyl}-piperidine-1-carboxylic acid ethyl ester was prepared from 1-phenyl-3-trifluoromethyl-1H-pyrazole-4-carboxylic acid (4-piperidin-4-yl-phenyl)-amide and ethyl chloroformate. LCMS calcd for C25H25F3N4O3 (m/e) 486, obsd 487 (M+H). The NMR spectrum obtained on the sample is compatible with its structure.

Example 167

Preparation of 4-(5-{[2-(2-methoxy-ethyl)-5-phenyl-2H-pyrazole-3-carbonyl]-amino}-pyridin-2-yl)-piperazine-1-carboxylic acid ethyl ester

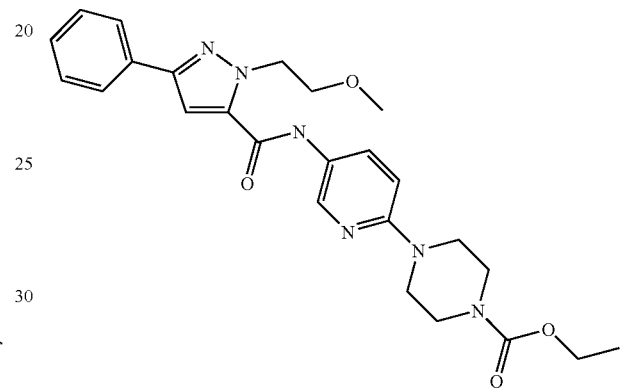

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-(5-{[2-(2-methoxy-ethyl)-5-phenyl-2H-pyrazole-3-carbonyl]-amino}-pyridin-2-yl)-piperazine-1-carboxylic acid ethyl ester was prepared from 2-(2-methoxy-ethyl)-5-phenyl-2H-pyrazole-3-carboxylic acid (6-piperazin-1-yl-pyridin-3-yl)-amide and ethyl chloroformate. LCMS calcd for C25H30N6O4 (m/e) 478, obsd 479 (M+H).

Example 168

Preparation of 4-{5-[(5-methoxymethyl-2-phenyl-2H-[1,2,3]triazole-4-carbonyl)-amino]-pyridin-2-yl}-piperazine-1-carboxylic acid ethyl ester

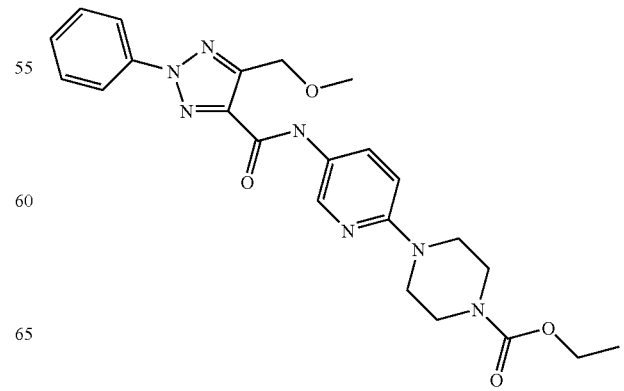

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{5-[(5-methoxymethyl-2-phenyl-2H-[1,2,3]triazole-4-carbonyl)-amino]-pyridin-2-yl}-piperazine-1-carboxylic acid ethyl ester was prepared from 5-methoxymethyl-2-phenyl-2H-[1,2,3]triazole-4-carboxylic acid (6-piperazin-1-yl-pyridin-3-yl)-amide and ethyl chloroformate. LCMS calcd for C23H27N7O4 (m/e) 465, obsd 466 (M+H).

Example 169

Preparation of 4-{4-[(5-methyl-2-phenyl-2H-[1,2,3]triazole-4-carbonyl)-amino]-phenyl}-piperidine-1-carboxylic acid ethyl ester

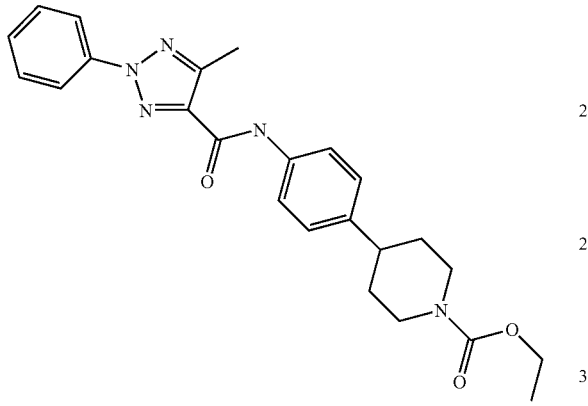

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{4-[(5-methyl-2-phenyl-2H-[1,2,3]triazole-4-carbonyl)-amino]-phenyl}-piperidine-1-carboxylic acid ethyl ester was prepared from 5-methyl-2-phenyl-2H-[1,2,3]triazole-4-carboxylic acid (4-piperidin-4-yl-phenyl)-amide and ethyl chloroformate. LCMS calcd for C24H27N5O3 (m/e) 433, obsd 434 (M+H). The NMR spectrum obtained on the sample is compatible with its structure.

Example 170

Preparation of 4-{4-[(5-methyl-2-phenyl-2H-[1,2,3]triazole-4-carbonyl)-amino]-phenyl}-piperidine-1-carboxylic acid methyl ester

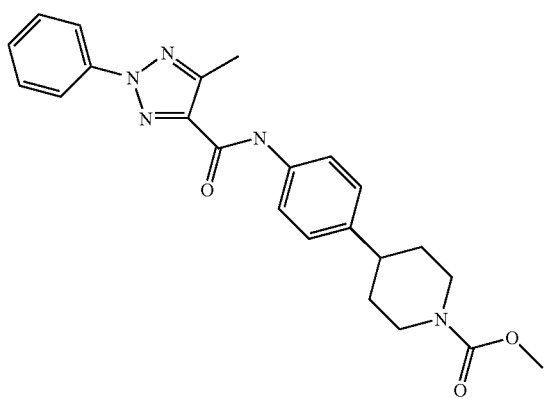

With a method similar to that use for the preparation of 4-{5-[(2-phenyl-5-trifluoromethyl-oxazole-4-carbonyl)-amino]-pyridin-2-yl}-piperazine-1-carboxylic acid isopropyl ester above, 4-{4-[(5-methyl-2-phenyl-2H-[1,2,3]triazole-4-carbonyl)-amino]-phenyl}-piperidine-1-carboxylic acid methyl ester was prepared from 5-methyl-2-phenyl-2H-[1,2,3]triazole-4-carboxylic acid (4-piperidin-4-yl-phenyl)-amide and methyl chloroformate. LCMS calcd for C23H25N5O3 (m/e) 419, obsd 420 (M+H). (37660-298-2)

Example 171

Preparation of 4-(4-{[1-(2-chloro-phenyl)-3-trifluoromethyl-1H-pyrazole-4-carbonyl]-amino}-phenyl)-piperidine-1-carboxylic acid ethyl ester

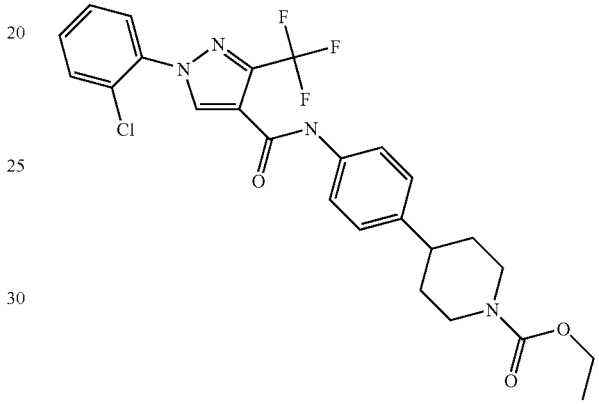

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-(4-{[1-(2-chloro-phenyl)-3-trifluoromethyl-1H-pyrazole-4-carbonyl]-amino}-phenyl)-piperidine-1-carboxylic acid ethyl ester was prepared from 1-(2-chloro-phenyl)-3-trifluoromethyl-1H-pyrazole-4-carboxylic acid (4-piperidin-4-yl-phenyl)-amide and ethyl chloroformate. LCMS calcd for C25H24ClF3N4O3 (m/e) 520, obsd 521 (M+H).

Example 172

Preparation of (S)-3-{5-[(2-phenyl-5-trifluoromethyl-oxazole-4-carbonyl)-amino]-pyridin-2-ylamino}-pyrrolidine-1-carboxylic acid ethyl ester

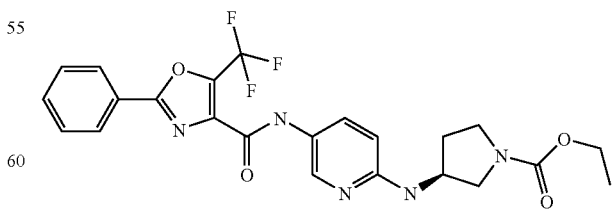

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, (S)-3-{5-[(2-phenyl-5-trifluoromethyl-oxazole-4-carbonyl)-amino]-pyridin-2-ylamino}-pyrrolidine-1-carboxylic acid ethyl ester was prepared from 2-phenyl-5-trifluoromethyl-oxazole-4-carboxylic acid [6-((S)-pyrrolidin-3-ylamino)-pyridin-3-yl]-amide and ethyl chloroformate. LCMS calcd for C23H22F3N5O4 (m/e) 489.45, obsd 490.17 (M+H).

Example 173

Preparation of (R)-3-{5-[(2-phenyl-5-trifluoromethyl-oxazole-4-carbonyl)-amino]-pyridin-2-ylamino}-pyrrolidine-1-carboxylic acid ethyl ester

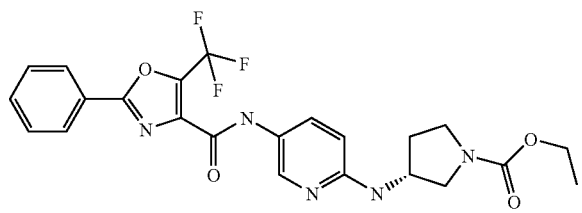

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, (R)-3-{5-[(2-phenyl-5-trifluoromethyl-oxazole-4-carbonyl)-amino]-pyridin-2-ylamino}-pyrrolidine-1-carboxylic acid ethyl ester was prepared from 2-phenyl-5-trifluoromethyl-oxazole-4-carboxylic acid [6-((R)-pyrrolidin-3-ylamino)-pyridin-3-yl]-amide and ethyl chloroformate. LCMS calcd for C23H22F3N5O4 (m/e) 489.45, obsd 490.17 (M+H).

Example 174

Preparation of (S)-3-{5-[(2-phenyl-5-trifluoromethyl-oxazole-4-carbonyl)-amino]-pyridin-2-ylamino}-pyrrolidine-1-carboxylic acid methyl ester

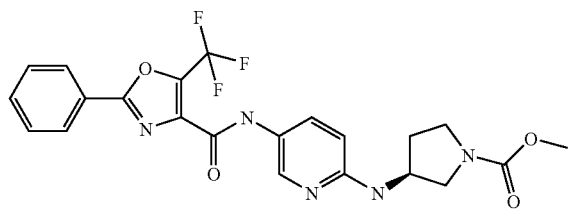

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, (S)-3-{5-[(2-phenyl-5-trifluoromethyl-oxazole-4-carbonyl)-amino]-pyridin-2-ylamino}-pyrrolidine-1-carboxylic acid methyl ester was prepared from 2-phenyl-5-trifluoromethyl-oxazole-4-carboxylic acid [6-((S)-pyrrolidin-3-ylamino)-pyridin-3-yl]-amide and methyl chloroformate. LCMS calcd for C22H20F3N5O4 (m/e) 475.43, obsd 476.15 (M+H).

Example 175

Preparation of (S)-3-{5-[(2-phenyl-5-trifluoromethyl-oxazole-4-carbonyl)-amino]-pyridin-2-ylamino}-pyrrolidine-1-carboxylic acid isopropyl ester

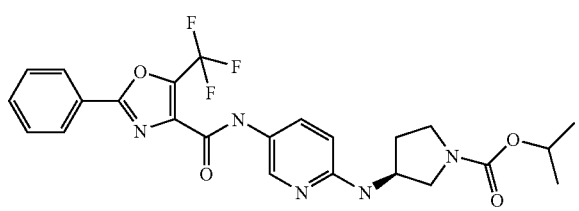

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, (S)-3-{5-[(2-phenyl-5-trifluoromethyl-oxazole-4-carbonyl)-amino]-pyridin-2-ylamino}-pyrrolidine-1-carboxylic acid isopropyl ester was prepared from 2-phenyl-5-trifluoromethyl-oxazole-4-carboxylic acid [6-((S)-pyrrolidin-3-ylamino)-pyridin-3-yl]-amide and isopropyl chloroformate. LCMS calcd for C24H24F3N5O4 (m/e) 503.48, obsd 504.19 (M+H).

Example 176

Preparation of (S)-3-{5-[(2-phenyl-5-trifluoromethyl-oxazole-4-carbonyl)-amino]-pyridin-2-ylamino}-pyrrolidine-1-carboxylic acid benzyl ester

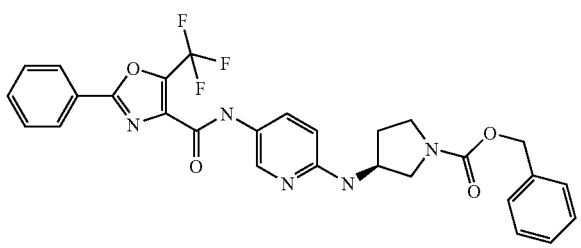

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, (S)-3-{5-[(2-phenyl-5-trifluoromethyl-oxazole-4-carbonyl)-amino]-pyridin-2-ylamino}-pyrrolidine-1-carboxylic acid benzyl ester was prepared from 2-phenyl-5-trifluoromethyl-oxazole-4-carboxylic acid [6-((S)- pyrrolidin-3-ylamino)-pyridin-3-yl]-amide and benzyl chloroformate. LCMS calcd for C28H24F3N5O4 (m/e) 551.52, obsd 552.18 (M+H).

Example 177

Preparation of (S)-3-(methyl-{5-[(2-phenyl-5-trifluoromethyl-oxazole-4-carbonyl)-amino]-pyridin-2-yl}-amino)-pyrrolidine-1-carboxylic acid ethyl ester

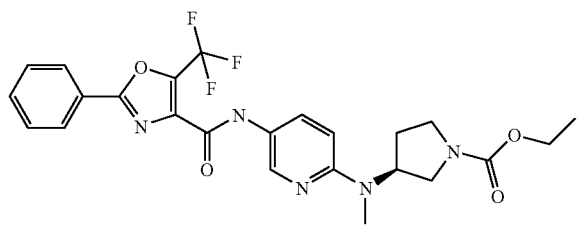

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, (S)-3-(methyl-{5-[(2-phenyl-5-trifluoromethyl-oxazole-4-carbonyl)-amino]-pyridin-2-yl}-amino)-pyrrolidine-1-carboxylic acid ethyl ester was prepared from 2-Phenyl-5-trifluoromethyl-oxazole-4-carboxylic acid [6-((S)-methyl-pyrrolidin-3-yl-amino)-pyridin-3-yl]-amide and ethyl chloroformate. LCMS calcd for C24H24F3N5O4 (m/e) 503.48, obsd 504.19 (M+H).

Example 178

Preparation of rac-methyl-(1-{5-[(2-phenyl-5-trifluoromethyl-oxazole-4-carbonyl)-amino]-pyridin-2-yl}-pyrrolidin-3-yl)-carbamic acid methyl ester

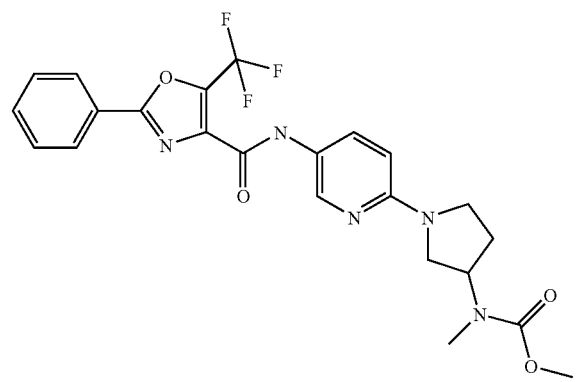

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, racemic methyl-(1-{5-[(2-phenyl-5-trifluoromethyl-oxazole-4-carbonyl)-amino]-pyridin-2-yl}-pyrrolidin-3-yl)-carbamic acid methyl ester was prepared from racemic 2-phenyl-5-trifluoromethyl-oxazole-4-carboxylic acid [6-(3-methylamino-pyrrolidin-1-yl)-pyridin-3-yl]-amide and methyl chloroformate. LCMS calcd for C23H22F3N5O4 (m/e) 489.45, obsd 490.17 (M+H).

Example 179

Preparation of (R)-(1-{5-[(2-phenyl-5-trifluoromethyl-oxazole-4-carbonyl)-amino]-pyridin-2-yl}-pyrrolidin-3-yl)-carbamic acid methyl ester

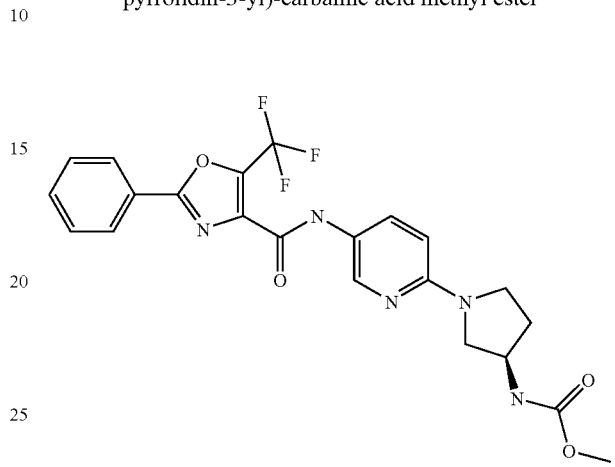

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, (R)-(1-{5-[(2-phenyl-5-trifluoromethyl-oxazole-4-carbonyl)-amino]-pyridin-2-yl}-pyrrolidin-3-yl)-carbamic acid methyl ester was prepared from 2-phenyl-5-trifluoromethyl-oxazole-4-carboxylic acid [6-((R)-3-amino-pyrrolidin-1-yl)-pyridin-3-yl]-amide and methyl chloroformate. LCMS calcd for C22H20F3N5O4 (m/e) 475.43, obsd 476.15 (M+H).

Example 180

Preparation of (S)-3-{5-[(2-phenyl-5-trifluoromethyl-oxazole-4-carbonyl)-amino]-pyrimidin-2-ylamino}-pyrrolidine-1-carboxylic acid methyl ester

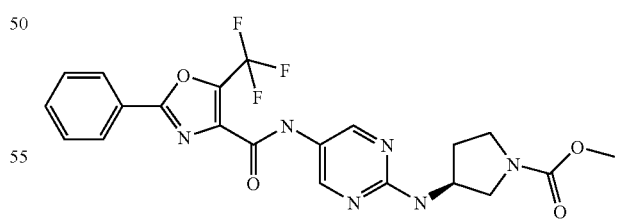

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, (S)-3-{5-[(2-phenyl-5-trifluoromethyl-oxazole-4-carbonyl)-amino]-pyrimidin-2-ylamino}-pyrrolidine-1-carboxylic acid methyl ester was prepared from 2-phenyl-5-trifluoromethyl-oxazole-4-carboxylic acid [2-((S)-pyrrolidin-3-ylamino)-pyrimidin-5-yl]-amide and methyl chloroformate. LCMS calcd for C21H19F3N6O4 (m/e) 476.41, obsd 477.15 (M+H).

Example 181

Preparation of (S)-3-{5-[(2-phenyl-5-trifluoromethyl-oxazole-4-carbonyl)-amino]-pyrimidin-2-ylamino}-pyrrolidine-1-carboxylic acid ethyl ester

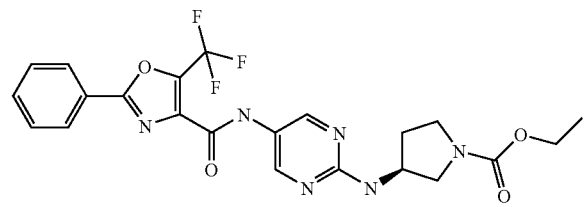

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, (S)-3-{5-[(2-phenyl-5-trifluoromethyl-oxazole-4-carbonyl)-amino]-pyrimidin-2-ylamino}-pyrrolidine-1-carboxylic acid ethyl ester was prepared from 2-phenyl-5-trifluoromethyl-oxazole-4-carboxylic acid [2-((S)-pyrrolidin-3-ylamino)-pyrimidin-5-yl]-amide and ethyl chloroformate. LCMS calcd for C22H21F3N6O4 (m/e) 490.44, obsd 491.16 (M+H).

Example 182

Preparation of (S)-3-{5-[(4-methyl-2-pyridin-2-yl-thiazole-5-carbonyl)-amino]-pyridin-2-ylamino}-pyrrolidine-1-carboxylic acid ethyl ester

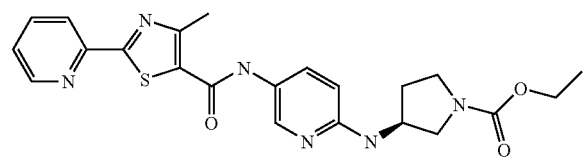

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, (S)-3-{5-[(4-methyl-2-pyridin-2-yl-thiazole-5-carbonyl)-amino]-pyridin-2-ylamino}-pyrrolidine-1-carboxylic acid ethyl ester was prepared from 4-methyl-2-pyridin-2-yl-thiazole-5-carboxylic acid [6-((S)-pyrrolidin-3-ylamino)-pyridin-3-yl]-amide and ethyl chloroformate. LCMS calcd for C22H24N6O3S (m/e) 452.54, obsd 453.17 (M+H).

Example 183

Preparation of 4-{2-cyano-4-[(2-phenyl-5-trifluoromethyl-oxazole-4-carbonyl)-amino]-phenyl}-piperazine-1-carboxylic acid ethyl ester

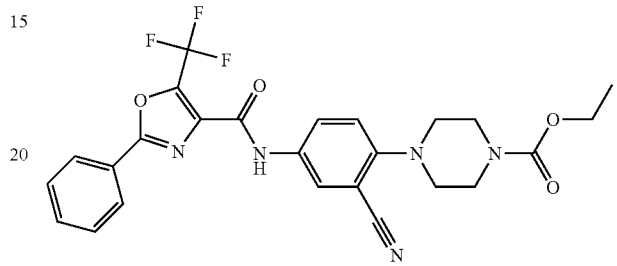

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{2-cyano-4-[(2-phenyl-5-trifluoromethyl-oxazole-4-carbonyl)-amino]-phenyl}-piperazine-1-carboxylic acid ethyl ester was prepared from 2-phenyl-5-trifluoromethyl-oxazole-4-carboxylic acid (3-cyano-4-piperazin-1-yl-phenyl)-amide and ethyl chloroformate. LCMS for C25H22F3N5O4 (m/e) calc. 513, obsd 514 (M+H).

Example 184

Preparation of 4-{4-[(2-phenyl-5-trifluoromethyl-oxazole-4-carbonyl)-amino]-phenyl}-piperazine-1-carboxylic acid butyl ester

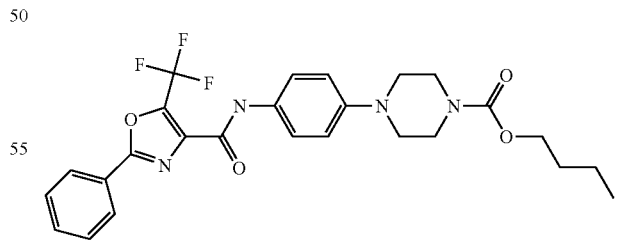

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{4-[(2-phenyl-5-trifluoromethyl-oxazole-4-carbonyl)-amino]-phenyl}-piperazine-1-carboxylic acid butyl ester was prepared from 2-phenyl-5-trifluoromethyloxazole-4-carboxylic acid (4-piperazin-1-yl-phenyl)-amide and butyl chloroformate. LCMS calcd for C26H27F3N4O4 (m/e) 516, obsd. 517 (M+H).

Example 185

Preparation of 4-{5-[(2-phenyl-5-trifluoromethyl-oxazole-4-carbonyl)-amino]-pyridin-2-ylamino}-piperidine-1-carboxylic acid isobutyl ester

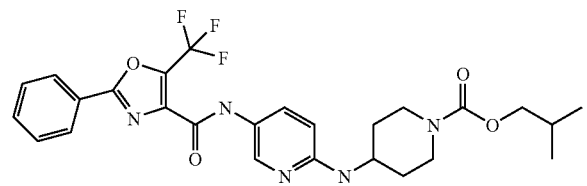

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{5-[(2-phenyl-5-trifluoromethyl-oxazole-4-carbonyl)-amino]-pyridin-2-ylamino}-piperidine-1-carboxylic acid isobutyl ester was prepared from 2-phenyl-5-trifluoromethyl-oxazole-4-carboxylic acid [6-(piperidin-4-ylamino)-pyridin-3-yl]-amide trifluoroacetate and isobutyl chloroformate. LCMS calcd for C26H28F3N5O4 (m/e) 531, obsd 532 (M+H).

Example 186

Preparation of 4-{5-[(2-phenyl-5-trifluoromethyl-oxazole-4-carbonyl)-amino]-pyridin-2-ylamino}-piperidine-1-carboxylic acid methyl ester

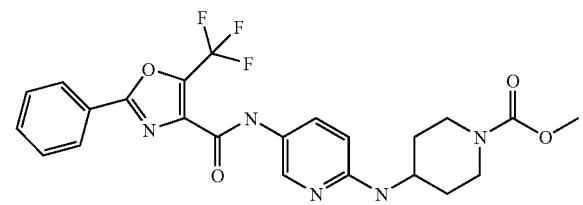

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{5-[(2-phenyl-5-trifluoromethyl-oxazole-4-carbonyl)-amino]-pyridin-2-ylamino}-piperidine-1-carboxylic acid methyl ester was prepared from 2-phenyl-5-trifluoromethyl-oxazole-4-carboxylic acid [6-(piperidin-4-ylamino)-pyridin-3-yl]-amide trifluoroacetate and methyl chloroformate. LCMS calcd for C23H22F3N5O4 (m/e) 489, obsd 490 (M+H).

Example 187

Preparation of 4-{5-[(2-phenyl-5-trifluoromethyl-oxazole-4-carbonyl)-amino]-pyridin-2-ylamino}-piperidine-1-carboxylic acid ethyl ester

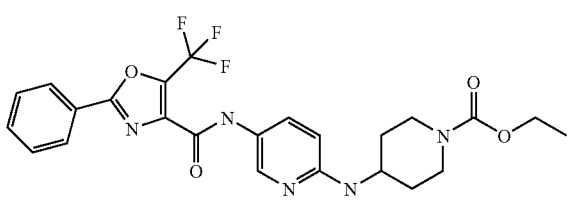

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{5-[(2-phenyl-5-trifluoromethyl-oxazole-4-carbonyl)-amino]-pyridin-2-ylamino}-piperidine-1-carboxylic acid ethyl ester was prepared from 2-phenyl-5-trifluoromethyl-oxazole-4-carboxylic acid [6-(piperidin-4-ylamino)-pyridin-3-yl]-amide trifluoroacetate and ethyl chloroformate. LCMS calcd for C24H24F3N5O4 (m/e) 503, obsd 504 (M+H).

Example 188

Preparation of 4-{5-[(2-phenyl-5-trifluoromethyl-oxazole-4-carbonyl)-amino]-pyridin-2-ylamino}-piperidine-1-carboxylic acid 2,2-dimethyl-propyl ester

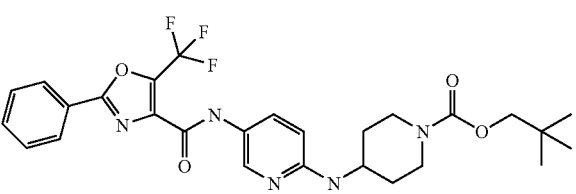

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{5-[(2-phenyl-5-trifluoromethyl-oxazole-4-carbonyl)-amino]-pyridin-2-ylamino}-piperidine-1-carboxylic acid 2,2-dimethyl-propyl ester was prepared from 2-phenyl-5-trifluoromethyl-oxazole-4-carboxylic acid [6-(piperidin-4-ylamino)-pyridin-3-yl]-amide trifluoroacetate and 2,2-dimethylpropyl chloroformate. LCMS calcd for C27H30F3N5O4 (m/e) 545, obsd 546 (M+H).

Example 189

Preparation of 4-{5-[(2-phenyl-5-trifluoromethyl-oxazole-4-carbonyl)-amino]-pyridin-2-ylamino}-piperidine-1-carboxylic acid isopropyl ester

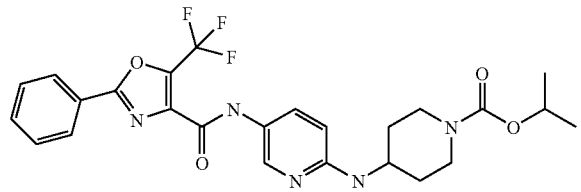

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{5-[(2-phenyl-5-trifluoromethyl-oxazole-4-carbonyl)-amino]-pyridin-2-ylamino}-piperidine-1-carboxylic acid isopropyl ester was prepared from 2-phenyl-5-trifluoromethyl-oxazole-4-carboxylic acid [6-(piperidin-4-ylamino)-pyridin-3-yl]-amide trifluoroacetate and isopropyl chloroformate. LCMS calcd for C25H26F3N5O4 (m/e) 517, obsd 518 (M+H).

Example 190

Preparation of methyl-{5'-[(2-phenyl-5-trifluoromethyl-oxazole-4-carbonyl)-amino]-3,4,5,6-tetrahydro-2H-[1,2']bipyridinyl-4-yl}-carbamic acid methyl ester

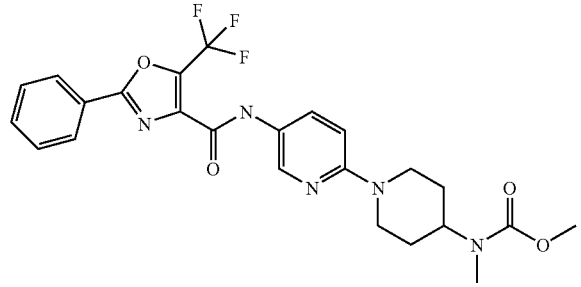

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, methyl-{5'-[(2-phenyl-5-trifluoromethyl-oxazole-4-carbonyl)-amino]-3,4,5,6-tetrahydro-2H-[1,2']bipyridinyl-4-yl}-carbamic acid methyl ester was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and methyl chloroformate. LCMS calcd for C24H24F3N5O4 (m/e) 503, obsd 504 (M+H).

Example 191

Preparation of methyl-{5'-[(2-phenyl-5-trifluoromethyl-oxazole-4-carbonyl)-amino]-3,4,5,6-tetrahydro-2H-[1,2']bipyridinyl-4-yl}-carbamic acid ethyl ester

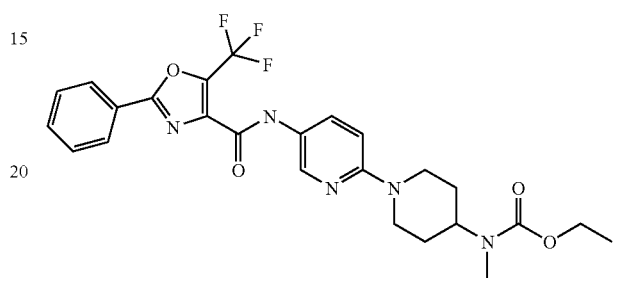

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, methyl-{5'-[(2-phenyl-5-trifluoromethyl-oxazole-4-carbonyl)-amino]-3,4,5,6-tetrahydro-2H-[1,2'] bipyridinyl-4-yl}-carbamic acid ethyl ester was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and ethyl chloroformate. LCMS calcd for C25H26F3N5O4 (m/e) 517, obsd 518 (M+H).

Example 192

Preparation of methyl-{5'-[(2-phenyl-5-trifluoromethyl-oxazole-4-carbonyl)-amino]-3,4,5,6-tetrahydro-2H-[1,2']bipyridinyl-4-yl}-carbamic acid isobutyl ester

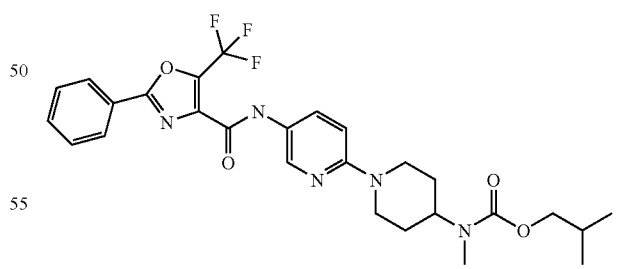

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, methyl-{5'-[(2-phenyl-5-trifluoromethyl-oxazole-4-carbonyl)-amino]-3,4,5,6-tetrahydro-2H-[1,2'] bipyridinyl-4-yl}-carbamic acid isobutyl ester was prepared from 2-phenyl-5-trifluoromethyl-oxazole-4-carboxylic acid (4-methylamino-3,4,5,6-tetrahydro-2H-[1,2']bipyridinyl-5'- yl)-amide trifluoroacetate and isobutyl chloroformate. LCMS calcd for C27H30F3N5O4 (m/e) 545, obsd 546 (M+H).

Example 193

Preparation of methyl-{5'-[(2-phenyl-5-trifluoromethyl-oxazole-4-carbonyl)-amino]-3,4,5,6-tetrahydro-2H-[1,2']bipyridinyl-4-yl}-carbamic acid 2,2-dimethyl-propyl ester

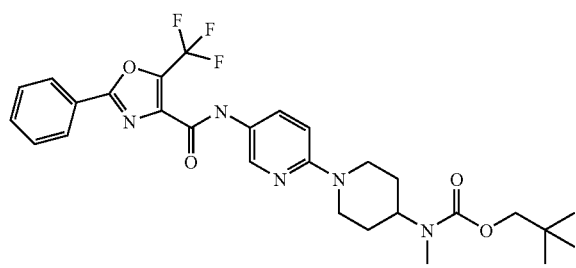

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, methyl-{5'-[(2-phenyl-5-trifluoromethyl-oxazole-4-carbonyl)-amino]-3,4,5,6-tetrahydro-2H-[1,2']bipyridinyl-4-yl}-carbamic acid 2,2-dimethyl-propyl ester was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and 2,2-dimethylpropyl chloroformate. LCMS calcd for C28H32F3N5O4 (m/e) 559, obsd 560 (M+H).

Example 194

Preparation of methyl-{5'-[(2-phenyl-5-trifluoromethyl-oxazole-4-carbonyl)-amino]-3,4,5,6-tetrahydro-2H-[1,2']bipyridinyl-4-yl}-carbamic acid isopropenyl ester

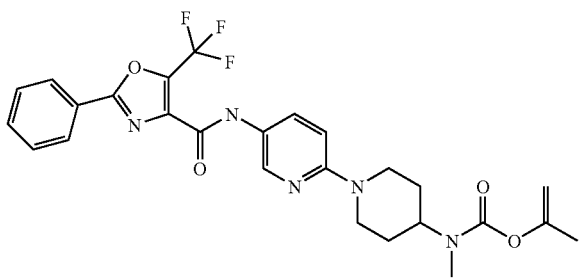

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester above, methyl-{5'-[(2-phenyl-5-trifluoromethyl-oxazole-4-carbonyl)-amino]-3,4,5,6-tetrahydro-2H-[1,2']bipyridinyl-4-yl}-carbamic acid isopropenyl ester was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and isopropenyl chloroformate. LCMS calcd for C26H26F3N5O4 (m/e) 529, obsd 530 (M+H).

Example 195

Preparation of 4-{4-[(2-phenyl-5-trifluoromethyl-oxazole-4-carbonyl)-amino]-phenyl}-piperazine-1-carboxylic acid propylamide

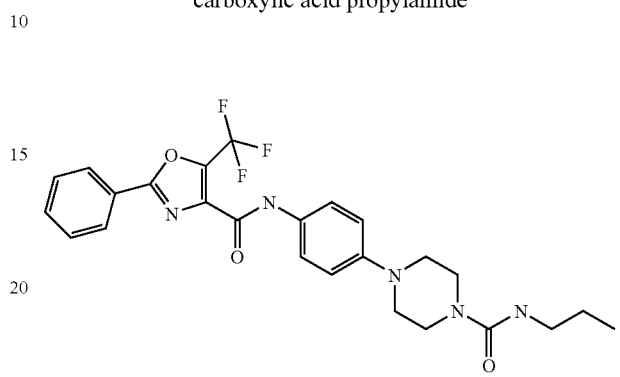

To a solution of 2-phenyl-5-trifluoromethyl-oxazole-4-carboxylic acid (4-piperazin-1-yl-phenyl)-amide hydrochloride (100 mg, 0.204 mmol) and triethylamine (57 μL, 0.408 mmol) in 5 mL THF at 0° C. was added n-propylisocyanate (21.6 mg, 0.255 mmol). The ice bath was removed and the reaction mixture was stirred at room temperature for 1 hr. The reaction mixture was diluted with ethyl acetate and washed with water. The organic layer was washed with saturated aqueous sodium bicarbonate solution, dried over magnesium sulfate, filtered, and evaporated under reduced pressure. The residue was crystallized from ethyl acetate/hexane to yield 4-{4-[(2-phenyl-5-trifluoromethyl-oxazole-4-carbonyl)-amino]-phenyl}-piperazine-1-carboxylic acid propylamide (83 mg, 81%). ES-MS calcd for C25H26F3N5O3 (m/e) 501.51, obsd 502.1 (M+H).

Example 196

Preparation of 4-{4-[(2-phenyl-5-trifluoromethyl-oxazole-4-carbonyl)-amino]-phenyl}-piperazine-1-carboxylic acid isopropylamide

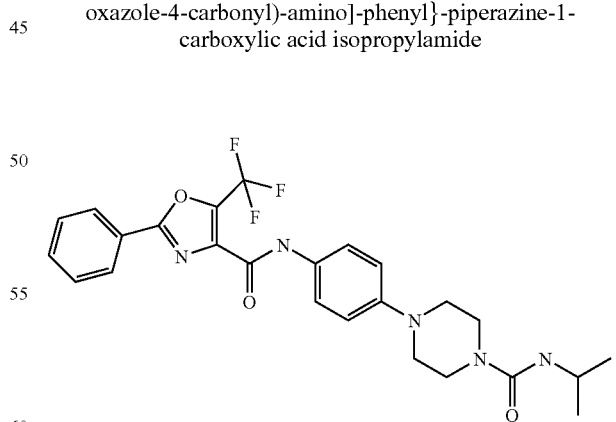

With a method similar to that used for the preparation of 4-{4-[(2-phenyl-5-trifluoromethyl-oxazole-4-carbonyl)-amino]-phenyl}-piperazine-1-carboxylic acid propylamide above, 4-{4-[(2-phenyl-5-trifluoromethyl-oxazole-4-carbonyl)-amino]-phenyl}-piperazine-1-carboxylic acid isopropylamide was prepared from 2-phenyl-5-trifluoromethyl-oxazole-4-carboxylic acid (4-piperazin-1-yl-phenyl)-amide hydrochloride and isopropylisocyanate. LC-MS calcd for C25H26F3N5O3 (m/e) 501.5, obsd 502.1 (M+H). The NMR spectrum obtained on the sample is compatible with its structure.

Example 197

Preparation of 4-{5-[(2-phenyl-5-trifluoromethyl-oxazole-4-carbonyl)-amino]-pyridin-2-yl}-piperazine-1-carboxylic acid propylamide

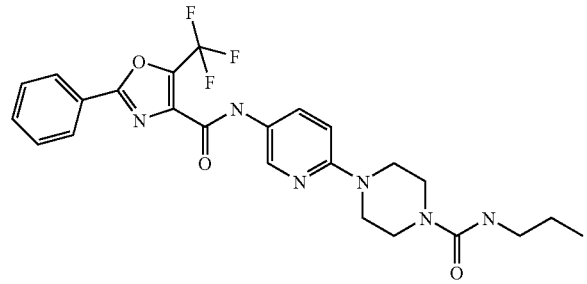

With a method similar to that used for the preparation of 4-{4-[(2-phenyl-5-trifluoromethyl-oxazole-4-carbonyl)-amino]-phenyl}-piperazine-1-carboxylic acid propylamide above, 4-{5-[(2-phenyl-5-trifluoromethyl-oxazole-4-carbonyl)-amino]-pyridin-2-yl}-piperazine-1-carboxylic acid propylamide was prepared from 2-phenyl-5-trifluoromethyl-oxazole-4-carboxylic acid (6-piperazin-1-yl-pyridin-3-yl)-amide hydrochloride and propylisocyanate. LC-MS calcd for C24H25F3N6O3 (m/e) 502.2, obsd 503.1 (M+H). The NMR spectrum obtained on the sample is compatible with its structure.

Example 198

Preparation of 2-phenyl-5-trifluoromethyl-oxazole-4-carboxylic acid [6-((S)-1-tert-butylcarbamoyl-pyrrolidin-3-ylamino)-pyridin-3-yl]-amide

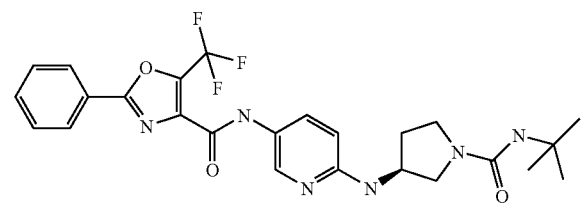

With a method similar to that used for the preparation of 4-{4-[(2-phenyl-5-trifluoromethyl-oxazole-4-carbonyl)-amino]-phenyl}-piperazine-1-carboxylic acid propylamide above, 2-phenyl-5-trifluoromethyl-oxazole-4-carboxylic acid [6-((S)-1-tert-butylcarbamoyl-pyrrolidin-3-ylamino)-pyridin-3-yl]-amide was prepared from 2-phenyl-5-trifluoromethyl-oxazole-4-carboxylic acid [6-((S)-pyrrolidin-3-ylamino)-pyridin-3-yl]-amide and tert-butyl isocyanate. LCMS calcd for C25H27F3N6O3 (m/e) 516.52, obsd 517.2 (M+H).

Example 199

Preparation of 4-{5-[(2-phenyl-5-trifluoromethyl-oxazole-4-carbonyl)-amino]-pyridin-2-ylamino}-piperidine-1-carboxylic acid butylamide

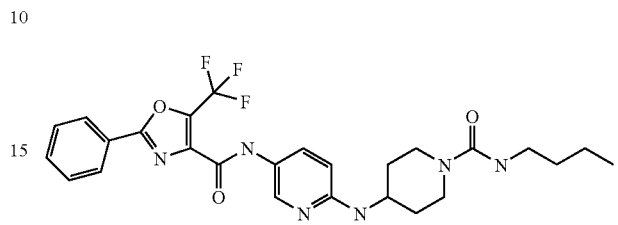

With a method similar to that used for the preparation of 4-{4-[(2-phenyl-5-trifluoromethyl-oxazole-4-carbonyl)-amino]-phenyl}-piperazine-1-carboxylic acid propylamide above, 4-{5-[(2-phenyl-5-trifluoromethyl-oxazole-4-carbonyl)-amino]-pyridin-2-ylamino}-piperidine-1-carboxylic acid butylamide was prepared from 2-phenyl-5-trifluoromethyl-oxazole-4-carboxylic acid [6-(piperidin-4-ylamino)-pyridin-3-yl]-amide trifluoroacetate and butyl isocyanate. LCMS calcd for C26H29F3N6O3 (m/e) 530, obsd 531 (M+H).

Example 200

Preparation of 4-{5-[(2-phenyl-5-trifluoromethyl-oxazole-4-carbonyl)-amino]-pyridin-2-ylamino}-piperidine-1-carboxylic acid cyclohexylamide

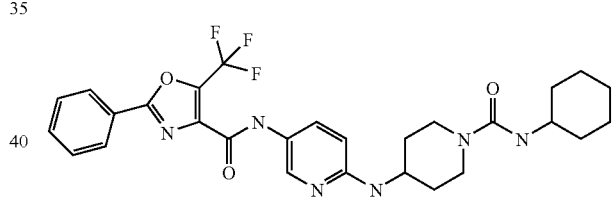

With a method similar to that used for the preparation of 4-{4-[(2-phenyl-5-trifluoromethyl-oxazole-4-carbonyl)-amino]-phenyl}-piperazine-1-carboxylic acid propylamide above, 4-{5-[(2-phenyl-5-trifluoromethyl-oxazole-4-carbonyl)-amino]-pyridin-2-ylamino}-piperidine-1-carboxylic acid cyclohexylamide was prepared from 2-phenyl-5-trifluoromethyl-oxazole-4-carboxylic acid [6-(piperidin-4-ylamino)-pyridin-3-yl]-amide trifluoroacetate and cyclohexyl isocyanate. LCMS calcd for C28H31F3N6O3 (m/e) 556, obsd 557 (M+H).

Example 201

Preparation of 4-{5-[(2-phenyl-5-trifluoromethyl-oxazole-4-carbonyl)-amino]-pyridin-2-ylamino}-piperidine-1-carboxylic acid benzylamide

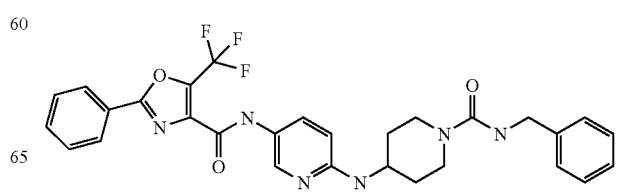

With a method similar to that used for the preparation of 4-{4-[(2-phenyl-5-trifluoromethyl-oxazole-4-carbonyl)-amino]-phenyl}-piperazine-1-carboxylic acid propylamide above, 4-{5-[(2-phenyl-5-trifluoromethyl-oxazole-4-carbonyl)-amino]-pyridin-2-ylamino}-piperidine-1-carboxylic acid benzylamide was prepared from 2-phenyl-5-trifluoromethyl-oxazole-4-carboxylic acid [6-(piperidin-4-ylamino)-pyridin-3-yl]-amide trifluoroacetate and benzyl isocyanate. LCMS calcd for C29H27F3N6O3 (m/e) 564, obsd 565 (M+H).

Example 202

Preparation of 4-{5-[(2-phenyl-5-trifluoromethyl-oxazole-4-carbonyl)-amino]-pyridin-2-ylamino}-piperidine-1-carboxylic acid methylamide

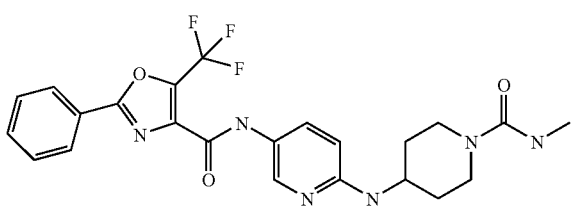

With a method similar to that used for the preparation of 4-{4-[(2-phenyl-5-trifluoromethyl-oxazole-4-carbonyl)-amino]-phenyl}-piperazine-1-carboxylic acid propylamide above, 4-{5-[(2-phenyl-5-trifluoromethyl-oxazole-4-carbonyl)-amino]-pyridin-2-ylamino}-piperidine-1-carboxylic acid methylamide was prepared from 2-phenyl-5-trifluoromethyl-oxazole-4-carboxylic acid [6-(piperidin-4-ylamino)-pyridin-3-yl]-amide trifluoroacetate and methyl isocyanate. LCMS calcd for C23H23F3N6O3 (m/e) 488, obsd 489 (M+H).

Example 203

Preparation of 2-phenyl-5-trifluoromethyl-oxazole-4-carboxylic acid [4-(3-isopropyl-1-methyl-ureido)-3,4,5,6-tetrahydro-2H-[1,2']bipyridinyl-5'-yl]-amide

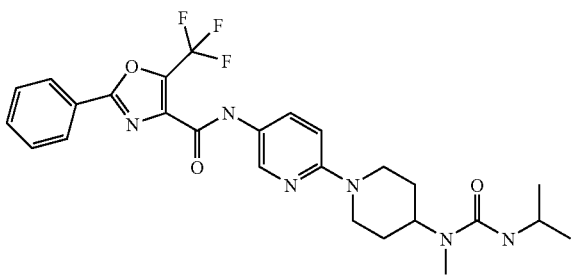

With a method similar to that used for the preparation of 4-{4-[(2-phenyl-5-trifluoromethyl-oxazole-4-carbonyl)-amino]-phenyl}-piperazine-1-carboxylic acid propylamide above, 2-phenyl-5-trifluoromethyl-oxazole-4-carboxylic acid [4-(3-isopropyl-1-methyl-ureido)-2H-[1,2']bipyridinyl-5'-yl]-amide was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and isopropyl isocyanate. LCMS calcd for C26H29F3N6O3 (m/e) 530, obsd 531 (M+H).

Example 204

Preparation of 2-phenyl-5-trifluoromethyl-oxazole-4-carboxylic acid [4-(3-butyl-1-methyl-ureido)-3,4,5,6-tetrahydro-2H-[1,2']bipyridinyl-5'-yl]-amide

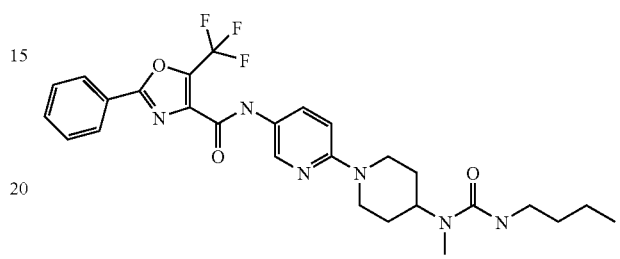

With a method similar to that used for the preparation of 4-{4-[(2-phenyl-5-trifluoromethyl-oxazole-4-carbonyl)-amino]-phenyl}-piperazine-1-carboxylic acid propylamide above, 2-phenyl-5-trifluoromethyl-oxazole-4-carboxylic acid [4-(3-butyl-1-methyl-ureido)-3,4,5,6-tetrahydro-2H-[1,2']bipyridinyl-5'-yl]-amide was prepared from 2-phenyl-5-trifluoromethyl-oxazole-4-carboxylic acid (4-methylamino-3,4,5,6-tetrahydro-2H-[1,2']bipyridinyl-5'-yl)-amide trifluoroacetate and butyl isocyanate. LCMS calcd for C27H31F3N6O3 (m/e) 544, obsd 545 (M+H).

Example 205

Preparation of 4-{5-[(2-phenyl-5-trifluoromethyl-oxazole-4-carbonyl)-amino]-pyridin-2-yl}-piperazine-1-carboxylic acid dimethylamide

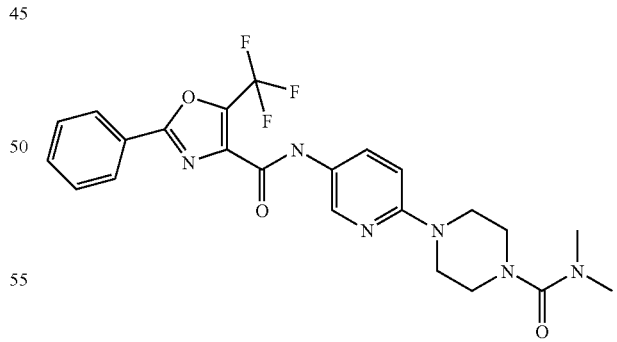

With a method similar to that used for the preparation of 4-{4-[(2-phenyl-5-trifluoromethyl-oxazole-4-carbonyl)-amino]-phenyl}-piperazine-1-carboxylic acid propylamide above, 4-{5-[(2-phenyl-5-trifluoromethyl-oxazole-4-carbonyl)-amino]-pyridin-2-yl}-piperazine-1-carboxylic acid dimethylamide was prepared from 2-phenyl-5-trifluoromethyl-oxazole-4-carboxylic acid (6-piperazin-1-yl-pyridin-3-yl)-amide hydrochloride and N,N-dimethylcarbamoyl chlo-

Example 206

Preparation of 2-phenyl-5-trifluoromethyl-oxazole-4-carboxylic acid [6-((S)-1-dimethylcarbamoyl-pyrrolidin-3-ylamino)-pyridin-3-yl]-amide

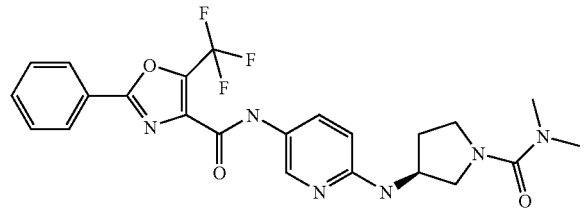

With a method similar to that used for the preparation of 4-{4-[(2-phenyl-5-trifluoromethyl-oxazole-4-carbonyl)-amino]-phenyl}-piperazine-1-carboxylic acid propylamide above, 2-phenyl-5-trifluoromethyl-oxazole-4-carboxylic acid [6-((S)-1-dimethylcarbamoyl-pyrrolidin-3-ylamino)-pyridin-3-yl]-amide was prepared from 2-phenyl-5-trifluoromethyl-oxazole-4-carboxylic acid [6-((S)-pyrrolidin-3-ylamino)-pyridin-3-yl]-amide and dimethyl carbamoyl chloride. LCMS calcd for C23H23F3N6O3 (m/e) 488.47, obsd 489.18 (M+H).

Example 207

Preparation of 4-{4-[(2-phenyl-5-trifluoromethyl-oxazole-4-carbonyl)-amino]-phenyl}-piperazine-1-carboxylic acid (3-methyl-pyridin-2-yl)-amide

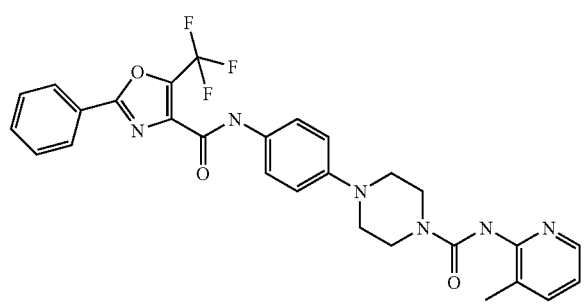

To a solution of 2-amino-3-picoline (26 μL, 0.204 mmol) and triethylamine (63 μL, 0.448 mmol) in 5 mL methylene chloride at −40° C. was slowly added a 20% solution of phosgene in THF (118 μL, 0.224 mmol). The reaction mixture was stirred at −40° C. for 1 hr and then a solution of 2-phenyl-5-trifluoromethyl-oxazole-4-carboxylic acid (4-piperazin-1-yl-phenyl)-amide hydrochloride (100 mg, 0.204 mmol) and triethylamine (57 μl, 0.408 mmol) in 8 ml of 1-methyl-2-pyrrolidinone was slowly added and stirred at room temperature overnight. The reaction mixture was diluted with ethyl acetate and washed with saturated sodium bicarbonate solution and water. The organic layer was dried over magnesium sulfate, filtered and evaporated to dryness. The residue was purified by flash chromatography (eluting with ethyl acetate/hexane) to yield 4-{4-[(2-phenyl-5-trifluoromethyl-oxazole-4-carbonyl)-amino]-phenyl}-piperazine-1-carboxylic acid (3-methyl-pyridin-2-yl)-amide (18 mg, 16%). ES-MS calcd for C28H25F3N6O3 (m/e) 550.6, obsd 551.1 (M+H).

Example 208

Preparation of 4-{4-[(2-phenyl-5-trifluoromethyl-oxazole-4-carbonyl)-amino]-phenyl}-piperazine-1-carboxylic acid ethylamide

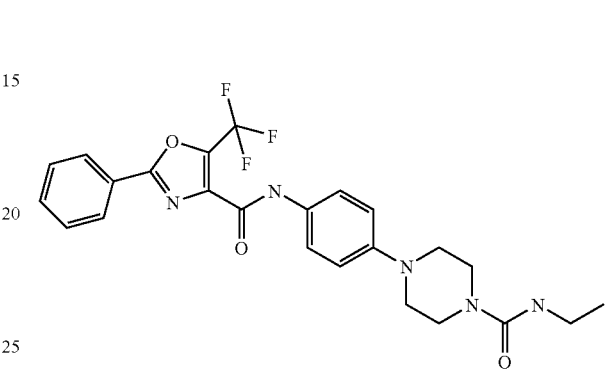

With a method similar to that used for the preparation of 4-{4-[(2-phenyl-5-trifluoromethyl-oxazole-4-carbonyl)-amino]-phenyl}-piperazine-1-carboxylic acid (3-methyl-pyridin-2-yl)-amide above, 4-{4-[(2-phenyl-5-trifluoromethyl-oxazole-4-carbonyl)-amino]-phenyl}-piperazine-1-carboxylic acid ethylamide was prepared from 2-phenyl-5-trifluoromethyl-oxazole-4-carboxylic acid (4-piperazin-1-yl-phenyl)-amide hydrochloride and ethylamine. LC-MS calcd for C24H24F3N5O3 (m/e) 487.5, obsd 488.1 (M+H).

Example 209

Preparation of 4-{4-[(2-phenyl-5-trifluoromethyl-oxazole-4-carbonyl)-amino]-phenyl}-piperazine-1-carboxylic acid ethyl-methyl-amide

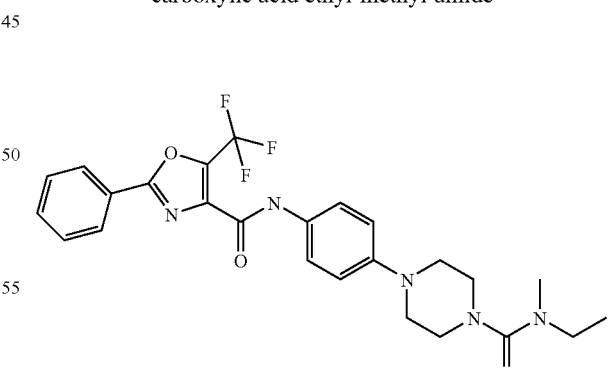

With a method similar to that used for the preparation of 4-{4-[(2-phenyl-5-trifluoromethyl-oxazole-4-carbonyl)-amino]-phenyl}-piperazine-1-carboxylic acid (3-methyl-pyridin-2-yl)-amide above, 4-{4-[(2-phenyl-5-trifluoromethyl-oxazole-4-carbonyl)-amino]-phenyl}-piperazine-1-carboxylic acid ethyl-methyl-amide was prepared from 2-phenyl-5-trifluoromethyl-oxazole-4-carboxylic acid (4-piperazin-1-yl-phenyl)-amide hydrochloride and N-ethylmethylamine. LC-MS calcd for C25H26F3N5O3 (m/e) 501.51, obsd 502.1 (M+H).

Example 210

Preparation of 4-{4-[(2-phenyl-5-trifluoromethyl-oxazole-4-carbonyl)-amino]-phenyl}-piperazine-1-carboxylic acid (5-methyl-isoxazol-3-yl)-amide

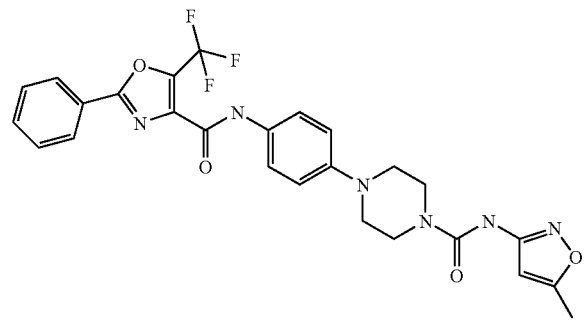

With a method similar to that used for the preparation of 4-{4-[(2-phenyl-5-trifluoromethyl-oxazole-4-carbonyl)-amino]-phenyl}-piperazine-1-carboxylic acid (3-methyl-pyridin-2-yl)-amide above, 4-{4-[(2-phenyl-5-trifluoromethyl-oxazole-4-carbonyl)-amino]-phenyl}-piperazine-1-carboxylic acid (5-methyl-isoxazol-3-yl)-amide was prepared from 2-phenyl-5-trifluoromethyl-oxazole-4-carboxylic acid (4-piperazin-1-yl-phenyl)-amide hydrochloride and 3-amino-5-methylisoxazole. LC-MS calcd for C26H23F3N6O4 (m/e) 540.4, obsd 541.1 (M+H).

Example 211

Preparation of rac-2-[(4-{4-[(2-phenyl-5-trifluoromethyl-oxazole-4-carbonyl)-amino]-phenyl}-piperazine-1-carbonyl)-amino]-cyclopentanecarboxylic acid methyl ester

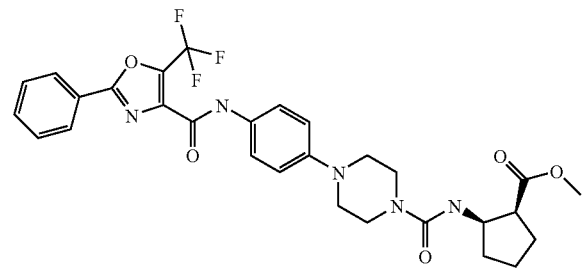

With a method similar to that used for the preparation of 4-{4-[(2-phenyl-5-trifluoromethyl-oxazole-4-carbonyl)-amino]-phenyl}-piperazine-1-carboxylic acid (3-methyl-pyridin-2-yl)-amide above, racemic 2-[(4-{4-[(2-phenyl-5-trifluoromethyl-oxazole-4-carbonyl)-amino]-phenyl}-piperazine-1-carbonyl)-amino]-cyclopentanecarboxylic acid methyl ester was prepared from 2-phenyl-5-trifluoromethyl-oxazole-4-carboxylic acid (4-piperazin-1-yl-phenyl)-amide hydrochloride and racemic cis-2-aminocyclopentanecarboxylic acid methyl ester hydrochloride. LC-MS calcd for C29H30F3N5O5 (m/e) 585.6, obsd 586.1 (M+H).

Example 212

Preparation of rac-1-(4-{4-[(2-phenyl-5-trifluoromethyl-oxazole-4-carbonyl)-amino]-phenyl}-piperazine-1-carbonyl)-pyrrolidine-3-carboxylic acid methyl ester

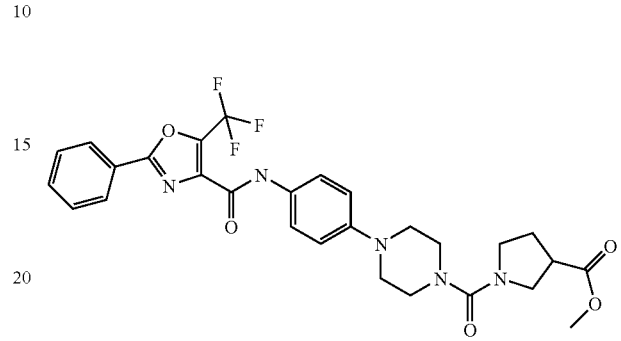

With a method similar to that used for the preparation of 4-{4-[(2-phenyl-5-trifluoromethyl-oxazole-4-carbonyl)-amino]-phenyl}-piperazine-1-carboxylic acid (3-methyl-pyridin-2-yl)-amide above, racemic 1-(4-{4-[(2-phenyl-5-trifluoromethyl-oxazole-4-carbonyl)-amino]-phenyl}-piperazine-1-carbonyl)-pyrrolidine-3-carboxylic acid methyl ester was prepared from 2-phenyl-5-trifluoromethyl-oxazole-4-carboxylic acid (4-piperazin-1-yl-phenyl)-amide hydrochloride and racemic pyrrolidine-3-carboxylic acid methyl ester hydrochloride. LC-MS calcd for C28H28F3N5O5 (m/e) 571.6, obsd 572.1 (M+H).

Example 213

Preparation of 3-chloro-4-{5-[(2-phenyl-5-trifluoromethyl-oxazole-4-carbonyl)-amino]-pyridin-2-yl}-benzoic acid

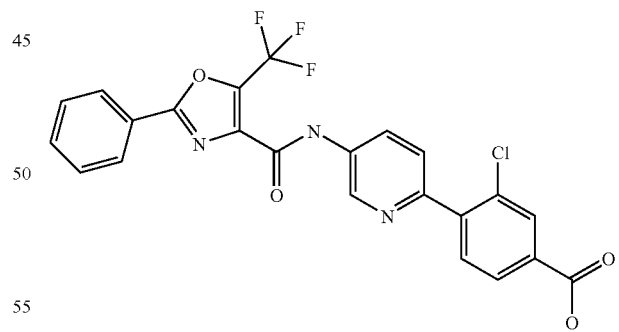

A mixture of 2-phenyl-5-trifluoromethyl-oxazole-4-carboxylic acid (6-bromo-pyridin-3-yl)-amide (600 mg, 1.46 mmol), (4-carboxy-2-chloro)benzeneboronic acid (437 mg, 2.18 mmol), tetrakis(triphenylphosphine)palladium(0) (84 mg, 0.07 mmol), and sodium carbonate (2M, 1.5 mL) in ethanol (10 mL) was microwaved at 160° C. for 30 min. The reaction was filtered and the precipitates were washed with ethanol. The combined filtrates were concentrated and purified by flash chromatography (Merck silica gel 60, 230-400 mesh, 0-25% methanol in methylene chloride) to give 3-chloro-4-{5-[(2-phenyl-5-trifluoromethyl-oxazole-4-carbonyl)-amino]-pyridin-2-yl}-benzoic acid (506 mg, 71%) as a light yellow solid. LCMS calcd for C23H13ClF3N3O4 (m/e) 487, obsd 488 (M+H).

Example 214

Preparation of 4-{5-[(2-phenyl-5-trifluoromethyl-oxazole-4-carbonyl)-amino]-pyridin-2-yl}-benzoic acid

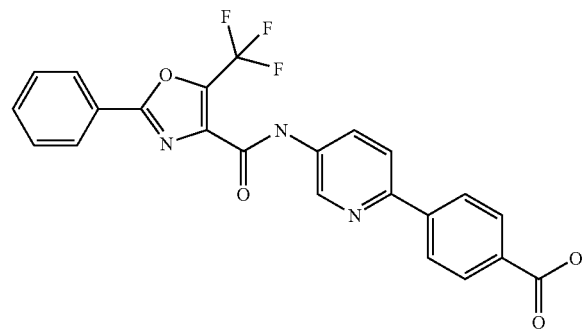

With a method similar to that used for the preparation of 3-chloro-4-{5-[(2-phenyl-5-trifluoromethyl-oxazole-4-carbonyl)-amino]-pyridin-2-yl}-benzoic acid above, 4-{5-[(2-phenyl-5-trifluoromethyl-oxazole-4-carbonyl)-amino]-pyridin-2-yl}-benzoic acid was prepared from 2-phenyl-5-trifluoromethyl-oxazole-4-carboxylic acid (6-bromo-pyridin-3-yl)-amide and 4-carboxyphenylboronic acid. LCMS calcd for C23H14F3N3O4 (m/e) 453, obsd 454 (M+H).

Example 215

Preparation of 2-chloro-4-{5-[(2-phenyl-5-trifluoromethyl-oxazole-4-carbonyl)-amino]-pyridin-2-yl}-benzoic acid

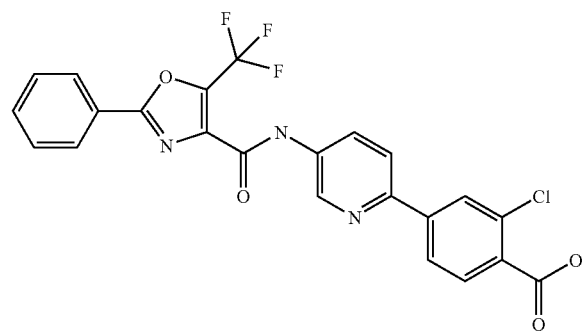

With a method similar to that used for the preparation of 3-chloro-4-{5-[(2-phenyl-5-trifluoromethyl-oxazole-4-carbonyl)-amino]-pyridin-2-yl}-benzoic acid above, 2-chloro-4-{5-[(2-phenyl-5-trifluoromethyl-oxazole-4-carbonyl)-amino]-pyridin-2-yl}-benzoic acid was prepared from 2-phenyl-5-trifluoromethyl-oxazole-4-carboxylic acid (6-bromo-pyridin-3-yl)-amide and 4-carboxy-3-chlorophenylboronic acid. LCMS calcd for C23H13ClF3N3O4 (m/e) 487, obsd 488 (M+H).

Example 216

Preparation of 2-phenyl-5-trifluoromethyl-oxazole-4-carboxylic acid [6-(4-isobutylcarbamoyl-phenyl)-pyridin-3-yl]-amide

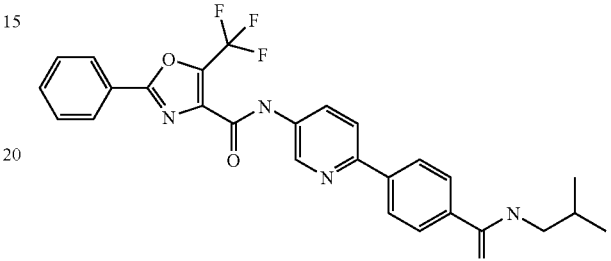

With a method similar to that used for the preparation of 3-chloro-4-{5-[(2-phenyl-5-trifluoromethyl-oxazole-4-carbonyl)-amino]-pyridin-2-yl}-benzoic acid above, 2-phenyl-5-trifluoromethyl-oxazole-4-carboxylic acid [6-(4-isobutylcarbamoyl-phenyl)-pyridin-3-yl]-amide was prepared from 2-phenyl-5-trifluoromethyl-oxazole-4-carboxylic acid (6-bromo-pyridin-3-yl)-amide and 4-(isobutylaminocarbonyl)benzeneboronic acid. LCMS calcd for C27H23F3N4O3 (m/e) 508, obsd 509 (M+H).

Example 217

Preparation of 2-phenyl-5-trifluoromethyl-oxazole-4-carboxylic acid (4'-isobutylcarbamoyl-biphenyl-4-yl)-amide

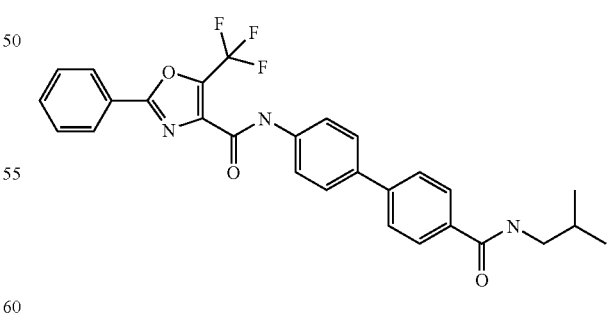

With a method similar to that used for the preparation of 3-chloro-4-{5-[(2-phenyl-5-trifluoromethyl-oxazole-4-carbonyl)-amino]-pyridin-2-yl}-benzoic acid above, 2-phenyl-5-trifluoromethyl-oxazole-4-carboxylic acid (4'-isobutylcarbamoyl-biphenyl-4-yl)-amide was prepared from 2-phenyl-5-trifluoromethyl-oxazole-4-carboxylic acid (4-iodophenyl)-amide and 4-(isobutylaminocarbonyl)benzeneboronic acid. LCMS calcd for C28H24F3N3O3 (m/e) 507, obsd 508 (M+H).

Example 218

Preparation of 4'-[(2-phenyl-5-trifluoromethyl-oxazole-4-carbonyl)-amino]-biphenyl-4-carboxylic acid

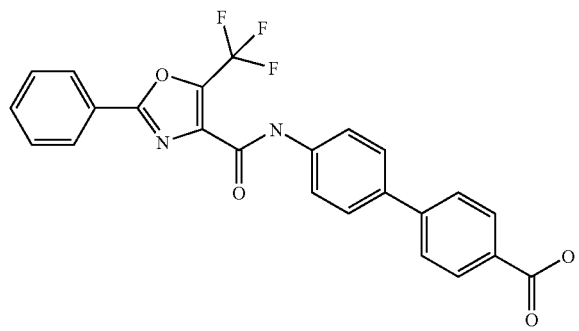

With a method similar to that used for the preparation of 3-chloro-4-{5-[(2-phenyl-5-trifluoromethyl-oxazole-4-carbonyl)-amino]-pyridin-2-yl}-benzoic acid above, 4'-[(2-phenyl-5-trifluoromethyl-oxazole-4-carbonyl)-amino]-biphenyl-4-carboxylic acid was prepared from 2-phenyl-5-trifluoromethyl-oxazole-4-carboxylic acid (4-iodo-phenyl)-amide and 4-carboxyphenylboronic acid. LCMS calcd for C24H15F3N2O4 (m/e) 452, obsd 453 (M+H).

Example 219

Preparation of 2-phenyl-5-trifluoromethyl-oxazole-4-carboxylic acid [6-(4-cyclopentylcarbamoyl-phenyl)-pyridin-3-yl]-amide

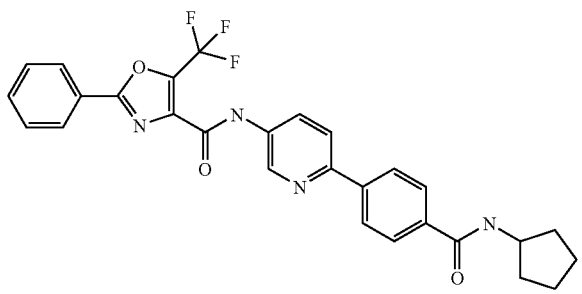

With a method similar to that used for the preparation of 3-chloro-4-{5-[(2-phenyl-5-trifluoromethyl-oxazole-4-carbonyl)-amino]-pyridin-2-yl}-benzoic acid above, 2-phenyl-5-trifluoromethyl-oxazole-4-carboxylic acid [6-(4-cyclopentylcarbamoyl-phenyl)-pyridin-3-yl]-amide was prepared from 2-phenyl-5-trifluoromethyl-oxazole-4-carboxylic acid (6-bromo-pyridin-3-yl)-amide and 4-(cyclopentylaminocarbonyl)benzeneboronic acid. LCMS calcd for C28H23F3N4O3 (m/e) 520, obsd 521 (M+H).

Example 220

Preparation of 2-phenyl-5-trifluoromethyl-oxazole-4-carboxylic acid [6-(4-cyclopropylcarbamoyl-phenyl)-pyridin-3-yl]-amide

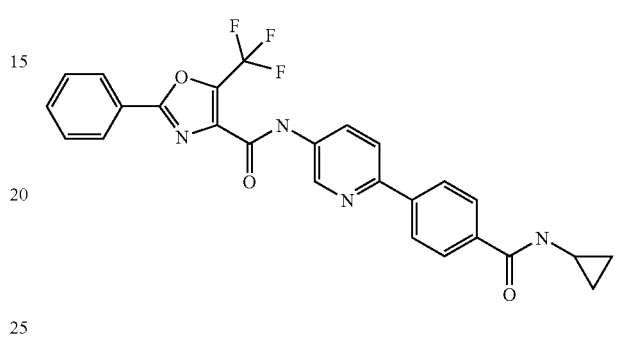

With a method similar to that used for the preparation of 3-chloro-4-{5-[(2-phenyl-5-trifluoromethyl-oxazole-4-carbonyl)-amino]-pyridin-2-yl}-benzoic acid above, 2-phenyl-5-trifluoromethyl-oxazole-4-carboxylic acid [6-(4-cyclopropylcarbamoyl-phenyl)-pyridin-3-yl]-amide was prepared from 2-phenyl-5-trifluoromethyl-oxazole-4-carboxylic acid (6-bromo-pyridin-3-yl)-amide and 4-(N-cyclopropylaminocarbonyl)phenylboronic acid. LCMS calcd for C26H19F3N4O3 (m/e) 492, obsd 493 (M+H).

Example 221

Preparation of 2-phenyl-5-trifluoromethyl-oxazole-4-carboxylic acid (4'-cyclopropylcarbamoyl-biphenyl-4-yl)-amide

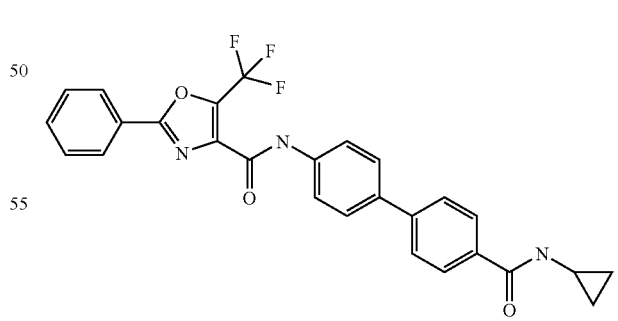

With a method similar to that used for the preparation of 3-chloro-4-{5-[(2-phenyl-5-trifluoromethyl-oxazole-4-carbonyl)-amino]-pyridin-2-yl}-benzoic acid above, 2-phenyl-5-trifluoromethyl-oxazole-4-carboxylic acid (4'-cyclopropylcarbamoyl-biphenyl-4-yl)-amide was prepared from 2-phenyl-5-trifluoromethyl-oxazole-4-carboxylic acid (4-iodo-phenyl)-amide and 4-(N-cyclopropylaminocarbonyl)phenylboronic acid. LCMS calcd for C27H20F3N3O3 (m/e) 491, obsd 492 (M+H).

Example 222

Preparation of (R)-1-(4-{5-[(2-phenyl-5-trifluoromethyl-oxazole-4-carbonyl)-amino]-pyridin-2-yl}-benzoyl)-pyrrolidine-2-carboxylic acid

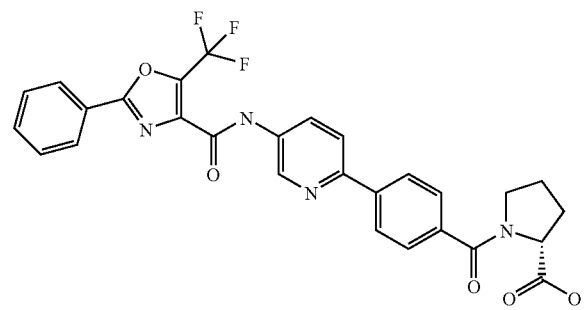

A mixture of 4-{5-[(2-phenyl-5-trifluoromethyl-oxazole-4-carbonyl)-amino]-pyridin-2-yl}-benzoic acid (45 mg, 0.1 mmol), D-proline t-butyl ester hydrochloride (31 mg, 0.15 mmol), triethylamine (50 µL, 0.3 mmol), 1-hydroxy-7-azabenzotriazole (HOAT) (20 mg, 0.15 mmol), and 1-ethyl-3-(3-dimethylaminopropyl)carbodiimide hydrochloride (30 mg, 0.15 mmol) in anhydrous dichloromethane (5 mL) and N,N-dimethylformamide (1.5 mL) was stirred at room temperature overnight. The reaction mixture was concentrated and purified by flash chromatography (Merck silica gel 60, 230-400 mesh, 0%-100% ethyl acetate in hexane) to give (R)-1-(4-{5-[(2-phenyl-5-trifluoromethyl-oxazole-4-carbonyl)-amino]-pyridin-2-yl}-benzoyl)-pyrrolidine-2-carboxylic acid tert-butyl ester (51 mg, 84%) as a white solid.

(R)-1-(4-{5-[(2-phenyl-5-trifluoromethyl-oxazole-4-carbonyl)-amino]-pyridin-2-yl}-benzoyl)-pyrrolidine-2-carboxylic acid tert-butyl ester (37 mg) from above was treated with 2 mL of trifluoroacetic acid and stirred at room temperature for one hour. The reaction was concentrated and the product was lyophilized to give 27 mg of (R)-1-(4-{5-[(2-phenyl-5-trifluoromethyl-oxazole-4-carbonyl)-amino]-pyridin-2-yl}-benzoyl)-pyrrolidine-2-carboxylic acid as a white powder. LCMS calcd for C28H21F3N4O5 (m/e) 550, obsd 551 (M+H).

Example 223

Preparation of (S)-1-(4-{5-[(2-phenyl-5-trifluoromethyl-oxazole-4-carbonyl)-amino]-pyridin-2-yl}-benzoyl)-pyrrolidine-2-carboxylic acid

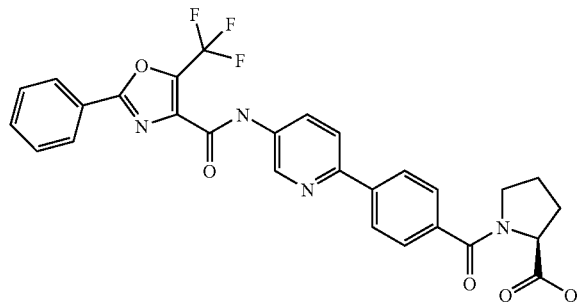

With a method similar to that used for the preparation of (R)-1-(4-{5-[(2-phenyl-5-trifluoromethyl-oxazole-4-carbonyl)-amino]-pyridin-2-yl}-benzoyl)-pyrrolidine-2-carboxylic acid above, (S)-1-(4-{5-[(2-phenyl-5-trifluoromethyl-oxazole-4-carbonyl)-amino]-pyridin-2-yl}-benzoyl)-pyrrolidine-2-carboxylic acid was prepared from 4-{5-[(2-phenyl-5-trifluoromethyl-oxazole-4-carbonyl)-amino]-pyridin-2-yl}-benzoic acid and L-proline t-butyl ester. LCMS calcd for C28H21F3N4O5 (m/e) 550, obsd 551 (M+H).

Example 224

Preparation of 2-phenyl-5-trifluoromethyl-oxazole-4-carboxylic acid [6-(2-chloro-4-cyclopropylcarbamoyl-phenyl)-pyridin-3-yl]-amide

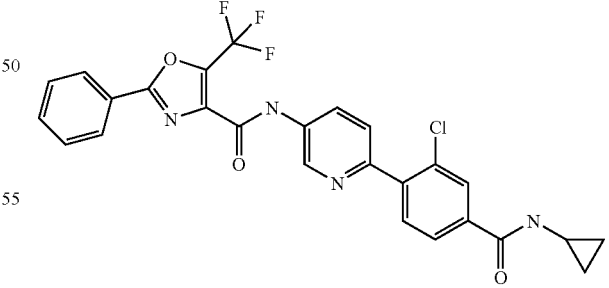

With a method similar to that used for the preparation of (R)-1-(4-{5-[(2-phenyl-5-trifluoromethyl-oxazole-4-carbonyl)-amino]-pyridin-2-yl}-benzoyl)-pyrrolidine-2-carboxylic acid above, 2-phenyl-5-trifluoromethyl-oxazole-4-carboxylic acid [6-(2-chloro-4-cyclopropylcarbamoyl-phenyl)-pyridin-3-yl]-amide was prepared from 4-{5-[(2-phenyl-5-trifluoromethyl-oxazole-4-carbonyl)-amino]-pyridin-2-yl}- benzoic acid and cyclopropylamine. LCMS calcd for C26H18ClF3N4O3 (m/e) 526, obsd 527 (M+H).

Example 225

Preparation of 2-phenyl-5-trifluoromethyl-oxazole-4-carboxylic acid [6-(2-chloro-4-isobutylcarbamoyl-phenyl)-pyridin-3-yl]-amide

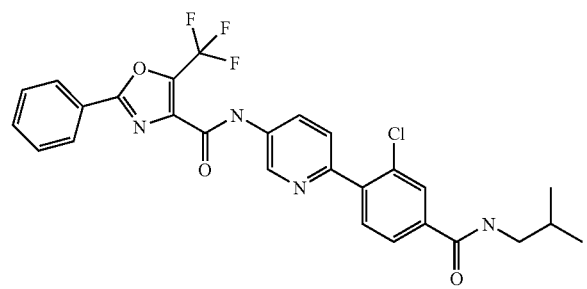

With a method similar to that used for the preparation of (R)-1-(4-{5-[(2-phenyl-5-trifluoromethyl-oxazole-4-carbonyl)-amino]-pyridin-2-yl}-benzoyl)-pyrrolidine-2-carboxylic acid above, 2-phenyl-5-trifluoromethyl-oxazole-4-carboxylic acid [6-(2-chloro-4-isobutylcarbamoyl-phenyl)-pyridin-3-yl]-amide was prepared from 3-chloro-4-{5-[(2-phenyl-5-trifluoromethyl-oxazole-4-carbonyl)-amino]-pyridin-2-yl}-benzoic acid and isobutylamine. LCMS calcd for C27H22ClF3N4O3 (m/e) 542, obsd 543 (M+H).

Example 226

Preparation of 2-phenyl-5-trifluoromethyl-oxazole-4-carboxylic acid [6-(2-chloro-4-methanesulfonylaminocarbonyl-phenyl)-pyridin-3-yl]-amide

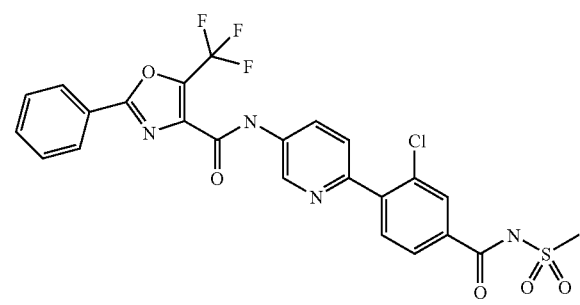

According to the procedures described in *Tetrahedron Lett.* 1998, 39, 5891 and *Org. Proc. Res. Dev.* 2004, 8, 952, 3-chloro-4-{5-[(2-phenyl-5-trifluoromethyl-oxazole-4-carbonyl)-amino]-pyridin-2-yl}-benzoic acid (30 mg, 0.06 mmol), methanesulfonamide (7 mg, 0.07 mmol), 4-dimethylaminopyridine (2 mg, 0.02 mmol) and 1-ethyl-3-(3-dimethylaminopropyl)carbodiimide hydrochloride (14 mg, 0.07 mmol) were suspended in 3 mL of dichloromethane and the mixture was refluxed for 3 h. The reaction mixture was cooled down to room temperature and filtered. The white precipitates were washed with ethyl acetate. The combined filtrate was stirred with 150 mg of Amberlyst-15 at room temperature for 2 h. The reaction was filtered to remove the resin, and the filtrate was concentrated and purified by flash chromatography (eluting with ethyl acetate and hexanes) to afford 12 mg of 2-phenyl-5-trifluoromethyl-oxazole-4-carboxylic acid [6-(2-chloro-4-methanesulfonylaminocarbonyl-phenyl)-pyridin-3-yl]-amide as a light yellow solid. LCMS calcd for C24H16ClF3N4O5S (m/e) 564, obsd 565 (M+H).

Example 227

Preparation of 2-phenyl-5-trifluoromethyl-oxazole-4-carboxylic acid {6-[2-chloro-4-(methanesulfonyl-methyl-aminocarbonyl)-phenyl]-pyridin-3-yl}-amide

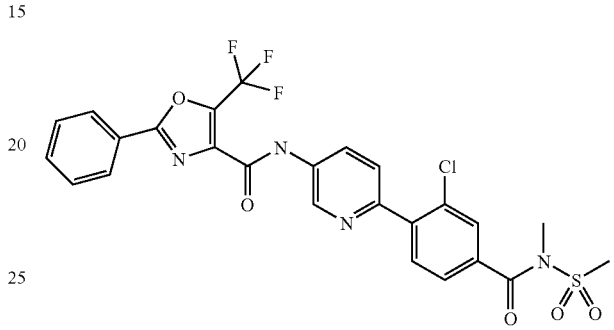

With a method similar to that used for the preparation of 2-phenyl-5-trifluoromethyl-oxazole-4-carboxylic acid [6-(2-chloro-4-methanesulfonylaminocarbonyl-phenyl)-pyridin-3-yl]-amide above, 2-phenyl-5-trifluoromethyl-oxazole-4-carboxylic acid {6-[2-chloro-4-(methanesulfonyl-methyl-aminocarbonyl)-phenyl]-pyridin-3-yl}-amide was prepared from 3-chloro-4-{5-[(2-phenyl-5-trifluoromethyl-oxazole-4-carbonyl)-amino]-pyridin-2-yl}-benzoic acid and N-methyl-methanesulfonamide. LCMS calcd for C25H18ClF3N4O5S (m/e) 578, obsd 579 (M+H).

Example 228

Preparation of 2-phenyl-5-trifluoromethyl-oxazole-4-carboxylic acid (6-{[2-chloro-4-(2-methyl-propane-2-sulfonylaminocarbonyl]-phenyl}-pyridin-3-yl)-amide

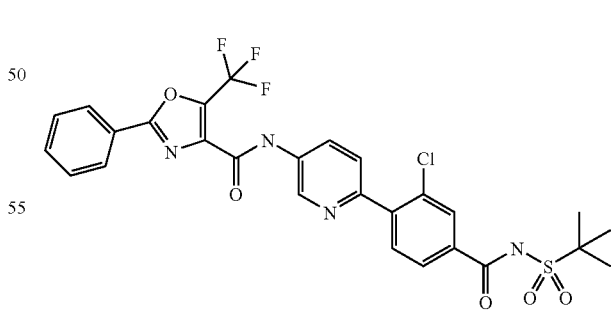

With a method similar to that used for the preparation of 2-phenyl-5-trifluoromethyl-oxazole-4-carboxylic acid [6-(2-chloro-4-methanesulfonylaminocarbonyl-phenyl)-pyridin-3-yl]-amide above, 2-phenyl-5-trifluoromethyl-oxazole-4-carboxylic acid (6-{[2-chloro-4-(2-methyl-propane-2-sulfonylaminocarbonyl]-phenyl}-pyridin-3-yl)-amide was prepared from 3-chloro-4-{5-[(2-phenyl-5-trifluoromethyl-

Example 229

Preparation of rac-2-phenyl-5-trifluoromethyl-oxazole-4-carboxylic acid {6-[4-(3,4-dihydroxy-cyclopentanecarbonyl)-piperazin-1-yl]-pyridin-3-yl}-amide

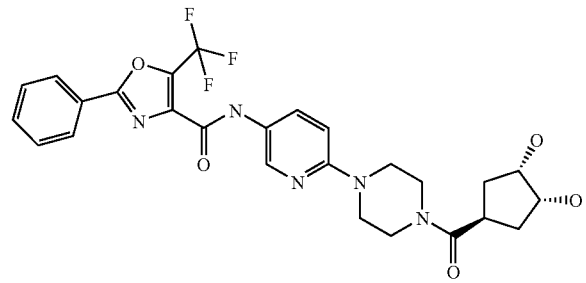

To a solution of 2-phenyl-5-trifluoromethyl-oxazole-4-carboxylic acid {6-[4-(cyclopent-3-enecarbonyl)-piperazin-1-yl]-pyridin-3-yl}-amide described previously (50 mg, 0.0978 mmol) in acetone (10 mL) was added two drops of osmium tetroxide in butanol (2.5% wt) and 4-methylmorpholine N-oxide (15 mg). The mixture was stirred at room temperature for 1 hr and the solvents were evaporated. The residue was extracted with methylene chloride and water. The organic layer was washed with citric acid solution and dried over sodium sulfate. The solvents were evaporated and the residue was purified using flash chromatography (eluting with methylene chloride and methanol) to give racemic 2-phenyl-5-trifluoromethyl-oxazole-4-carboxylic acid {6-[4-(3,4-dihydroxy-cyclopentanecarbonyl)-piperazin-1-yl]-pyridin-3-yl}-amide (25.7 mg) as a solid. LC-MS calcd for C26H26F3N5O5 (m/e) 545.2, obsd 546.1 (M+H). The NMR spectrum obtained on the sample is compatible with its structure.

Example 230

Preparation of rac-2-phenyl-5-trifluoromethyl-oxazole-4-carboxylic acid {4-[1-(3,4-dihydroxy-cyclopentanecarbonyl)-piperidin-4-yl]-phenyl}-amide

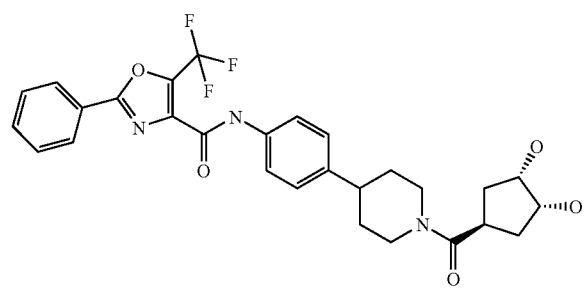

With a method similar to that used for the preparation of racemic 2-phenyl-5-trifluoromethyl-oxazole-4-carboxylic acid {6-[4-(3,4-dihydroxy-cyclopentanecarbonyl)-piperazin-1-yl]-pyridin-3-yl}-amide above, racemic 2-phenyl-5-trifluoromethyl-oxazole-4-carboxylic acid {4-[1-(3,4-dihydroxy-cyclopentanecarbonyl)-piperidin-4-yl]-phenyl}-amide was prepared from 2-phenyl-5-trifluoromethyl-oxazole-4-carboxylic acid {4-[1-(cyclopent-3-enecarbonyl)-piperidin-4-yl]-phenyl}-amide and osmium tetroxide. LC-MS calcd for C28H28F3N3O5 (m/e) 543.2, obsd 544.1 (M+H). The NMR spectrum obtained on the sample is compatible with its structure.

Example 231

Preparation of (S)-3-(5-{[2-(2-bromo-phenyl)-5-propyl-oxazole-4-carbonyl]-amino}-pyridin-2-ylamino)-pyrrolidine-1-carboxylic acid ethyl ester

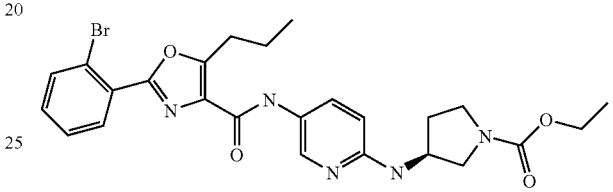

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-(5-{[2-(2-bromo-phenyl)-5-propyl-oxazole-4-carbonyl]-amino}-pyridin-2-ylamino)-pyrrolidine-1-carboxylic acid ethyl ester was prepared from 2-(2-bromo-phenyl)-5-propyl-oxazole-4-carboxylic acid and (S)-3-(5-amino-pyridin-2-ylamino)-pyrrolidine-1-carboxylic acid ethyl ester. HRMS calcd for C25H28BrN5O4 (M+H) 542.1398, obsd 542.1396.

Example 232

Preparation of (S)-3-(5-{[2-(2-bromo-phenyl)-5-trifluoromethyl-oxazole-4-carbonyl]-amino}-pyridin-2-ylamino)-pyrrolidine-1-carboxylic acid ethyl ester

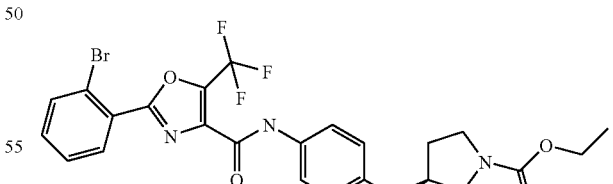

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-(5-{[2-(2-bromo-phenyl)-5-trifluoromethyl-oxazole-4-carbonyl]-amino}-pyridin-2-ylamino)-pyrrolidine-1-carboxylic acid ethyl ester was prepared from 2-(2-bromo-phenyl)-5-trifluoromethyl-oxazole-4-carboxylic acid and (S)-3-(5-amino-pyridin-2-ylamino)-pyrrolidine- 1-carboxylic acid ethyl ester. HRMS calcd for C23H21BrF3N5O4 (M+H) 568.0802, obsd 568.0801.

Example 233

Preparation of (S)-3-{5-[(1-phenyl-3-trifluoromethyl-1H-pyrazole-4-carbonyl)-amino]-pyridin-2-ylamino}-pyrrolidine-1-carboxylic acid ethyl ester

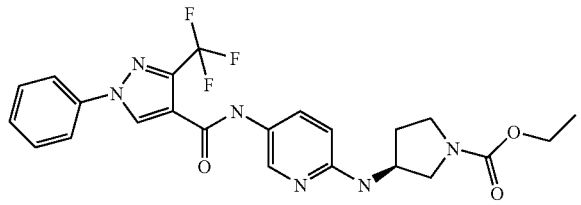

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-{5-[(1-phenyl-3-trifluoromethyl-1H-pyrazole-4-carbonyl)-amino]-pyridin-2-ylamino}-pyrrolidine-1-carboxylic acid ethyl ester was prepared from 1-phenyl-3-trifluoromethyl-1H-pyrazole-4-carboxylic acid and (S)-3-(5-amino-pyridin-2-ylamino)-pyrrolidine-1-carboxylic acid ethyl ester. HRMS calcd for C23H23F3N6O3 (M+H) 489.1857, obsd 489.1853.

Example 234

Preparation of (S)-3-{5-[(1-Pyridin-2-yl-3-trifluoromethyl-1H-pyrazole-4-carbonyl)-amino]-pyridin-2-ylamino}-pyrrolidine-1-carboxylic acid ethyl ester

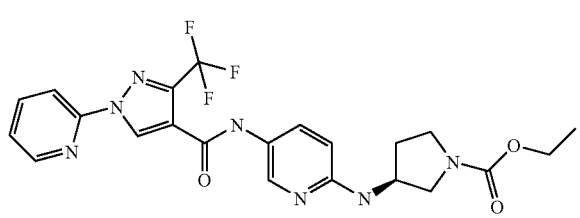

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-{5-[(1-pyridin-2-yl-3-trifluoromethyl-1H-pyrazole-4-carbonyl)-amino]-pyridin-2-ylamino}-pyrrolidine-1-carboxylic acid ethyl ester was prepared from 1-pyridin-2-yl-3-trifluoromethyl-1H-pyrazole-4-carboxylic acid and (S)-3-(5-amino-pyridin-2-ylamino)-pyrrolidine-1-carboxylic acid ethyl ester. HRMS calcd for C22H22F3N7O3 (M+H) 490.1809, obsd 490.1807.

Example 235

Preparation of (S)-3-(4-{[2-(2-Trifluoromethoxy-phenyl)-5-trifluoromethyl-oxazole-4-carbonyl]-amino}-phenylamino)-pyrrolidine-1-carboxylic acid tert butyl ester

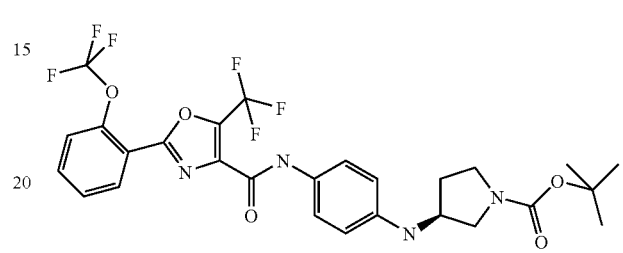

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-(4-{[2-(2-trifluoromethoxy-phenyl)-5-trifluoromethyl-oxazole-4-carbonyl]-amino}-phenylamino)-pyrrolidine-1-carboxylic acid tert butyl ester was prepared from 2-(2-trifluoromethoxy-phenyl)-5-trifluoromethyl-oxazole-4-carboxylic acid and (S)-3-(4-amino-phenylamino)-pyrrolidine-1-carboxylic acid tert butyl ester. HRMS calcd for C27H26F6N4O5 (M+H) 601.188, obsd 601.1877.

Example 236

Preparation of (S)-3-(4-{[2-(2-Trifluoromethoxy-phenyl)-5-trifluoromethyl-oxazole-4-carbonyl]-amino}-phenylamino)-pyrrolidine-1-carboxylic acid ethyl ester

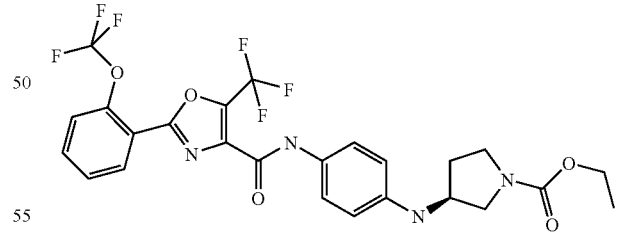

With a method similar to that used for the preparation of (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid ethyl ester above, (S)-3-(4-{[2-(2-trifluoromethoxy-phenyl)-5-trifluoromethyl-oxazole-4-carbonyl]-amino}-phenylamino)-pyrrolidine-1-carboxylic acid ethyl ester was prepared from 2-(2-trifluoromethoxy-phenyl)-5-trifluoromethyl-oxazole-4-carboxylic acid and (S)-3-(4-amino-phenylamino)-pyrrolidine-1-carboxylic acid tert butyl ester, followed by deprotection with trifluoroacetic acid and subsequent treatment with ethyl chloroformate. HRMS calcd for C25H22F6N4O5 (M+H) 573.1567, obsd 573.1565.

Example 237

Preparation of (S)-3-{4-[(1-phenyl-3-trifluoromethyl-1H-pyrazole-4-carbonyl)-amino]-phenylamino}-pyrrolidine-1-carboxylic acid ethyl ester

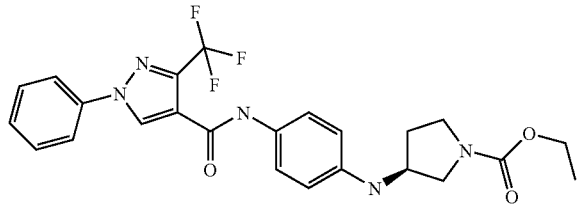

With a method similar to that used for the preparation of (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid ethyl ester above, (S)-3-{4-[(1-phenyl-3-trifluoromethyl-1H-pyrazole-4-carbonyl)-amino]-phenylamino}-pyrrolidine-1-carboxylic acid ethyl ester was prepared from 1-phenyl-3-trifluoromethyl-1H-pyrazole-4-carboxylic acid and (S)-3-(4-amino-phenylamino)-pyrrolidine-1-carboxylic acid tert butyl ester, followed by deprotection with trifluoroacetic acid and subsequent treatment with ethyl chloroformate. HRMS calcd for C24H24F3N5O3 (M+H) 488.1904, obsd 488.1904.

Example 238

Preparation of 1-{4-[(2-phenyl-5-trifluoromethyl-oxazole-4-carbonyl)-amino]-phenyl}-piperidine-4-carboxylic acid ethyl ester

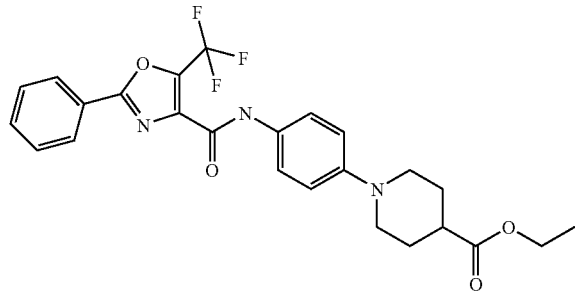

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 1-{4-[(2-phenyl-5-trifluoromethyl-oxazole-4-carbonyl)-amino]-phenyl}-piperidine-4-carboxylic acid ethyl ester was prepared from 2-phenyl-5-trifluoromethyl-oxazole-4-carboxylic acid and 1-(4-amino-phenyl)-piperidine-4-carboxylic acid ethyl ester. HRMS calcd for C25H24F3N3O4 (M+H) 488.1792, obsd 488.1792.

Example 239

Preparation of 1-{5-[(2-phenyl-5-trifluoromethyl-oxazole-4-carbonyl)-amino]-pyrimidin-2-yl}-piperidine-4-carboxylic acid ethyl ester

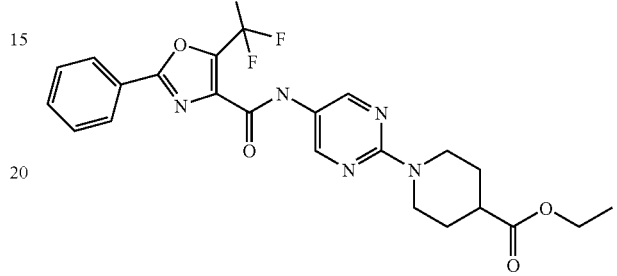

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 1-{5-[(2-phenyl-5-trifluoromethyl-oxazole-4-carbonyl)-amino]-pyrimidin-2-yl}-piperidine-4-carboxylic acid ethyl ester was prepared from 2-phenyl-5-trifluoromethyl-oxazole-4-carboxylic acid and 1-(5-amino-pyrimidin-2-yl)-piperidine-4-carboxylic acid ethyl ester. HRMS calcd for C23H22F3N5O4 (M+H) 490.1697, obsd 490.1695.

Example 240

Preparation of Methyl-[2-(methyl-{5-[(2-phenyl-5-trifluoromethyl-oxazole-4-carbonyl)-amino]-pyridin-2-yl}-amino)-ethyl]-carbamic acid ethyl ester

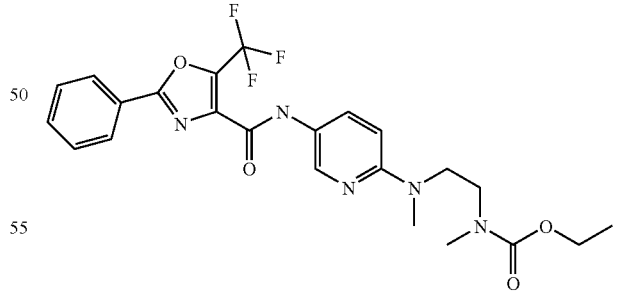

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, methyl-[2-(methyl-{5-[(2-phenyl-5-trifluoromethyl-oxazole-4-carbonyl)-amino]-pyridin-2-yl}-amino)-ethyl]-carbamic acid ethyl ester was prepared from 2-phenyl-5-trifluoromethyl-oxazole-4-carboxylic acid and {2-[(5-amino-pyridin-2-yl)-methyl-amino]-ethyl}-methylcarbamic acid ethyl ester. HRMS calcd for C23H24F3N5O4 (M+H) 492.1853, obsd 492.1855.

Example 241

Preparation of (S)-3-{5-[(2-phenyl-5-trifluoromethyl-oxazole-4-carbonyl)amino]-pyridin-2-yloxy}-pyrrolidine-1-carboxylic acid tert butyl ester

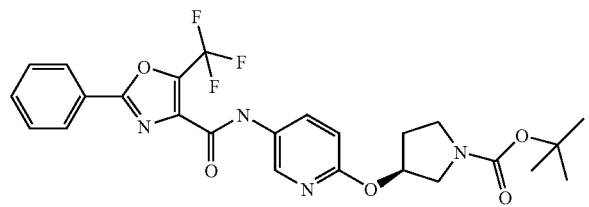

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-{5-[(2-phenyl-5-trifluoromethyl-oxazole-4-carbonyl)-amino]-pyridin-2-yloxy}-pyrrolidine-1-carboxylic acid tert butyl ester was prepared from 2-phenyl-5-trifluoromethyl-oxazole-4-carboxylic acid and (S)-3-(5-amino-pyridin-2-yloxy)-pyrrolidine-1-carboxylic acid tert butyl ester. HRMS calcd for C25H25F3N4O5 (M+Na) 541.1669, obsd 541.1664.

Example 242

Preparation of (S)-3-{5-[(2-phenyl-5-trifluoromethyl-oxazole-4-carbonyl)amino]-pyridin-2-yloxy}-pyrrolidine-1-carboxylic acid ethyl ester

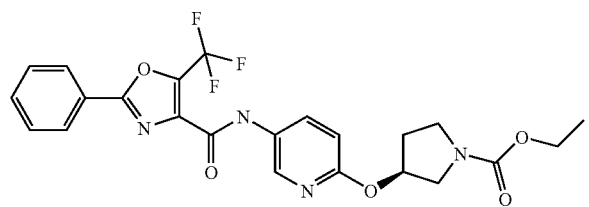

With a method similar to that used for the preparation of (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid ethyl ester above, (S)-3-{5-[(2-phenyl-5-trifluoromethyl-oxazole-4-carbonyl)-amino]-pyridin-2-yloxy}-pyrrolidine-1-carboxylic acid ethyl ester was prepared from (S)-3-{5-[(2-phenyl-5-trifluoromethyl-oxazole-4-carbonyl)-amino]-pyridin-2-yloxy}-pyrrolidine-1-carboxylic acid tert butyl ester, by deprotection with trifluoroacetic acid and subsequent treatment with ethyl chloroformate. HRMS calcd for C23H21F3N4O5 (M+H) 491.1537, obsd 491.1537.

Example 243

Preparation of (S)-3-{4-[(2-phenyl-5-trifluoromethyl-oxazole-4-carbonyl)-amino]-phenoxy}-pyrrolidine-1-carboxylic acid tert butyl ester

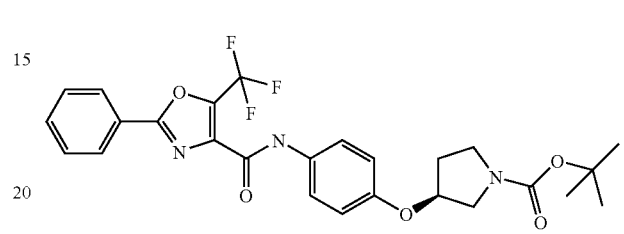

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-{4-[(2-phenyl-5-trifluoromethyl-oxazole-4-carbonyl)-amino]-phenoxy}-pyrrolidine-1-carboxylic acid tert butyl ester was prepared from 2-phenyl-5-trifluoromethyl-oxazole-4-carboxylic acid and (S)-3-(4-amino-phenoxy)-pyrrolidine-1-carboxylic acid tert butyl ester. HRMS calcd for C26H26F3N3O5 (M+Na) 540.1717, obsd 540.1716.

Example 244

Preparation of (S)-3-(4-{[(2-(2-Trifluoromethoxy-phenyl)-5-trifluoromethyl-oxazole-4-carbonyl]-amino}-phenoxy)-pyrrolidine-1-carboxylic acid tert butyl ester

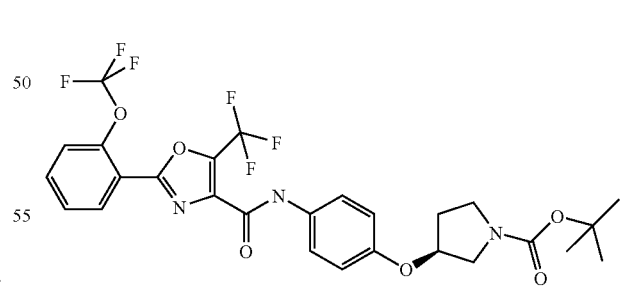

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-(4-{[(2-(2-trifluoromethoxy-phenyl)-5-trifluoromethyl-oxazole-4-carbonyl]-amino}-phenoxy)-pyrrolidine-1-carboxylic acid tert butyl ester was prepared from 2-(2-trifluoromethoxy-phenyl)-5-trifluoromethyl-oxazole-4-carboxylic acid and (S)-3-(4-amino-phenoxy)-pyrrolidine-1-carboxylic acid tert butyl ester. HRMS calcd for C27H25F6N3O6 (M+Na) 624.154, obsd 624.1539.

Example 245

Preparation of (S)-3-{4-[(2-phenyl-5-trifluoromethyl-oxazole-4-carbonyl)-amino]-phenoxy}-pyrrolidine-1-carboxylic acid ethyl ester

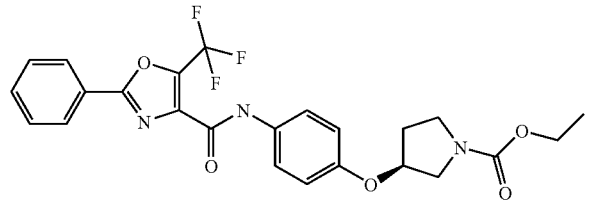

With a method similar to that used for the preparation of (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid ethyl ester above, (S)-3-{4-[(2-phenyl-5-trifluoromethyl-oxazole-4-carbonyl)-amino]-phenoxy}-pyrrolidine-1-carboxylic acid ethyl ester was prepared from (S)-3-{4-[(2-phenyl-5-trifluoromethyl-oxazole-4-carbonyl)-amino]-phenoxy}-pyrrolidine-1-carboxylic acid tert butyl ester, by deprotection with trifluoroacetic acid and subsequent treatment with ethyl chloroformate. HRMS calcd for C24H22F3N3O5 (M+H) 490.1585, obsd 490.1585.

Example 246

Preparation of (S)-3-(4-{[(2-(2-trifluoromethoxy-phenyl)-5-trifluoromethyl-oxazole-4-carbonyl]-amino}-phenoxy)-pyrrolidine-1-carboxylic acid ethyl ester

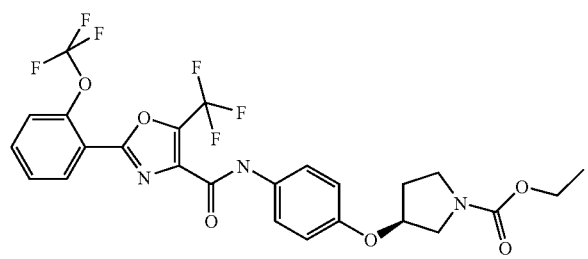

With a method similar to that used for the preparation of (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid ethyl ester above, (S)-3-(4-{[(2-(2-trifluoromethoxy-phenyl)-5-trifluoromethyl-oxazole-4-carbonyl]-amino}-phenoxy)-pyrrolidine-1-carboxylic acid ethyl ester was prepared from (S)-3-(4-{[(2-(2-trifluoromethoxy-phenyl)-5-trifluoromethyl-oxazole-4-carbonyl]-amino}-phenoxy)-pyrrolidine-1-carboxylic acid tert butyl ester, by deprotection with trifluoroacetic acid and subsequent treatment with ethyl chloroformate. HRMS calcd for C25H21F6N3O6 (M+Na) 596.1227, obsd 596.1223.

Example 247

Preparation of (S)-3-(5-{[(2-(2-trifluoromethoxy-phenyl)-5-trifluoromethyl-oxazole-4-carbonyl]-amino}-pyrimidin-2-yloxy)-pyrrolidine-1-carboxylic acid tert butyl ester

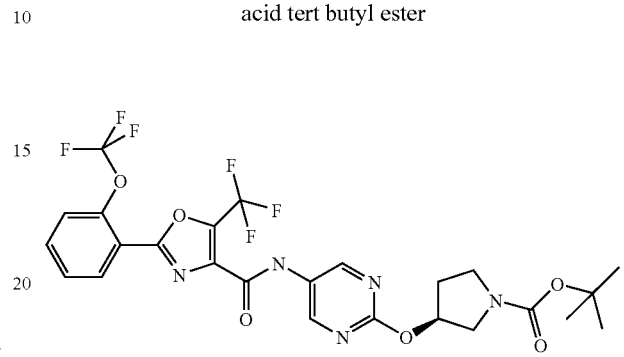

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, (S)-3-(5-{[(2-(2-trifluoromethoxy-phenyl)-5-trifluoromethyl-oxazole-4-carbonyl]-amino}-pyrimidin-2-yloxy)-pyrrolidine-1-carboxylic acid tert butyl ester was prepared from 2-(2-trifluoromethoxy-phenyl)-5-trifluoromethyl-oxaxole-4-carboxylic acid and (S)-3-(5-amino-pyrimidin-2-yloxy)-pyrrolidine-1-carboxylic acid tert butyl ester. HRMS calcd for C25H23F6N5O6 (M+Na) 626.1445, obsd 626.1447.

Example 248

Preparation of (S)-3-(5-{[(2-(2-trifluoromethoxy-phenyl)-5-trifluoromethyl-oxazole-4-carbonyl]-amino}-pyrimidin-2-yloxy)-pyrrolidine-1-carboxylic acid ethyl ester

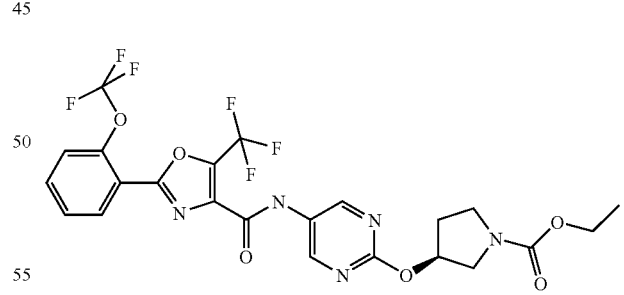

With a method similar to that used for the preparation of (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid ethyl ester above, (S)-3-(5-{[(2-(2-trifluoromethoxy-phenyl)-5-trifluoromethyl-oxazole-4-carbonyl]-amino}-pyrimidin-2-yloxy)-pyrrolidine-1-carboxylic acid ethyl ester was prepared from (S)-3-(5-{[(2-(2-trifluoromethoxy-phenyl)-5-trifluoromethyl-oxazole-4-carbonyl]amino}-pyrimidin-2-yloxy)-pyrrolidine-1-carboxylic acid tert butyl ester, by deprotection with

Example 249

Preparation of (S)-3-{5-[(2-phenyl-5-trifluoromethyl-oxazole-4-carbonyl)-amino]-pyrimidin-2-yloxy}-pyrrolidine-1-carboxylic acid ethyl ester

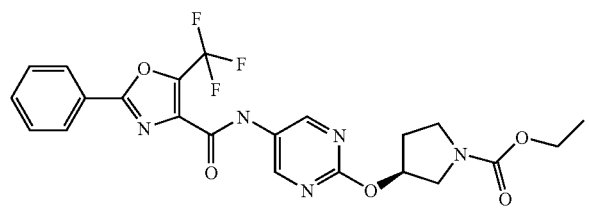

With a method similar to that used for the preparation of (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid ethyl ester above, (S)-3-{5-[(2-phenyl-5-trifluoromethyl-oxazole-4-carbonyl)-amino]-pyrimidin-2-yloxy}-pyrrolidine-1-carboxylic acid ethyl ester was prepared from (S)-3-{5-[(2-phenyl-5-trifluoromethyl-oxazole-4-carbonyl)-amino]-pyrimidin-2-yloxy}-pyrrolidine-1-carboxylic acid tert butyl ester, by deprotection with trifluoroacetic acid and subsequent treatment with ethyl chloroformate. HRMS calcd for C22H20F3N5O5 (M+H) 492.149, obsd 492.149.

Example 250

Preparation of (1R,2R)-2-((S)-3-{4-[(2-phenyl-5-trifluoromethyl-oxazole-4-carbonyl)-amino]-phenylamino}-pyrrolidine-1-carbonyl)-cyclopentanecarboxylic acid

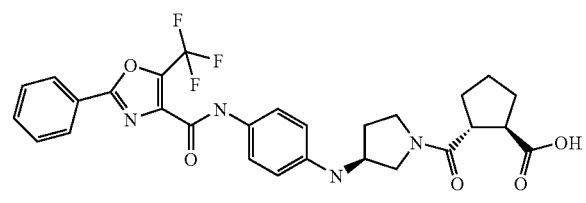

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 2-((S)-3-{4-[(2-phenyl-5-trifluoromethyl-oxazole-4-carbonyl)-amino]-phenylamino}-pyrrolidine-1-carbonyl)-cyclopentanecarboxylic acid was prepared as a mixture of diastereomers. The diastereomeric mixture was purified by chiral supercritical fluid chromatography (the first eluting peak) to yield (1R,2R)-2-((S)-3-{4-[(2-phenyl-5-trifluoromethyl-oxazole-4-carbonyl)-amino]-phenylamino}-pyrrolidine-1-carbonyl)-cyclopentanecarboxylic acid as a yellow oil. HRMS calcd for C28H27F3N4O5 (M+H) 557.2007, obsd 557.2004

Example 251

Preparation of (1S,2S)-2-((S)-3-{4-[(2-phenyl-5-trifluoromethyl-oxazole-4-carbonyl)-amino]-phenylamino}-pyrrolidine-1-carbonyl)-cyclopentanecarboxylic acid

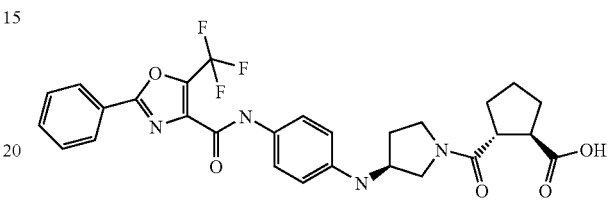

From the above chiral supercritical fluid chromatography of racemic 2-((S)-3-{4-[(2-phenyl-5-trifluoromethyl-oxazole-4-carbonyl)-amino]-phenylamino}-pyrrolidine-1-carbonyl)-cyclopentanecarboxylic acid, the second eluting peak was isolated to yield (1S,2S)-2-((S)-3-{4-[(2-phenyl-5-trifluoromethyl-oxazole-4-carbonyl)-amino]-phenylamino}-pyrrolidine-1-carbonyl)-cyclopentanecarboxylic acid as a yellow oil. HRMS calcd for C28H27F3N4O5 (M+H) 557.2007, obsd 557.2004.

Example 252

Preparation of 4-((S)-3-{5-[(2-phenyl-5-trifluoromethyl-oxazole-4-carbonyl)-amino]-pyridin-2-ylamino}-pyrrolidine-1-carbonyl)-cyclohexanecarboxylic acid

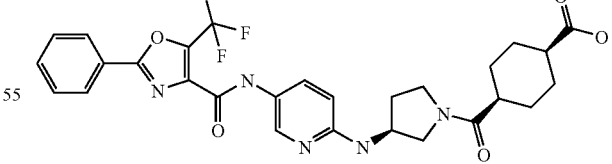

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-((S)-3-{5-[(2-phenyl-5-trifluoromethyl-oxazole-4-carbonyl)-amino]-pyridin-2-ylamino}-pyrrolidine-1-carbonyl)-cyclohexanecarboxylic acid was prepared from 2-phenyl-5-trifluoromethyl-oxazole-4-carboxylic acid [6-((S)-pyrrolidine-3-yl-amino)-pyridin-3-yl]- amide and cis-cyclohexane-1,4-dicarboxylic acid. HRMS calcd for C28H28F3N5O5 (M+H) 572.2116, obsd 572.2113.

Example 253

Preparation of 4-{4-[(1-pyridin-2-yl-3-trifluoromethyl-1H-pyrazole-4-carbonyl)-amino]-phenyl}-piperidine-1-carboxylic acid ethyl ester

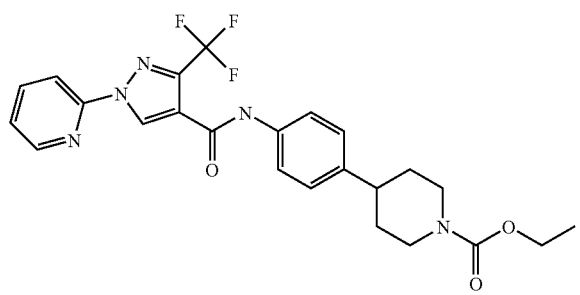

With a similar method to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{4-[(1-pyridin-2-yl-3-trifluoromethyl-1H-pyrazole-4-carbonyl)-amino]-phenyl}-piperidine-1-carboxylic acid ethyl ester was prepared from 1-pyridin-2-yl-3-trifluoromethyl-1H-pyrazole-4-carboxylic acid (4-piperidin-4-yl-phenyl)-amide hydrochloride and ethyl chloroformate. LCMS calcd for C24H24F3N5O3 (m/e) 487.18, obsd 488 (M+H).

Example 254

Preparation of 4-{4-[(1-pyridin-2-yl-3-trifluoromethyl-1H-pyrazole-4-carbonyl)-amino]-phenyl}-piperidine-1-carboxylic acid isopropyl ester

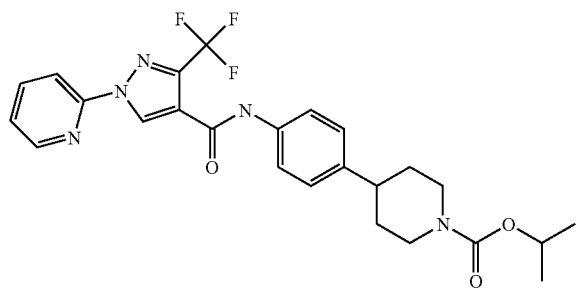

With a similar method to that used for the preparation of 4-{5-[(2-phenyl-5-trifluoromethyl-oxazole-4-carbonyl)-amino]-pyridin-2-yl}-piperazine-1-carboxylic acid isopropyl ester above, 4-{4-[(1-pyridin-2-yl-3-trifluoromethyl-1H-pyrazole-4-carbonyl)-amino]-phenyl}-piperidine-1-carboxylic acid isopropyl ester was prepared from 1-pyridin-2-yl-trifluoromethyl-1H-pyrazole-4-carboxylic acid (4-piperidin-4-yl-phenyl)-amide hydrochloride and isopropyl chloroformate. LCMS calcd for C25H26F3N5O3 (m/e) 501.2, obsd 502 (M+H).

Example 255

Preparation of 1-pyridin-2-yl-3-trifluoromethyl-1H-pyrazole-4-carboxylic acid [4-(1-cyclopropanecarbonyl-piperidin-4-yl)-phenyl]-amide

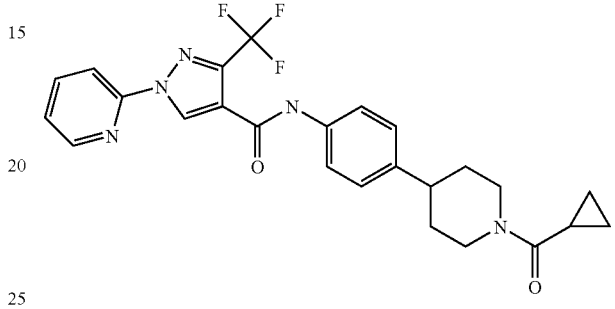

With a similar method to that used for the preparation of 2-phenyl-5-trifluoromethyl-oxazole-4-carboxylic acid [6-(4-acetyl-piperazin-1-yl)-pyridin-3-yl]-amide from above, 1-pyridin-2-yl-3-trifluoromethyl-1H-pyrazole-4-carboxylic acid [4-(1-cyclopropanecarbonyl-piperidin-4-yl)-phenyl]-amide was prepared from 1-pyridin-2-yl-3-trifluoromethyl-1H-pyrazole-4-carboxylic acid (4-piperidin-4-yl-phenyl)-amide hydrochloride and cyclopropanecarbonyl chloride. LCMS calcd for C25H24F3N5O2 (m/e) 483.2, obsd 484 (M+H).

Example 256

Preparation of 1-pyridin-2-yl-3-trifluoromethyl-1H-pyrazole-4-carboxylic acid [4-(1-cyclopentanecarbonyl-piperidin-4-yl)-phenyl]-amide

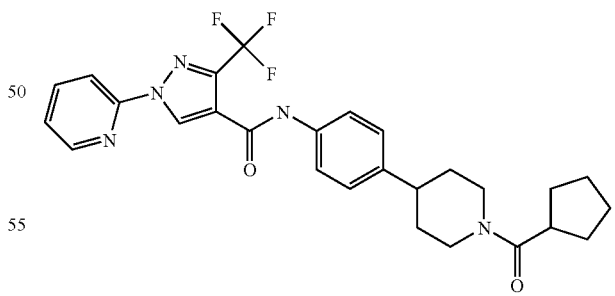

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 1-pyridin-2-yl-3-trifluoromethyl-1H-pyrazole-4-carboxylic acid [4-(1-cyclopentanecarbonyl-piperidin-4-yl)-phenyl]-amide was prepared from 1-pyridin-2-yl-3-trifluoromethyl-1H-pyrazole-4-carboxylic acid (4-piperidin-4-yl-phenyl)-amide and cyclopentanecarboxylic acid. LC-MS calcd for C27H28F3N5O2 (m/e) 511.2, obsd 512 (M+H). The NMR spectrum obtained on the sample is compatible with its structure.

Example 257

Preparation of 4-{4-[(1-pyridin-2-yl-3-trifluoromethyl-1H-pyrazole-4-carbonyl)-amino]-phenyl}-piperidine-1-carboxylic acid propylamide

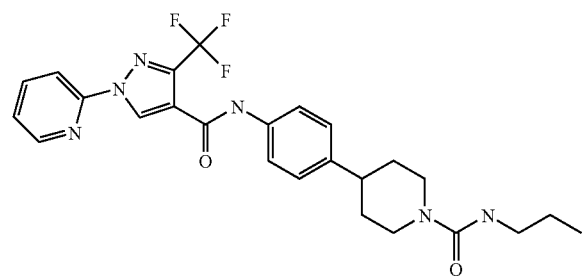

With a method similar to that used for the preparation of 4-{4-[(2-phenyl-5-trifluoromethyl-oxazole-4-carbonyl)-amino]-phenyl}-piperazine-1-carboxylic acid propylamide above, 4-{4-[(1-pyridin-2-yl-3-trifluoromethyl-1H-pyrazole-4-carbonyl)-amino]-phenyl}-piperidine-1-carboxylic acid propylamide was prepared from 1-pyridin-2-yl-3-trifluoromethyl-1H-pyrazole-4-carboxylic acid (4-piperidin-4-yl-phenyl)-amide and propylisocyanate. LC-MS calcd for C25H27F3N6O2 (m/e) 500.2, obsd 501 (M+H). The NMR spectrum obtained on the sample is compatible with its structure.

Example 258

Preparation of 4-{4-[(5-Methyl-2-phenyl-2H-[1,2,3]-triazole-4-carbonyl)-amino]-phenyl}-piperidine-1-carboxylic acid propylamide

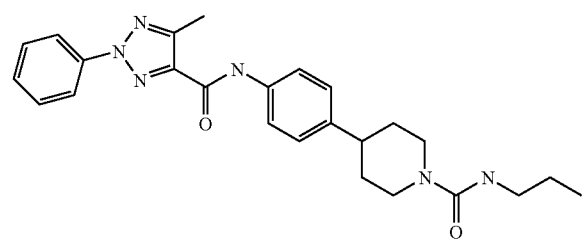

With a method similar to that used for the preparation of 4-{4-[(2-phenyl-5-trifluoromethyl-oxazole-4-carbonyl)-amino]-phenyl}-piperazine-1-carboxylic acid propylamide above, 4-{4-[(5-Methyl-2-phenyl-2H-[1,2,3]-triazole-4-carbonyl)-amino]-phenyl}-piperidine-1-carboxylic acid propylamide was prepared from 5-Methyl-2-phenyl-2H-[1,2,3] triazole-4-carboxylic acid (4-piperidin-4-yl-phenyl)-amide and propylisocyanate. LCMS calcd for C25H30N6O2 (m/e) 446.24, obsd 447 (M+H).

Example 259

Preparation of 4-[4-(4-{[1-(4-fluoro-phenyl)-3-trifluoromethyl-1H-pyrazole-4-carbonyl]-amino}-phenyl)-piperidine-1-carbonyl]-benzoic acid

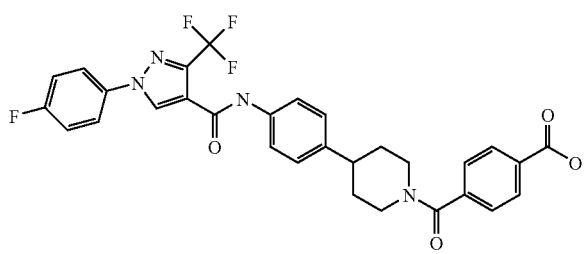

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 4-[4-(4-{[1-(4-fluoro-phenyl)-3-trifluoromethyl-1H-pyrazole-4-carbonyl]-amino}-phenyl)-piperidine-1-carbonyl]-benzoic acid was prepared from 1-(4-fluoro-phenyl)-3-trifluoromethyl-1H-pyrazole-4-carboxylic acid (4-piperidin-4-yl-phenyl)-amide and terephthalic acid monomethyl ester, followed by basic hydrolysis. LC-MS calcd for C30H24F4N4O4 (m/e) 580.2, obsd 581 (M+H). The NMR spectrum obtained on the sample is compatible with its structure.

Example 260

Preparation of 3-chloro-4-(5-{[1-(4-fluoro-phenyl)-3-trifluoromethyl-1H-pyrazole-4-carbonyl]-amino}-pyridin-2-yl)-benzoic acid

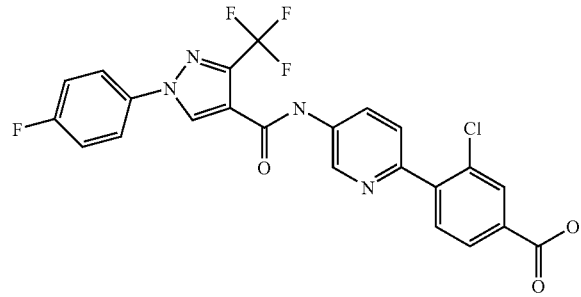

With a method similar to that used for the preparation of 3-chloro-4-{5-[(2-phenyl-5-trifluoromethyl-oxazole-4-carbonyl)-amino]-pyridin-2-yl}-benzoic acid above, 3-chloro-4-(5-{[1-(4-fluoro-phenyl)-3-trifluoromethyl-1H-pyrazole-4-carbonyl]-amino}-pyridin-2-yl)-benzoic acid was prepared from 1-(4-fluoro-phenyl)-3-trifluoromethyl-1H-pyrazole-4-carboxylic acid (6-bromo-pyridin-3-yl)-amide and 2-chloro-4-carboxyphenylboronic acid. LCMS calcd for C23H13F4N4O3 (m/e) 504, obsd 505 (M+H). The NMR spectrum obtained on the sample is compatible with its structure.

Example 261

Preparation of (1R,2R)-2-(4-{4-[(5-phenyl-2-trifluoromethyl-furan-3-carbonyl)-amino]-phenyl}-piperazine-1-carbonyl)-cyclopentanecarboxylic acid

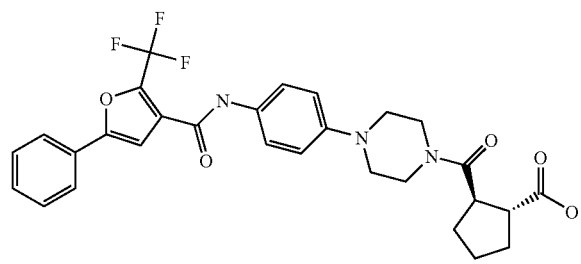

With a similar procedure as above (1R,2R)-2-(4-{4-[(5-phenyl-2-trifluoromethyl-furan-3-carbonyl)-amino]-phenyl}-piperazine-1-carbonyl)-cyclopentanecarboxylic acid was prepared from (1R,2R)-2-(4-{4-[(5-phenyl-2-trifluoromethyl-furan-3-carbonyl)-amino]-phenyl}-piperazine-1-carbonyl)-cyclopentanecarboxylic acid benzyl ester. The product was isolated as an off-white solid (183 mg, 99% yield). HRMS m/z calcd. for C29H29F3N3O5 [M+H]+: 556.2054; found: 556.2054.

Example 262

Preparation of 2-fluoro-4-{5-[(2-phenyl-5-trifluoromethyl-oxazole-4-carbonyl)-amino]-pyridin-2-yl}-benzoic acid

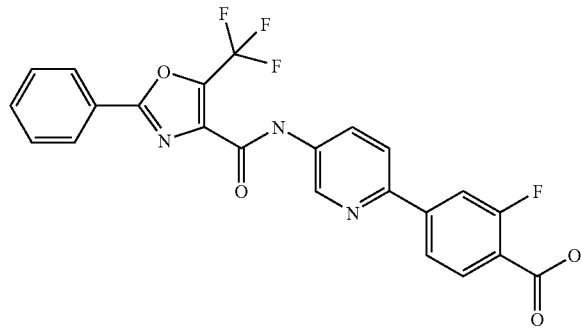

With a method similar to that used for the preparation of 3-chloro-4-{5-[(2-phenyl-5-trifluoromethyl-oxazole-4-carbonyl)-amino]-pyridin-2-yl}-benzoic acid above, 2-fluoro-4-{5-[(2-phenyl-5-trifluoromethyl-oxazole-4-carbonyl)-amino]-pyridin-2-yl}-benzoic acid was prepared from 2-phenyl-5-trifluoromethyl-oxazole-4-carboxylic acid (6-bromo-pyridin-3-yl)-amide and 4-carboxy-3-fluorophenylboronic acid. LCMS calcd for C23H13F4N3O4 (m/e) 471, obsd 472 (M+H).

Example 263

Preparation of (S)-2-(3-chloro-4-{5-[(2-phenyl-5-trifluoromethyl-oxazole-4-carbonyl)-amino]-pyridin-2-yl}-benzoylamino)-3-methyl-butyric acid methyl ester

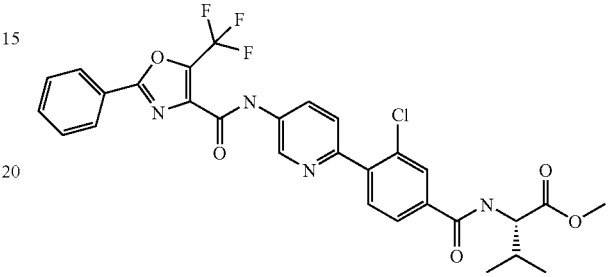

A mixture of 3-chloro-4-{5-[(2-phenyl-5-trifluoromethyl-oxazole-4-carbonyl)-amino]-pyridin-2-yl}-benzoic acid (50 mg, 0.1 mmol), (S)-2-amino-3-methyl-butyric acid methyl ester (17 mg, 0.1 mmol), 1-hydroxy-7-azabenzotriazole (HOAT) (21 mg, 0.15 mmol), and 1-ethyl-3-(3-dimethylaminopropyl)carbodiimide hydrochloride (30 mg, 0.15 mmol) in anhydrous dichloromethane (3 mL) was stirred at room temperature for 3 h. The reaction mixture was concentrated and partitioned between water and ethyl acetate. The organic layer was washed with brine, dried and concentrated to give a solid. The solid was purified by flash chromatography (Merck silica gel 60, 230-400 mesh, 0%-100% ethyl acetate in hexane) to give 2-(3-chloro-4-{5-[(2-phenyl-5-trifluoromethyl-oxazole-4-carbonyl)-amino]-pyridin-2-yl}-benzoylamino)-3-methyl-butyric acid methyl ester (41 mg, 66%) as a white solid. LCMS calcd for C29H24ClF3N4O5 (m/e) 600, obsd 601 (M+H).

Example 264

Preparation of (S)-2-(3-chloro-4-{5-[(2-phenyl-5-trifluoromethyl-oxazole-4-carbonyl)-amino]-pyridin-2-yl}-benzoylamino)-3-methyl-butyric acid

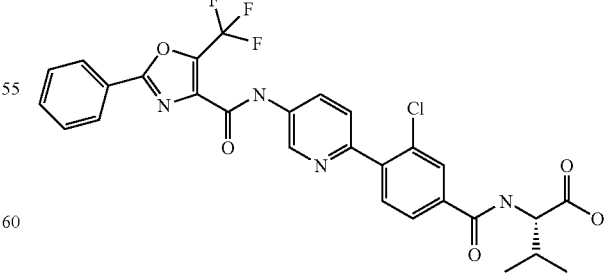

A solution of (S)-2-(3-chloro-4-{5-[(2-phenyl-5-trifluoromethyl-oxazole-4-carbonyl)-amino]-pyridin-2-yl}-benzoylamino)-3-methyl-butyric acid methyl ester (30 mg, 0.05 mmol) in a mixture of tetrahydrofuran, methanol and water (3:1:1, 2 mL) was treated with lithium hydroxide monohydrate (6 mg, 0.15 mmol) at 50° C. for an hour. The reaction mixture was concentrated, diluted with water and the pH was adjusted to 1~2 with dilute hydrochloric acid (1N). The white precipitate was collected by centrifugation, and then was dried under vacuum to give 2-(3-chloro-4-{5-[(2-phenyl-5-trifluoromethyl-oxazole-4-carbonyl)-amino]-pyridin-2-yl}-benzoylamino)-3-methyl-butyric acid (27 mg, 93%) as a white solid. LCMS calcd for C28H22ClF3N4O5 (m/e) 586, obsd 587 (M+H).

Example 265

Preparation of 1-(3-chloro-4-{5-[(2-phenyl-5-trifluoromethyl-oxazole-4-carbonyl)-amino]-pyridin-2-yl}-benzoyl)-piperidine-4-carboxylic acid

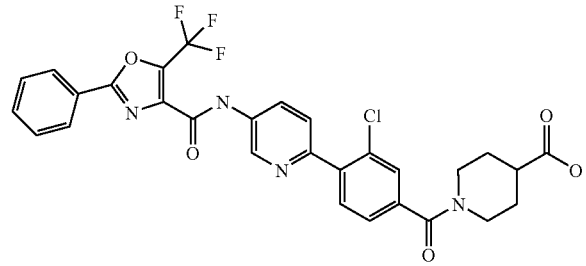

With a method similar to that used for the preparation of (S)-2-(3-chloro-4-{5-[(2-phenyl-5-trifluoromethyl-oxazole-4-carbonyl)-amino]-pyridin-2-yl}-benzoylamino)-3-methyl-butyric acid above, 1-(3-chloro-4-{5-[(2-phenyl-5-trifluoromethyl-oxazole-4-carbonyl)-amino]-pyridin-2-yl}-benzoyl)-piperidine-4-carboxylic acid was prepared from 3-chloro-4-{5-[(2-phenyl-5-trifluoromethyl-oxazole-4-carbonyl)-amino]-pyridin-2-yl}-benzoic acid and piperidine-4-carboxylic acid ethyl ester. LCMS calcd for C29H22ClF3N4O5 (m/e) 598, obsd 599 (M+H).

Example 266

Preparation of 1-({4'-[(2-phenyl-5-trifluoromethyl-oxazole-4-carbonyl)-amino]-biphenyl-4-carbonyl}-amino)-cyclopropanecarboxylic acid

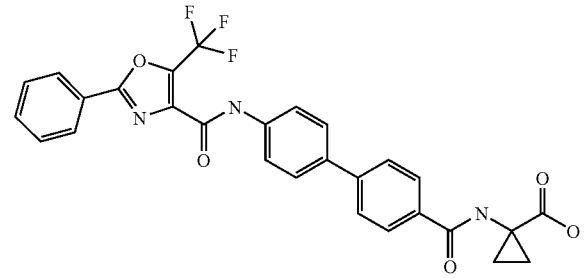

With a method similar to that used for the preparation of (S)-2-(3-chloro-4-{5-[(2-phenyl-5-trifluoromethyl-oxazole-4-carbonyl)-amino]-pyridin-2-yl}-benzoylamino)-3-methyl-butyric acid above, 1-({4'-[(2-phenyl-5-trifluoromethyl-oxazole-4-carbonyl)-amino]-biphenyl-4-carbonyl}-amino)-cyclopropanecarboxylic acid was prepared from 4'-[(2-phenyl-5-trifluoromethyl-oxazole-4-carbonyl)-amino]-biphenyl-4-carboxylic acid and 1-amino-cyclopropanecarboxylic acid ethyl ester. LCMS calcd for C28H20F3N3O5 (m/e) 535, obsd 536 (M+H).

Example 267

Preparation of 1-({4'-[(2-phenyl-5-trifluoromethyl-oxazole-4-carbonyl)-amino]-biphenyl-4-carbonyl}-amino)-cyclobutanecarboxylic acid

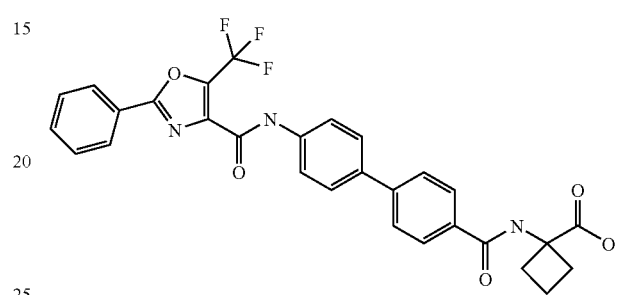

With a method similar to that used for the preparation of (S)-2-(3-chloro-4-{5-[(2-phenyl-5-trifluoromethyl-oxazole-4-carbonyl)-amino]-pyridin-2-yl}-benzoylamino)-3-methyl-butyric acid above, 1-({4'-[(2-phenyl-5-trifluoromethyl-oxazole-4-carbonyl)-amino]-biphenyl-4-carbonyl}-amino)-cyclobutanecarboxylic acid was prepared from 4'-[(2-phenyl-5-trifluoromethyl-oxazole-4-carbonyl)-amino]-biphenyl-4-carboxylic acid and 1-amino-cyclobutanecarboxylic acid ethyl ester. LCMS calcd for C29H22F3N3O5 (m/e) 549, obsd 550 (M+H).

Example 268

Preparation of 1-({4'-[(2-phenyl-5-trifluoromethyl-oxazole-4-carbonyl)-amino]-biphenyl-4-carbonyl}-amino)-cyclopentanecarboxylic acid

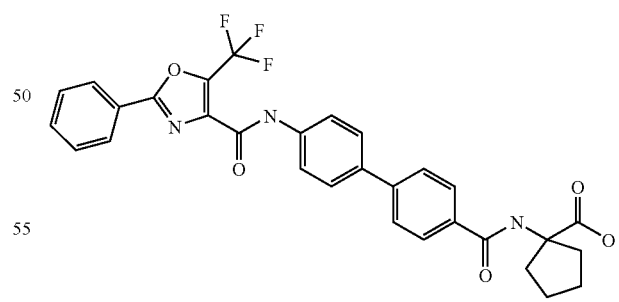

With a method similar to that used for the preparation of (S)-2-(3-chloro-4-{5-[(2-phenyl-5-trifluoromethyl-oxazole-4-carbonyl)-amino]-pyridin-2-yl}-benzoylamino)-3-methyl-butyric acid above, 1-({4'-[(2-phenyl-5-trifluoromethyl-oxazole-4-carbonyl)-amino]-biphenyl-4-carbonyl}-amino)-cyclopentanecarboxylic acid was prepared from 4'-[(2-phenyl-5-trifluoromethyl-oxazole-4-carbonyl)-amino]-biphenyl-4-carboxylic acid and 1-aminocyclopentanecarboxylic acid methyl ester. LCMS calcd for C30H24F3N3O5 (m/e) 563, obsd 564 (M+H).

Example 269

Preparation of (S)-3,3-dimethyl-2-({4'-[(2-phenyl-5-trifluoromethyl-oxazole-4-carbonyl)-amino]-biphenyl-4-carbonyl}-amino)-butyric acid

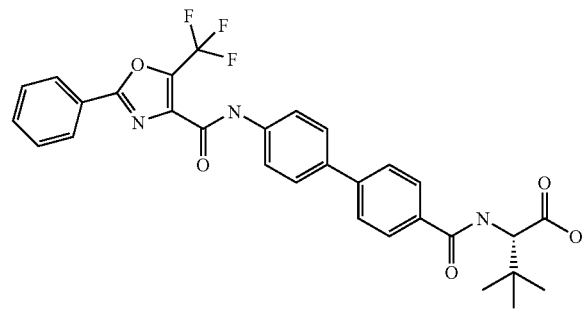

With a method similar to that used for the preparation of (S)-2-(3-chloro-4-{5-[(2-phenyl-5-trifluoromethyl-oxazole-4-carbonyl)-amino]-pyridin-2-yl}-benzoylamino)-3-methyl-butyric acid above, (S)-3,3-dimethyl-2-({4'-[(2-phenyl-5-trifluoromethyl-oxazole-4-carbonyl)-amino]-biphenyl-4-carbonyl}-amino)-butyric acid was prepared from 4'-[(2-phenyl-5-trifluoromethyl-oxazole-4-carbonyl)-amino]-biphenyl-4-carboxylic acid and (S)-2-Amino-3,3-dimethyl-butyric acid tert-butyl ester. LCMS calcd for C30H26F3N3O5 (m/e) 565, obsd 566 (M+H).

Example 270

Preparation of 2-phenyl-5-trifluoromethyl-oxazole-4-carboxylic acid [6-(3-fluoro-4-isobutylcarbamoyl-phenyl)-pyridin-3-yl]-amide

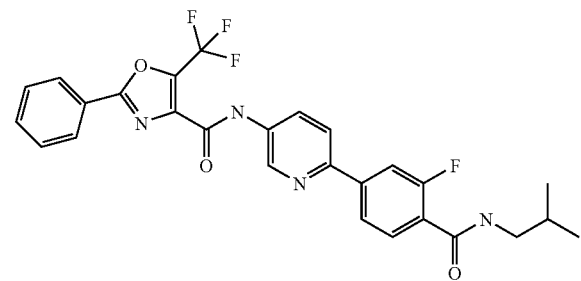

With a method similar to that used for the preparation of (S)-2-(3-chloro-4-{5-[(2-phenyl-5-trifluoromethyl-oxazole-4-carbonyl)-amino]-pyridin-2-yl}-benzoylamino)-3-methyl-butyric acid above, 2-phenyl-5-trifluoromethyl-oxazole-4-carboxylic acid [6-(3-fluoro-4-isobutylcarbamoyl-phenyl)-pyridin-3-yl]-amide was prepared from 2-fluoro-4-{5-[(2-phenyl-5-trifluoromethyl-oxazole-4-carbonyl)-amino]-pyridin-2-yl}-benzoic acid and isobutylamine. LCMS calcd for C27H22F4N4O3 (m/e) 526, obsd 527 (M+H).

Example 271

Preparation of 2-phenyl-5-trifluoromethyl-oxazole-4-carboxylic acid [6-(2-chloro-4-methylcarbamoyl-phenyl)-pyridin-3-yl]-amide

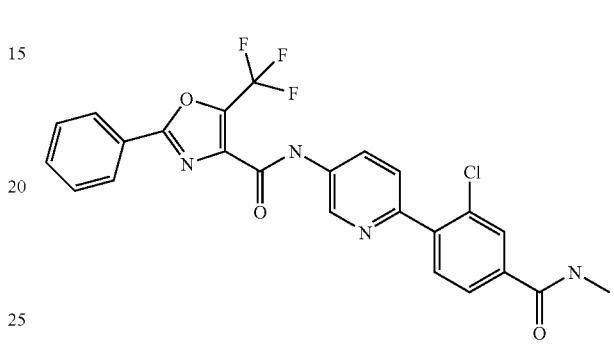

With a method similar to that used for the preparation of (S)-2-(3-chloro-4-{5-[(2-phenyl-5-trifluoromethyl-oxazole-4-carbonyl)-amino]-pyridin-2-yl}-benzoylamino)-3-methyl-butyric acid above, 2-phenyl-5-trifluoromethyl-oxazole-4-carboxylic acid [6-(2-chloro-4-methylcarbamoyl-phenyl)-pyridin-3-yl]-amide was prepared from 3-chloro-4-{5-[(2-phenyl-5-trifluoromethyl-oxazole-4-carbonyl)-amino]-pyridin-2-yl}-benzoic acid and methylamine. LCMS calcd for C24H16ClF3N4O3 (m/e) 500, obsd 501 (M+H).

Example 272

Preparation of (S)-3-methyl-2-({4'-[(2-phenyl-5-trifluoromethyl-oxazole-4-carbonyl)-amino]-biphenyl-4-carbonyl}-amino)-butyric acid

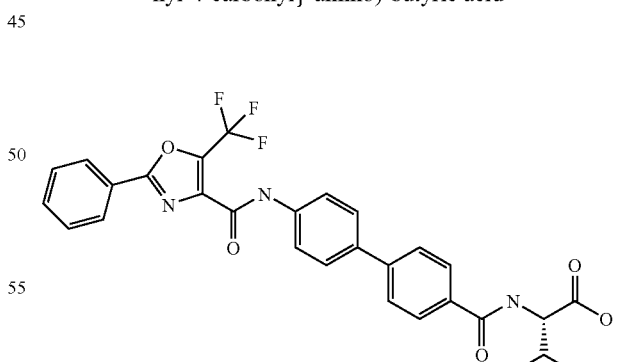

With a method similar to that used for the preparation of (S)-2-(3-chloro-4-{5-[(2-phenyl-5-trifluoromethyl-oxazole-4-carbonyl)-amino]-pyridin-2-yl}-benzoylamino)-3-methyl-butyric acid above, (S)-3-methyl-2-({4'-[(2-phenyl-5-trifluoromethyl-oxazole-4-carbonyl)-amino]-biphenyl-4-carbonyl}-amino)-butyric acid was prepared from 4'-[(2-phenyl-5-trifluoromethyl-oxazole-4-carbonyl)-amino]- biphenyl-4-carboxylic acid and (S)-2-amino-3-methyl-butyric acid methyl ester. LCMS calcd for C29H24F3N3O5 (m/e) 551, obsd 552 (M+H).

Example 273

Preparation of racemic trans-2-{5-[(2-phenyl-5-trifluoromethyl-oxazole-4-carbonyl)-amino]-[2,3']bipyridinyl-6'-ylcarbamoyl}-cyclopentanecarboxylic acid

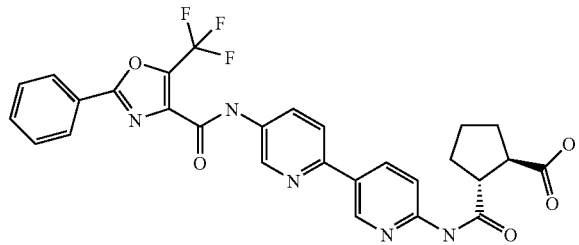

With a method similar to that used for the preparation of (S)-2-(3-chloro-4-{5-[(2-phenyl-5-trifluoromethyl-oxazole-4-carbonyl)-amino]-pyridin-2-yl}-benzoylamino)-3-methyl-butyric acid above, racemic trans-2-{5-[(2-phenyl-5-trifluoromethyl-oxazole-4-carbonyl)-amino]-[2,3']bipyridinyl-6'-ylcarbamoyl}-cyclopentanecarboxylic acid was prepared from 2-phenyl-5-trifluoromethyl-oxazole-4-carboxylic acid (6-bromo-pyridin-3-yl)-amide, 2-tert-butyloxycarbonylaminopyridine-5-boronic acid pinacol ester and racemic trans-cyclopentane-1,2-dicarboxylic acid monobenzyl ester. LCMS calcd for C28H22F3N5O5 (m/e) 565, obsd 566 (M+H).

Example 274

Preparation of (1R,2R)-2-{4'-[(2-phenyl-5-trifluoromethyl-oxazole-4-carbonyl)-amino]-biphenyl-4-ylcarbamoyl}-cyclopentanecarboxylic acid (or enantiomer)

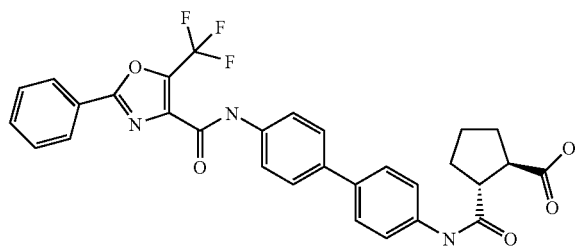

With a method similar to that used for the preparation of (S)-2-(3-chloro-4-{5-[(2-phenyl-5-trifluoromethyl-oxazole-4-carbonyl)-amino]-pyridin-2-yl}-benzoylamino)-3-methyl-butyric acid above, racemic trans-2-{4'-[(2-phenyl-5-trifluoromethyl-oxazole-4-carbonyl)-amino]-biphenyl-4-ylcarbamoyl}-cyclopentanecarboxylic acid was prepared from 2-phenyl-5-trifluoromethyl-oxazole-4-carboxylic acid (4-iodo-phenyl)-amide, 4-(4,4,5,5-tetramethyl-1,3,2-dioxaborolan-2-yl)aniline and cyclopentane-1,2-dicarboxylic acid monobenzyl ester. The benzyl ester was then removed by hydrogenolysis. The racemic mixture was separated by chiral SFC to afford (1R,2R)-2-{4'-[(2-phenyl-5-trifluoromethyl-oxazole-4-carbonyl)-amino]-biphenyl-4-carbonyl}-cyclopentanecarboxylic acid (or enantiomer). LCMS calcd for C30H24F3N3O5 (m/e) 563, obsd 564 (M+H).

Example 275

Preparation of (1S,2S)-2-{4'-[(2-phenyl-5-trifluoromethyl-oxazole-4-carbonyl)-amino]-biphenyl-4-ylcarbamoyl}-cyclopentanecarboxylic acid (or enantiomer)

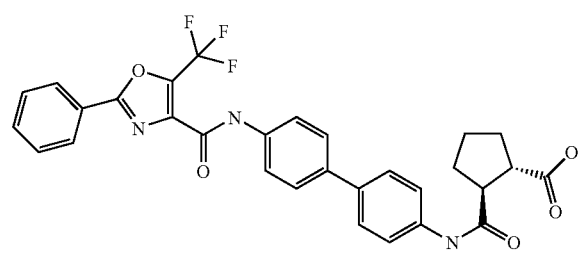

With a method similar to that used for the preparation of (1R,2R)-2-{4'-[(2-phenyl-5-trifluoromethyl-oxazole-4-carbonyl)-amino]-biphenyl-4-carbonyl}-cyclopentanecarboxylic acid above, (1S,2S)-2-{4'-[(2-phenyl-5-trifluoromethyl-oxazole-4-carbonyl)-amino]-biphenyl-4-carbonyl}-cyclopentanecarboxylic acid (or enantiomer) was obtained by chiral SFC separation. LCMS calcd for C30H24F3N3O5 (m/e) 563, obsd 564 (M+H).

Example 276

Preparation of racemic trans-2-(methyl-{4'-[(2-phenyl-5-trifluoromethyl-oxazole-4-carbonyl)-amino]-biphenyl-4-yl}-carbamoyl)-cyclopentanecarboxylic acid

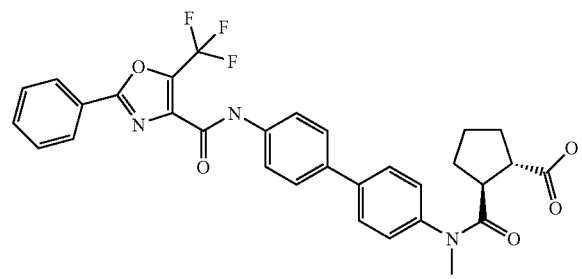

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester, racemic trans-2-(methyl-{4'-[(2-phenyl-5-trifluoromethyl-oxazole-4-carbonyl)-amino]-biphenyl-4-yl}-carbamoyl)-cyclopentanecarboxylic acid was prepared from 2-phenyl-5-trifluoromethyl-oxazole-4-carboxylic acid and racemic trans-2-[(4'-amino-biphenyl-4-yl)-methyl-carbamoyl]-cyclopentanecarboxylic acid. LCMS calcd for C31H26F3N3O5 (m/e) 577, obsd 578 (M+H).

Example 277

Preparation of 2-pyridin-2-yl-4-trifluoromethyl-oxazole-5-carboxylic acid [6-(4-isobutylcarbamoyl-phenyl)-pyridin-3-yl]-amide

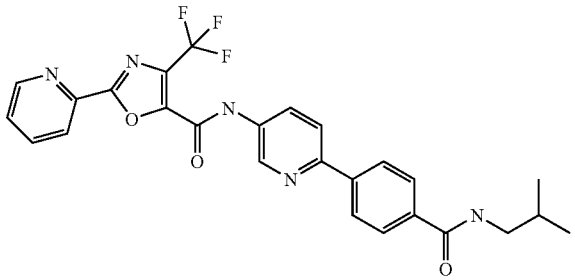

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester above, 2-pyridin-2-yl-4-trifluoromethyl-oxazole-5-carboxylic acid [6-(4-isobutylcarbamoyl-phenyl)-pyridin-3-yl]-amide was prepared from 2-pyridin-2-yl-4-trifluoromethyl-oxazole-5-carboxylic acid and 4-(5-amino-pyridin-2-yl)-N-isobutyl-benzamide. LCMS calcd for C26H22F3N5O3 (m/e) 509, obsd 510 (M+H).

Example 278

Preparation of methyl-(1-{5-[(2-phenyl-5-trifluoromethyl-oxazole-4-carbonyl)-amino]-pyrimidin-2-yl}-piperidin-4-yl)-carbamic acid ethyl ester

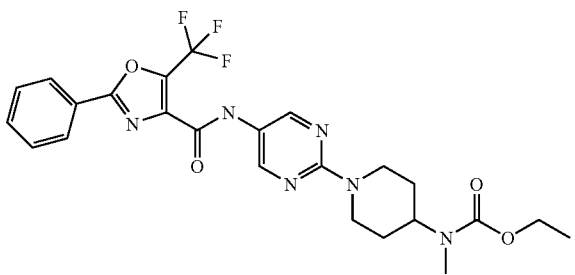

With a method similar to that used for the preparation of 4-{5-[(2-phenyl-5-trifluoromethyl-oxazole-4-carbonyl)-amino]-pyridin-2-yl}-piperazine-1-carboxylic acid isopropyl ester, methyl-(1-{5-[(2-phenyl-5-trifluoromethyl-oxazole-4-carbonyl)-amino]-pyrimidin-2-yl}-piperidin-4-yl)-carbamic acid ethyl ester was prepared from 2-phenyl-5-trifluoromethyl-oxazole-4-carboxylic acid [2-(4-methylamino-piperidin-1-yl)-pyrimidin-5-yl]-amide and ethyl chloroformate. LC-MS calcd for C24H25F3N6O4 (m/e) 518, obsd 519 (M+H). The NMR spectrum obtained on the sample is compatible with its structure.

Example 279

Preparation of 2-phenyl-5-trifluoromethyl-oxazole-4-carboxylic acid (2-{4-[methyl-(2,2,2-trifluoro-acetyl)-amino]-piperidin-1-yl}-pyrimidin-5-yl)-amide

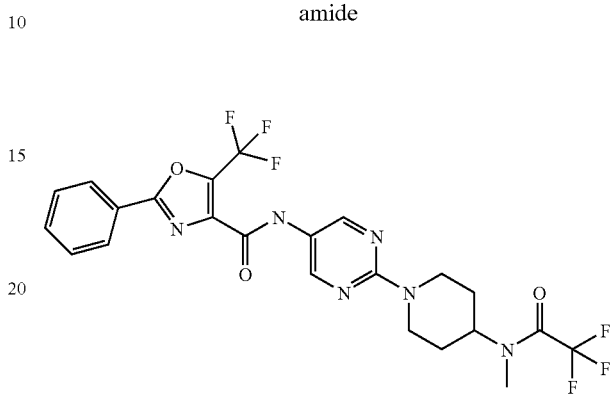

With a method similar to that used for the preparation of 2-phenyl-5-trifluoromethyl-oxazole-4-carboxylic acid [6-(4-acetyl-piperazin-1-yl)-pyridin-3-yl]-amide above, 2-phenyl-5-trifluoromethyl-oxazole-4-carboxylic acid (2-{4-[methyl-(2,2,2-trifluoro-acetyl)-amino]-piperidin-1-yl}-pyrimidin-5-yl)-amide was prepared from 2-phenyl-5-trifluoromethyl-oxazole-4-carboxylic acid [2-(4-methylamino-piperidin-1-yl)-pyrimidin-5-yl]-amide hydrochloride salt and trifluoroacetic anhydride. LCMS calcd for C23H20F6N6O3 (m/e) 542, obsd 543 (M+H).

Example 280

Preparation of (1R,2R)-2-[methyl-(1-{5-[(2-phenyl-5-trifluoromethyl-oxazole-4-carbonyl)-amino]-pyrimidin-2-yl}-piperidin-4-yl)-carbamoyl]-cyclopentanecarboxylic acid (or enantiomer)

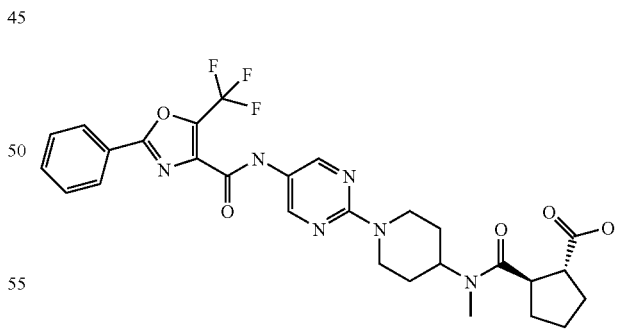

With a method similar to that used for the preparation of (1R,2R)-2-{4'-[(2-phenyl-5-trifluoromethyl-oxazole-4-carbonyl)-amino]-biphenyl-4-carbonyl}-cyclopentanecarboxylic acid above, (1R,2R)-2-[methyl-(1-{5-[(2-phenyl-5-trifluoromethyl-oxazole-4-carbonyl)-amino]-pyrimidin-2-yl}-piperidin-4-yl)-carbamoyl]-cyclopentanecarboxylic acid (or enantiomer) was prepared from 2-phenyl-5-trifluoromethyl-oxazole-4-carboxylic acid [2-(4-methylamino-piperidin-1-yl)-pyrimidin-5-yl]-amide hydrochloride salt and racemic

Example 281

Preparation of (1S,2S)-2-[methyl-(1-{5-[(2-phenyl-5-trifluoromethyl-oxazole-4-carbonyl)-amino]-pyrimidin-2-yl}-piperidin-4-yl)-carbamoyl]-cyclopentanecarboxylic acid (or enantiomer)

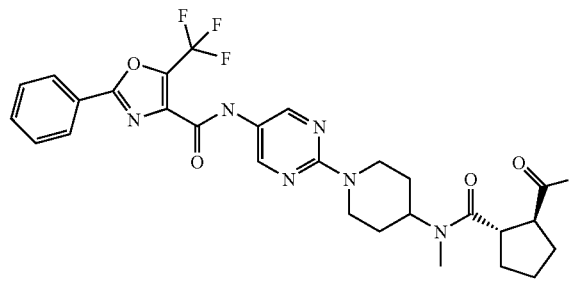

With a method similar to that used for the preparation of (1R,2R)-2-{4'-[(2-phenyl-5-trifluoromethyl-oxazole-4-carbonyl)-amino]-biphenyl-4-carbonyl}-cyclopentanecarboxylic acid above, (1S,2S)-2-[methyl-(1-{5-[(2-phenyl-5-trifluoromethyl-oxazole-4-carbonyl)-amino]-pyrimidin-2-yl}-piperidin-4-yl)-carbamoyl]-cyclopentanecarboxylic acid (or enantiomer) was prepared from 2-phenyl-5-trifluoromethyl-oxazole-4-carboxylic acid [2-(4-methylamino-piperidin-1-yl)-pyrimidin-5-yl]-amide hydrochloride salt and racemic trans-1,2-cyclopentanedicarboxylic acid, followed by chiral SFC. LCMS calcd for C28H29F3N6O5 (m/e) 586, obsd 587 (M+H).

Example 282

Preparation of (R)-2-(4-{4-[(2-phenyl-5-trifluoromethyl-oxazole-4-carbonyl)-amino]-phenyl}-piperazine-1-carbonyl)-pyrrolidine-1-carboxylic acid benzyl ester

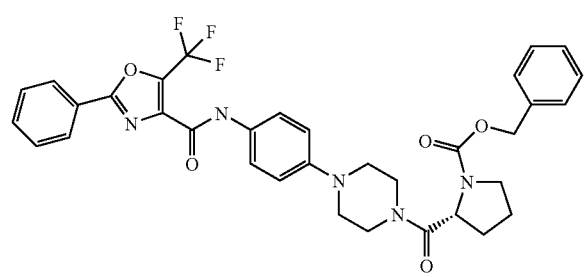

With a method similar to that used for the preparation of (1R,2R)-2-{4'-[(2-phenyl-5-trifluoromethyl-oxazole-4-carbonyl)-amino]-biphenyl-4-carbonyl}-cyclopentanecarboxylic acid above, (R)-2-(4-{4-[(2-phenyl-5-trifluoromethyl-oxazole-4-carbonyl)-amino]-phenyl}-piperazine-1-carbonyl)-pyrrolidine-1-carboxylic acid benzyl ester was prepared from 2-phenyl-5-trifluoromethyl-oxazole-4-carboxylic acid (4-piperazin-1-yl-phenyl)-amide hydrochloride salt and (R)-pyrrolidine-1,2-dicarboxylic acid 1-benzyl ester. LCMS calcd for C34H32F3N5O5 (m/e) 647, obsd 648 (M+H).

Example 283

Preparation of (R)-2-(4-{4-[(2-phenyl-5-trifluoromethyl-oxazole-4-carbonyl)-amino]-phenyl}-piperazine-1-carbonyl)-pyrrolidine-1-carboxylic acid ethyl ester

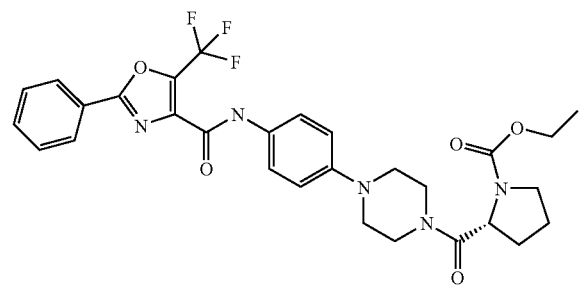

With a method similar to that used for the preparation of (1R,2R)-2-{4'-[(2-phenyl-5-trifluoromethyl-oxazole-4-carbonyl)-amino]-biphenyl-4-carbonyl}-cyclopentanecarboxylic acid above, (R)-2-(4-{4-[(2-phenyl-5-trifluoromethyl-oxazole-4-carbonyl)-amino]-phenyl}-piperazine-1-carbonyl)-pyrrolidine-1-carboxylic acid ethyl ester was prepared by hydrogenolysis of (R)-2-(4-{4-[(2-phenyl-5-trifluoromethyl-oxazole-4-carbonyl)-amino]-phenyl}-piperazine-1-carbonyl)-pyrrolidine-1-carboxylic acid benzyl ester followed by reaction with ethyl chloroformate. LCMS calcd for C29H30F3N5O5 (m/e) 585, obsd 586 (M+H).

Example 284

Preparation of 2-phenyl-5-trifluoromethyl-oxazole-4-carboxylic acid (4-methanesulfonylaminocarbonyl-3,4,5,6-tetrahydro-2H-[1,2']bipyridinyl-5'-yl)-amide

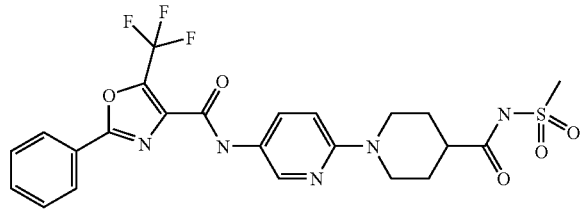

To a suspension of 5'-[(2-phenyl-5-trifluoromethyl-oxazole-4-carbonyl)-amino]-3,4,5,6-tetrahydro-2H-[1,2']bipyridinyl-4-carboxylic acid (39.4 mg, 0.085 mmol) in methylene chloride (5 mL) was added methanesulfonamide (8.2 mg, 0.086 mmol). Then 4-dimethylaminopyridine (10.45 mg, 0.085 mmol) and EDCl (16.4 mg, 0.085 mmol) was added. The mixture was stirred at room temperature overnight. Solvents were evaporated and the residue was purified by flash column chromatography using a linear gradient of ethyl acetate containing 1% acetic acid in hexanes (20% to 100% in 15 minutes) to give the desired compound as a pale yellow solid (16.5 mg). ¹H-NMR is consistent with the desired structure. LRMS for C23H22F3N5O5S (m/e) calcd 537.13, obsd 538.1 (M+1).

Example 285

Preparation of 1-{4-[(2-phenyl-5-trifluoromethyl-oxazole-4-carbonyl)-amino]-phenyl}-piperidine-4-carboxylic acid methyl ester

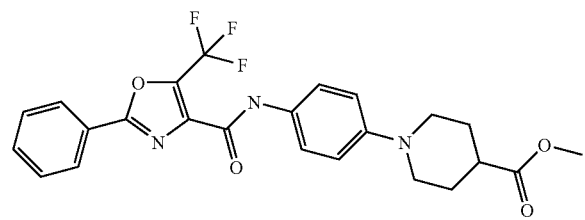

To a solution of 4-fluoronitrobenzene (0.70 g, 4.96 mmol) in THF (8 mL) was added piperadine-4-carboxylic acid methyl ester (0.71 g, 4.96 mmol) and diisopropylethylamine (0.66 g, 5.11 mmol). The mixture was heated in a microwave oven at 150° C. for 1.5 hr. The resulting mixture was extracted with ethyl acetate and hydrochloric acid (0.2 N). The organic layer was washed with brine and concentrated sodium bicarbonate solution. After the evaporation of solvents, the residue was purified through a Biotage flash column chromatography using ethyl acetate and hexanes (1:1 ratio) to give a yellow solid as 1-(4-nitrophenyl)-piperidine-4-carboxylic acid methyl ester (490 mg). ¹H-NMR is consistent with the structure.

The yellow solid prepared above (463 mg, 1.75 mmol) was dissolved into methanol (25 ml) and THF (5 mL). To this solution was added 10% palladium on carbon (100 mg) and the mixture was hydrogenated at 50 psi for 2 hrs. The mixture was filtered and solvents were evaporated to give a purple residue. This material was dissolved in methylene chloride (5 mL) containing triethyl amine (0.4 mL) and the solution was added to a methylene chloride solution of 2-phenyl-5-trifluoromethyloxazole-4-carbonyl chloride which was prepared from 2-phenyl-5-trifluoromethyloxazole-4-carboxylic acid (450.7 mg, 1.753 mmol) and oxalyl chloride. The mixture was stirred at r.t for 3 hrs and solvents were evaporated. The residue was extracted with ethyl acetate and diluted hydrochloric acid and solvents were evaporated. The resulting mixture was purified through a flash column chromatography using ethyl acetate and hexanes (1:1 ratio) to give a white solid as 1-{4-[(2-phenyl-5-trifluoromethyl-oxazole-4-carbonyl)-amino]-phenyl}-piperidine-4-carboxylic acid methyl ester (650 mg). ¹H-NMR is consistent with the structure. LC-MS indicated a single peak (R_f=3.85 min). LRMS for C24H22F3N3O4 (m/e) calcd 473.16, obsd 474.3 (M+1).

Example 286

1-{4-[(2-Phenyl-5-trifluoromethyl-oxazole-4-carbonyl)-amino]-phenyl}-piperidine-4-carboxylic acid

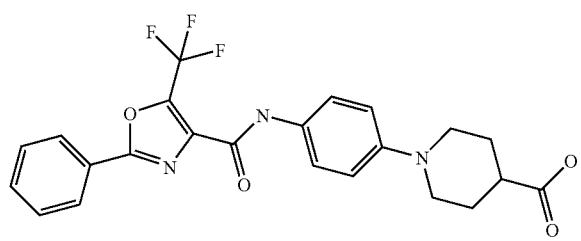

The above 1-{4-[(2-phenyl-5-trifluoromethyl-oxazole-4-carbonyl)-amino]-phenyl}-piperidine-4-carboxylic acid methyl ester (470 mg, 1 mmol) was dissolved in a mixture of methanol (7 mL) and THF (2 mL). To this solution was added 1N sodium hydroxide solution (3 mL). The mixture was stirred at room temperature for 4 hrs until all starting material was consumed. Solvents were evaporated and the residue was diluted with water (8 mL). The solution was filtered and the filtrate was acidified with 1N hydrochloric acid (3.5 mL). The yellow precipitate was filtered and dried in the air to give 1-{4-[(2-phenyl-5-trifluoromethyl-oxazole-4-carbonyl)-amino]-phenyl}-piperidine-4-carboxylic acid (395 mg). ¹H-NMR is consistent with the desired structure. LC-MS indicated a single peak (R_f=3.23 min). LRMS for C23H20F3N3O4 (m/e) calcd 459.14, obsd 460.2 (M+1).

Example 287

Preparation of 2-phenyl-5-trifluoromethyl-oxazole-4-carboxylic acid [4-(4-methanesulfonylaminocarbonyl-piperidin-1-yl)-phenyl]-amide

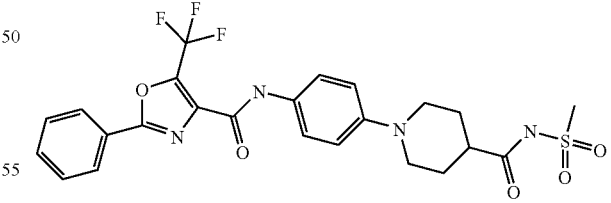

With a method similar to that used for the preparation of 2-phenyl-5-trifluoromethyl-oxazole-4-carboxylic acid (4-methanesulfonylaminocarbonyl-3,4,5,6-tetrahydro-2H-[1,2']bipyridinyl-5'-yl)-amide, 2-phenyl-5-trifluoromethyl-oxazole-4-carboxylic acid [4-(4-methanesulfonylaminocarbonyl-piperidin-1-yl)-phenyl]-amide was prepared from 1-{4-[(2-phenyl-5-trifluoromethyl-oxazole-4-carbonyl)-amino]-phenyl}-piperidine-4-carboxylic acid and methanesulfonamide. LRMS for C24H23F3N4O5S (m/e) calcd 536.13, obsd 537.1 (M+1). The ¹H-NMR obtained on the sample is consistent with the desired structure.

Example 288

Preparation of 2-phenyl-5-trifluoromethyl-oxazole-4-carboxylic acid [4-(4-ethanesulfonylaminocarbonyl-piperidin-1-yl)-phenyl]-amide

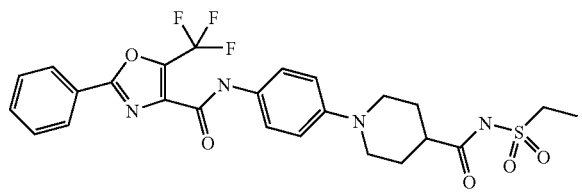

With a method similar to that used for the preparation of 2-phenyl-5-trifluoromethyl-oxazole-4-carboxylic acid (4-methanesulfonylaminocarbonyl-3,4,5,6-tetrahydro-2H-[1,2']bipyridinyl-5'-yl)-amide, 2-phenyl-5-trifluoromethyl-oxazole-4-carboxylic acid [4-(4-ethanesulfonylaminocarbonyl-piperidin-1-yl)-phenyl]-amide was prepared from 1-{4-[(2-phenyl-5-trifluoromethyl-oxazole-4-carbonyl)-amino]-phenyl}-piperidine-4-carboxylic acid and ethanesulfonamide. LRMS for C25H25F3N4O5S (m/e) calcd 550.15, obsd 551.1 (M+H). The ¹H-NMR obtained on the sample is consistent with the desired structure.

Example 289

Preparation of 2-phenyl-5-trifluoromethyl-oxazole-4-carboxylic acid {4-[4-(2-methyl-propane-2-sulfonylaminocarbonyl)-piperidin-1-yl]-phenyl}-amide

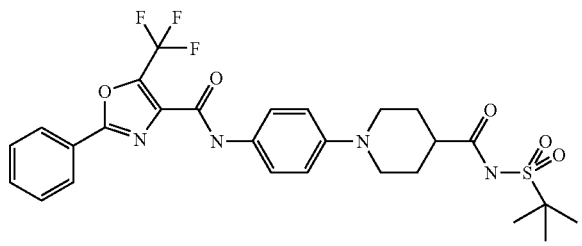

With a method similar to that used for the preparation of 2-phenyl-5-trifluoromethyl-oxazole-4-carboxylic acid (4-methanesulfonylaminocarbonyl-3,4,5,6-tetrahydro-2H-[1,2']bipyridinyl-5'-yl)-amide, 2-phenyl-5-trifluoromethyl-oxazole-4-carboxylic acid {4-[4-(2-methyl-propane-2-sulfonylaminocarbonyl)-piperidin-1-yl]-phenyl}-amide was prepared from 1-{4-[(2-phenyl-5-trifluoromethyl-oxazole-4-carbonyl)-amino]-phenyl}-piperidine-4-carboxylic acid and tert-butylsulfonamide. LRMS for C27H29F3N4O5S (m/e) calcd 578.18, obsd 579.2 (M+H). The ¹H-NMR obtained on the sample is consistent with the desired structure.

Example 290

Preparation of (S)-3-{4-[(1-Phenyl-3-trifluoromethyl-1H-pyrazole-4-carbonyl)-amino]-phenoxy}-pyrrolidine-1-carboxylic acid ethyl ester

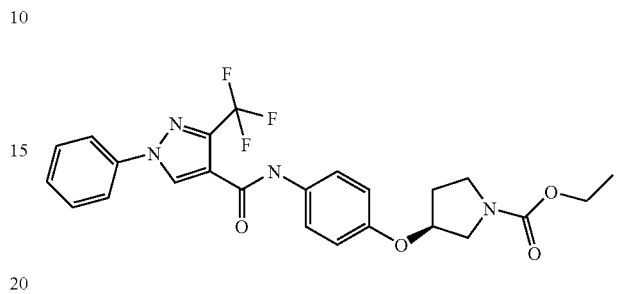

With a method similar to that used for the preparation of 4-{5-[(2-phenyl-5-trifluoromethyl-oxazole-4-carbonyl)-amino]-pyridin-2-yl}-piperazine-1-carboxylic acid tert-butyl ester, (S)-3-{4-[(1-Phenyl-3-trifluoromethyl-1H-pyrazole-4-carbonyl)-amino]-phenoxy}-pyrrolidine-1-carboxylic acid t-butyl ester was prepared from 2-phenyl-5-trifluoromethyl-1H-pyrazole-4-carboxylic acid and (S)-3-(5-amino-phenoxy)-pyrrolidine-1-carboxylic acid tert butyl ester. LRMS calcd for C26H28F3N5O3 (M−1) 516.56, obsd 515.1

With a method similar to that used for the preparation of (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid ethyl ester, (S)-3-{4-[(1-Phenyl-3-trifluoromethyl-1H-pyrazole-4-carbonyl)-amino]-phenoxy}-pyrrolidine-1-carboxylic acid ethyl ester was prepared from (S)-3-{4-[(1-Phenyl-3-trifluoromethyl-1H-pyrazole-4-carbonyl)-amino]-phenoxy}-pyrrolidine-1-carboxylic acid t-butyl ester, by deprotection with trifluoroacetic acid and subsequent treatment with ethyl chloroformate. HRMS calcd for C24H23F3N4O4 (M+H) 489.1745, obsd 489.1744.

Example 291

Preparation of 2-phenyl-5-trifluoromethyl-oxazole-4-carboxylic acid (4-{4-[4-(1H-tetrazol-5-yl)-cyclohexanecarbonyl]-piperazin-1-yl}-phenyl)-amide

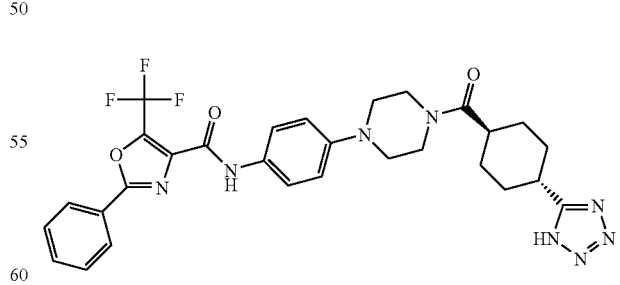

A mixture of 2-phenyl-5-trifluoromethyl-oxazole-4-carboxylic acid (4-piperazin-1-yl-phenyl)-amide (130 mg, 0.31 mmol), 4-(1H-tetrazol-5-yl)-cyclohexanecarboxylic acid (61 mg, 0.31 mmol), DMAP (2 mg, 0.016 mmol), and 1-ethyl-3-(3-dimethylaminopropyl)carbodiimide hydrochloride (71 mg, 0.37 mmol) in anhydrous DMF (2 mL) was stirred at room temperature for 2.5 days. The reaction was diluted in water (100 mL) and extracted with dichloromethane (2×100 mL) and ethyl acetate (1×100 mL), the organic layers combined, dried over sodium sulfate and purified by flash chromatograph with increasing concentrations of methanol in dichloromethane (0 to 10% over 20 min) to give 2-phenyl-5-trifluoromethyl-oxazole-4-carboxylic acid (4-{4-[4-(1H-tetrazol-5-yl)-cyclohexanecarbonyl]-piperazin-1-yl}-phenyl)-amide (90 mg, 49%) as a light yellow solid. LCMS calcd for C29H29F3N8O3 (m/e) 594, obsd 595 (M+H).

Example 292

Preparation of 2-phenyl-5-trifluoromethyl-oxazole-4-carboxylic acid (4-{1-[4-(1H-tetrazol-5-yl)-cyclohexanecarbonyl]-piperidin-4-yl}-phenyl)-amide

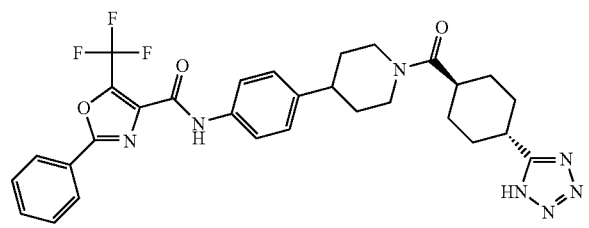

With a procedure similar to example 1,2-phenyl-5-trifluoromethyl-oxazole-4-carboxylic acid (4-{1-[4-(1H-tetrazol-5-yl)-cyclohexanecarbonyl]-piperidin-4-yl}-phenyl)-amide was prepared from 2-phenyl-5-trifluoromethyl-oxazole-4-carboxylic acid (4-piperidin-4-yl-phenyl)-amide (212 mg, 0.51 mmol) and 4-(1H-tetrazol-5-yl)-cyclohexanecarboxylic acid (100 mg, 0.51 mmol) as an off white solid (147 mg, 49%). LCMS calcd for C30H30F3N7O3 (m/e) 593, obsd 594 (M+H).

Example 293

Preparation 2-phenyl-5-trifluoromethyl-oxazole-4-carboxylic acid (4-{1-[4-(5-oxo-4,5-dihydro-[1,2,4]oxadiazol-3-yl)-cyclohexanecarbonyl]-piperidin-4-yl}-phenyl)-amide

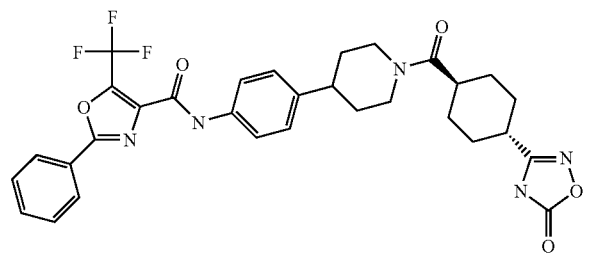

With a procedure similar to example 1,2-phenyl-5-trifluoromethyl-oxazole-4-carboxylic acid (4-{1-[4-(5-oxo-4,5-dihydro-[1,2,4]oxadiazol-3-yl)-cyclohexanecarbonyl]-piperidin-4-yl}-phenyl)-amide was prepared from 2-phenyl-5-trifluoromethyl-oxazole-4-carboxylic acid (4-piperidin-4-yl-phenyl)-amide (202 mg, 0.49 mmol) and 4-(5-Oxo-4,5-dihydro-[1,2,4]oxadiazol-3-yl)-cyclohexanecarboxylic acid (104 mg, 0.49 mmol) as an off white solid (13 mg, 4%). LCMS calcd for C31H30F3N5O5 (m/e) 609, obsd 610 (M+H).

Example 294

Preparation of 5'-[(2-phenyl-5-trifluoromethyl-oxazole-4-carbonyl)-amino]-3,4,5,6-tetrahydro-2H-[1,2']bipyridinyl-4-carboxylic acid amide

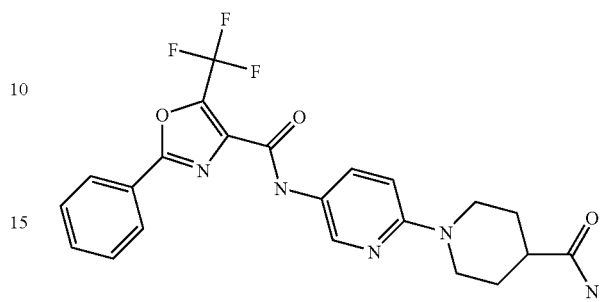

A mixture of 2-phenyl-5-trifluoromethyl-oxazole-4-carboxylic acid (3.42 g, 12.6 mmol), 5'-amino-3,4,5,6-tetrahydro-2H-[1,2']bipyridinyl-4-carboxylic acid amide (which was the product from the catalytic hydrogenation of 5'-nitro-3,4,5,6-tetrahydro-2H-[1,2']bipyridinyl-4-carboxylic acid amide: 2.93 g, 12.6 mmol, 200 mL EtOH/THF/EtOAc mixture, 50 psi H₂, 7 hr, with 300 mg of Pd/C 10%), 1-ethyl-3-(3-dimethylaminopropyl)carbodiimide hydrochloride (2.89 g, 15.1 mmol) and DMAP (catalytic) in anhydrous DMF (25 mL) was stirred at room temperature overnight. The reaction was diluted with ethyl acetate (400 mL) and washed with aqueous ammonium chloride (saturated, 200 mL), sodium bicarbonate (saturated, 200 mL with addition of brine to clear emulsion) and brine (100 mL). The aqueous ammonium chloride was extracted with ethyl acetate (200 mL) which was subsequently washed with brine (100 mL). The organic layers were combined, dried over sodium sulfate, concentrated, and tritrated from boiling ethyl acetate to give 5'-[(2-phenyl-5-trifluoromethyl-oxazole-4-carbonyl)-amino]-3,4,5,6-tetrahydro-2H-[1,2']bipyridinyl-4-carboxylic acid amide (1.5 g, 26%) as a light brown solid. LCMS calcd for C22H20F3N5O3 (m/e) 459, obsd 460 (M+H).

Example 295

Preparation of [1-(4-{4-[(2-phenyl-5-trifluoromethyl-oxazole-4-carbonyl)-amino]-phenyl}-piperidine-1-carbonyl)-piperidin-4-yl]-acetic acid

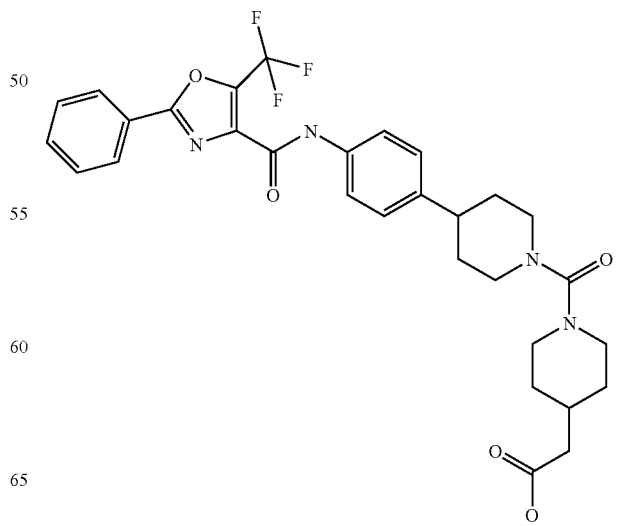

To a mixture of 4-{4-[(2-phenyl-5-trifluoromethyl-oxazole-4-carbonyl)-amino]-phenyl}-piperidine-1-carboxylic acid 4-nitro-phenyl ester (150 mg, 0.26 mmol) in 1-methyl-pyrrolidin-2-one (10 mL) at room temperature was added piperidin-4-yl-acetic acid methyl ester (0.04 g, 0.25 mmol) followed by N,N-diisopropylethylamine (0.14 mL, 0.8 mmol). The mixture was stirred in a 90° C. oil bath overnight. The mixture was blown to dryness and the crude was purified by flash chromatography (Merck silica gel 60, 230-400 mesh, gradient elution with 0%-60% ethyl acetate in hexane) to give [1-(4-{4-[(2-phenyl-5-trifluoromethyl-oxazole-4-carbonyl)-amino]-phenyl}-piperidine-1-carbonyl)-piperidin-4-yl]-acetic acid methyl ester (70 mg). LCMS calcd for C31H33F3N4O5 (m/e) 598, obsd 599 (M+H).

To a mixture of [1-(4-{4-[(2-phenyl-5-trifluoromethyl-oxazole-4-carbonyl)-amino]-phenyl}-piperidine-1-carbonyl)-piperidin-4-yl]-acetic acid methyl ester (70 mg, 0.117 mmol) in dioxane (3 mL) and water (3 mL) at room temperature was added lithium hydroxide (0.01 g, 0.24 mmol). The mixture was stirred at room temperature for about an hour. The mixture was acidified to pH of about 2 and then blown to dryness. Purification by reversed-phase HPLC gave [1-(4-{4-[(2-phenyl-5-trifluoromethyl-oxazole-4-carbonyl)-amino]-phenyl}-piperidine-1-carbonyl)-piperidin-4-yl]-acetic acid. LCMS calcd for C30H31F3N4O5 (m/e) 584, obsd 585 (M+H). The NMR spectrum obtained on the sample is compatible with its structure.

Example 296

Preparation of 1-(4-{4-[(2-phenyl-5-trifluoromethyl-oxazole-4-carbonyl)-amino]-phenyl}-piperidine-1-carbonyl)-piperidine-4-carboxylic acid

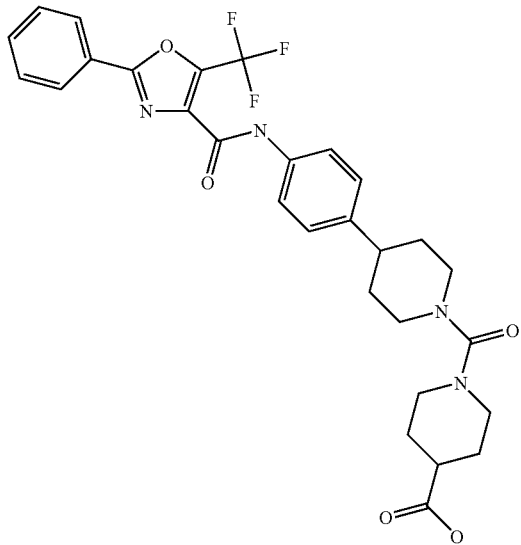

With a procedure similar to above, 1-(4-{4-[(2-phenyl-5-trifluoromethyl-oxazole-4-carbonyl)-amino]-phenyl}-piperidine-1-carbonyl)-piperidine-4-carboxylic acid was prepared from 4-{4-[(2-phenyl-5-trifluoromethyl-oxazole-4-carbonyl)-amino]-phenyl}-piperidine-1-carboxylic acid 4-nitro-phenyl ester and piperidine-4-carboxylic acid ethyl ester. LCMS calcd for C29H29F3N4O5 (m/e) 570, obsd 571 (M+H). The NMR spectrum obtained on the sample is compatible with its structure.

Example 297

Preparation of 1-(4-{4-[(2-phenyl-5-trifluoromethyl-oxazole-4-carbonyl)-amino]-phenyl}-piperidine-1-carbonyl)-pyrrolidine-3-carboxylic acid

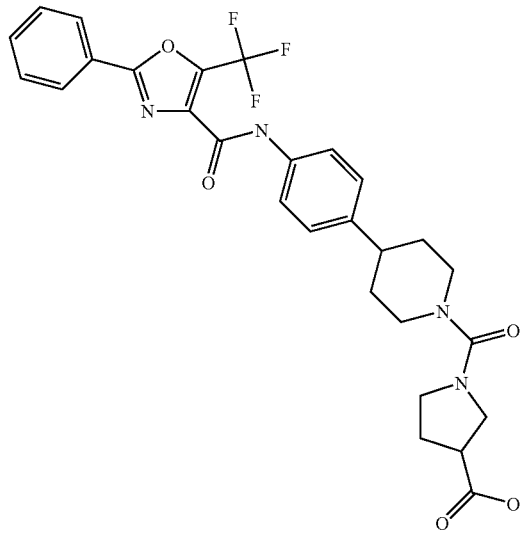

With a procedure similar to above, 1-(4-{4-[(2-phenyl-5-trifluoromethyl-oxazole-4-carbonyl)-amino]-phenyl}-piperidine-1-carbonyl)-pyrrolidine-3-carboxylic acid was prepared from 4-{4-[(2-phenyl-5-trifluoromethyl-oxazole-4-carbonyl)-amino]-phenyl}-piperidine-1-carboxylic acid 4-nitro-phenyl ester and pyrrolidine-3-carboxylic acid methyl ester. LCMS calcd for C28H27F3N4O5 (m/e) 556, obsd 557 (M+H). The NMR spectrum obtained on the sample is compatible with its structure.

Example 298

Preparation of 3-[1-(4-{4-[(2-phenyl-5-trifluoromethyl-oxazole-4-carbonyl)-amino]-phenyl}-piperidine-1-carbonyl)-piperidin-4-yl]-propionic acid

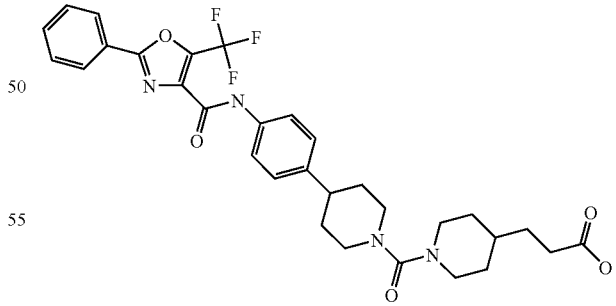

With a procedure similar to above, 3-[1-(4-{4-[(2-phenyl-5-trifluoromethyl-oxazole-4-carbonyl)-amino]-phenyl}-piperidine-1-carbonyl)-piperidin-4-yl]-propionic acid was prepared from 4-{4-[(2-phenyl-5-trifluoromethyl-oxazole-4-carbonyl)-amino]-phenyl}-piperidine-1-carboxylic acid 4-nitro-phenyl ester and 3-piperidin-4-yl-propionic acid methyl ester. LCMS calcd for C31H33F3N4O5 (m/e) 598, obsd 599 (M+H). The NMR spectrum obtained on the sample is compatible with its structure.

Example 299

Preparation of 4-[1-(4-{4-[(2-phenyl-5-trifluoromethyl-oxazole-4-carbonyl)-amino]-phenyl}-piperidine-1-carbonyl)-piperidin-4-yl]-butyric acid

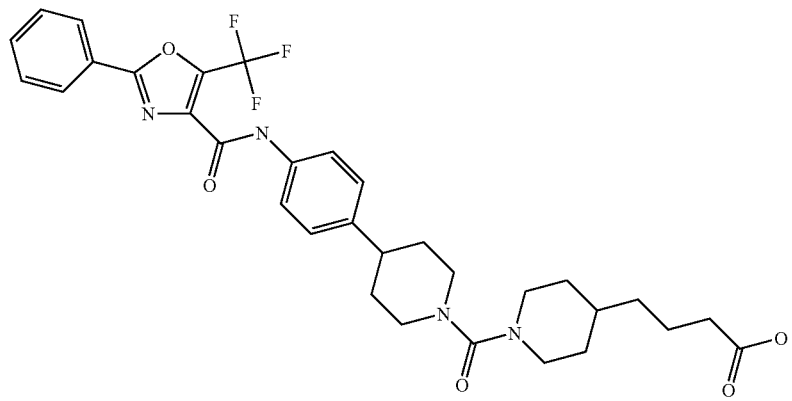

With a procedure similar to above, 4-[1-(4-{4-[(2-phenyl-5-trifluoromethyl-oxazole-4-carbonyl)-amino]-phenyl}-piperidine-1-carbonyl)-piperidin-4-yl]-butyric acid was prepared from 4-{4-[(2-phenyl-5-trifluoromethyl-oxazole-4-carbonyl)-amino]-phenyl}-piperidine-1-carboxylic acid 4-nitro-phenyl ester and 3-piperidin-4-yl-butyric acid methyl ester. LCMS calcd for C32H35F3N4O5 (m/e) 612, obsd 613 (M+H). The NMR spectrum obtained on the sample is compatible with its structure.

Example 300

Preparation of (R)-3-{5-[(2-phenyl-5-trifluoromethyl-oxazole-4-carbonyl)-amino]-pyrimidin-2-yloxy}-pyrrolidine-1-carboxylic acid ethyl ester

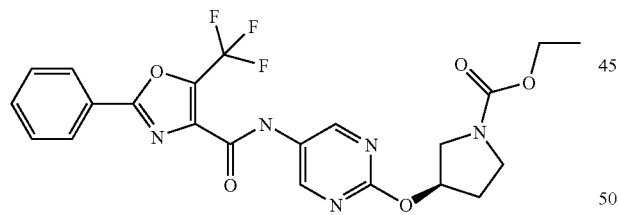

This compound was prepared using the same method described in the preparation of (S)-3-{5-[(2-phenyl-5-trifluoromethyl-oxazole-4-carbonyl)-amino]-pyrimidin-2-yloxy}-pyrrolidine-1-carboxylic acid ethyl ester. LC-MS showed a single peak with retention time of 4.09 min. LRMS calcd for C22H20F3N5O5 (M+H) 492.14, obsd 492.1

Example 301

Preparation of 1-(1-{4-[(2-phenyl-5-trifluoromethyl-oxazole-4-carbonyl)-amino]-phenyl}-piperidine-4-carbonyl)-piperidine-4-carboxylic acid ethyl ester

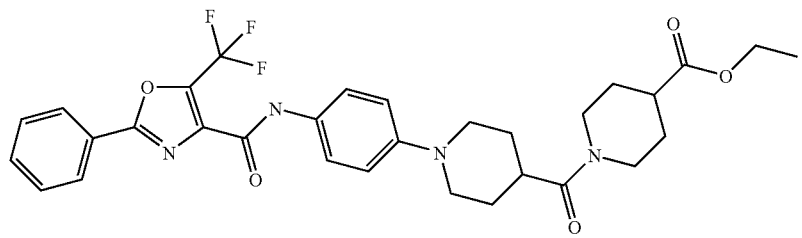

To a solution of 1-{4-[(2-phenyl-5-trifluoromethyl-oxazole-4-carbonyl)-amino]-phenyl}-piperidine-4-carboxylic acid (229.5 mg, 0.5 mmol) in DMF (4 mL) was added piperidine-4-carboxylic acid ethyl ester (79 mg, 0.5 mmol), PyBrop (233.1 mg, 0.5 mmol) and triethylamine (0.1 mL). The mixture was stirred overnight and solvents were evaporated. The residue was extracted with ethyl acetate and water. After the evaporation of solvents, the residue was purified through flash column chromatography using ethyl acetate and hexanes. The desired fraction was evaporated and triturated with ether and petroleum ether (2:1) to give a yellow solid as 1-(1-{4-[(2-phenyl-5-trifluoromethyl-oxazole-4-carbonyl)-amino]-phenyl}-piperidine-4-carbonyl)-piperidine-4-carboxylic acid ethyl ester. LC-MS showed a single peak with a retention time of 3.54 min. LRMS calcd for C31H33F3N4O5 (M+H) 599.24, obsd 599.3

Example 302

Preparation of 1-(1-{4-[(2-phenyl-5-trifluoromethyl-oxazole-4-carbonyl)-amino]-phenyl}-piperidine-4-carbonyl)-piperidine-4-carboxylic acid

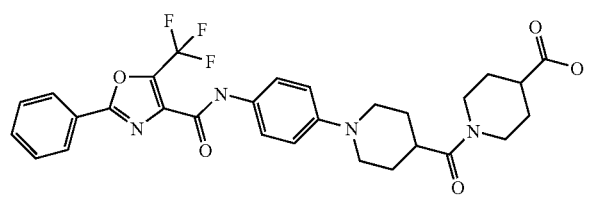

This compound was prepared from the hydrolysis of the corresponding ethyl ester. LC-MS showed a single peak with a retention time of 3.09 min. LRMS calcd for C29H29F3N4O5 (M+H) 571.21, obsd 571.2

Example 303

Preparation of 1-(1-{4-[(2-phenyl-5-trifluoromethyl-oxazole-4-carbonyl)-amino]-phenyl}-piperidine-4-carbonyl)-piperidine-3-carboxylic acid ethyl ester

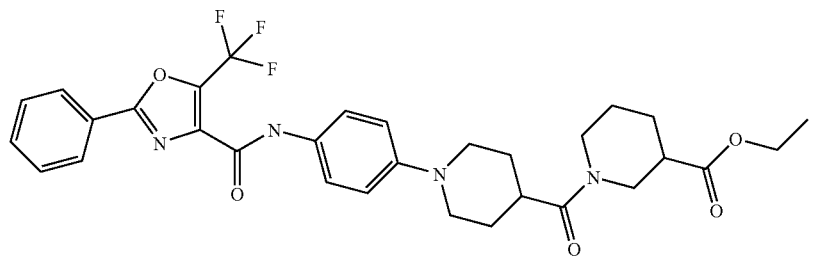

This compound was prepared from 1-{4-[(2-phenyl-5-trifluoromethyl-oxazole-4-carbonyl)-amino]-phenyl}-piperidine-4-carboxylic acid and piperidine-3-carboxylic acid ethyl ester using the same method describer in earlier example. LC-MS showed a single peak with a retention time of 3.62 min. LRMS calcd for C31H33F3N4O5 (M+H) 599.24, obsd 599.2

Example 304

Preparation of 1-(1-{4-[(2-phenyl-5-trifluoromethyl-oxazole-4-carbonyl)-amino]-phenyl}-piperidine-4-carbonyl)-piperidine-3-carboxylic acid

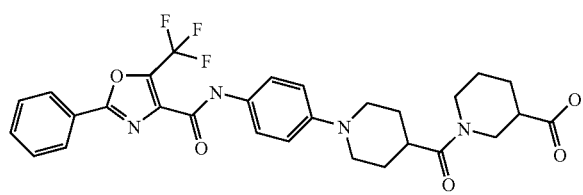

This compound was prepared from the hydrolysis of the corresponding ethyl ester. LC-MS showed a single peak with a retention time of 3.12 min. LRMS calcd for C29H29F3N4O5 (M+H) 571.21, obsd 571.2

Example 305

Preparation of 2,2-dimethyl-4-oxo-4-(4-{4-[(2-phenyl-5-trifluoromethyl-oxazole-4-carbonyl)-amino]-phenoxy}-piperidin-1-yl)-butyric acid

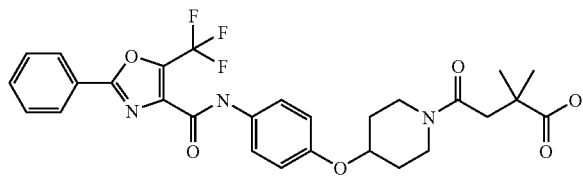

To a solution of 4-fluoronitrobenzene (1.41 g, 10 mmol) in THF (50 mL) was added N-Boc-4-hydroxypiperidine (2.01 g, 10 mmol) and sodium hydride (60% in mineral oil, 583 mg, 14.5 mmol). The mixture was stirred at room temperature for 14 hrs. After purification through flash column chromatography, 4-(4-nitro-phenoxy)-piperidine-1-carboxylic acid tert-butyl ester (2.51 g, 78% yield) was obtained as a solid. This nitro compound was hydrogenated to the corresponding amine and coupled with 2-phenyl-5-trifluoromethyloxazole-4-carboxylic acid to give 4-{4-[(2-phenyl-5-trifluoromethyl-oxazole-4-carbonyl)-amino]-phenoxy}-piperidine-1-carboxylic acid tert-butyl ester. LC-MS showed a single peak with a retention time of 4.08 min. LRMS calcd for C27H28F3N3O5 (M+1) 532.20, obsd 532.1

The above compound (1.89 g, 3.56 mmol) was dissolved in methylene chloride (6 mL) and treated with gaseous hydrogen chloride in ether (3.8M, 10 mL). The mixture was stirred at room temperature for 4 hrs and then diluted with ether (20 mL). The white solid was filtered to give 2-phenyl-5-trifluoromethyl-oxazole-4-carboxylic acid [4-(piperidin-4-yloxy)-phenyl]-amide hydrochloride. LC-MS showed a single peak with a retention time of 3.03 min. LRMS calcd for C22H20F3N3O3 (M+1) 432.15, obsd 432.1

The above hydrochloride salt (101 mg, 0.2 mmol) was dissolved in methylene chloride (5 mL) and triethylamine (0.12 mL) was added followed by the addition of 2,2-dimethylsuccinic anhydride (38.4 mg, 0.3 mmol). The mixture was stirred at room temperature overnight. Solvents were evaporated and the residue was extracted with ethyl acetate and 1N hydrochloric acid. The organic layer was washed with brine and solvents were evaporated. The residue was triturated with ether and the white solid was filtered to give 2,2-dimethyl-4-oxo-4-(4-{4-[(2-phenyl-5-trifluoromethyl-oxazole-4-carbonyl)-amino]-phenoxy}-piperidin-1-yl)-butyric acid (97 mg). LC-MS showed a single peak with a retention time of 4.14 min. LRMS calcd for C28H28F3N3O6 (M+1) 560.19, obsd 560.4

Example 306

Preparation of 2,2-dimethyl-4-oxo-4-((S)-3-{4-[(2-phenyl-5-trifluoromethyl-oxazole-4-carbonyl)-amino]-phenoxy}-pyrrolidin-1-yl)-butyric acid

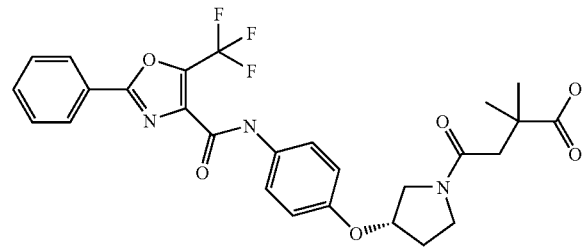

This compound was prepared using the same method as the preparation of 2,2-dimethyl-4-oxo-4-(4-{4-[(2-phenyl-5-trifluoromethyl-oxazole-4-carbonyl)-amino]-phenoxy}-piperidin-1-yl)-butyric acid. LC-MS showed a single peak with a retention time of 4.02 min. LRMS calcd for C27H26F3N3O6 (M+1) 546.18, obsd 546.2

Example 307

Preparation of 4-((S)-3-{4-[(2-phenyl-5-trifluoromethyl-oxazole-4-carbonyl)-amino]-phenoxy}-pyrrolidine-1-carbonyl)-trans-cyclohexanecarboxylic acid

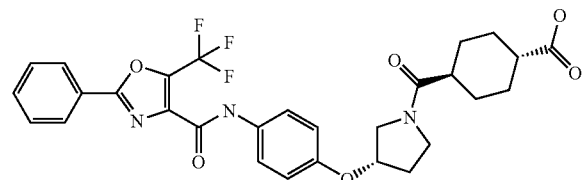

This compound was prepared by the hydrogenation of the corresponding benzyl ester. The benzyl ester was synthesized by coupling 2-phenyl-5-trifluoromethyl-oxazole-4-carboxylic acid [4-((S)-pyrrolidin-3-yloxy)-phenyl]-amide with trans-1,4-cyclohexane-dicarboxylic acid mono-benzyl ester through an acid chloride intermediate. After the hydrogenation and evaporation of solvents, the residue was triturated with ether to give a white solid. LC-MS showed a single peak with a retention time of 3.75 min. LRMS calcd for C29H28F3N3O6 (M+1) 572.19, obsd 572.3

Example 308

Preparation of 1-[2-oxo-2-((S)-3-{4-[(2-phenyl-5-trifluoromethyl-oxazole-4-carbonyl)-amino]-phenoxy}-pyrrolidin-1-yl)-ethyl]-cyclopentanecarboxylic acid

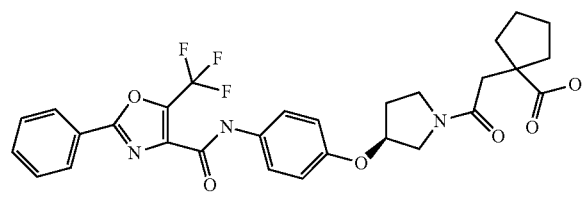

This compound was prepared with the same method described previously by treating the amine hydrochloride salt with an anhydride in the presence of triethylamine. LC-MS showed a single peak with a retention time of 4.17 min. LRMS calcd for C29H28F3N3O6 (M+1) 572.19, obsd 572.4

Example 309

Preparation of 2,2-dimethyl-4-(4-{4-[(5-methyl-2-phenyl-oxazole-4-carbonyl)-amino]-phenyl}-piperidin-1-yl)-4-oxo-butyric acid

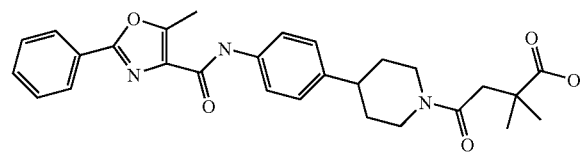

This compound was prepared with the same method described in previous examples. LC-MS showed a single peak with a retention time of 4.05 min. LRMS calcd for C28H31N3O5 (M+1) 490.23, obsd 490.5

Example 310

Preparation of (1R,2R)-2-((S)-3-{4-[(2-phenyl-5-trifluoromethyl-oxazole-4-carbonyl)-amino]-phenoxy}-pyrrolidine-1-carbonyl)-cyclopentanecarboxylic acid

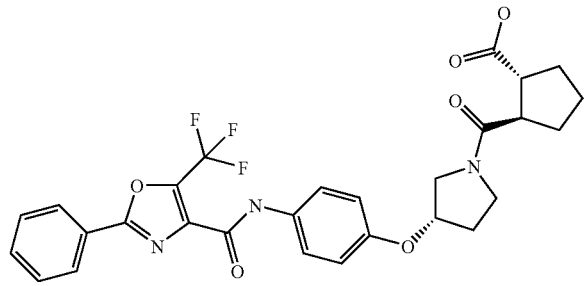

215

This compound was prepared through the hydrogenation of the corresponding benzyl ester. The benzyl ester was synthesized through the coupling of 2-phenyl-5-trifluoromethyl-oxazole-4-carboxylic acid [4-((S)-pyrrolidin-3-yloxy)-phenyl]-amide with (1R,2R)-2-benzyloxycarbonyl-cyclopantane carboxylic acid. LC-MS showed a single peak with a retention time of 3.93 min. LRMS calcd for C28H26F3N3O6 (M+1) 558.18, obsd 558.4

Example 311

Preparation of 1-(1-{4-[(2-phenyl-5-trifluoromethyl-oxazole-4-carbonyl)-amino]-phenyl}-piperidine-4-carbonyl)-pyrrolidine-3-carboxylic acid methyl ester; hydrochloride

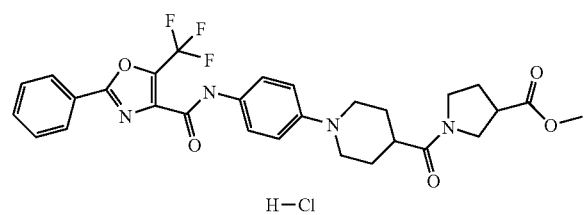

With a method similar to that used for the preparation of compounds in previous examples. LRMS calcd for C29H29F3N4O5 (M+H) 571.21, obsd 571.1

Example 312

Preparation of (S)-1-(1-{4-[(2-phenyl-5-trifluoromethyl-oxazole-4-carbonyl)-amino]-phenyl}-piperidine-4-carbonyl)-pyrrolidine-2-carboxylic acid methyl ester; hydrochloride

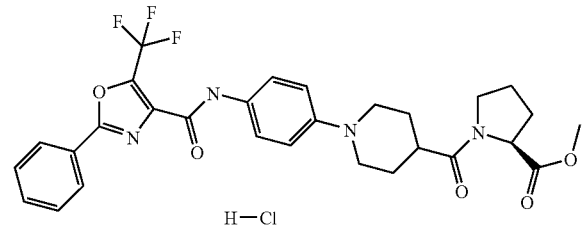

With a method similar to that used for the preparation of compounds in previous examples. LRMS calcd for C29H29F3N4O5 (M+H) 571.21, obsd 571.1

Example 313

Preparation of (S)-1-(1-{4-[(2-phenyl-5-trifluoromethyl-oxazole-4-carbonyl)-amino]-phenyl}-piperidine-4-carbonyl)-pyrrolidine-2-carboxylic acid

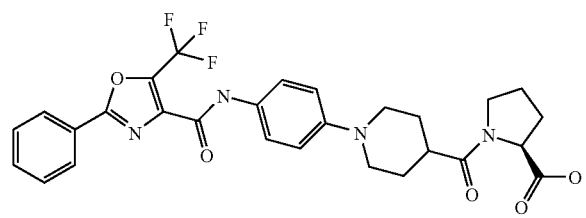

With a method similar to that used for the preparation of compounds in previous examples. LRMS calcd for C28H27F3N4O5 (M+H) 557.19, obsd 557.2

Example 314

Preparation of 1-(1-{4-[(2-phenyl-5-trifluoromethyl-oxazole-4-carbonyl)-amino]-phenyl}-piperidine-4-carbonyl)-piperidine-2-carboxylic acid; hydrochloride

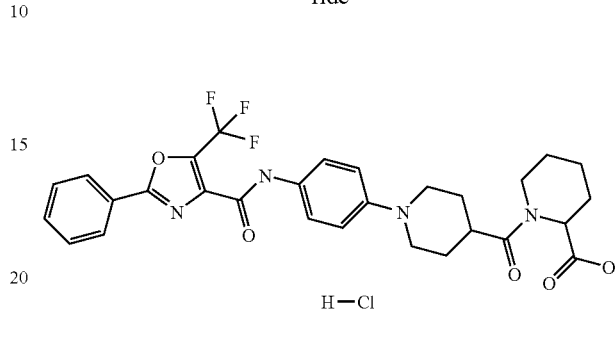

With a method similar to that used for the preparation of compounds in previous examples. LRMS calcd for C29H29F3N4O5 (M+H) 571.21, obsd 571.2

Example 315

Preparation of (1S,2S)-2-(4-{4-[(2-tert-butyl-5-methyl-oxazole-4-carbonyl)-amino]-phenyl}-piperazine-1-carbonyl)-cyclopentanecarboxylic acid; hydrochloride

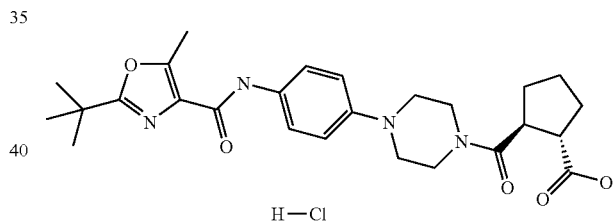

With a method similar to that used for the preparation of compounds in previous examples. The 2-tert-butyl-5-methyl-oxazole-4-carboxylic acid was prepared from (L)-threonine methyl ester according to known procedure in literature. LRMS calcd for C26H34N4O5 (M+H) 483.25, obsd 483.2

Example 316

Preparation of 4-((S)-3-{4-[(2-phenyl-5-trifluoromethyl-oxazole-4-carbonyl)-amino]-phenoxy}-pyrrolidine-1-carbonyl)-cis-cyclohexanecarboxylic acid

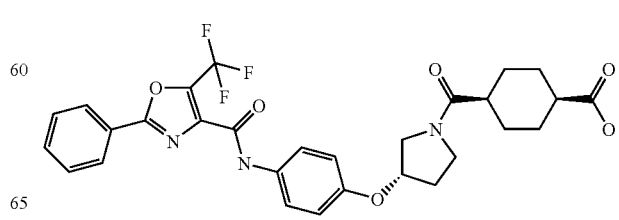

With a method similar to that used for the preparation of compounds in previous examples. LRMS calcd for C29H28F3N3O6 (M+H) 572.19, obsd 572.30

Example 317

Preparation of 2-phenyl-thiazole-4-carboxylic acid (4-{4-[2-(2,4-dioxo-thiazolidin-5-yl)-acetyl]-piperazin-1-yl}-phenyl)-amide; hydrochloride

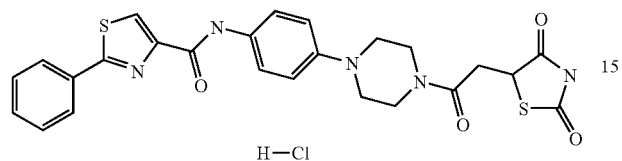

With a method similar to that used for the preparation of compounds in previous examples. LRMS calcd for C25H23N5O4S2 (M+H) 522.12, obsd 522.2

Example 318

Preparation of (1S,2S)-2-(4-{3-fluoro-4-[(2-phenyl-5-trifluoromethyl-oxazole-4-carbonyl)-amino]-phenyl}-piperazine-1-carbonyl)-cyclopentanecarboxylic acid

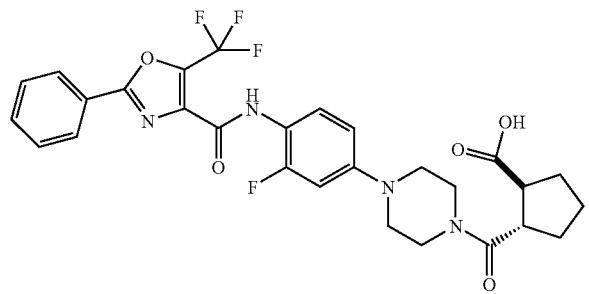

A mixture of 2-phenyl-5-trifluoromethyl-oxazole-4-carboxylic acid (2-fluoro-4-piperazin-1-yl-phenyl)-amide (0.22 g, 0.5 mmol) prepared from 2-phenyl-5-trifluoromethyl-oxazole-4-carboxylic acid and 4-(4-amino-3-fluoro-phenyl)-piperazine using a procedure similar to the one described above, (1S,2S)-cyclopentane-1,2-dicarboxylic acid monobenzyl ester (0.26 g, 0.5 mmol), N-hydroxybenzotriazole (0.1 g, 0.74 mmol), and 1-ethyl-3-(3-dimethylaminopropyl)carbodiimide hydrochloride (0.14 g, 0.74 mmol), N,N-diisopropylethylamine (0.26 mL, 1.5 mmol) in anhydrous dichloromethane (4 mL) was stirred at room temperature for overnight. After the reaction, solvent was evaporated. The resulted mixture was mixed with water and extracted with ethyl acetate twice. The organic layers were collected, combined, washed with brine before dried over sodium sulfate, and then concentrated to give a solid. The crude product was purified by reverse phase HPLC (10%-80% acetonitrile in water) to gave (1S,2S)-2-(4-{3-fluoro-4-[(2-phenyl-5-trifluoromethyl-oxazole-4-carbonyl)-amino]-phenyl}-piperazine-1-carbonyl)-cyclopentanecarboxylic acid benzyl ester as a yellow solid. LCMS calcd for C35H32F4N4O5 (m/e) 664, obsd 665 (M+H).

To the solution of (1S,2S)-2-(4-{3-fluoro-4-[(2-phenyl-5-trifluoromethyl-oxazole-4-carbonyl)-amino]-phenyl}-piperazine-1-carbonyl)-cyclopentanecarboxylic acid benzyl ester in methanol, lithium hydroxide and water were added. The so formed mixture was stirred at 25° C. overnight. Solvent was removed and the residue was resuspended in ethyl acetate and water. Citric acid was added to acidify the mixture. Organic layer was concentrated and the residue was purified on a reverse phase HPLC system to give (1S,2S)-2-(4-{3-fluoro-4-[(2-phenyl-5-trifluoromethyl-oxazole-4-carbonyl)-amino]-phenyl}-piperazine-1-carbonyl)-cyclopentanecarboxylic acid as a white solid. LCMS calcd for C28H26F4N4O5 (m/e) 574, obsd 575 (M+H).

Example 319

Preparation of trans-4-(4-{3-fluoro-4-[(2-phenyl-5-trifluoromethyl-oxazole-4-carbonyl)-amino]-phenyl}-piperazine-1-carbonyl)-cyclohexanecarboxylic acid

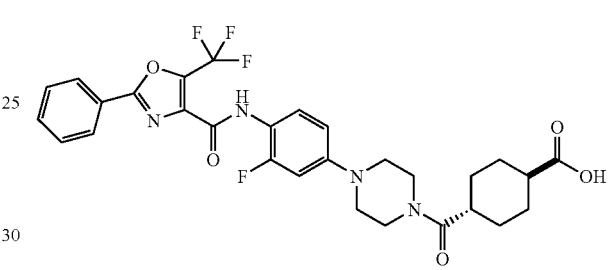

With a procedure similar to the one described above, trans-4-(4-{3-fluoro-4-[(2-phenyl-5-trifluoromethyl-oxazole-4-carbonyl)-amino]-phenyl}-piperazine-1-carbonyl)-cyclohexanecarboxylic acid methyl ester was prepared from 2-phenyl-5-trifluoromethyl-oxazole-4-carboxylic acid (2-fluoro-4-piperazin-1-yl-phenyl)-amide and trans-cyclohexane-1,4-dicarboxylic acid monomethyl ester. LC-MS calcd for C30H30F4N4O5 (m/e) 602, obsd 603 (M+H).

trans-4-(4-{3-fluoro-4-[(2-phenyl-5-trifluoromethyl-oxazole-4-carbonyl)-amino]-phenyl}-piperazine-1-carbonyl)-cyclohexanecarboxylic acid methyl ester was hydrolized using a procedure similar to the one described above to give trans-4-(4-{3-fluoro-4-[(2-phenyl-5-trifluoromethyl-oxazole-4-carbonyl)-amino]-phenyl}-piperazine-1-carbonyl)-cyclohexanecarboxylic acid as a white solid. LC-MS calcd for C29H28F4N4O5 (m/e) 588, obsd 589 (M+H).

Example 320

Preparation of trans-2-[methyl-(1-{4-[(2-phenyl-5-trifluoromethyl-oxazole-4-carbonyl)-amino]-phenyl}-piperidin-4-yl)-carbamoyl]-cyclopentanecarboxylic acid

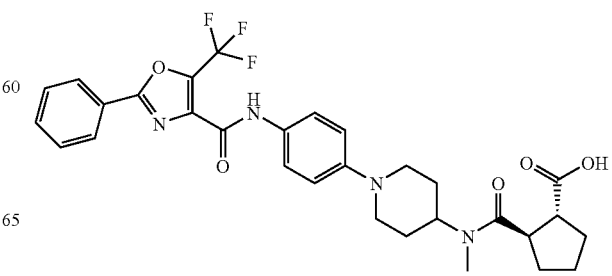

With a similar coupling procedure as described above, trans-2-[methyl-(1-{4-[(2-phenyl-5-trifluoromethyl-oxazole-4-carbonyl)-amino]-phenyl}-piperidin-4-yl)-carbamoyl]-cyclopentanecarboxylic acid benzyl ester was prepared from 2-phenyl-5-trifluoromethyl-oxazole-4-carboxylic acid [4-(4-methylamino-piperidin-1-yl)-phenyl]-amide and cyclopentane-trans-1,2-dicarboxylic acid monobenzyl ester. LCMS calcd for C37H37F3N4O5 (m/e) 674, obsd 675 (M+H).

Trans-2-[methyl-(1-{4-[(2-phenyl-5-trifluoromethyl-oxazole-4-carbonyl)-amino]-phenyl}-piperidin-4-yl)-carbamoyl]-cyclopentanecarboxylic acid benzyl ester was hydrolyzed with lithium hydroxide in methanol and water. The resulted crude mixture was concentrated and the residue was dissolved in ethyl acetate and water with citric acid as acidifying agent. The organic layer then was concentrated and purified by reverse phase HPLC. The mixture of isomers was obtained as a yellow solid. LCMS calcd for C30H31F3N4O5 (m/e) 584, obsd 585 (M+H).

Example 321

Preparation of (1R,2R)-2-[methyl-(1-{4-[(2-phenyl-5-trifluoromethyl-oxazole-4-carbonyl)-amino]-phenyl}-piperidin-4-yl)-carbamoyl]-cyclopentanecarboxylic acid

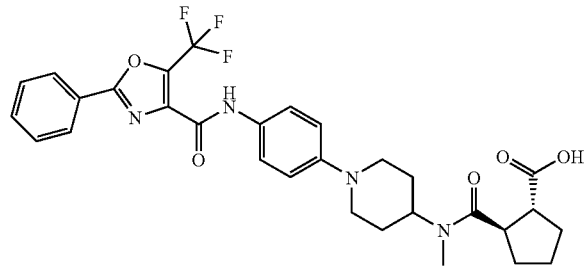

(1R,2R)-2-[methyl-(1-{4-[(2-phenyl-5-trifluoromethyl-oxazole-4-carbonyl)-amino]-phenyl}-piperidin-4-yl)-carbamoyl]-cyclopentanecarboxylic acid was obtained from SFC chiral purification of trans-2-[methyl-(1-{4-[(2-phenyl-5-trifluoromethyl-oxazole-4-carbonyl)-amino]-phenyl}-piperidin-4-yl)-carbamoyl]-cyclopentanecarboxylic acid LCMS calcd for C30H31F3N4O5 (m/e) 584, obsd 585 (M+H).

Example 322

Preparation of (1S,2S)-2-[methyl-(1-{4-[(2-phenyl-5-trifluoromethyl-oxazole-4-carbonyl)-amino]-phenyl}-piperidin-4-yl)-carbamoyl]-cyclopentanecarboxylic acid

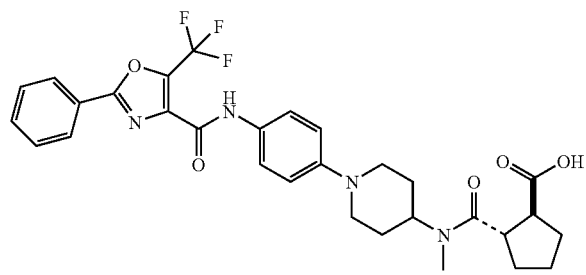

(1S,2S)-2-[methyl-(1-{4-[(2-phenyl-5-trifluoromethyl-oxazole-4-carbonyl)-amino]-phenyl}-piperidin-4-yl)-carbamoyl]-cyclopentanecarboxylic acid was obtained from SFC chiral purification of trans-2-[methyl-(1-{4-[(2-phenyl-5-trifluoromethyl-oxazole-4-carbonyl)-amino]-phenyl}-piperidin-4-yl)-carbamoyl]-cyclopentanecarboxylic acid LCMS calcd for C30H31F3N4O5 (m/e) 584, obsd 585 (M+H).

Example 323

Preparation of (1S,2S)-2-(methyl-{5'-[(2-phenyl-5-trifluoromethyl-oxazole-4-carbonyl)-amino]-3,4,5,6-tetrahydro-2H-[1,2']bipyridinyl-4-yl}-carbamoyl)-cyclopentanecarboxylic acid

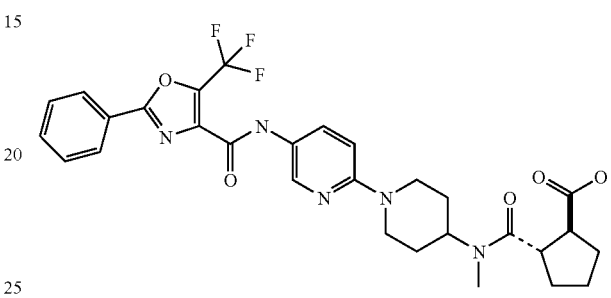

With a similar coupling procedure as described above, (1S,2S)-2-(methyl-{5'-[(2-phenyl-5-trifluoromethyl-oxazole-4-carbonyl)-amino]-3,4,5,6-tetrahydro-2H-[1,2']bipyridinyl-4-yl}-carbamoyl)-cyclopentanecarboxylic acid benzyl ester was prepared from 2-phenyl-5-trifluoromethyl-oxazole-4-carboxylic acid (4-methylamino-3,4,5,6-tetrahydro-2H-[1,2']bipyridinyl-5'-yl)-amide and (1S,2S)-cyclopentane-dicarboxylic acid monobenzyl ester. LCMS calcd for C36H36F3N5O5 (m/e) 675, obsd 676 (M+H).

With a similar procedure as described above, (1S,2S)-2-(methyl-{5'-[(2-phenyl-5-trifluoromethyl-oxazole-4-carbonyl)-amino]-3,4,5,6-tetrahydro-2H-[1,2']bipyridinyl-4-yl}-carbamoyl)-cyclopentanecarboxylic acid was prepared from (1S,2S)-2-(methyl-{5'-[(2-phenyl-5-trifluoromethyl-oxazole-4-carbonyl)-amino]-3,4,5,6-tetrahydro-2H-[1,2']bipyridinyl-4-yl}-carbamoyl)-cyclopentanecarboxylic acid benzyl ester. LCMS calcd for C29H30F3N5O5 (m/e) 585, obsd 586 (M+H).

Example 324

Preparation of 2-phenyl-5-trifluoromethyl-oxazole-4-carboxylic acid {4-[4-((R)-1-methanesulfonyl-pyrrolidine-2-carbonyl)-piperazin-1-yl]-phenyl}-amide

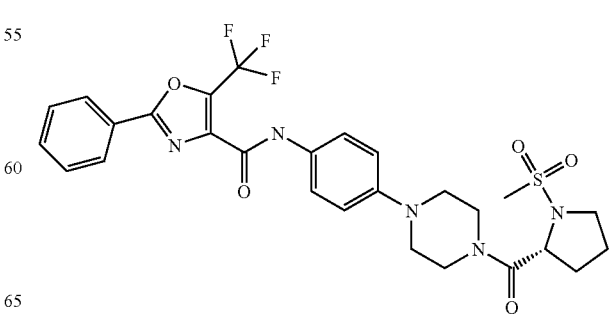

With a similar coupling procedure as described above, 2-phenyl-5-trifluoromethyl-oxazole-4-carboxylic acid {4-[4-((R)-pyrrolidine-2-carbonyl)-piperazin-1-yl]-phenyl}-amide was prepared from 2-phenyl-5-trifluoromethyl-oxazole-4-carboxylic acid (4-piperazin-1-yl-phenyl)-amide and (R)-pyrrolidine-1,2-dicarboxylic acid 1-tert-butyl ester. LCMS calcd for C26H26F3N5O3 (m/e) 513, obsd 514 (M+H).

With a similar procedure as described above, 2-phenyl-5-trifluoromethyl-oxazole-4-carboxylic acid {4-[4-((R)-1-methanesulfonyl-pyrrolidine-2-carbonyl)-piperazin-1-yl]-phenyl}-amide was prepared from 2-phenyl-5-trifluoromethyl-oxazole-4-carboxylic acid {4-[4-((R)-pyrrolidine-2-carbonyl)-piperazin-1-yl]-phenyl}-amide and methanesulfonyl chloride. LCMS calcd for C27H28F3N5O5S (m/e) 591, obsd 592 (M+H).

Example 325

Preparation of 2-phenyl-5-trifluoromethyl-oxazole-4-carboxylic acid {4-[4-((R)-1-dimethylsulfamoyl-pyrrolidine-2-carbonyl)-piperazin-1-yl]-phenyl}-amide

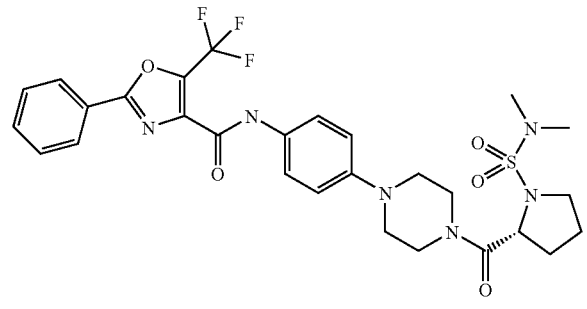

With a similar procedure as described above, 2-phenyl-5-trifluoromethyl-oxazole-4-carboxylic acid {4-[4-((R)-1-dimethylsulfamoyl-pyrrolidine-2-carbonyl)-piperazin-1-yl]-phenyl}-amide was prepared from 2-phenyl-5-trifluoromethyl-oxazole-4-carboxylic acid {4-[4-((R)-pyrrolidine-2-carbonyl)-piperazin-1-yl]-phenyl}-amide and dimethylsulfamoyl chloride. LCMS calcd for C28H31F3N6O5S (m/e) 620, obsd 621 (M+H).

Example 326

Preparation of 2-phenyl-5-trifluoromethyl-oxazole-4-carboxylic acid {4-[4-((S)-1-methanesulfonyl-pyrrolidine-2-carbonyl)-piperazin-1-yl]-phenyl}-amide

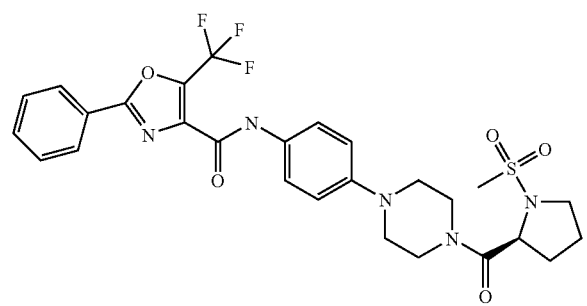

With a similar coupling procedure as described above, 2-phenyl-5-trifluoromethyl-oxazole-4-carboxylic acid {4-[4-((S)-pyrrolidine-2-carbonyl)-piperazin-1-yl]-phenyl}-amide was prepared from 2-phenyl-5-trifluoromethyl-oxazole-4-carboxylic acid (4-piperazin-1-yl-phenyl)-amide and (S)-pyrrolidine-1,2-dicarboxylic acid 1-tert-butyl ester. LCMS calcd for C26H26F3N5O3 (m/e) 513, obsd 514 (M+H).

With a similar procedure as described above, 2-phenyl-5-trifluoromethyl-oxazole-4-carboxylic acid {4-[4-((S)-1-methanesulfonyl-pyrrolidine-2-carbonyl)-piperazin-1-yl]-phenyl}-amide was prepared from 2-phenyl-5-trifluoromethyl-oxazole-4-carboxylic acid {4-[4-((S)-pyrrolidine-2-carbonyl)-piperazin-1-yl]-phenyl}-amide and methanesulfonyl chloride. LCMS calcd for C27H28F3N5O5S (m/e) 591, obsd 592 (M+H).

Example 327

Preparation of 2-phenyl-5-trifluoromethyl-oxazole-4-carboxylic acid {4-[4-((S)-1-dimethylsulfamoyl-pyrrolidine-2-carbonyl)-piperazin-1-yl]-phenyl}-amide

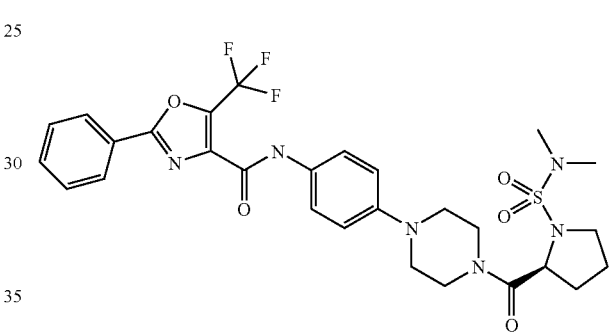

With a similar procedure as described above, 2-phenyl-5-trifluoromethyl-oxazole-4-carboxylic acid {4-[4-((S)-1-dimethylsulfamoyl-pyrrolidine-2-carbonyl)-piperazin-1-yl]-phenyl}-amide was prepared from 2-phenyl-5-trifluoromethyl-oxazole-4-carboxylic acid {4-[4-((R)-pyrrolidine-2-carbonyl)-piperazin-1-yl]-phenyl}-amide and dimethylsulfamoyl chloride. LCMS calcd for C28H31F3N6O5S (m/e) 620, obsd 621 (M+H).

Example 328

Preparation of 2-(4-{5-[(2-phenyl-5-trifluoromethyl-oxazole-4-carbonyl)-amino]-pyridin-2-yl}-benzoyl)-cyclopentanecarboxylic acid methyl ester

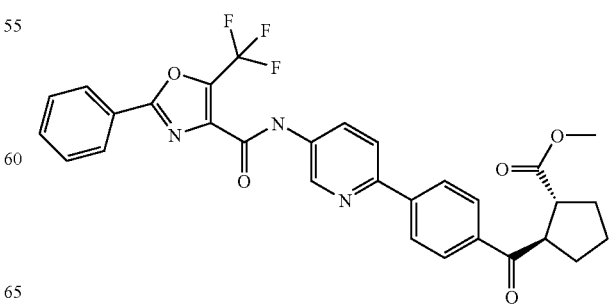

2-(4-{5-[(2-Phenyl-5-trifluoromethyl-oxazole-4-carbonyl)-amino]-pyridin-2-yl}-benzoyl)-cyclopentanecarboxylic acid methyl ester was prepared through a standard Suzuki coupling procedure by mixing 2-phenyl-5-trifluoromethyl-oxazole-4-carboxylic acid (6-bromo-pyridin-3-yl)-amide (prepared using a similar coupling procedure as described above from 2-phenyl-5-trifluoromethyl-oxazole-4-carboxylic acid and 6-bromo-pyridin-3-ylamine), 2-[4-(4,4,5,5-tetramethyl-[1,3,2]dioxaborolan-2-yl)-benzoyl]-cyclopentanecarboxylic acid methyl ester, palladium tetrakis (triphenylphosphine) and aqueous sodium bicarbonate solution in toluene and ethanol, and heating this mixture to 160° C. under microwave condition for 20 min. Aqueous workup followed by silica gel chromatography separation gave 2-(4-{5-[(2-phenyl-5-trifluoromethyl-oxazole-4-carbonyl)-amino]-pyridin-2-yl}-benzoyl)-cyclopentanecarboxylic acid methyl ester as light yellow solid. LCMS calcd for C30H24F3N3O5 (m/e) 563, obsd 564 (M+H).

Example 329

Preparation of 2-(4-{5-[(2-phenyl-5-trifluoromethyl-oxazole-4-carbonyl)-amino]-pyridin-2-yl}-benzoyl)-cyclopentanecarboxylic acid

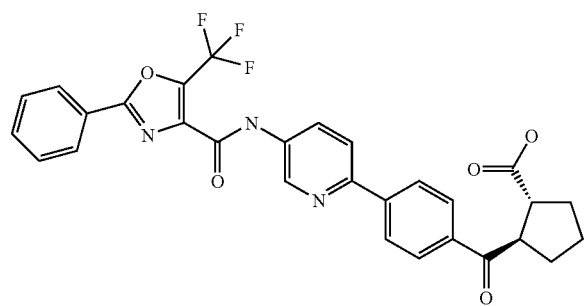

With a similar hydrolysis procedure as described above, 2-(4-{5-[(2-Phenyl-5-trifluoromethyl-oxazole-4-carbonyl)-amino]-pyridin-2-yl}-benzoyl)-cyclopentanecarboxylic acid was obtained by a hydrolysis of 2-(4-{5-[(2-phenyl-5-trifluoromethyl-oxazole-4-carbonyl)-amino]-pyridin-2-yl}-benzoyl)-cyclopentanecarboxylic acid methyl ester with lithium hydroxide in THF, methanol and water. LCMS calcd for C29H22F3N3O5 (m/e) 549, obsd 550 (M+H).

Example 330

Preparation of 3-{5-[(2-phenyl-5-trifluoromethyl-oxazole-4-carbonyl)-amino]-pyridin-2-yloxy}-piperidine-1-carboxylic acid ethyl ester

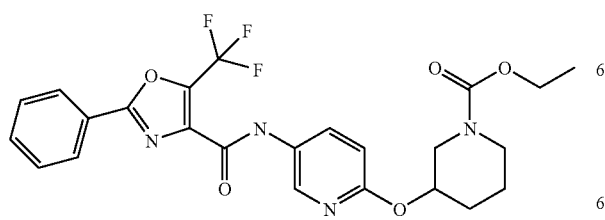

With a similar procedure to that used for the preparation of 3-{4-[(2-phenyl-5-trifluoromethyl-oxazole-4-carbonyl)-amino]-phenoxy}-pyrrolidine-1-carboxylic acid ethyl ester (example in the application), 3-{5-[(2-phenyl-5-trifluoromethyl-oxazole-4-carbonyl)-amino]-pyridin-2-yloxy}-piperidine-1-carboxylic acid ethyl ester was prepared from 5-ethyl-2-phenyl-oxazole-4-carboxylic acid, 2-chloro-5-nitro-pyridine, 3-hydroxy-piperidine-1-carboxylic acid tert-butyl ester and ethyl chloroformate. LCMS calcd for C24H23F3N4O5 (m/e) 504, obsd 505 (M+H).

Example 331

Preparation of 2-phenyl-5-trifluoromethyl-oxazole-4-carboxylic acid {4-[4-(3-propyl-1-methyl-ureido)-piperidin-1-yl]-phenyl}-amide

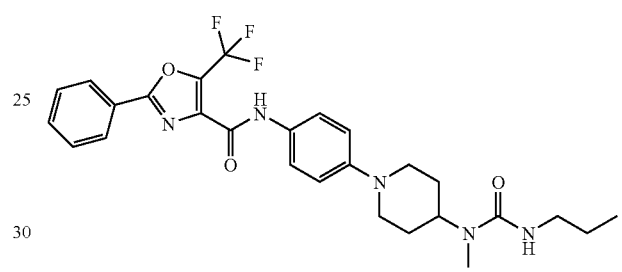

With a similar procedure as described above, 2-phenyl-5-trifluoromethyl-oxazole-4-carboxylic acid {4-[4-(3-propyl-1-methyl-ureido)-piperidin-1-yl]-phenyl}-amide was prepared from 2-phenyl-5-trifluoromethyl-oxazole-4-carboxylic acid [4-(4-methylamino-piperidin-1-yl)-phenyl]-amide and propylisocyanate. LCMS calcd for C27H30F3N5O3 (m/e) 529, obsd 530 (M+H).

Example 332

Preparation of 2-phenyl-5-trifluoromethyl-oxazole-4-carboxylic acid {4-[4-(3-ethyl-1-methyl-ureido)-piperidin-1-yl]-phenyl}-amide

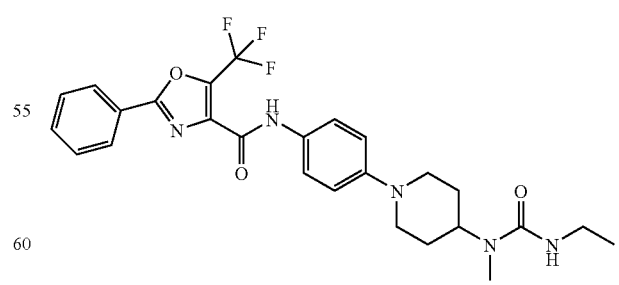

With a similar procedure as described above, 2-phenyl-5-trifluoromethyl-oxazole-4-carboxylic acid {4-[4-(3-ethyl-1-methyl-ureido)-piperidin-1-yl]-phenyl}-amide was prepared from 2-phenyl-5-trifluoromethyl-oxazole-4-carboxylic acid

[4-(4-methylamino-piperidin-1-yl)-phenyl]-amide and ethylisocyanate. LCMS calcd for C26H28F3N5O3 (m/e) 515, obsd 516 (M+H).

Example 333

Preparation of 2,2,N-trimethyl-N-(1-{4-[(2-phenyl-5-trifluoromethyl-oxazole-4-carbonyl)-amino]-phenyl}-piperidin-4-yl)-succinamic acid

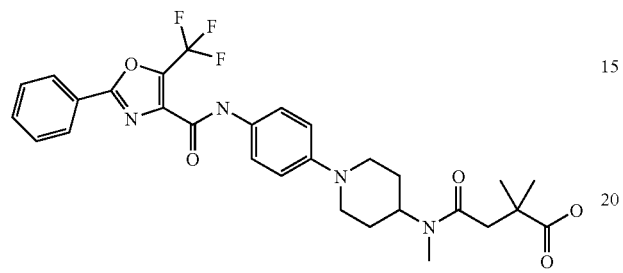

With a similar procedure as described above, 2,2,N-trimethyl-N-(1-{4-[(2-phenyl-5-trifluoromethyl-oxazole-4-carbonyl)-amino]-phenyl}-piperidin-4-yl)-succinamic acid was prepared from 2-phenyl-5-trifluoromethyl-oxazole-4-carboxylic acid [4-(4-methylamino-piperidin-1-yl)-phenyl]-amide and 2,2-dimethyl-succinic acid. LCMS calcd for C29H31F3N4O5 (m/e) 572, obsd 573 (M+H).

Example 334

Preparation of 2-phenyl-5-trifluoromethyl-oxazole-4-carboxylic acid {4-[4-(2-1H-tetrazol-5-yl-acetyl)-piperazin-1-yl]-phenyl}-amide

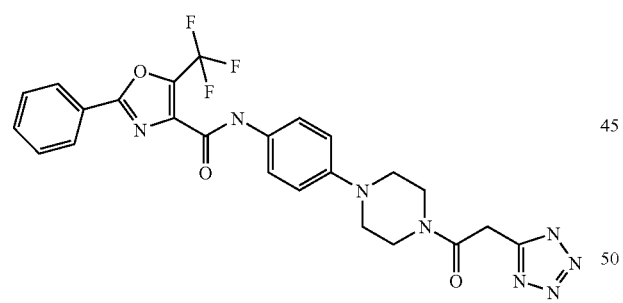

2-Phenyl-5-trifluoromethyl-oxazole-4-carboxylic acid (4-piperazin-1-yl-phenyl)-amide, hydrochloride (53 mg, 0.117 mmol), (1H-tetrazol-5-yl)-acetic acid (15 mg, 0.117 mmol), and triethylamine (49 uL, 0.351 mmol) were dissolved in 1.5 mL of DMF and chilled in an ice bath. To this solution was added BOP (52 mg, 0.122 mmol) in one portion. The mixture was stirred at room temperature for 30 minutes and then diluted with 30 ml CH$_2$Cl$_2$. The organic phase was washed with 1N citric acid (1×8 mL), water (3×8 mL) and saturated sodium chloride (10 mL). The organic layer was dried over MgSO$_4$, filtered and evaporated to dryness under vacuum. The residue was crystallized from acetonitrile to yield 2-phenyl-5-trifluoromethyl-oxazole-4-carboxylic acid {4-[4-(2-1H-tetrazol-5-yl-acetyl)-piperazin-1-yl]-phenyl}-amide as light yellow crystals (26 mg, 42%). ES-MS calcd for C24H21F3N8O3 (m/e) 526.48, obsd 527 (M+H).

Example 335

Preparation of 3-(4-{4-[(2-phenyl-5-trifluoromethyl-oxazole-4-carbonyl)-amino]-phenyl}-piperazine-1-carbonyl)-adamantane-1-carboxylic acid

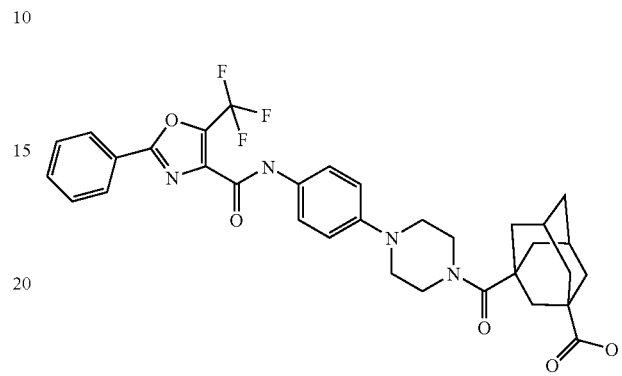

2-Phenyl-5-trifluoromethyl-oxazole-4-carboxylic acid (4-piperazin-1-yl-phenyl)-amide, hydrochloride (51.5 mg, 0.113 mmol), adamantane-1,3-dicarboxylic acid (51 mg, 0.227 mmol), and triethylamine (48 uL, 0.341 mmol) were dissolved in 1 mL of DMF. To this solution was added BOP (52 mg, 0.122 mmol) in one portion. The mixture was stirred at room temperature overnight. 4-N,N-dimethylamino-pyridine (5 mg) was added and the reaction was stirred for an additional 72 hours and then diluted with 30 ml ethyl acetate. The organic phase was washed with saturated ammonium chloride (1×5 mL), 2.5% KHSO$_4$ (3×5 mL), water (2×5 mL) and saturated sodium chloride. The organic layer was dried over MgSO$_4$, filtered, passed through a plug of silica gel and evaporated to dryness under vacuum to a light brown solid. The residue was purified by flash chromatography to yield 3-(4-{4-[(2-phenyl-5-trifluoromethyl-oxazole-4-carbonyl)-amino]-phenyl}-piperazine-1-carbonyl)-adamantane-1-carboxylic acid as light yellow crystals (9.4 mg, 13%). ES-MS calcd for C33H33F3N4O5 (m/e) 622.65, obsd 623 (M+H).

Example 336

Preparation of 2-phenyl-5-trifluoromethyl-oxazole-4-carboxylic acid {4-[1-(2-1H-tetrazol-5-yl-acetyl)-piperidin-4-yl]-phenyl}-amide

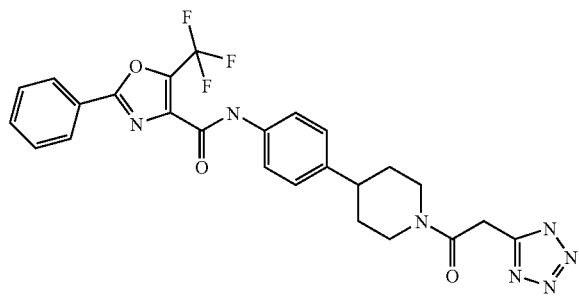

2-Phenyl-5-trifluoromethyl-oxazole-4-carboxylic acid (4-piperidin-4-yl-phenyl)-amide (50.7 mg, 0.122 mmol), (1H-tetrazol-5-yl)-acetic acid (15.6 mg, 0.122 mmol), triethylamine (51 uL, 0.366 mmol) and BOP (54 mg, 0.128 mmol) in 1 mL DMF were reacted as above to give a clear oil. The crude product was crystallized from methanol/acetonitrile to yield 2-phenyl-5-trifluoromethyl-oxazole-4-carboxylic acid {4-[1-(2-1H-tetrazol-5-yl-acetyl)-piperidin-4-yl]-phenyl}-amide as off-white crystals (11 mg, 17%). ES-MS calcd for C25H22F3N7O3 (m/e) 525.49, obsd 526 (M+H).

Example 337

Preparation of 1-methyl-4-(4-{4-[(2-phenyl-5-trifluoromethyl-oxazole-4-carbonyl)-amino]-phenyl}-piperidine-1-carbonyl)-cyclohexanecarboxylic acid

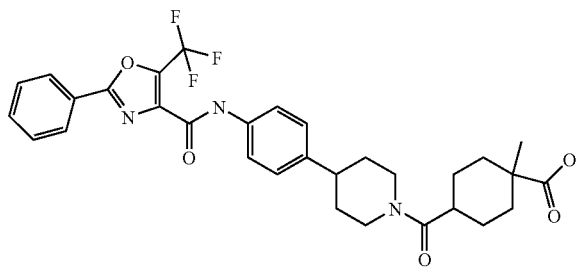

Methyl-cyclohexane-1,4-dicarboxylic acid (34.1 mg, 0.183 mmol) in dry $CH_2Cl_2$ (3 mL) was treated with phosgene (2M in $CH_2Cl_2$, 366 uL, 0.732 mmol) for 30 minutes. THF (0.5 mL) was added and stirred for an additional 30 minutes. The reaction was evaporated and re-evaporated from toluene three times and re-dissolved in 5 mL $CH_2Cl_2$. 2-Phenyl-5-trifluoromethyl-oxazole-4-carboxylic acid (4-piperidin-4-yl-phenyl)-amide (76.2 mg, 0.183 mmol) and triethylamine (77 uL, 0.549 mmol) in 3 mL of $CH_2Cl_2$ were added dropwise over 15 minutes to the above solution. The mixture was stirred at room temperature for 90 minutes and then diluted with 10 mL $CH_2Cl_2$. Following work-up, the crude residue was purified by flash chromatography to yield 1-methyl-4-(4-{4-[(2-phenyl-5-trifluoromethyl-oxazole-4-carbonyl)-amino]-phenyl}-piperidine-1-carbonyl)-cyclohexanecarboxylic acid as a white solid (26 mg, 24%). ES-MS calcd for C31H32F3N3O5 (m/e) 583.61, obsd 584 (M+H).

Example 338

Preparation of 2-phenyl-5-trifluoromethyl-oxazole-4-carboxylic acid (4-{1-[2-(2,4-dioxo-thiazolidin-5-yl)-acetyl]-piperidin-4-yl}-phenyl)-amide

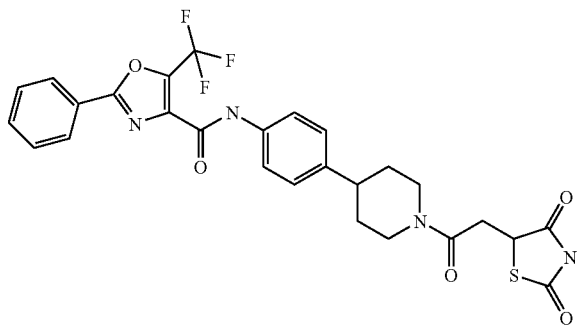

2-Phenyl-5-trifluoromethyl-oxazole-4-carboxylic acid (4-piperidin-4-yl-phenyl)-amide (60.1 mg, 0.149 mmol), (2,4-dioxo-thiazolidin-5-yl)-acetic acid (26.2 mg, 0.149 mmol), triethylamine (63 uL, 0.448 mmol) and BOP (63.2 mg, 0.149 mmol) in 1 mL DMF were reacted as above. The crude product was purified by flash chromatography to yield 2-phenyl-5-trifluoromethyl-oxazole-4-carboxylic acid (4-{1-[2-(2,4-dioxo-thiazolidin-5-yl)-acetyl]-piperidin-4-yl}-phenyl)-amide as a white solid (76.9 mg, 90%). ES-MS calcd for C27H23F3N4O5S (m/e) 572.57, obsd 573 (M+H).

Example 339

Preparation of 2-phenyl-5-trifluoromethyl-oxazole-4-carboxylic acid (4-{1-[3-(3-hydroxy-isoxazol-5-yl)-propionyl]-piperidin-4-yl}-phenyl)-amide

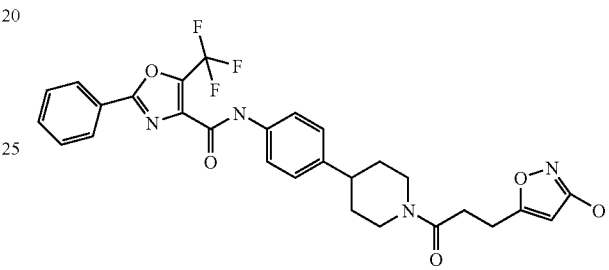

2-Phenyl-5-trifluoromethyl-oxazole-4-carboxylic acid (4-piperidin-4-yl-phenyl)-amide (46.8 mg, 0.112 mmol), 3-(3-hydroxy-isoxazol-5-yl)-propionic acid (17.7 mg, 0.112 mmol), triethylamine (47 uL, 0.337 mmol) and BOP (47.6 mg, 0.112 mmol) in 1 mL DMF were reacted as above. The crude product was purified by flash chromatography to yield 2-phenyl-5-trifluoromethyl-oxazole-4-carboxylic acid (4-{1-[3-(3-hydroxy-isoxazol-5-yl)-propionyl]-piperidin-4-yl}-phenyl)-amide as a white solid (15.5 mg, 25%). ES-MS calcd for C28H25F3N4O5 (m/e) 554.53, obsd 555 (M+H).

Example 340

Preparation of 2,2-dimethyl-4-oxo-4-(3-{4-[(2-phenyl-5-trifluoromethyl-oxazole-4-carbonyl)-amino]-phenoxy}-piperidin-1-yl)-butyric acid

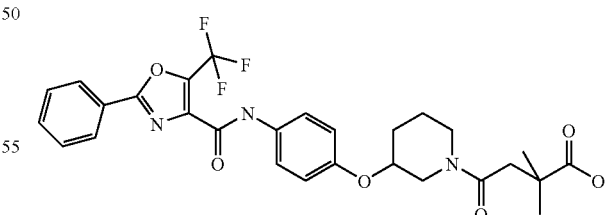

2-Phenyl-5-trifluoromethyl-oxazole-4-carboxylic acid [4-(piperidin-3-yloxy)-phenyl]-amide (52.3 mg, 0.121 mmol), 3,3-dimethyl-dihydro-furan-2,5-dione (17 mg, 0.133 mmol) and triethylamine (34 uL, 0.242 mmol) in 1 mL DMSO were stirred at room temperature for 30 minutes and then diluted with 30 ml ethyl acetate. The organic phase was washed with 2.5% $KHSO_4$ (5 mL) and saturated sodium chloride (2×5 mL), dried over $MgSO_4$, filtered and evaporated to dryness under vacuum. The crude product was purified by flash chromatography to yield 2,2-dimethyl-4-oxo-4-(3-{4-[(2-phenyl-5-trifluoromethyl-oxazole-4-carbonyl)-amino]-phenoxy}-piperidin-1-yl)-butyric acid as a white solid (46.4 mg, 68%). ES-MS calcd for C28H28F3N3O6 (m/e) 559.55, obsd 560 (M+H).

Example 341

Preparation of 2,2-dimethyl-5-oxo-5-(3-{4-[(2-phenyl-5-trifluoromethyl-oxazole-4-carbonyl)-amino]-phenoxy}-piperidin-1-yl)-pentanoic acid

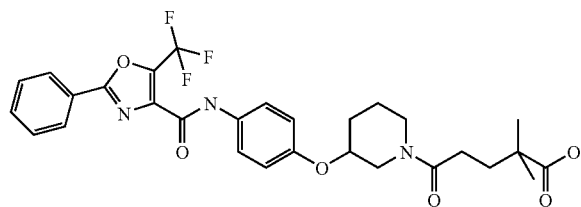

2-Phenyl-5-trifluoromethyl-oxazole-4-carboxylic acid [4-(piperidin-3-yloxy)-phenyl]-amide (44.1 mg, 0.102 mmol), 3,3-dimethyl-dihydro-pyran-2,6-dione (17.5 mg, 0.122 mmol) and triethylamine (28.5 uL, 0.204 mmol) in 1 mL DMSO were treated as above. The crude product was purified by flash chromatography to yield 2,2-dimethyl-5-oxo-5-(3-{4-[(2-phenyl-5-trifluoromethyl-oxazole-4-carbonyl)-amino]-phenoxy}-piperidin-1-yl)-pentanoic acid as a white solid (33 mg, 56%). ES-MS calcd for C29H30F3N3O6 (m/e) 573.57, obsd 574 (M+H).

Example 342

Preparation of 3,3-dimethyl-5-oxo-5-(3-{4-[(2-phenyl-5-trifluoromethyl-oxazole-4-carbonyl)-amino]-phenoxy}-piperidin-1-yl)-pentanoic acid

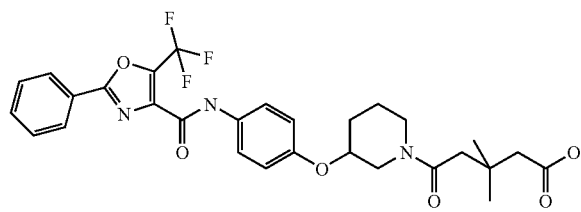

2-Phenyl-5-trifluoromethyl-oxazole-4-carboxylic acid [4-(piperidin-3-yloxy)-phenyl]-amide (46.2 mg, 0.107 mmol), 4,4-dimethyl-dihydro-pyran-2,6-dione (18.3 mg, 0.128 mmol) and triethylamine (30 uL, 0.214 mmol) in 1 mL DMSO were treated as above. The crude product was purified by flash chromatography to yield 3,3-dimethyl-5-oxo-5-(3-{4-[(2-phenyl-5-trifluoromethyl-oxazole-4-carbonyl)-amino]-phenoxy}-piperidin-1-yl)-pentanoic acid as a white solid (34 mg, 55%). ES-MS calcd for C29H30F3N3O6 (m/e) 573.57, obsd 574 (M+H).

Example 343

DGAT Phospholipid FlashPlate Assay

Materials for the assay were: PL-FlashPlate: Phospholipid FlashPlates from PerkinElmer, catalog number SMP108; DAG (1,2-Dioleoyl-sn-glycerol) 10 mM suspended in water containing 0.1% Triton X-100; $^{14}$C-Pal-CoA (palmitoyl coenzyme A, [palmitoyl-1-$^{14}$C]) from PerkinElmer, catalog number NEC-555 with a specific activity of 55 mCi/mmol; and DGAT pellet, with a protein concentration of 9.85 mg/ml.

Aqueous buffers were prepared or purchased as follows: The coating buffer (CB) was purchased from PerkinElmer, catalog number SMP900A; the reaction buffer (RB) was 50 mM Tris-HCl, pH 7.5, 100 mM NaCl, 0.01% BSA in water; the washing buffer (WB) is 50 mM Tris-HCl, pH 7.5, 100 mM NaCl, 0.05% deoxycholic acid sodium salt in water; the dilution buffer (DB) was 50 mM Tris-HCl, pH 7.5, 100 mM NaCl, 1 mM EDTA, 0.2% Triton X-100 in water.

1,2-Dioleoyl-sn-glycerol (DAG, 10 mmoles) was diluted to 500 μM with coating buffer (CB). The diluted DAG solution was then added to 384-well PL-FlashPlates at 60 μl per well, and incubated at room temperature for 2 days. The coated plates were then washed twice with washing buffer (WB) before use. Test compounds were serial diluted to 2000, 666.7, 222.2, 74.1, 24.7, 8.2, 2.7 and 0.9 μM in 100% DMSO. Diluted compound were further diluted 10 fold with reaction buffer (RB). $^{14}$C-Pal-CoA was diluted to 8.3 μM with RB. The DGAT pellet was diluted to 0.13 mg protein/ml with dilution buffer (DB) immediately before it was added to the PL-FlashPlates to start the reaction. 20 μl of the RB-diluted compounds (or 10% DMSO in RB for Total and Blank), 15 μl of RB diluted 14C-Pal-CoA and 15 μl of DB diluted DGAT pellet (DB without DGAT for Blanks) were transferred to each well of the PL-FlashPlates. The reaction mixtures were incubated at 37° C. for 1 hour. The reactions were stopped by washing 3 times with WB. Plates were sealed with Top-seal and read on a Topcount instrument.

Calculation of IC$_{50}$: The IC$_{50}$ values for each compound were generated using an Excel template. The Topcount rpm readings of Total and Blank were used as 0% and 100% inhibition. The percent inhibition values of reactions in the presence of compounds were calculated, and plotted against compound concentrations. All data were fitted into a Dose Response One Site model (4 parameter logistic model) as the following:

$$(A+((B-A)/(1+((x/C)^D)))),$$

with A and B as the bottom and top of the curve (highest and lowest inhibition), respectively, and C as IC$_{50}$ and D as Hill Coefficient of the compound. The results are summarized in Table 1 below:

TABLE 1

| Compound in | Activity in DGAT Phospholipid FlashPlate Assay (A = IC$_{50}$ < 0.10 μM, B = IC$_{50}$ ≥ 0.10 μM) |
|---|---|
| Example 1 | A |
| Example 2 | A |
| Example 3 | A |
| Example 4 | B |
| Example 5 | A |
| Example 6 | A |
| Example 7 | A |
| Example 8 | B |
| Example 9 | A |
| Example 10 | B |
| Example 11 | A |
| Example 12 | A |
| Example 13 | A |
| Example 14 | B |
| Example 15 | B |
| Example 16 | B |
| Example 17 | B |

TABLE 1-continued

Activity in DGAT Phospholipid FlashPlate Assay

| Compound in | (A = IC$_{50}$ < 0.10 μM, B = IC$_{50}$ ≧ 0.10 μM) |
|---|---|
| Example 18 | A |
| Example 19 | B |
| Example 20 | A |
| Example 21 | B |
| Example 22 | B |
| Example 23 | B |
| Example 24 | A |
| Example 25 | B |
| Example 26 | A |
| Example 27 | B |
| Example 28 | B |
| Example 29 | A |
| Example 30 | B |
| Example 31 | A |
| Example 32 | A |
| Example 33 | A |
| Example 34 | A |
| Example 35 | A |
| Example 36 | B |
| Example 37 | B |
| Example 38 | B |
| Example 39 | B |
| Example 40 | A |
| Example 41 | B |
| Example 42 | B |
| Example 43 | A |
| Example 44 | A |
| Example 45 | B |
| Example 46 | B |
| Example 47 | A |
| Example 48 | B |
| Example 49 | B |
| Example 50 | B |
| Example 51 | B |
| Example 52 | B |
| Example 53 | B |
| Example 54 | B |
| Example 55 | A |
| Example 56 | B |
| Example 57 | B |
| Example 58 | B |
| Example 59 | A |
| Example 60 | B |
| Example 61 | A |
| Example 62 | B |
| Example 63 | A |
| Example 64 | B |
| Example 65 | A |
| Example 66 | A |
| Example 67 | B |
| Example 68 | A |
| Example 69 | B |
| Example 70 | A |
| Example 71 | B |
| Example 72 | A |
| Example 73 | A |
| Example 74 | B |
| Example 75 | B |
| Example 76 | B |
| Example 77 | A |
| Example 78 | A |
| Example 79 | A |
| Example 80 | A |
| Example 81 | B |
| Example 82 | B |
| Example 83 | A |
| Example 84 | A |
| Example 85 | B |
| Example 86 | B |
| Example 87 | B |
| Example 88 | B |
| Example 89 | B |
| Example 90 | B |
| Example 91 | B |
| Example 92 | B |
| Example 93 | A |
| Example 94 | A |
| Example 95 | A |
| Example 96 | A |
| Example 97 | B |
| Example 98 | B |
| Example 99 | A |
| Example 100 | A |
| Example 101 | A |
| Example 102 | A |
| Example 103 | A |
| Example 104 | B |
| Example 105 | B |
| Example 106 | A |
| Example 107 | A |
| Example 108 | A |
| Example 109 | A |
| Example 110 | B |
| Example 111 | A |
| Example 112 | A |
| Example 113 | B |
| Example 114 | B |
| Example 115 | A |
| Example 116 | B |
| Example 117 | A |
| Example 118 | B |
| Example 119 | B |
| Example 120 | B |
| Example 121 | A |
| Example 122 | B |
| Example 123 | A |
| Example 124 | A |
| Example 125 | B |
| Example 126 | B |
| Example 127 | A |
| Example 128 | B |
| Example 129 | A |
| Example 130 | A |
| Example 131 | B |
| Example 132 | B |
| Example 133 | B |
| Example 134 | B |
| Example 135 | A |
| Example 136 | B |
| Example 137 | B |
| Example 138 | B |
| Example 139 | A |
| Example 140 | B |
| Example 141 | B |
| Example 142 | A |
| Example 143 | A |
| Example 144 | A |
| Example 145 | A |
| Example 146 | A |
| Example 147 | A |
| Example 148 | A |
| Example 149 | A |
| Example 150 | A |
| Example 151 | B |
| Example 152 | B |
| Example 153 | A |
| Example 154 | A |
| Example 155 | A |
| Example 156 | A |
| Example 157 | A |
| Example 158 | A |
| Example 159 | A |
| Example 160 | A |
| Example 161 | B |
| Example 162 | B |
| Example 163 | A |
| Example 164 | A |
| Example 165 | B |
| Example 166 | A |
| Example 167 | B |
| Example 168 | A |
| Example 169 | B |

TABLE 1-continued

Activity in DGAT Phospholipid FlashPlate Assay

| Compound in | ($A = IC_{50} < 0.10$ μM, $B = IC_{50} \geqq 0.10$ μM) |
|---|---|
| Example 170 | B |
| Example 171 | B |
| Example 172 | A |
| Example 173 | B |
| Example 174 | A |
| Example 175 | A |
| Example 176 | A |
| Example 177 | A |
| Example 178 | A |
| Example 179 | A |
| Example 180 | A |
| Example 181 | A |
| Example 182 | B |
| Example 183 | B |
| Example 184 | B |
| Example 185 | A |
| Example 186 | A |
| Example 187 | A |
| Example 188 | B |
| Example 189 | A |
| Example 190 | A |
| Example 191 | A |
| Example 192 | B |
| Example 193 | B |
| Example 194 | A |
| Example 195 | A |
| Example 196 | B |
| Example 197 | A |
| Example 198 | B |
| Example 199 | B |
| Example 200 | A |
| Example 201 | A |
| Example 202 | B |
| Example 203 | B |
| Example 204 | B |
| Example 205 | A |
| Example 206 | B |
| Example 207 | B |
| Example 208 | A |
| Example 209 | B |
| Example 210 | B |
| Example 211 | B |
| Example 212 | A |
| Example 213 | A |
| Example 214 | B |
| Example 215 | A |
| Example 216 | A |
| Example 217 | A |
| Example 218 | A |
| Example 219 | B |
| Example 220 | A |
| Example 221 | B |
| Example 222 | B |
| Example 223 | B |
| Example 224 | A |
| Example 225 | A |
| Example 226 | A |
| Example 227 | A |
| Example 228 | B |
| Example 229 | B |
| Example 230 | B |
| Example 231 | B |
| Example 232 | B |
| Example 233 | A |
| Example 234 | A |
| Example 235 | A |
| Example 236 | B |
| Example 237 | A |
| Example 238 | A |
| Example 239 | B |
| Example 240 | B |
| Example 241 | B |
| Example 242 | B |
| Example 243 | A |
| Example 244 | B |
| Example 245 | B |
| Example 246 | B |
| Example 247 | B |
| Example 248 | B |
| Example 249 | B |
| Example 250 | B |
| Example 251 | B |
| Example 252 | B |
| Example 253 | A |
| Example 254 | B |
| Example 255 | B |
| Example 256 | B |
| Example 257 | B |
| Example 258 | B |
| Example 259 | B |
| Example 260 | A |
| Example 261 | B |
| Example 262 | A |
| Example 263 | B |
| Example 264 | B |
| Example 265 | B |
| Example 266 | A |
| Example 267 | A |
| Example 268 | B |
| Example 269 | B |
| Example 270 | B |
| Example 271 | A |
| Example 272 | B |
| Example 273 | A |
| Example 274 | B |
| Example 275 | B |
| Example 276 | B |
| Example 277 | A |
| Example 278 | A |
| Example 279 | B |
| Example 280 | A |
| Example 281 | A |
| Example 282 | B |
| Example 283 | B |
| Example 284 | A |
| Example 285 | B |
| Example 286 | B |
| Example 287 | B |
| Example 288 | A |
| Example 289 | B |
| Example 290 | A |
| Example 291 | B |
| Example 292 | B |
| Example 293 | B |
| Example 294 | B |
| Example 295 | A |
| Example 296 | B |
| Example 297 | B |
| Example 298 | A |
| Example 299 | B |
| Example 300 | B |
| Example 301 | B |
| Example 302 | B |
| Example 303 | B |
| Example 304 | B |
| Example 305 | B |
| Example 306 | A |
| Example 307 | A |
| Example 308 | A |
| Example 309 | B |
| Example 310 | B |
| Example 311 | B |
| Example 312 | B |
| Example 313 | B |
| Example 314 | B |
| Example 315 | B |
| Example 316 | B |
| Example 317 | A |
| Example 318 | B |
| Example 319 | B |
| Example 320 | B |
| Example 321 | B |

TABLE 1-continued

| Compound in | Activity in DGAT Phospholipid FlashPlate Assay (A = IC$_{50}$ < 0.10 μM, B = IC$_{50}$ ≧ 0.10 μM) |
|---|---|
| Example 322 | B |
| Example 323 | B |
| Example 324 | B |
| Example 325 | A |
| Example 326 | B |
| Example 327 | B |
| Example 328 | A |
| Example 329 | A |
| Example 330 | B |
| Example 331 | B |
| Example 332 | B |
| Example 333 | A |
| Example 334 | B |
| Example 335 | B |
| Example 336 | B |
| Example 337 | B |
| Example 338 | A |
| Example 339 | B |
| Example 340 | B |
| Example 341 | B |
| Example 342 | B |

It is to be understood that the invention is not limited to the particular embodiments of the invention described above, as variations of the particular embodiments may be made and still fall within the scope of the appended claims.

What is claimed is:
1. A compound of formula (I):

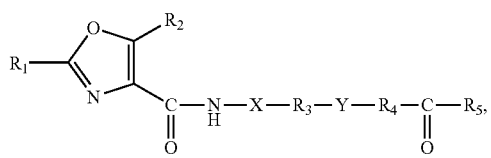

(I)

wherein:
R$_1$ is phenyl or 5- or 6-membered heteroaryl, said phenyl and heteroaryl being unsubstituted or substituted with halogen, lower alkyl, alkoxy or O—CF$_3$;
R$_2$ is halogen, lower alkyl, haloloweralkyl or alkoxy;
R$_3$ is nitrogen, oxygen or absent, said nitrogen being unsubstituted or substituted with lower alkyl;
R$_4$ is carbon, NH, oxygen or absent, said carbon being unsubstituted or substituted with lower alkyl,
wherein both R3 and R4 are not absent;
R$_5$ is -lower alkyl,
-alkoxy,
-hydroxy,
-amine,
-lower alkyl amine,
-haloloweralkyl,
-lower alkoxy,
-lower alkenyloxy,
-cycloloweralkyl, unsubstituted or substituted with one to four substituents from lower alkyl, hydroxy, halogen, —C(O)OH, —C(O)O-lower alkyl or —C(O)O-lower alkyl-phenyl,
-5- or 6-membered heterocycloalkyl, unsubstituted or substituted, with one to four substituents from lower alkyl, hydroxy, halogen, —SO$_2$-loweralkyl, —C(O)OH, —C(O)O-lower alkyl or —C(O)O-lower alkyl-phenyl,
-6-membered aryl, unsubstituted or substituted with one to four substituents from lower alkyl, hydroxy, halogen, —C(O)OH, —C(O)O-lower alkyl or —C(O)O-lower alkyl-phenyl,
-5- or 6-membered heteroaryl, unsubstituted or substituted with one to four substituents from lower alkyl, hydroxy, halogen, —C(O)OH, C(O)O-lower alkyl or —C(O)O -lower alkyl-phenyl,
—(CH$_2$)$_n$C(O)OH,
—CH$_2$C(lower alkyl)$_2$C(O)OH,
—CH$_2$(cycloalkyl)C(O)OH,
-(cycloalkyl)C(O)OH,
—CH$_2$C(CH$_3$)$_3$,
—(CH$_2$)$_n$-cycloalkyl,
-cycloalkenyl,
-bicycloalkenyl-C(O)OH,
—(CH$_2$)$_n$—O-alkyl,
—O—C(=C)-lower alkyl,
—O—(CH$_2$)$_n$-phenyl,
—NSO$_2$-loweralkyl,
—NSO$_2$-cycloalkyl,
—NSO$_2$-aryl,
—N-lower alkyl,
—N-cycloalkyl, said cycloalkyl being unsubstituted or substituted with —C(O)OH,
—N-heterocycloalkyl,
—N-aryl,
—N—(CH$_2$)$_n$-aryl,
—N-heteroaryl, said heteroaryl being unsubstituted or substituted with alkyl,
—N—CH(lower alkyl)C(O)OH,
—N-(cycloalkyl)C(O)OH,
—N—CH(lower alkyl)C(O)O-lower alkyl, or
-phenyl-C(O)OH,
X is 6-membered aryl or 5- or 6-membered heteroaryl, said aryl or heteroaryl being unsubstituted or substituted with lower alkyl, halogen or cyano;
Y is phenyl, heteroaryl, cycloloweralkyl, 5- or 6-membered heterocycloalkyl, or —N(CH$_2$)$_n$)N—, said phenyl, cycloloweralkyl or heterocycloalkyl being unsubstituted or substituted with lower alkyl, halogen or cyano; and
n is 1, 2 or 3,
or pharmaceutically acceptable salts thereof.
2. The compound according to claim 1, wherein:
R$_1$ is phenyl, unsubstituted or substituted with halogen, lower alkyl, alkoxy or O—CF$_3$;
R$_2$ is halogen, lower alkyl, haloloweralkyl or alkoxy;
R$_3$ is nitrogen, oxygen or absent, said nitrogen being unsubstituted or substituted with lower alkyl;
R$_4$ is carbon, NH, oxygen or absent, said carbon being unsubstituted or substituted with lower alkyl;
wherein both R$_3$ and R$_4$ are not absent;
R$_5$ is -lower alkyl,
-alkoxy,
-hydroxy,
-amine,
-lower alkyl amine,
-haloloweralkyl,
-lower alkoxy,
-lower alkenyloxy,
-cycloloweralkyl, unsubstituted or substituted with one to four substituents from lower alkyl, hydroxy, halogen, —C(O)OH, —C(O)O-lower alkyl or —C(O)O-lower alkyl-phenyl,
-5- or 6-membered heterocycloalkyl, unsubstituted or substituted, with one to four substituents from lower alkyl, hydroxy, halogen, —SO$_2$-loweralkyl, —C(O)OH, —C(O)O-lower alkyl or —C(O)O-lower alkyl-phenyl,
-6-membered aryl, unsubstituted or substituted with one to four substituents from lower alkyl, hydroxy, halogen, —C(O)OH, —C(O)O-lower alkyl or —C(O)O-lower alkyl-phenyl,
-5- or 6-membered heteroaryl, unsubstituted or substituted with one to four substituents from lower alkyl, hydroxy, halogen, —C(O)OH, C(O)O-lower alkyl or —C(O)O-lower alkyl-phenyl,
—(CH$_2$)$_n$C(O)OH,
—CH$_2$C(lower alkyl)$_2$C(O)OH,
—CH$_2$(cycloalkyl)C(O)OH,
-(cycloalkyl)C(O)OH,
—CH$_2$C(CH$_3$)$_3$,
—(CH$_2$)$_n$-cycloalkyl,
-cycloalkenyl,
-bicycloalkenyl-C(O)OH,
—(CH$_2$)$_n$—O-alkyl,
—O—C(=C)-lower alkyl,
—O—(CH$_2$)$_n$-phenyl,
—NSO$_2$-loweralkyl,
—NSO$_2$-cycloalkyl,
—NSO$_2$-aryl,
—N-lower alkyl,
—N-cycloalkyl, said cycloalkyl being unsubstituted or substituted with —C(O)OH,
—N-heterocycloalkyl,
—N-aryl,
—N—(CH$_2$)n-aryl,
—N-heteroaryl, said heteroaryl being unsubstituted or substituted with alkyl,
—N—CH(lower alkyl)C(O)OH,
—N-(cycloalkyl)C(O)OH,
—N—CH(lower alkyl)C(O)O-lower alkyl, or
-phenyl-C(O)OH,
X is 6-membered aryl or 5- or 6-membered heteroaryl, said aryl or heteroaryl being unsubstituted or substituted with lower alkyl, halogen or cyano;
Y is phenyl, heteroaryl, cycloloweralkyl, 5- or 6-membered heterocycloalkyl, or —N(CH$_2$)$_n$)N—, said phenyl, cycloloweralkyl or heterocycloalkyl being unsubstituted or substituted with lower alkyl, halogen or cyano; and
n is 1, 2 or 3.

3. The compound according to claim 1, wherein:
R$_1$ is 5- or 6-membered heteroaryl unsubstituted or substituted with halogen, lower alkyl, alkoxy or O—CF$_3$;
R$_2$ is halogen, lower alkyl, haloloweralkyl or alkoxy;
R$_3$ is nitrogen, oxygen or absent, said nitrogen being unsubstituted or substituted with lower alkyl;
R$_4$ is carbon, NH, oxygen or absent, said carbon being unsubstituted or substituted with lower alkyl;
wherein both R$_3$ and R$_4$ are not absent;
R$_5$ is -lower alkyl,
-alkoxy,
-hydroxy,
-amine,
-lower alkyl amine,
-haloloweralkyl,
-lower alkoxy,
-lower alkenyloxy,
-cycloloweralkyl, unsubstituted or substituted with one to four substituents from lower alkyl, hydroxy, halogen, —C(O)OH, —C(O)O-lower alkyl or —C(O)O-lower alkyl-phenyl,
-5- or 6-membered heterocycloalkyl, unsubstituted or substituted, with one to four substituents from lower alkyl, hydroxy, halogen, —SO$_2$-loweralkyl, —C(O)OH, —C(O)O-lower alkyl or —C(O)O-lower alkyl-phenyl,
-6-membered aryl, unsubstituted or substituted with one to four substituents from lower alkyl, hydroxy, halogen, —C(O)OH, —C(O)O-lower alkyl or —C(O)O-lower alkyl-phenyl,
-5- or 6-membered heteroaryl, unsubstituted or substituted with one to four substituents from lower alkyl, hydroxy, halogen, —C(O)OH, C(O)O-lower alkyl or —C(O)O-lower alkyl-phenyl,
—(CH$_2$)$_n$C(O)OH,
—CH$_2$C(lower alkyl)$_2$C(O)OH,
—CH$_2$(cycloalkyl)C(O)OH,
-(cycloalkyl)C(O)OH,
—CH$_2$C(CH$_3$)$_3$,
—(CH$_2$)$_n$-cycloalkyl,
-cycloalkenyl,
-bicycloalkenyl-C(O)OH,
—(CH$_2$)$_n$—O-alkyl,
—O—C(=C)-lower alkyl,
—O—(CH$_2$)$_n$-phenyl,
—NSO$_2$-loweralkyl,
—NSO$_2$-cycloalkyl,
—NSO$_2$-aryl,
—N-lower alkyl,
—N-cycloalkyl, said cycloalkyl being unsubstituted or substituted with —C(O)OH,
—N-heterocycloalkyl,
—N-aryl,
—N—(CH$_2$)$_n$-aryl,
—N-heteroaryl, said heteroaryl being unsubstituted or substituted with alkyl,
—N—CH(lower alkyl)C(O)OH,
—N-(cycloalkyl)C(O)OH,
—N—CH(lower alkyl)C(O)O-lower alkyl, or
-phenyl-C(O)OH,
X is 6-membered aryl or 5- or 6-membered heteroaryl, said aryl or heteroaryl being unsubstituted or substituted with lower alkyl, halogen or cyano;
Y is phenyl, heteroaryl, cycloloweralkyl, 5- or 6-membered heterocycloalkyl, or —N(CH$_2$)$_n$)N—, said phenyl, cycloloweralkyl or heterocycloalkyl being unsubstituted or substituted with lower alkyl, halogen or cyano; and
n is 1, 2 or 3.

4. The compound according to claim 1, wherein:
R$_1$ is phenyl or 5- or 6-membered heteroaryl, said phenyl and heteroaryl being unsubstituted or substituted with halogen, lower alkyl, alkoxy or O—CF$_3$;
R$_2$ is halogen, lower alkyl, haloloweralkyl or alkoxy;
R$_3$ is nitrogen, oxygen or absent, said nitrogen being unsubstituted or substituted with lower alkyl;
R$_4$ is carbon, NH, oxygen or absent, said carbon being unsubstituted or substituted with lower alkyl;
wherein both R$_3$ and R$_4$ are not absent;
R$_5$ is -lower alkyl,
-alkoxy,
-hydroxy,
-amine,
-lower alkyl amine,
-haloloweralkyl,
-lower alkoxy,
-lower alkenyloxy,

- cycloloweralkyl, unsubstituted or substituted with one to four substituents from lower alkyl, hydroxy, halogen, —C(O)OH, —C(O)O-lower alkyl or —C(O)O-lower alkyl-phenyl,
- 5- or 6-membered heterocycloalkyl, unsubstituted or substituted, with one to four substituents from lower alkyl, hydroxy, halogen, —SO$_2$-loweralkyl, —C(O)OH, —C(O)O-lower alkyl or —C(O)O-lower alkyl-phenyl,
- 6-membered aryl, unsubstituted or substituted with one to four substituents from lower alkyl, hydroxy, halogen, —C(O)OH, —C(O)O-lower alkyl or —C(O)O-lower alkyl-phenyl,
- 5- or 6-membered heteroaryl, unsubstituted or substituted with one to four substituents from lower alkyl, hydroxy, halogen, —C(O)OH, C(O)O-lower alkyl or —C(O)O-lower alkyl-phenyl,
- —(CH$_2$)$_n$C(O)OH,
- —CH$_2$C(lower alkyl)$_2$C(O)OH,
- —CH$_2$(cycloalkyl)C(O)OH,
- -(cycloalkyl)C(O)OH,
- —CH$_2$C(CH$_3$)$_3$,
- —(CH$_2$)$_n$-cycloalkyl,
- -cycloalkenyl,
- -bicycloalkenyl-C(O)OH,
- —(CH$_2$)$_n$—O-alkyl,
- —O—C(═C)-lower alkyl,
- —O—(CH$_2$)$_n$-phenyl,
- —NSO$_2$-loweralkyl,
- —NSO$_2$-cycloalkyl,
- —NSO$_2$-aryl,
- —N-lower alkyl,
- —N-cycloalkyl, said cycloalkyl being unsubstituted or substituted with —C(O)OH,
- —N-heterocycloalkyl,
- —N-aryl,
- —N—(CH$_2$)$_n$-aryl,
- —N-heteroaryl, said heteroaryl being unsubstituted or substituted with alkyl,
- —N—CH(lower alkyl)C(O)OH,
- —N-(cycloalkyl)C(O)OH,
- —N—CH(lower alkyl)C(O)O-lower alkyl, or
- -phenyl-C(O)OH, X is 6-membered aryl, unsubstituted or substituted with lower alkyl, halogen or cyano;

Y is phenyl, heteroaryl, cycloloweralkyl, 5- or 6-membered heterocycloalkyl, or —N(CH$_2$)$_n$)N—, said phenyl, cycloloweralkyl or heterocycloalkyl being unsubstituted or substituted with lower alkyl, halogen or cyano; and n is 1, 2 or 3.

5. The compound according to claim 1, wherein:

R$_1$ is phenyl or 5- or 6-membered heteroaryl, said phenyl and heteroaryl being unsubstituted or substituted with halogen, lower alkyl, alkoxy or O—CF$_3$;

R$_2$ is halogen, lower alkyl, haloloweralkyl or alkoxy;

R$_3$ is nitrogen, oxygen or absent, said nitrogen being unsubstituted or substituted with lower alkyl;

R$_4$ is carbon, NH, oxygen or absent, said carbon being unsubstituted or substituted with lower alkyl;

wherein both R$_3$ and R$_4$ are not absent;

R5 is -lower alkyl,
- -alkoxy,
- -hydroxy,
- -amine,
- -lower alkyl amine,
- -haloloweralkyl,
- -lower alkoxy,
- -lower alkenyloxy,
- -cycloloweralkyl, unsubstituted or substituted with one to four substituents from lower alkyl, hydroxy, halogen, —C(O)OH, —C(O)O-lower alkyl or —C(O)O-lower alkyl-phenyl,
- -5- or 6-membered heterocycloalkyl, unsubstituted or substituted, with one to four substituents from lower alkyl, hydroxy, halogen, —SO$_2$-loweralkyl, —C(O)OH, —C(O)O-lower alkyl or —C(O)O-lower alkyl-phenyl,
- -6-membered aryl, unsubstituted or substituted with one to four substituents from lower alkyl, hydroxy, halogen, —C(O)OH, —C(O)O-lower alkyl or —C(O)O-lower alkyl-phenyl,
- -5- or 6-membered heteroaryl, unsubstituted or substituted with one to four substituents from lower alkyl, hydroxy, halogen, —C(O)OH, C(O)O-lower alkyl or —C(O)O-lower alkyl-phenyl,
- —(CH$_2$)$_n$C(O)OH,
- —CH$_2$C(lower alkyl)$_2$C(O)OH,
- —CH$_2$(cycloalkyl)C(O)OH,
- -(cycloalkyl)C(O)OH,
- —CH$_2$C(CH$_3$)$_3$,
- —(CH$_2$)$_n$-cycloalkyl,
- -cycloalkenyl,
- -bicycloalkenyl-C(O)OH,
- —(CH$_2$)$_n$—O-alkyl,
- —O—C(═C)-lower alkyl,
- —O—(CH$_2$)$_n$-phenyl,
- —NSO$_2$-loweralkyl,
- —NSO$_2$-cycloalkyl,
- —NSO$_2$-aryl,
- —N-lower alkyl,
- —N-cycloalkyl, said cycloalkyl being unsubstituted or substituted with —C(O)OH,
- —N-heterocycloalkyl,
- —N-aryl,
- —N—(CH$_2$)$_n$-aryl,
- —N-heteroaryl, said heteroaryl being unsubstituted or substituted with alkyl,
- —N—CH(lower alkyl)C(O)OH,
- —N-(cycloalkyl)C(O)OH,
- —N—CH(lower alkyl)C(O)O-lower alkyl, or
- -phenyl-C(O)OH, X is 5- or 6-membered heteroaryl, unsubstituted or substituted with lower alkyl, halogen or cyano;

Y is phenyl, heteroaryl, cycloloweralkyl, 5- or 6-membered heterocycloalkyl, or —N(CH$_2$)$_n$)N—, said phenyl, cycloloweralkyl or heterocycloalkyl being unsubstituted or substituted with lower alkyl, halogen or cyano; and n is 1, 2 or 3.

6. The compound according to claim 1, wherein:

R$_1$ is phenyl or 5- or 6-membered heteroaryl, said phenyl and heteroaryl being unsubstituted or substituted with halogen, lower alkyl, alkoxy or O—CF$_3$;

R$_2$ is halogen, lower alkyl, haloloweralkyl or alkoxy;

R$_3$ is nitrogen, oxygen or absent, said nitrogen being unsubstituted or substituted with lower alkyl;

R$_4$ is carbon, NH, oxygen or absent, said carbon being unsubstituted or substituted with lower alkyl;

wherein both R3 and R$_4$ are not absent;

R$_5$ is -lower alkyl,
- -alkoxy,
- -hydroxy,
- -amine,

- -lower alkyl amine,
- -haloloweralkyl,
- -lower alkoxy,
- -lower alkenyloxy,
- -cycloloweralkyl, unsubstituted or substituted with one to four substituents from lower alkyl, hydroxy, halogen, —C(O)OH, —C(O)O-lower alkyl or —C(O)O-lower alkyl-phenyl,
- -5- or 6-membered heterocycloalkyl, unsubstituted or substituted, with one to four substituents from lower alkyl, hydroxy, halogen, —SO$_2$-loweralkyl, —C(O)OH, —C(O)O-lower alkyl or —C(O)O-lower alkyl-phenyl,
- -6-membered aryl, unsubstituted or substituted with one to four substituents from lower alkyl, hydroxy, halogen, —C(O)OH, —C(O)O-lower alkyl or —C(O)O-lower alkyl-phenyl,
- -5- or 6-membered heteroaryl, unsubstituted or substituted with one to four substituents from lower alkyl, hydroxy, halogen, —C(O)OH, —C(O)O-lower alkyl or —C(O)O-lower alkyl-phenyl,
- —(CH$_2$)$_n$C(O)OH,
- —CH$_2$C(lower alkyl)$_2$C(O)OH,
- —CH$_2$(cycloalkyl)C(O)OH,
- -(cycloalkyl)C(O)OH,
- —CH$_2$C(CH$_3$)$_3$,
- —(CH$_2$)$_n$-cycloalkyl,
- -cycloalkenyl,
- -bicycloalkenyl-C(O)OH,
- —(CH$_2$)$_n$—O-alkyl,
- —O—C(=C)-lower alkyl,
- —O—(CH$_2$)$_n$-phenyl,
- —NSO$_2$-loweralkyl,
- —NSO$_2$-cycloalkyl,
- —NSO$_2$-aryl,
- —N-lower alkyl,
- —N-cycloalkyl, said cycloalkyl being unsubstituted or substituted with —C(O)OH,
- —N-heterocycloalkyl,
- —N-aryl,
- —N—(CH$_2$)$_n$-aryl,
- —N-heteroaryl, said heteroaryl being unsubstituted or substituted with alkyl,
- —N—CH(lower alkyl)C(O)OH,
- —N-(cycloalkyl)C(O)OH,
- —N—CH(lower alkyl)C(O)O-lower alkyl, or
- -phenyl-C(O)OH, X is 6-membered aryl or 5- or 6-membered heteroaryl, said aryl or heteroaryl being unsubstituted or substituted with lower alkyl, halogen or cyano;

Y is phenyl, unsubstituted or substituted with lower alkyl, halogen or cyano; and n is 1, 2 or 3.

7. The compound according to claim 1, wherein:

R$_1$ is phenyl or 5- or 6-membered heteroaryl, said phenyl and heteroaryl being unsubstituted or substituted with halogen, lower alkyl, alkoxy or O—CF$_3$; is halogen, lower alkyl, haloloweralkyl or alkoxy;

R$_3$ is nitrogen, oxygen or absent, said nitrogen being unsubstituted or substituted with lower alkyl;

R$_4$ is carbon, NH, oxygen or absent, said carbon being unsubstituted or substituted with lower alkyl;

wherein both R$_3$ and R$_4$ are not absent;

R$_5$ is -lower alkyl,
- -alkoxy,
- -hydroxy,
- -amine,
- -lower alkyl amine,
- -haloloweralkyl,
- -lower alkoxy,
- -lower alkenyloxy,
- -cycloloweralkyl, unsubstituted or substituted with one to four substituents from lower alkyl, hydroxy, halogen, —C(O)OH, —C(O)O-lower alkyl or —C(O)O-lower alkyl-phenyl,
- -5- or 6-membered heterocycloalkyl, unsubstituted or substituted, with one to four substituents from lower alkyl, hydroxy, halogen, —SO$_2$-loweralkyl, —C(O)OH, —C(O)O-lower alkyl or —C(O)O-lower alkyl-phenyl,
- -6-membered aryl, unsubstituted or substituted with one to four substituents from lower alkyl, hydroxy, halogen, —C(O)OH, —C(O)O-lower alkyl or —C(O)O-lower alkyl-phenyl,
- -5- or 6-membered heteroaryl, unsubstituted or substituted with one to four substituents from lower alkyl, hydroxy, halogen, —C(O)OH, —C(O)O-lower alkyl or —C(O)O-lower alkyl-phenyl,
- —(CH$_2$)$_n$C(O)OH,
- —CH$_2$C(lower alkyl)$_2$C(O)OH,
- —CH$_2$(cycloalkyl)C(O)OH,
- -(cycloalkyl)C(O)OH,
- —CH$_2$C(CH$_3$)$_3$,
- —(CH$_2$)$_n$-cycloalkyl,
- -cycloalkenyl,
- -bicycloalkenyl-C(O)OH,
- —(CH$_2$)$_n$—O-alkyl,
- —O—C(=C)-lower alkyl,
- —O—(CH$_2$)$_n$-phenyl,
- —NSO$_2$-loweralkyl,
- —NSO$_2$-cycloalkyl,
- —NSO$_2$-aryl,
- —N-lower alkyl,
- —N-cycloalkyl, said cycloalkyl being unsubstituted or substituted with —C(O)OH,
- —N-heterocycloalkyl,
- —N-aryl,
- —N—(CH$_2$)$_n$-aryl,
- —N-heteroaryl, said heteroaryl being unsubstituted or substituted with alkyl,
- —N—CH(lower alkyl)C(O)OH,
- —N-(cycloalkyl)C(O)OH,
- —N—CH(lower alkyl)C(O)O-lower alkyl, or
- -phenyl-C(O)OH, X is 6-membered aryl or 5- or 6-membered heteroaryl, said aryl or heteroaryl being unsubstituted or substituted with lower alkyl, halogen or cyano;

Y is cycloloweralkyl or 5- or 6-membered heterocycloalkyl, said cycloloweralkyl or heterocycloalkyl being unsubstituted or substituted with lower alkyl, halogen or cyano; and n is 1, 2 or 3.

8. The compound according to claim 1, wherein:

R$_1$ is phenyl, unsubstituted or substituted with halogen, lower alkyl, alkoxy or O—CF$_3$; and X is 6-membered aryl, unsubstituted or substituted with lower alkyl, halogen or cyano.

9. The compound according to claim 1, wherein:

R$_1$ is phenyl, unsubstituted or substituted with halogen, lower alkyl, alkoxy or O—CF$_3$; and X is 5- or 6-membered heteroaryl, unsubstituted or substituted with lower alkyl, halogen or cyano.

10. The compound according to claim 1, wherein:
$R_1$ is 5- or 6-membered heteroaryl, unsubstituted or substituted with halogen, lower alkyl, alkoxy or O—$CF_3$; and
X is 6-membered aryl, unsubstituted or substituted with lower alkyl, halogen or cyano.

11. The compound according to claim 1, wherein:
$R_1$ is 5- or 6-membered heteroaryl, unsubstituted or substituted with halogen, lower alkyl, —O-lower alkyl or O—$CF_3$; and
X is 5- or 6-membered heteroaryl, unsubstituted or substituted with lower alkyl, halogen or cyano.

12. The compound according to claim 1, wherein:
$R_1$ is phenyl, unsubstituted or substituted with halogen, lower alkyl, alkoxy or O—$CF_3$; and
Y is phenyl, unsubstituted or substituted with lower alkyl, halogen or cyano.

13. The compound according to claim 1, wherein:
$R_1$ is 5- or 6-membered heteroaryl, unsubstituted or substituted with halogen, lower alkyl, alkoxy or O—$CF_3$; and
Y is phenyl, unsubstituted or substituted with lower alkyl, halogen or cyano.

14. The compound according to claim 1, wherein:
$R_1$ is phenyl, unsubstituted or substituted with halogen, lower alkyl, alkoxy or O—$CF_3$; and
Y is cycloloweralkyl or 5- or 6-membered heterocycloalkyl, said cycloloweralkyl or heterocycloalkyl being unsubstituted or substituted with lower alkyl, halogen or cyano.

15. The compound according to claim 1, wherein:
$R_1$ is 5- or 6-membered heteroaryl, unsubstituted or substituted with halogen, lower alkyl, alkoxy or O—$CF_3$; and
Y is cycloloweralkyl or 5- or 6-membered heterocycloalkyl, said cycloloweralkyl or heterocycloalkyl being unsubstituted or substituted with lower alkyl, halogen or cyano.

16. The compound according to claim 1, wherein:
X is 6-membered aryl, unsubstituted or substituted with lower alkyl, halogen or cyano; and
Y is phenyl, heteroaryl, cycloloweralkyl, 5- or 6-membered heterocycloalkyl, or —N($CH_2$)$_n$N—, said phenyl, cycloloweralkyl or heterocycloalkyl being unsubstituted or substituted with lower alkyl, halogen or cyano.

17. The compound according to claim 1, wherein:
X is 5- or 6-membered heteroaryl, unsubstituted or substituted with lower alkyl, halogen or cyano; and
Y is phenyl, heteroaryl, cycloloweralkyl, 5- or 6-membered heterocycloalkyl, or —N($CH_2$)$_n$N—, said phenyl, cycloloweralkyl or heterocycloalkyl being unsubstituted or substituted with lower alkyl, halogen or cyano.

18. The compound according to claim 1, wherein:
X is 6-membered aryl or 5- or 6-membered heteroaryl, said aryl or heteroaryl being unsubstituted or substituted with lower alkyl, halogen or cyano; and
Y is phenyl, unsubstituted or substituted with lower alkyl, halogen or cyano.

19. The compound according to claim 1, wherein:
X is 6-membered aryl or 5- or 6-membered heteroaryl, said aryl or heteroaryl being unsubstituted or substituted with lower alkyl, halogen or cyano; and
Y is cycloloweralkyl or 5- or 6-membered heterocycloalkyl, said cycloloweralkyl or heterocycloalkyl being unsubstituted or substituted with lower alkyl, halogen or cyano.

20. The compound according to claim 1, wherein $R_1$ is phenyl, unsubstituted or substituted with halogen.

21. The compound according to claim 1, wherein $R_1$ is pyridine, unsubstituted or substituted with halogen.

22. The compound according to claim 1, wherein $R_2$ is halogen, trifluoromethyl, trifluoroethyl, methyl, ethyl, propyl, methoxymethyl or methoxyethyl.

23. The compound according to claim 1, wherein $R_5$ is lower alkyl, alkoxy, hydroxy, lower alkyl amine; cycloloweralkyl, unsubstituted or substituted with one to four substituents from loweralkyl, hydroxy, halogen, —C(O)OH, —C(O)O -lower alkyl or —C(O)O-lower alkyl-phenyl; 5- or 6-membered heterocycloalkyl, unsubstituted or substituted, with one to four substituents from lower alkyl, hydroxy, halogen, —$SO_2$-loweralkyl, —C(O)OH, —C(O)O-lower alkyl or —C(O)O-lower alkyl-phenyl; ($CH_2$)$_n$C(O)OH; $CH_2$C(lower alkyl)$_2$C(O)OH; $CH_2$(cycloalkyl)C(O)OH; (cycloalkyl)C(O)OH; $NSO_2$-loweralkyl; N-lower alkyl; N-cycloalkyl, said cycloalkyl being unsubstituted or substituted with —C(O)OH; N—CH(lower alkyl)C(O)OH; or N-(cycloalkyl)C(O)OH.

24. The compound according to claim 1, wherein X is phenyl, pyridine or pyrimidine.

25. The compound according to claim 1, wherein Y is phenyl, pyridine, piperazine, piperidine, pyrrolidine or cyclopentane.

26. The compound according to claim 1, wherein $R_3$ is nitrogen, unsubstituted or substituted with lower alkyl.

27. The compound according to claim 1, wherein $R_4$ is NH.

28. The compound according to claim 1, wherein n is 1.

29. The compound according to claim 1, selected from the group consisting of:

(1R,2R)-2-{4'-[(2-phenyl-5-trifluoromethyl-oxazole-4-carbonyl-amino]-biphenyl-4-ylcarbamoyl}-cyclopentanecarboxylic acid, (1S,2S)-2-{4'-[(2-phenyl-5-trifluoromethyl-oxazole-4-carbonyl-amino]-biphenyl-4-ylcarbamoyl}-cyclopentanecarboxylic acid, (S)-3-(5-{[2-(2-trifluoromethoxy-phenyl)-5-trifluoromethyl-oxazole-4-carbonyl]-amino}-pyrimidin-2-yloxy)-pyrrolidine-1-carboxylic acid ethyl ester, (S)-3-{5-[(2-phenyl-5-trifluoromethyl-oxazole-4-carbonyl)-amino]-pyridin-2-yloxy}-pyrrolidine-1-carboxylic acid ethyl ester, (S)-3-(4-{[2-(2-trifluoromethoxy-phenyl)-5-trifluoromethyl-oxazole-4-carbonyl]-amino}-phenylamino)-pyrrolidine-1-carboxylic acid ethyl ester, 2-phenyl-5-trifluoromethyl-oxazole-4-carboxylic acid [6((S)-1-isobutyryl-pyrrolidin-3-ylamino)-pyridin-3-yl]-amide, 2,2-dimethyl-3-{5'-[(2-phenyl-5-trifluoromethyl-oxazole-4-carbonyl)-amino]-3,4,5,6-tetrahydro-2H-[1,2']bipyridinyl-4-yl}-propionic acid, (S)-3-(5-{[2-(2-trifluoromethoxy-phenyl)-5-trifluoromethyl-oxazole-4-carbonyl]-amino}-pyridin-2-ylamino)-pyrrolidine-1-carboxylic acid ethyl ester, (S)-3-{4-[(2-phenyl-5-trifluoromethyl-oxazole-4-carbonyl)-amino]-phenylamino}-pyrrolidine-1-carboxylic acid ethyl ester, and (S)-3-(5-{[2-(2-trifluoromethoxy-phenyl)-5-trifluoromethyl-oxazole-4-carbonyl]-amino}-pyrimidin-2-ylarnino)-pyrrolidine-1-carboxylic acid ethyl ester.

30. The compound of claim 1 wherein:

$R_1$ is unsubstituted phenyl or phenyl substituted with halogen, lower alkyl, alkoxy or O—CF$_3$;

$R_2$ is halogen, lower alkyl, haloloweralkyl or alkoxy;

X is a 6-membered aryl or 5- or 6-membered heteroaryl, said aryl or heteroaryl being unsubstituted or substituted with lower alkyl, halogen or cyano;

$R_3$ is nitrogen, oxygen or absent, said nitrogen being unsubstituted or substituted with lower alkyl;

$R_4$ is carbon, NH, oxygen or absent, said carbon being unsubstituted or substituted with lower alkyl;

wherein both $R_3$ and $R_4$ are not absent;

$R_5$ is lower alkyl, lower alkoxy, -hydroxy, -cycloloweralkyl, which is unsubstituted or substituted with one to four substituents selected from the group consisting of lower alkyl, hydroxy, halogen, —C(O)OH, —C(O)O-lower alkyl or —C(O)O-lower alkyl-phenyl, or 5 or 6-membered heterocycloalkyl, unsubstituted or substituted, with one substituent selected from the group consisting of lower alkyl, —C(O)OH, or —C(O)O-lower alkyl or pharmaceutically acceptable salts thereof.

31. The compound of claim 30 wherein $R_3$ is absent.

32. The compound of claim 31 wherein X is phenyl.

33. The compound of claim 30 wherein $R_5$ is a 5 or 6-membered heterocycloalkyl ring, said ring being unsubstituted or substituted in one position with C(O)OH or —C(O)O-lower alkyl.

34. The compound of claim 30 wherein $R_3$ is nitrogen or lower alkyl substituted nitrogen.

35. The compound of claim 34 wherein X is phenyl.

36. The compound of claim 35 wherein said compound is 3-{4-[(2-phenyl-5-trifluoromethyl-oxazole-4-carbonyl)-amino]-phenylamino}-pyrrolidine-1-carboxylic acid ethyl ester or its pharmaceutically acceptable salts.

37. The compound of claim 34 wherein X is 5 or 6-membered heteroaryl ring containing from 1 to 2 heteroatoms.

38. The compound of claim 37 wherein said heteroatoms are nitrogen atoms.

39. The compound of claim 38 wherein said compound is 3-(5-{[2-(2-trifluoromethoxy-phenyl)-5-trifluoromethyl-oxazole-4-carbonyl]-amino}-pyrimidin-2-ylamino)-pyrrolidine-1 -carboxylic acid ethyl ester or its pharmaceutically acceptable salts.

40. The compound of claim 38 wherein said compound is 3-(5-{[2-(2-trifluoromethoxy-phenyl)-5-trifluoromethyl-oxazole-4-carbonyl]amino}-pyridin-2-ylamino)-pyrrolidine-1-carboxylic acid ethyl ester or its pharmaceutically acceptable salts.

41. The compound of claim 38 wherein said compound is 2-phenyl-5-trifluoromethyl-oxazole-4-carboxylic acid [6-(1-isobutyryl-pyrrolidin-3-ylamino)-pyridin-3-yl]-amide ethyl ester.

42. The compound of claim 30 wherein $R_3$ is oxygen.

43. The compound of claim 42 wherein X is 5 or 6-membered heteroaryl ring containing from 1 to 2 heteroatoms.

44. The compound of claim 43 wherein said compound is 3-{5-[(2-phenyl-5-trifluoromethyl-oxazole-4-carbony)amino]-pyridin-2-yloxy}-pyrrolidine-1-carboxylic acid ethyl ester or its pharmaceutically acceptable salts.

45. The compound of claim 38 wherein said compound is 3-(5-{[(2-(2-trifluoromethoxy-phenyl)-5-trifluoromethyl-oxazole-4-carbonyl]-amino}-pyrimidin-2-yloxy)-pyrrolidine-1-carboxylic acid ethyl ester or its pharmaceutically acceptable salts.

46. The compound of claim 33 wherein Y is 5- or 6-membered heterocycloalkyl being unsubstituted or substituted with lower alkyl, halogen or cyano.

47. The compound of claim 46 wherein said compound is 2,2-dimethyl-3-{5'-[(2-phenyl-5-trifluoromethyl-oxazole-4-carbonyl)-amino]-3,4,5,6-tetrahydro-2H-[1,2']bipyridinyl-4-yl}-propionic acid or its pharmaceutically acceptable salts.

48. The compound of claim 32 wherein $R_5$ is cycloloweralkyl unsubstituted or substituted in one position with C(O)OH or —C(O)O-lower alkyl.

49. The compound of claim 33 wherein said compound is 3-(4-{[2-(2-trifluoromethoxy-phenyl)-5-trifluoromethyl-oxazole-4-carbonyl]-amino}-phenylamino)-pyrrolidine-1-carboxylic acid ethyl ester or its pharmaceutically acceptable salts.

50. The compound of claim 48 wherein said compound is 2-{4'-[(2-phenyl-5-trifluoromethyl-oxazole-4-carbonyl)-amino]-biphenyl-4-ylcarbamoyl}-cyclopentanecarboxylic acid, its lower alkyl esters or their pharmaceutically acceptable salts.

51. The compound of claim 50 wherein said compound is (1S,2S)-2-{4'-[(2-phenyl-5-trifluoromethyl-oxazole-4-carbonyl)-amino]-biphenyl-4-ylcarbamoyl}-cyclopentanecarboxylic acid ethyl ester or its pharmaceutically acceptable salts.

* * * * *